US010421975B2

(12) United States Patent
Benning et al.

(10) Patent No.: US 10,421,975 B2
(45) Date of Patent: Sep. 24, 2019

(54) 14-3-3 PROTEINS ENHANCE WRINKLED1 TRANSCRIPTION FACTOR-REGULATED OIL PRODUCTION

(71) Applicant: Board of Trustees of Michigan State University, East Lansing, MI (US)

(72) Inventors: Christoph Benning, East Lansing, MI (US); John B. Ohlrogge, Okemos, MI (US); Wei Ma, Lansing, MI (US); Que Kong, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 15/627,006

(22) Filed: Jun. 19, 2017

(65) Prior Publication Data

US 2018/0094274 A1 Apr. 5, 2018

Related U.S. Application Data

(60) Provisional application No. 62/352,246, filed on Jun. 20, 2016.

(51) Int. Cl.
*C12N 15/82* (2006.01)
*C07K 14/415* (2006.01)

(52) U.S. Cl.
CPC ........ *C12N 15/8247* (2013.01); *C07K 14/415* (2013.01); *C12N 15/8261* (2013.01); *Y02A 40/146* (2018.01)

(58) Field of Classification Search
None
See application file for complete search history.

(56) References Cited

U.S. PATENT DOCUMENTS 4,053,646 A * 10/1977 Wright ................. A23K 20/158 426/62

OTHER PUBLICATIONS

Ma et al, The Plant Journal, published online Aug. 30, 2016 (Year: 2016).*
Kong and Ma, Plant Signaling and Behavior, vol. 13, Issue 8, published online Aug. 1, 2018 (Year: 2018).*
Baud, S., et al., "WRINKLED1 specifies the regulatory action of LEAFY COTYLEDON2 towrds fatty acid metabolism during seed maturation in *Arabidopis*", Plant J., 50(5), (2007), 825-838.
Blom, N., et al., "Sequence and Structure-Based Prediction of Eukaryotic Protein Phosphorylation Sites", J Mol Biol, 294(5), (1999), 1351-1362.
Cernac, A., et al., "WRINKLED1 encodes an AP2/EREB domain protein involved in the control of storage compound biosynthesis in *Arabidopsis*", Plant J, 40(4), (2004), 575-585.
Chen, L., et al., "*Arabidopsis* BPM Proteins Function as Substrate Adaptors to a CULLIN3-Based E3 Ligase to Affect Fatty Acid Metabolism in Plants", Plant Cell, 25(6), (2013), 2253-2264.
Duek, P. D., et al., "The Degradation of HFR1, a Putative bHLH Class Transcription Factor Involved in Light Signaling, Is Regulated by Phosphorylation and Requires COP1", Curr Biol, 14(24), (2004), 2296-2301.
Dunker, A. K., et al., "Intrinsic Disorder and Protein Function", Biochemistry, 41(21), (2002), 6573-6582.
Dyson, H. J., et al., "Intrinsically Unstructured Proteins and Their Functions", Nat. Rev. Mol. Cell. Biol., 6(3), (2005), 197-208.
Evrard, A., et al., "Regulation of the heat stress response in *Arabidopsis* by MPK6-targeted phosphorylation of the heat stress factor HsfA2", PeerJ, 1, e59, (2013), 21 pgs.
Focks, N., et al., "wrinkied1: A Novel, Low-Seed-Oil Mutant of *Arabidopsis* with a Deficiency in the Seed-Specific Regulation of Carbohydrate Metabolism", Plant Physiol. 118(1), (1998), 91-101.
Gao, J., et al., "Correlation between posttranslational modification and intrinsic disorder in protein", Pacific Symposium on Biocomputing. (2012), 94-103, (2012), 12 pgs.
Garcia-Alai, M. M., "Molecular basis for phosphorylation-dependent, PEST-mediated protein turnover", Structure, 14(2), (2006), 309-319.
Hara, A., "Lipid Extraction of Tissues with a Low-Toxicity Solvent", Analytical Biochemistry, 90(1), (1978), 420-426.
Hardtke, C. S., et al., "HY5 stability and activity in *Arabidopsis* is regulated by phosphorylation in its COP1 binding domain", EMBO J, 19(18), (2000), 4997-5006.
Iakoucheva, L. M., et al., "The importance of intrinsic disorder for protein phosphorylation", Nucleic Acids Res, 32(3), (2004), 1037-1049.
Kjaersgaard, T., et al., "Senescence-associated barley NAC (NAM, ATAF1,2, CUC) transcription factor interacts with radical-induced cell death 1 through a disordered regulatory domain", J Biol Chem, 286(41)(2011), 35418-35429.
Kong, Q., et al., "Regulatory switch enforced by basic helix-loop-helix and ACT-domain mediated dimerizations of the maize transcription factor R", Proc Natl Acad Sci USA, 109(30), (2012), E2091-E2097.
Kragelund, B B., et al., "Order by disorder in plant signaling", Trends in Plant Science, 17(11), (2012), 625-632.
Kurotani, A., et al., "Correlations between predicted protein disorder and post-translational modifications in plants", Bioinformatics, 30(8), (2014), 1095-1103.
Li, Y., et al., "Oil content of *Arabidopsis* seeds: the influence of seed anatomy, light and plant-to-plant variation", Phytochemistry, 67(9), (2006), 904-915.
Lindemose, S., et al., "Structure, Function and Networks of Transcription Factors Involved in Abiotic Stress Responses", Int J Mol Sci, 14(3), (2013), 5842-5878.
Liu, D., et al., "Validation of Reference Genes for Gene Expression Studies in Virus-Infected *Nicotiana benthamiana* Using Quantitative Real-Time PCR", PloS One, 7(9), e46451, (2012), 1-14.

(Continued)

*Primary Examiner* — Eileen B O Hara
(74) *Attorney, Agent, or Firm* — Schwegman Lundberg & Woessner, P.A.

(57) ABSTRACT

The application describes plants, plant cells, and seeds that express WRINKLED1 transcription factors and/or 14-3-3 proteins that are useful for increasing production of oils in plants and seeds. Also described are expression systems and cassettes that encode and express such WRINKLED1 transcription factors and/or 14-3-3 proteins.

20 Claims, 23 Drawing Sheets
(10 of 23 Drawing Sheet(s) Filed in Color)

Specification includes a Sequence Listing.

(56) References Cited

OTHER PUBLICATIONS

Liu, H., et al., "Cytoplasmic degradation of the *Arabidopsis* transcription factor abscisic acid insensitive 5 is mediated by the RING-type E3 ligase Keep on Going", J Biol Chem, 288(28), (2013), 20267-20279.
Liu, J., et al., "Increasing seed mass and oil content in transgenic *Arabidopsis* by the overexpression of wri1-like gene from *Brassica napus*", Plant Physiol Biochem, 48(1), (2010), 9-15.
Liu, J., et al., "Intrinsic Disorder in Transcription Factors", Biochemistry, 45(22), (2006), 6873-6888.
Liu, Z. P., et al., "A role for CKII phosphorylation of the cactus PEST domain in dorsoventral patterning of the *Drosophila* embryo", Genes Dev, 11(24), (1997), 3413-3422.
Lu, Q. S., et al., "The C-terminal domain of FUSCA3 negatively regulates mRNA and protein levels, and mediates sensitivity to the hormones abscisic acid and gibberellic acid in *Arabidopsis*", Plant J, 64(1), (2010), 100-113.
Ma, W., et al., "Deletion of a C-terminal intrinsically disordered region of WRINKLED1 affects its stability and enhances oil accumulation in *Arabidopsis*", The Plant Journal, 83(5), (2015), 864-674.
Ma, W., et al., "Wrinkled1 , a Ubiquitous Regulator in Oil Accumulating Tissues from *Arabidopsis* Embryos to Oil Palm Mesocarp", PloS One, 8(7), e68887, (2013), 1-13.
Maeo, K., et al., "An AP2-type transcription factor, WRINKLED1, of *Arabidopsis thaliana* binds to the AW-box sequence conserved among proximal upstream regions of genes involved in fatty acid synthesis", Plant J, 60(3), (2009), 476-487.
Marchive, C., et al., "Transcriptional regulation of fatty acid production in higher plants: Molecular bases and biotechnological outcomes", Eur J Lipid Sci Technol, 11, (2014), 1332-1343.
Marin, M., et al., "The intrinsically Disordered N-termina Region of AtREM1.3 Remorin Protein Mediates Protein-Protein Interactions", J Biol Chem, 287(47), (2012), 39982-39991.
Masaki, Takeshi, et al., "ACTIVATOR of $Spo^{min}$::LUC1/ WRINKLED1 of *Arabidopsis thaliana* Transactivates Sugar-inducible Promoters", Plant Cell Physiol. 46(4), (2005), 547-556.
Meyer, R. D., et al., "PEST Motif Serine and Tyrosine Phosphorylation Controls Vascular Endothelial Growth Factor Receptor 2 Stability and Downregulation", Mol. Cell Biol, 31(10), (2011), 2010-2025.
Mitchell, P., et al., "Transcriptional Regulation in Mammalian Cells by Sequence-Specific DNA Binding Proteins", Science, 245(4916), (Jul. 21, 1989), 371-378.
Miura, K., et al., "ICE1 Ser403 is necessary for protein stabilization and regulation of cold signaling and tolerance", Plant J, 67(2), (2011), 269-279.
Mizoi, J., et al., "GmDREB2A;2, a Canonical Dehydration-Responsive Element-Binding Protein2-Type Transcription Factor in Soybean, Is Posttranslationally Regulated and Mediates Dehydration-Responsive Element-Dependent Gene Expression[1[W][OA]]", Plant Physiol, 161(1), (2013), 346-361.
Oldfield, C. J., et al., "Comparing and Combining Predictors of Mostly Disordered Proteins", Biochemistry, 44(6), (2005), 1989-2000.
Pazos. F., et al., "Protein intrinsic disorder in plants", Frontiers in Plant Science, 4, Article 363, (2013), 1-5.
Pouvreau, B., et al., "Duplicate maize Wrinkled1 Transcription Factors Activate Target Genes Involved in Seed Oil Biosynthesis[1[C][W]]", Plant Physiol, 156(2), (2011), 674-686.
Radivojac, P., et al., "Prediction of boundaries between intrinsically ordered and disordered protein regions", Pacific Symposium on Biocomputing, 8, (2003), 216-227.
Rechsteiner, M., et al., "PEST sequences and regulation by proteolysis", Trends Biochem Sci, 21(7), (1996), 267-271.
Rogers, Scott, et al., "Amino Acid Sequences Common to Rapidly Degraded Proteins: The PEST Hypothesis", Science, 234(4774), (Oct. 1986), 364-368.
Romero, P., et al., "Sequence Complexity of Disordered Protein", Proteins, 42(1), (2001), 38-48.
Ruuska, S. A., et al., "Contrapuntal Networks of Gene Expression during *Arabidopsis* Seed Filling", Plant Cell 14(6), (2002), 1191-1206.
Sakuma, Y., et al., "Dual function of an *Arabidopsis* transcription factor DREB2A in water-stress-responsive and heat-stress-responsive gene expression", Proc Natl Acad Sci USA, 103(49), (2006), 18822-18827.
Sakuma, Y., et al., "Functional Analysis of an *Arabidopsis* Transcription Factor, DREB2A, Involved in Drought-Responsive Gene Expression", Plant Cell, 18(5), (2006), 1292-1309.
Salmeron, A., et al., "Direct phosphorylation of NF-κB1 p105 by the IκB kinase complex on serine 927 is essential for signal-induced p105 proteolysis", J Biol Chem, 276(25), (2001), 22215-22222.
Sanjaya, et al., "Increasing the energy density of vegetative tissues by diverting carbon from starch to oil biosynthesis in transgenic *Arabidopsis*", Plant Biotechnology Journal, 9(8), (2011), 874-883.
Shen, B., et al., "Expression of ZmLEC1 and ZmWRI1 Increases Seed Oil Production in Maize[1[W][OA]]", Plant Physiol, 153(3), (2010), 980-987.
Singh, G. P., et al., "Intrinsic Unstructuredness and Abundance of PEST Motifs in Eukaryotic Proteomes", Proteins, 62(2), (2006), 309-315.
Sirichandra, C., et al., "The *Arabidopsis* ABA-Activated Kinase OST1 Phosphorylates the bZIP Transcription Factor ABF3 and Creates a 14-3-3 Binding Site Involved in its Turnover", PloS One, 5(11), e13935, (Nov. 2010), 1-13.
Tsai, A. Y-L., et al., "AKIN10 and FUSCA3 interact to control lateral rgan development and phase transitions in *Arabidopsis*", Plant J, 69(5), (2012), 809-821.
Vacic, V., et al., "Composition Profiler: a tool for discovery and visualization of amino acid composition differences", BMC Bioinformatics, 8: 211, (2007), 7 pages.
Valsecchi, I., et al., "The intrinsically disordered C-terminal region of *Arabidopsis thaliana* TCP8 transcription factor acts both as a transactivation and self-assembly domai", Molecular ,BioSysterns, 9(9), (2013), 2282-2295.
Vanhercke, T., et al., "Synergistic effect of WRI1 and DGAT1 coexpression on triacylglycerol biosynthesis in plants", FEBS Lett, 587 (4), (2013), 364-369.
Wang, F., et al., "Biochemical Insights on Degradation of *Arabidopsis* DELLA Proteins Gained From a Cell-Free Assay System", Plant Cell, 21(8), (Aug. 2009), 2378-2390.
Ward, J. J., et al., "Prediction and functional analysis of native disorder in proteins from the three kingdoms of life", J. Mol Biol, 337(3), (2004), 635-645.
Wu, X, L., et al., "BnWRI1 coordinates fatty acid biosynthesis and photosynthesis pathways during oil accumulation in rapeseed", J Integr Plant Biol, 56, (2014), 582-593.
Xue, B., et al., "PONDR-FIT: a meta-predictor of intrinsically disordered amino acids", Biochim Biophys Acta, 1804(4), (2010), 966-1010.
Yamaguchi, M., et al., "VND-INTERACTING2, a NAC Domain Transcription Factor, Negatively Regulates Xylem Vessel Formation in *Arabidopsis*", Plant Cell, 22(4), (2010), 1249-1263.
Yang, Z. R., et al., "RONN: the bio-basis function neural network technique applied to the detection of natively disordered regions in proteins", Bioinformatics, 21(16), (2005), 3369-3376.
Yin, Y., et al, "BES1 Accumulates in the Nucleus in Response to Brassinosteroids to Regulate Gene Expression and Promote Stem Elongation", Cell, 109, (2002), 181-191.
Zhai, Q., et al., "Phosphorylation-coupled proteolysis of the transcription factor MYC2 is important for jasmonate-signaled plant immunity", PLoS Genetics, 9, e1003422, (Apr. 2013), 1-14.

* cited by examiner

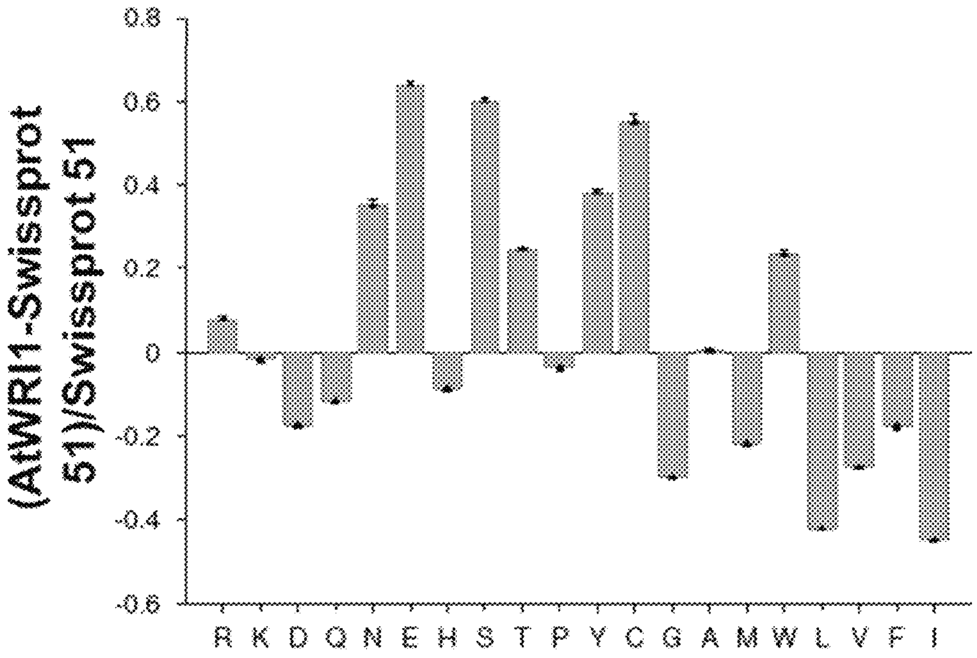
FIG. 1E
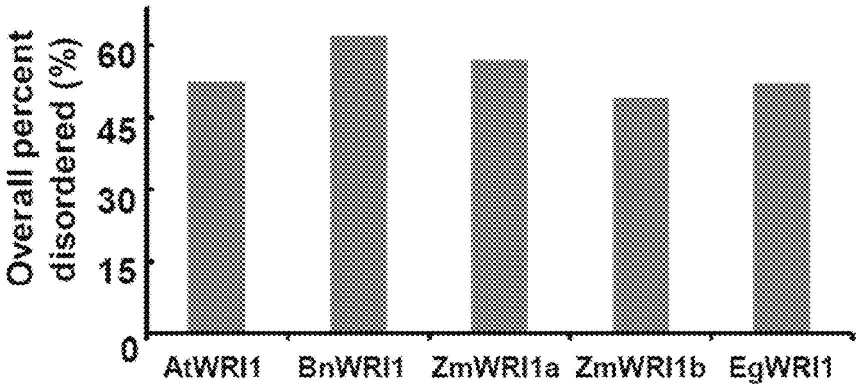
FIG. 1F
| Program used for prediction | Disordered region 1 | Disordered region2 | Disordered region3 |
|---|---|---|---|
| PONDR_VL3 | [1]-[71] | [249]-[313] | [368]-[430] |
| RONN | [1]-[66] | [244]-[302] | [395]-[430] |
| PONDR_FIT | [1]-[83] | [263]-[307] | [396]-[430] |
FIG. 1G

| | AtWRI1 | AtWRI1$^{1-302}$ | AtWRI1$^{1-366}$ |
|---|---|---|---|
| YFP signal (Fluorescence/pixel) | 46.017±7.276 | 158.852±1.497 | 149.136±4.795 |

14-3-3 PROTEINS ENHANCE WRINKLED1 TRANSCRIPTION FACTOR-REGULATED OIL PRODUCTION

RELATED APPLICATIONS

This patent application claims the benefit of priority, under 35 U.S.C. § 119(e), to U.S. Provisional Patent Application Ser. No. 62/352,246, filed on Jun. 20, 2016, the contents of which application are specifically incorporated herein by reference in their entirety.

GOVERNMENT FUNDING

This invention was made with government support under DE-FC02-07ER64494 awarded by the U.S. Department of Energy. The government has certain rights in the invention.

BACKGROUND

Plant oils such as triacylglycerols (TAGs) are useful for food, industrial feedstock and biofuel production. TAG is generally harvested from the seeds of oil crop species, such as canola. However, engineering of crops that product oils in non-seed tissues (leaves and roots) is an alternative way to produce feed stocks for high energy transportation biofuels or even jet fuels.

Fuels are typically produced from petroleum products, but such production involves considerable cost, both financially and environmentally. Sources of petroleum must be discovered, but petroleum exploration is an expensive and risky venture. The cost of exploring deep water wells can exceed $100 million. In addition to the economic cost, petroleum exploration carries a high environmental cost. For example, offshore exploration frequently disturbs the surrounding marine environments.

After a productive well is discovered, the petroleum must be extracted from the Earth, but such extraction is expensive and, even under the best circumstances, only 50% of the petroleum in a well can be extracted. Petroleum extraction also carries an environmental cost. For example, petroleum extraction can result in large seepages of petroleum rising to the surface. Offshore drilling involves dredging the seabed which disrupts or destroys the surrounding marine environment.

After extraction, petroleum must be transported over great distances from petroleum producing regions to petroleum consuming regions. In addition to the shipping costs, there is also the environmental risk of oil spills.

In its natural form, crude petroleum extracted from the Earth has few commercial uses. It is a mixture of hydrocarbons (e.g., paraffins (or alkanes), olefins (or alkenes), alkynes, napthenes (or cycloalkanes), aliphatic compounds, aromatic compounds, etc.) of varying length and complexity. In addition, crude petroleum contains other organic compounds (e.g., organic compounds containing nitrogen, oxygen, sulfur, etc.) and impurities (e.g., sulfur, salt, acid, metals, etc.). Hence, crude petroleum must be refined and purified before it can be used commercially.

Due to the inherent challenges posed by petroleum, there is a need for a renewable petroleum source which does not need to be located by extensive exploration, extracted, transported over long distances, or substantially refined like petroleum. There is also a need for a renewable oil source that can be produced economically without environmental damage.

SUMMARY

As described herein plant 14-3-3 proteins are phosphopeptide-binding proteins that interact with WRINKLED (WRI1), both in yeast and plant cells. Co-expression of 14-3-3 proteins with WRI1 proteins leads to increased plant vegetative tissue oil content as well as increased seed oil content. The 14-3-3 protein stabilized and enhanced the transcriptional activity of WRI1.

Plants, plant cells and seeds are described herein that include heterologous 14-3-3 and/or WRI1 nucleic acids and/or proteins. Also described are nucleic acids and expression cassettes that encode and express 14-3-3 and/or WRI1. When expressed in plants, the 14-3-3 and/or WRI1 proteins are useful for increasing production of oils in plants and seeds. In some cases both 14-3-3 and WRI1 are heterologously expressed in plants, plant cells and seeds.

Methods are also described herein that can involve isolating oils from plants, plant cells, seeds, or combinations thereof that include heterologous 14-3-3 and/or WRI1 nucleic acids and/or proteins. Further methods involve generating one or more transgenic plants, plant cells, or seeds that include introducing heterologous 14-3-3 and/or WRI1 nucleic acids to a yeast, algae, or plant cell to thereby generate one or more transgenic plants, plant cells, or seeds. The methods can include generating one or more transgenic plants from the transgenic plant cells.

This application relates to U.S. Application Ser. No. 62/187,419, the contents of which are incorporated herein by reference in their entirety.

DESCRIPTION OF THE FIGURES

The patent or application file contains at least one drawing executed in color. Copies of this patent or patent application publication with color drawing(s) will be provided by the Office upon request and payment of the necessary fee.

FIG. 1A-1G illustrates that there are three main intrinsically disordered regions (IDRs) in the *Arabidopsis thaliana* WRINKLED1 (AtWRI1) transcription factor that are predicted by three different programs. FIG. 1A is a schematic diagram of AtWRI1. FIG. 1B illustrates the disorder of AtWRI1 as predicted by PONDR-VL3. FIG. 1C illustrates the disorder of AtWRI1 as predicted by RONN. FIG. 1D illustrates the disorder of AtWRI1 as predicted by PONDR-FIT. FIG. 1E graphically illustrates the amino acid composition of AtWRI1. The full length AtWRI1 protein sequence was analyzed by Composition Profiler (see website at cprofiler.org). The SwissProt 51 dataset was chosen as a background dataset. FIG. 1F graphically illustrates the overall disorder as predicted by PONDR VL3. FIG. 1G is a chart summarizing the three main IDRs predicted in AtWRI1 by the different programs.

FIG. 2A shows confocal images of cells transiently expressing YFP fused AtWRI1 (WT form) and AtWRI1 truncated variants in *N. benthamiana* leaves. FIG. 2B shows the YFP fluorescence intensity of AtWRI1 and its variants in the cells of *N. benthamiana* leaves. FIG. 2C graphically illustrates the fatty acid content of seeds of WT, wri1-1 and transgenic wri1-1 that express YFP-AtWRI1. Results are mean+SE (n=3).

FIG. 3A is a schematic diagram of the AtWRI1 structure. The acidic amino acids within the C-terminal region of the WRI1 sequence (SEQ ID NO:65) shown below the diagram are the ones with lighter (red) letters, also shown in the sequence below (SEQ ID NO:65) where the same acidic amino acids are identified in bold and with underlining.

307 AAVV NCCIDSSTIM EMDRCGDNNE LAWNFC-MMDT

341 GFSPFLTDQN LANENPIEYP ELFNELAFED NI DFMFDDGK

381 HECLNLENLD CCVVGRESPP SSSSPLSCLS TD-SASSTTTT

421 TTSVSCNYLV

Figure 3A:
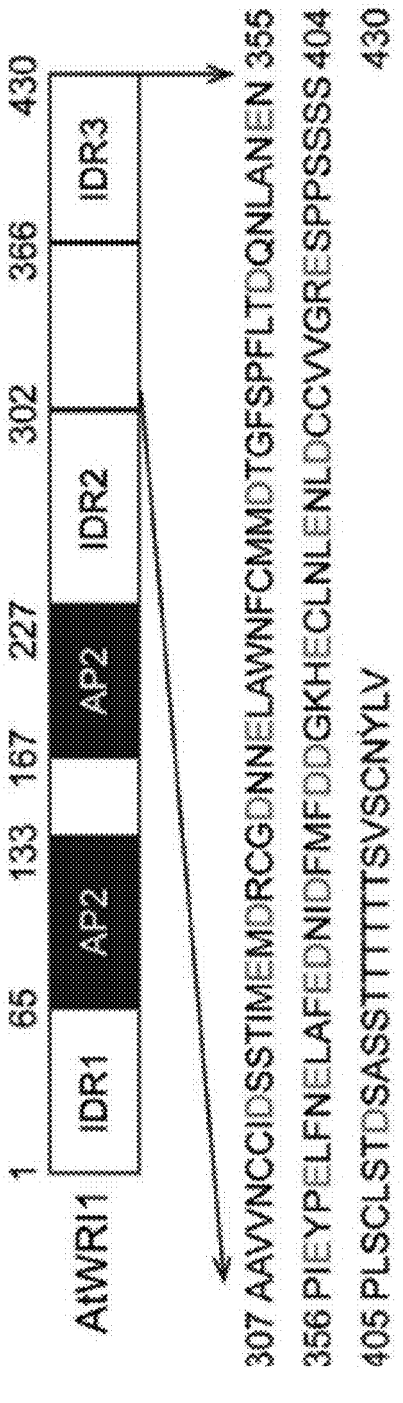
FIG. 3A-3B illustrates a correlation between the structure and the domains that affect the transactivation activity of WRI
Figure 3B:
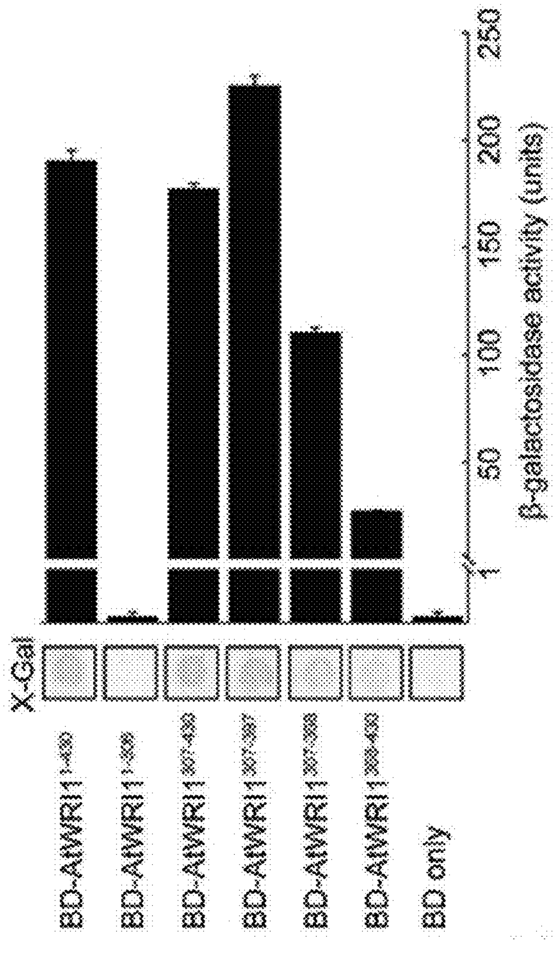

FIG. 3B graphically illustrates the transactivation activity of AtWRI1 and of AtWRI1 deletion mutants in yeast. Full-length AtWRI1$^{1-430}$ and AtWRI1 truncated variants were fused to yeast GAL4 DNA binding domain (BD). Colony-lift filter assay and β-galactosidase assay of liquid cultures were used to measure the transactivation activity. Results are shown as mean±SE (n=3). As illustrated, there was no transactivation activity of AtWRI1$^{1-306}$ carrying a deletion of the C-terminal 124 amino acids, but At-WRI1$^{307-397}$ displayed a similar transcriptional activity compared to wild-type AtWRI1.

Figure 4A:
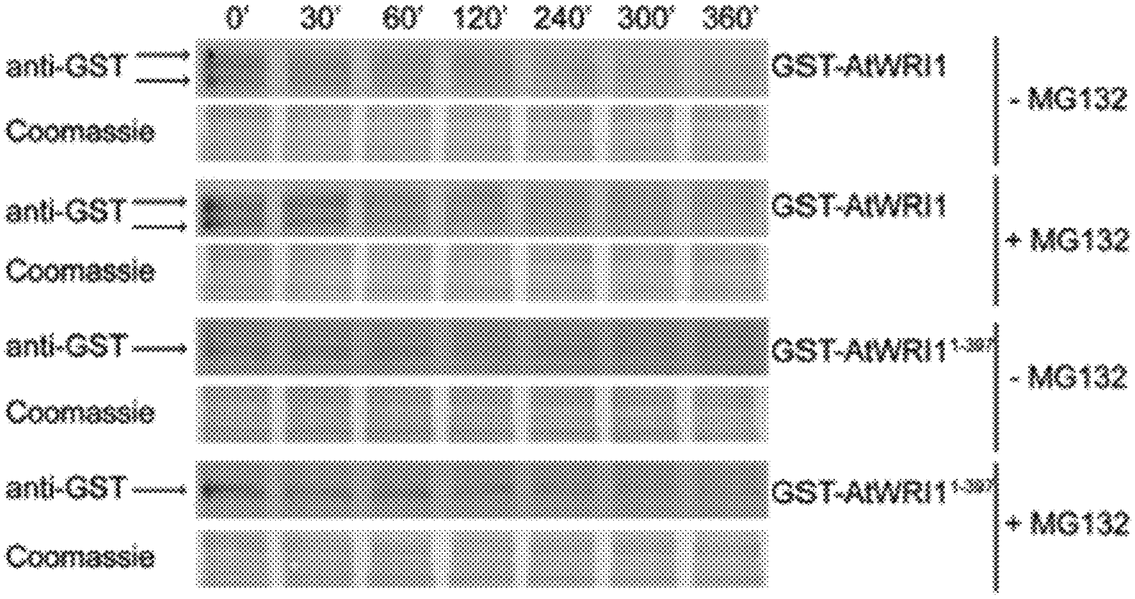
Figure 4B:
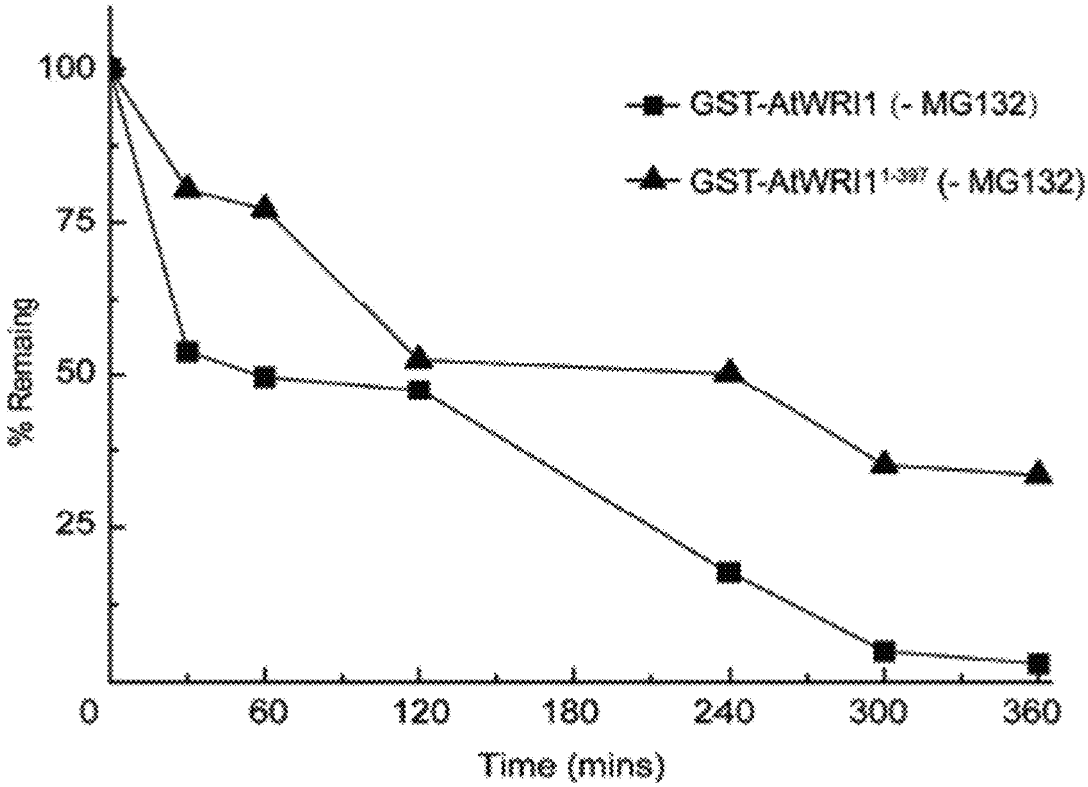
Figure 4C:
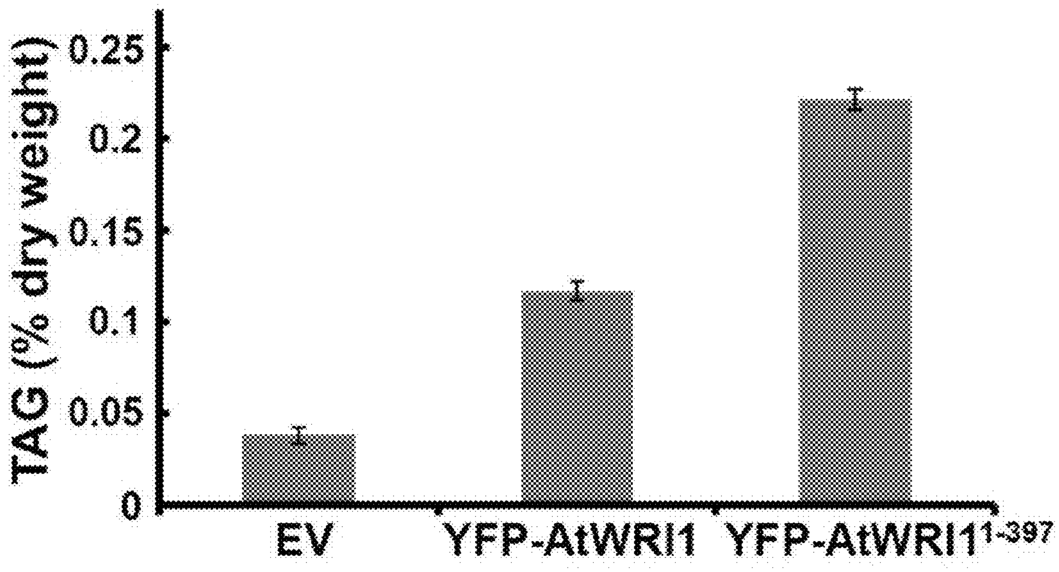
Figure 4D:
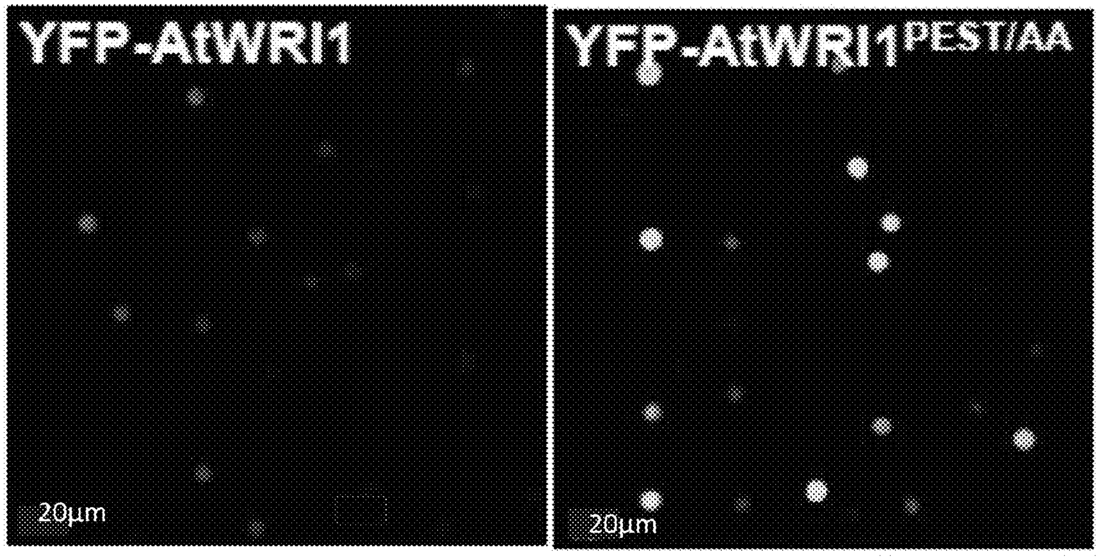
Figure 4E:
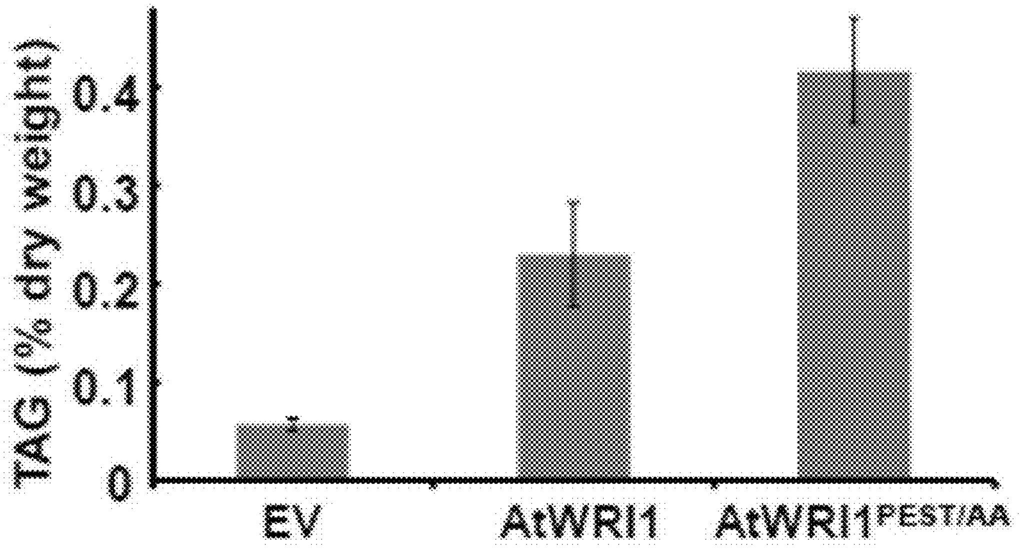
Figure 4F:
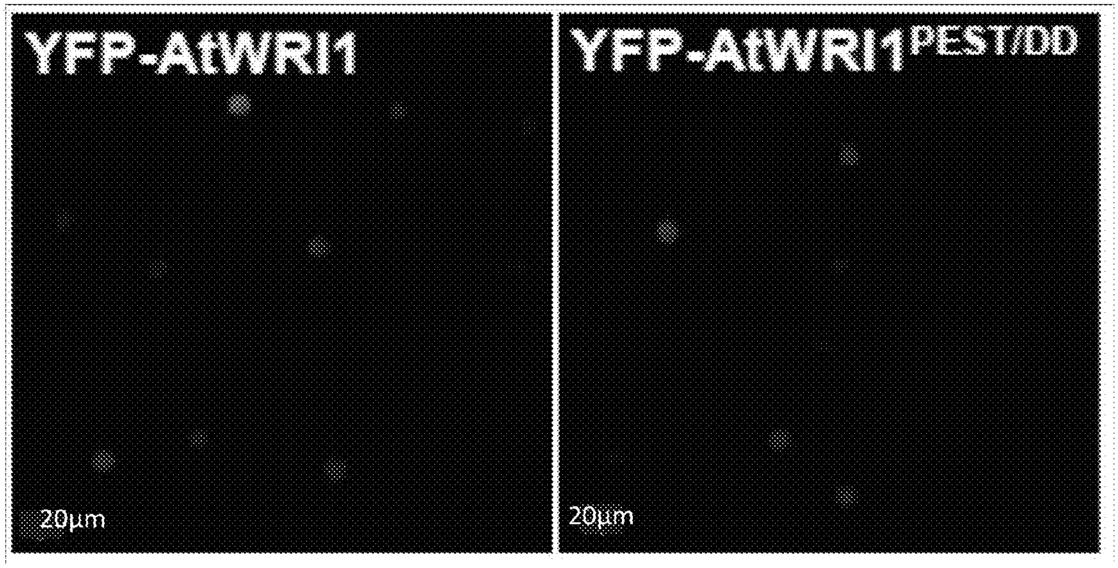
Figure 4G:
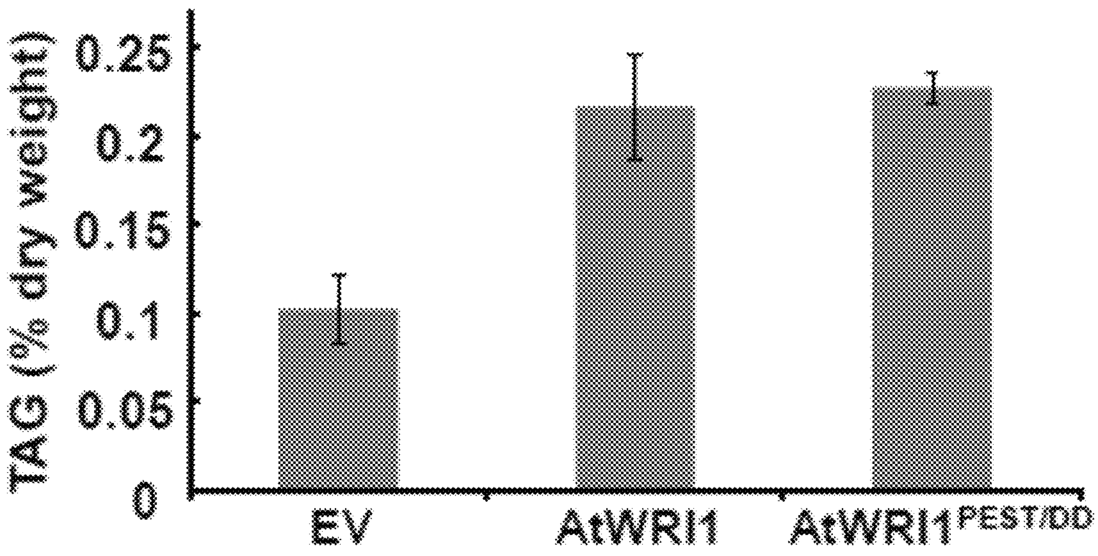

FIG. 4A-4G shows that the C-terminally truncated AtWRI1$^{1-397}$ protein displayed less degradation compared to AtWRI1 wild type (WT). FIG. 4A shows electrophoretically separated GST-AtWRI1 proteins subjected to degradation in WT protein extracts in cell-free degradation in vitro assay. The MG132 proteasome inhibitor (10 μM) was added into some WT protein extracts as indicated. After GST purification, two protein bands were eluted for GST-At-WRI1. Protein mass spectrometry confirmed that both bands correspond to GST-AtWRI1 protein. However, only one band was observed for GST-AtWRI1$^{1-397}$. This difference might result from different protein modifications in *E. coli* associated with the IDR3 of AtWRI1. FIG. 4B graphically illustrates the percent remaining of the GST-AtWRI1 and GST-AtWRI1$^{1-397}$ proteins as detected by western blot signals during the cell-free degradation assay. Image analysis indicated similar degradation patterns when the double bands of GST-AtWRI1 were analyzed individually. FIG. 4C graphically illustrates that transient expression of the C-terminally truncated YFP-AtWRI1$^{1-397}$ protein in *N. benthamiana* leaves generated leaves with approximately 2 fold higher TAG content than in leaves expressing YFP-AtWRI1. FIG. 4D shows confocal images illustrating the fluorescence of YFP fused AtWRI and AtWRI1 phosphorylation-deficient mutant AtWRI1$^{S398A/S401A/S402A/S407A/S415A/S416A/T420A/T421A/T422A/S423A}$ (AtWRI1$^{PEST/AA}$; SEQ ID NO:30) proteins in *N. benthamiana* leaves. FIG. 4E graphically illustrates TAG content in *N. benthamiana* leaves that transiently express AtWRI1 or AtWRI1$^{PEST/AA}$. Empty vector (EV) is used as a control. Results are shown as mean±SE (n=3). FIG. 4F shows confocal images illustrating the fluorescence of YFP-fused AtWRI1 and AtWRI1 phosphorylation mimic mutant (AtWRI1$^{S398D/S401D/S402D/S407D/S415D/S416D/T420D/T421D/T422D/S423D}$ (AtWRI1$^{PEST/DD}$; SEQ ID NO:31) protein in *N. benthamiana* leaves. FIG. 4G graphically illustrates TAG content in *N. benthamiana* leaves that transiently express YFP fused AtWRI and AtWRI1$^{PEST/DD}$ proteins. Results are shown as means±SE (n=3).

Figure 5:
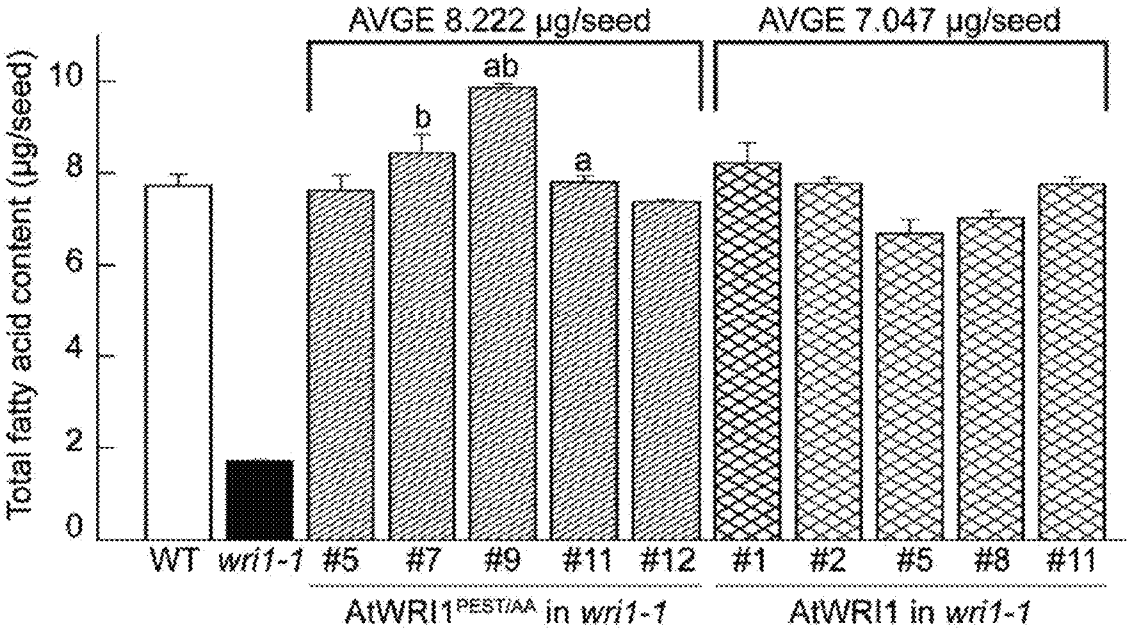

FIG. 5 graphically illustrates the total fatty acid content of seeds of WT, wri1-1 and transgenic wri1-1 plants that express AtWRI1 and AtWRI1$^{PEST/AA}$. Results are the mean±SE of three analyses (n=3). The average total fatty acid content of transgenic wri1-1 lines expressing AtWRI1 and AtWRI1$^{PEST/AA}$ are indicated above the respective bar graphs. The letters "a" and "b" indicate significant difference (P<0.05, t-test, and one-way ANOVA, respectively) between transgenic wri1-1 lines expressing AtWRI1$^{PEST/AA}$, and transgenic wri1-1 lines expressing AtWRI1.

Figure 6A:
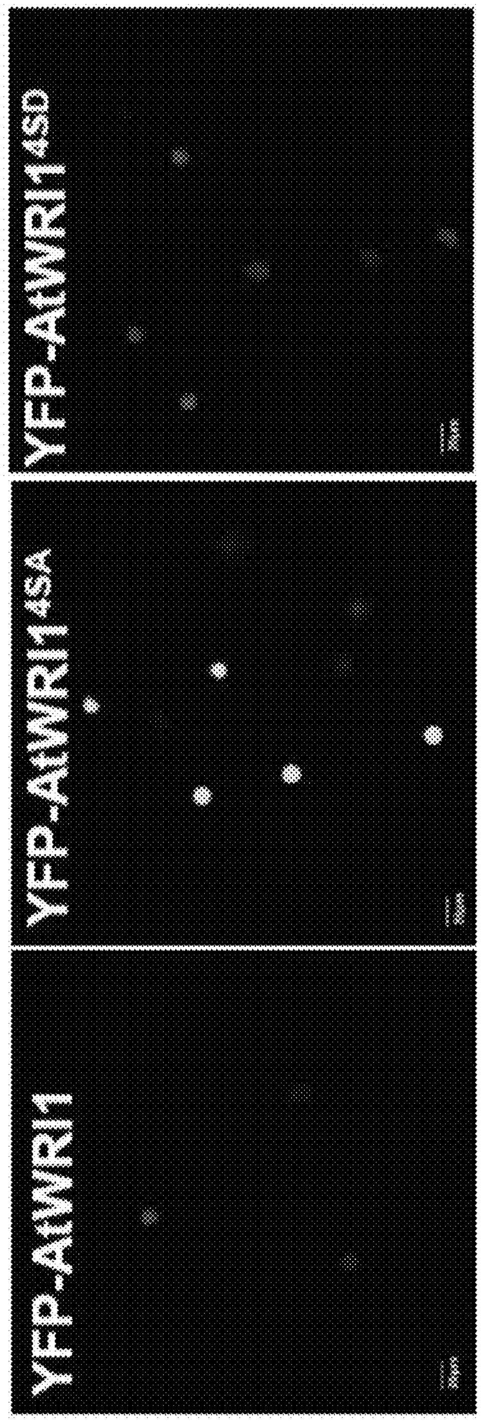
Figure 6B:
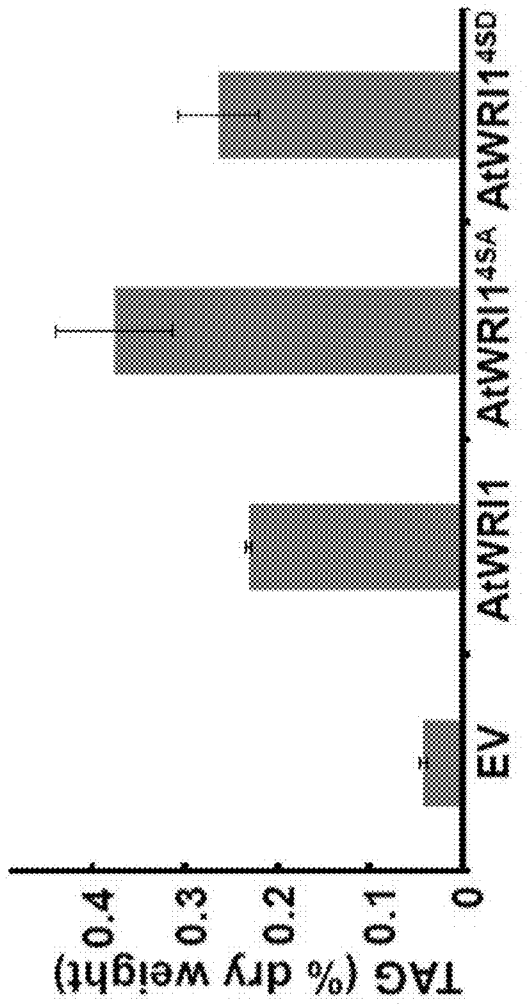

FIG. 6A-6B illustrate the function of AtWRI1 phosphorylation deficient and phosphorylation mimic mutants in *N. benthamiana* transient expression assays. The expressed proteins were the phosphorylation deficient protein AtWRI1$^{S398A/S401A/S402A/S407A}$ (AtWRI1$^{4SA}$; SEQ ID NO:62) fused to YFP and the phosphorylation mimic mutant AtWRI1$^{S398D/S401D/S402D/S407D}$ (AtWRI1$^{4SD}$; SEQ ID NO:63) fused to YFP. FIG. 6A shows confocal images of *N. benthamiana* cells expressing YFP fused to AtWRI1, YFP fused to AtWRI1$^{S398A/S401A/S402A/S407A}$ (AtWRI1$^{4SA}$), and TYP fused to AtWRI1$^{S398D/S401D/S402D/S407D}$ (AtWRI1$^{4SD}$) proteins. FIG. 6B graphically illustrates TAG content in *N. benthamiana* leaves that transiently express YFP-fused AtWRI1 and YFP-fused AtWRI1 mutants. Results are shown as mean±SE of three analyses (n=3).

Figure 7:
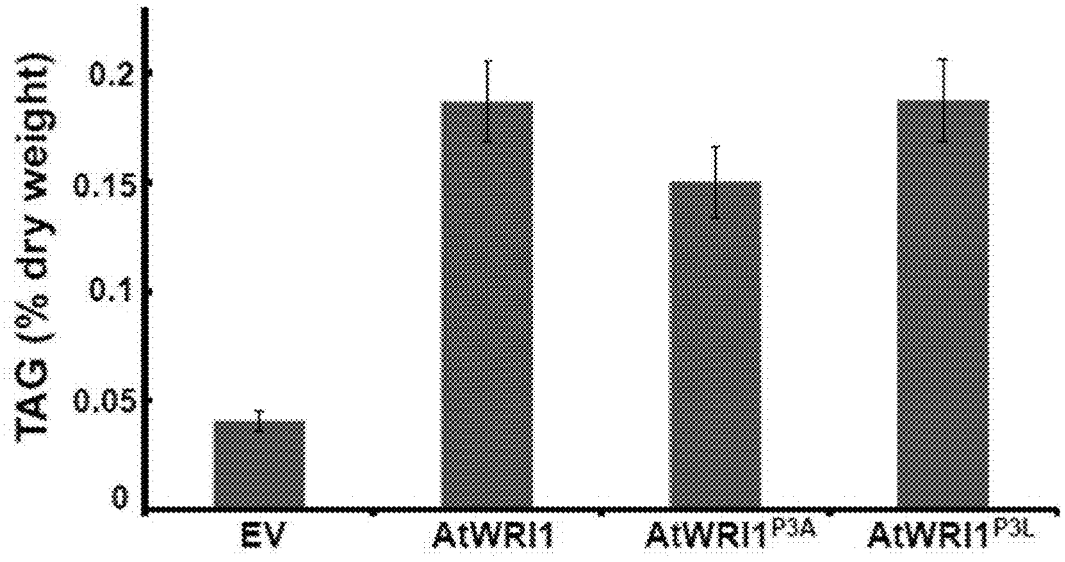

FIG. 7 graphically illustrates the percent dry weight of TAG detected in transient expression assays of *N. benthamiana* leaves expressing AtWRI1 mutants AtWRI1$^{P399A/P400A/P405A}$ (AtWRI1$^{P3A}$) and AtWRI1$^{P399L/P400L/P405L}$ (AtWRI1$^{P3L}$) that were fused to YFP. Results are shown as a mean±SE of 3-4 analyses (n=3-4).

Figure 8:
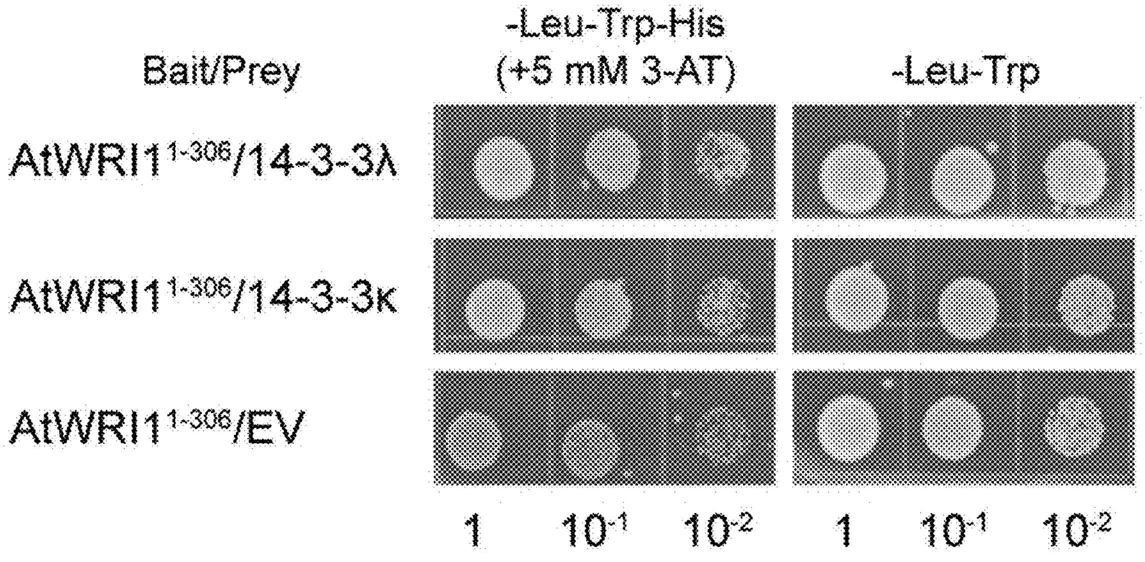

FIG. 8 illustrates AtWRI1 physical interaction with *Arabidopsis* 14-3-3 proteins as shown by yeast-two hybrid (Y2H) assay. Yeast growth on either permissive (-Leu/-Trp) or stringent selective (-Leu/-Trp/-His) media are illustrated. Yeast strains expressing the full length AtWRI1 (bait fusion) and 14-3-3s (prey fusion) were used in the assays. A yeast strain with an empty vector (EV) was used as a negative control.

Figure 9A:
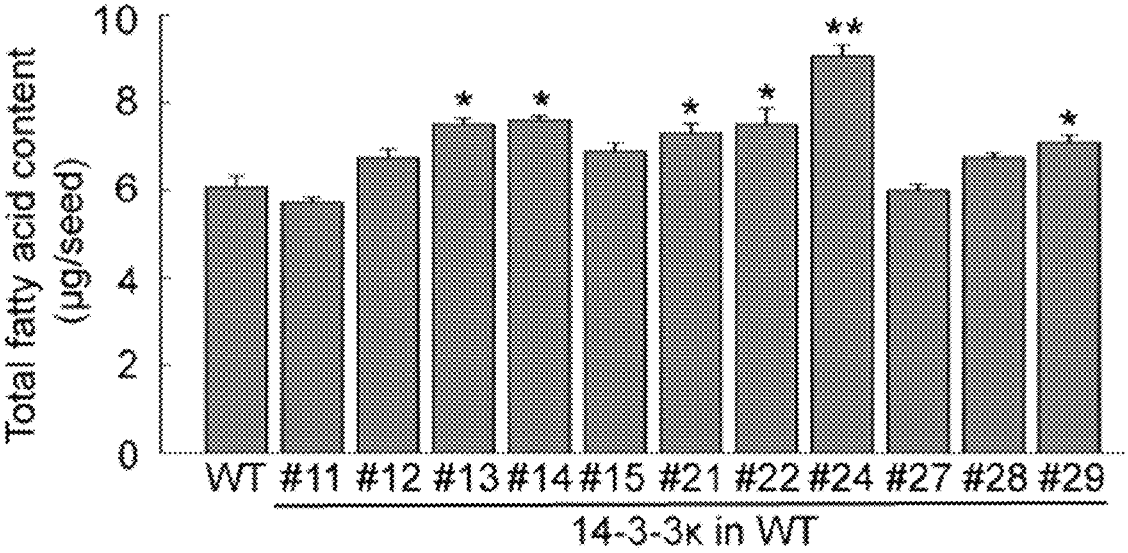
Figure 9B:
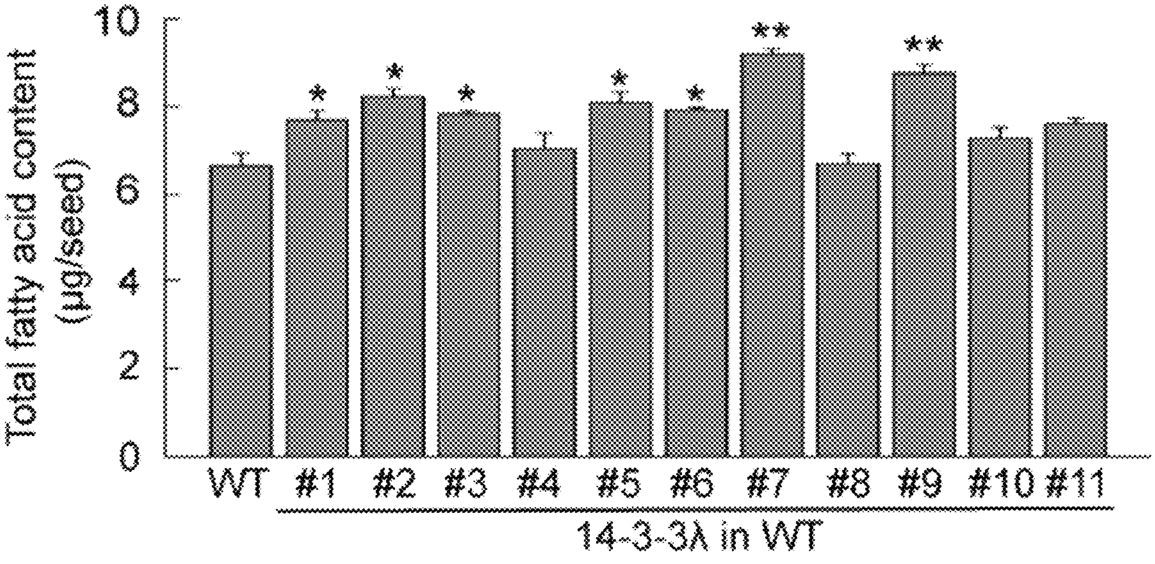
Figure 9C:
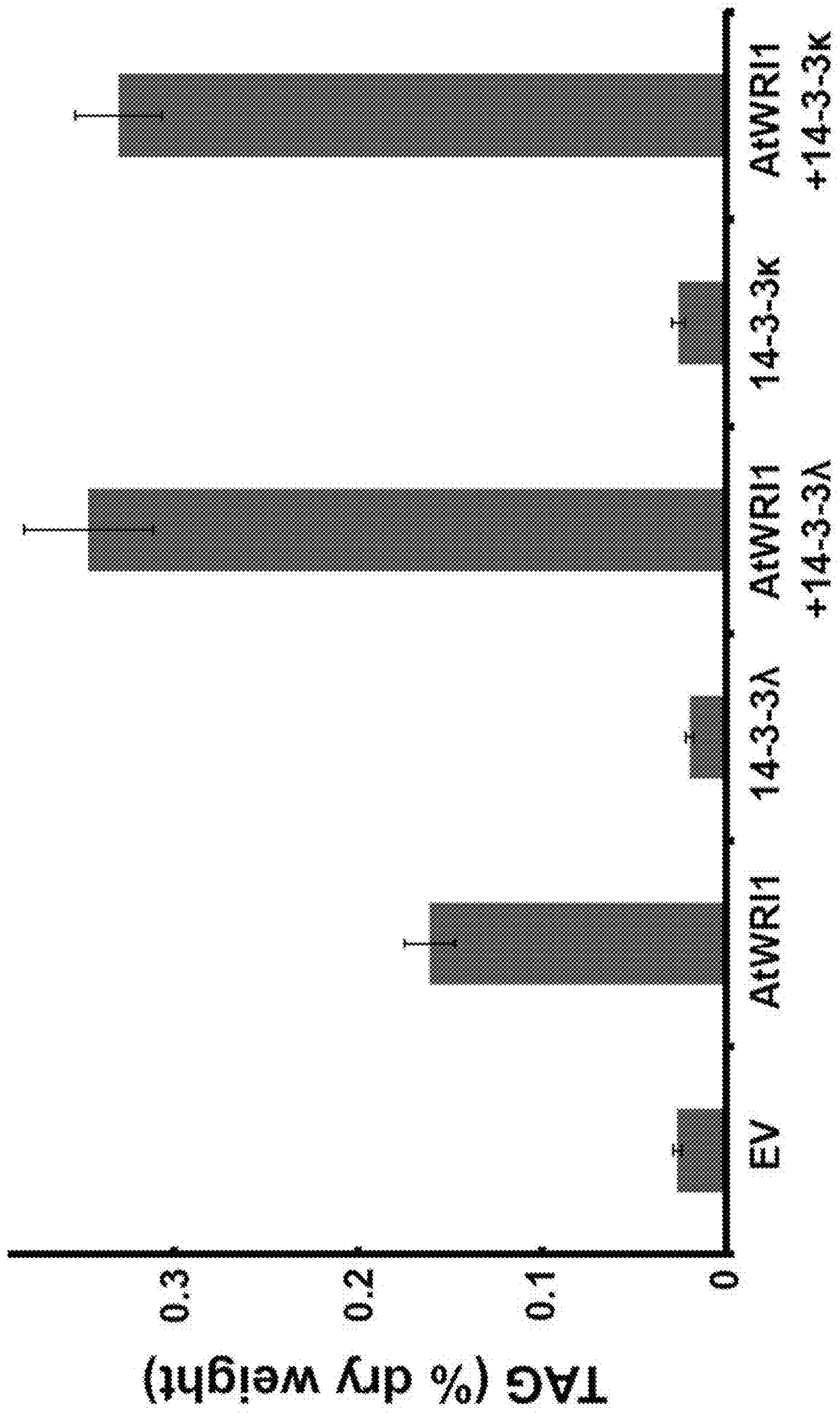

FIG. 9A-9C illustrate the fatty acid content of seeds of WT and transgenic plants overexpressing 14-3-3 isoforms. FIG. 9A graphically illustrates the fatty acid content of seeds of WT and 14-3-3K transgenic plants. FIG. 9B graphically illustrates the fatty acid content of seeds of WT and 14-3-3× transgenic plants. Results are shown as mean±SE (n=3). Symbols "*" and "" indicate a significant differences (P<0.05 and P<0.01 respectively, Student's t-test) between transgenic lines overexpressing 14-3-3 isoforms and WT. FIG. 9**C graphically illustrates the amounts of triacylglycerols as a percent of the dry weight of *N. benthamiana* leaves that transiently co-expressed AtWRI1 and 14-3-3s (14-3-3λ or 14-3-3κ) encoding cDNAs. Results are shown as mean+SE of three analyses (n=3). Empty vector (EV) is used as a control.

Figure 10A:
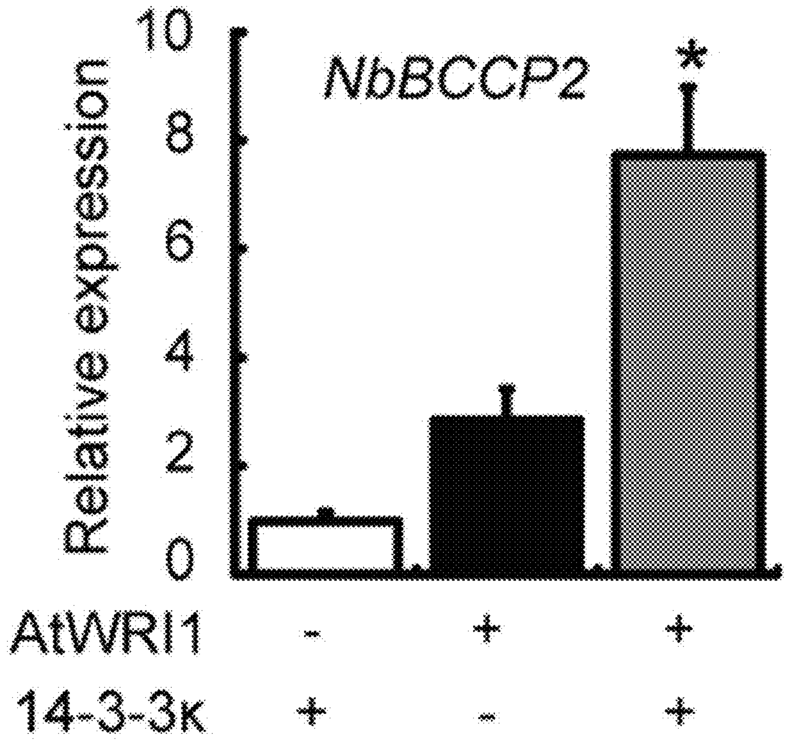
Figure 10B:
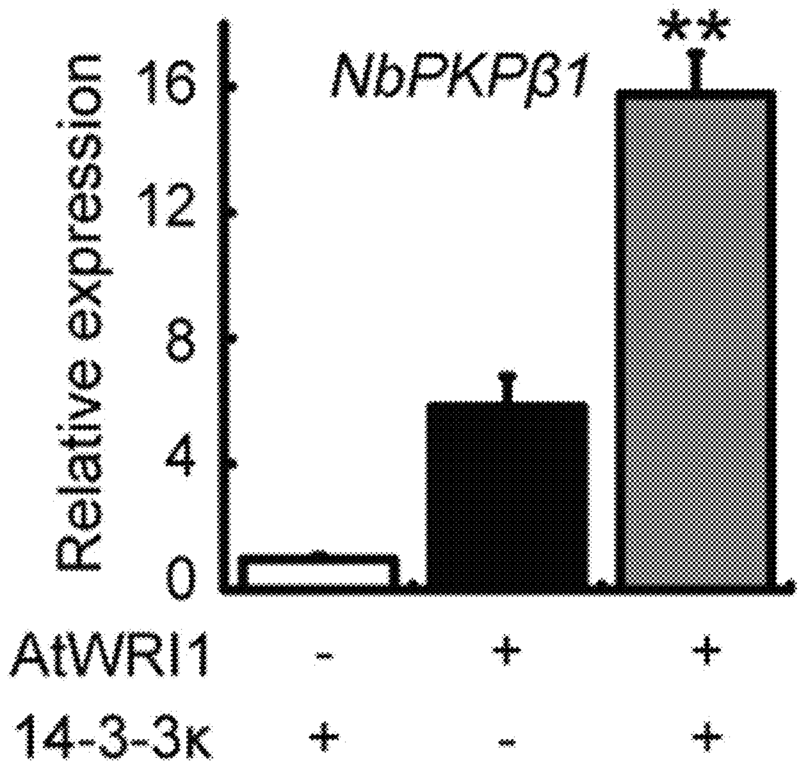
Figure 10C:
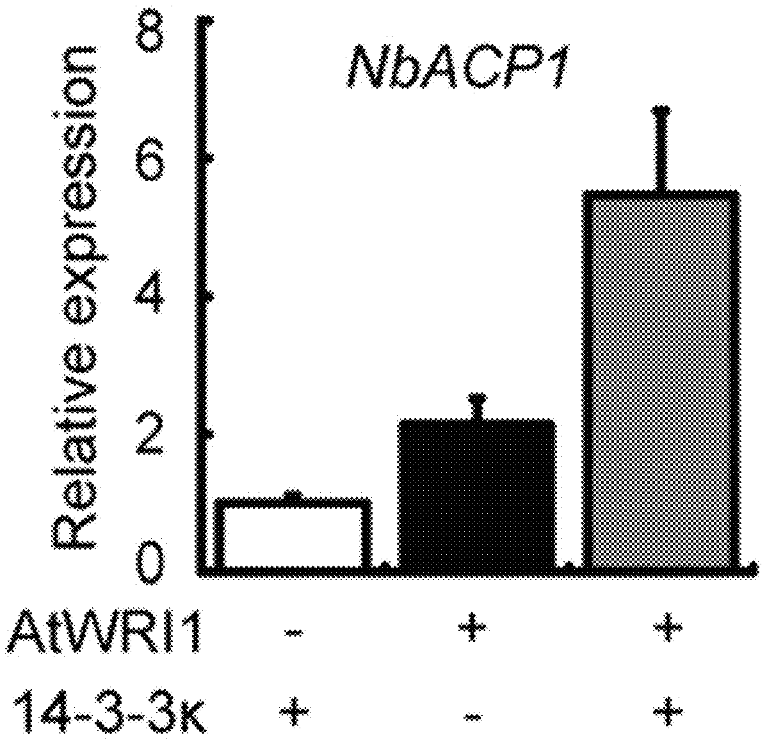
Figure 10D:
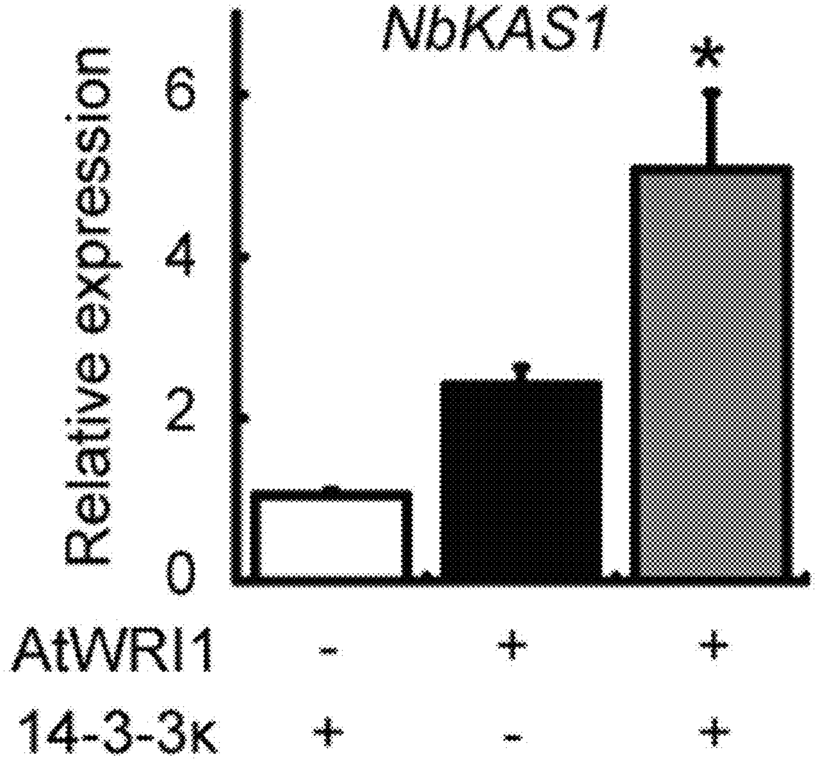
Figure 10E:
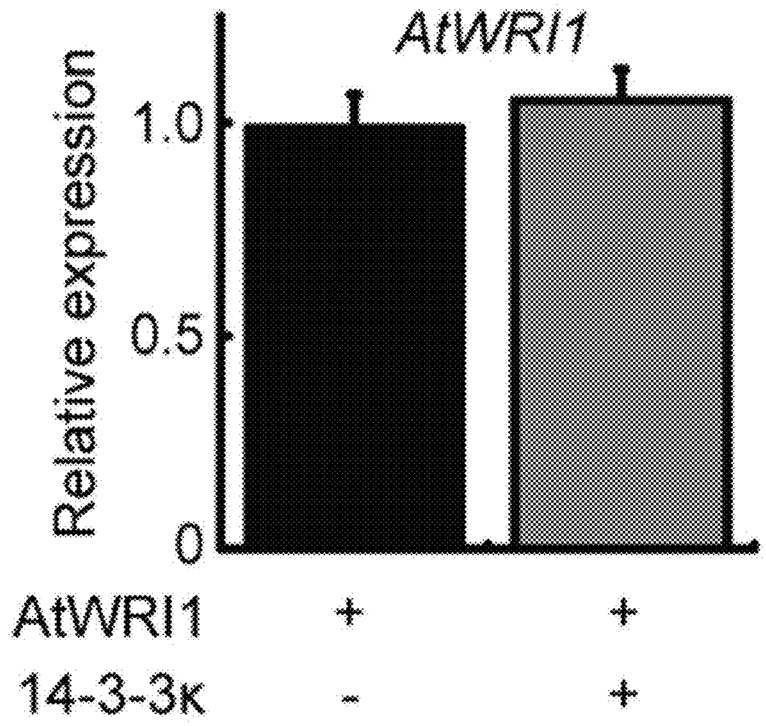
Figure 10F:
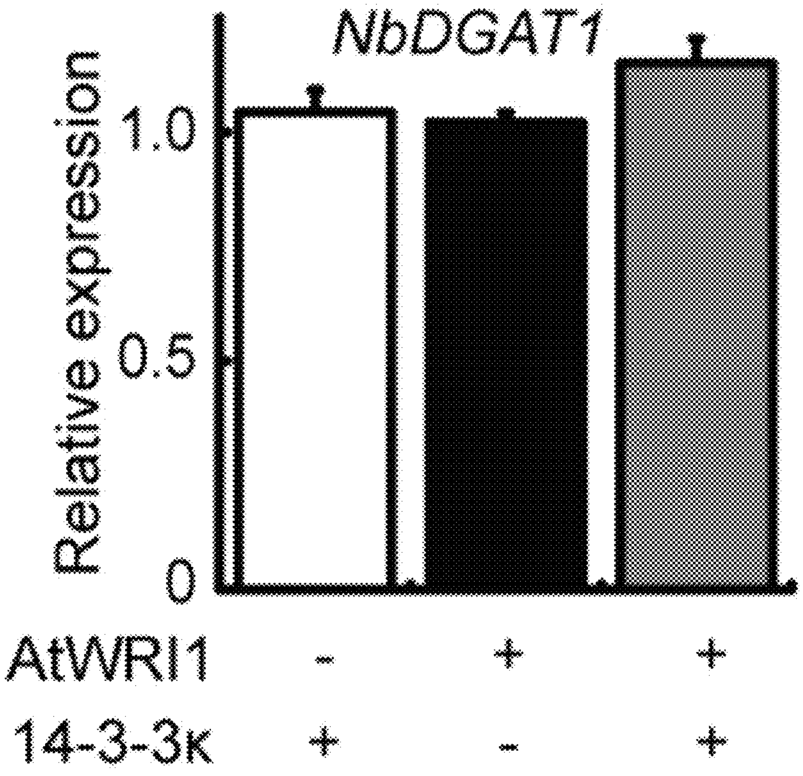

FIG. 10A-10F graphically illustrates that 14-3-3K enhanced the transcriptional activity of AtWRI1. FIG. 10A graphically illustrates NbBCCP2 expression levels with and without transgenic expression of WRI1 and 14-3-3κ. FIG. 10B graphically illustrates NbPKPβ1 expression levels with and without transgenic expression of WRI1 and 14-3-3K. FIG. 10C graphically illustrates NbACP1 expression levels with and without transgenic expression of WRI1 and 14-3-3κ. FIG. 10D graphically illustrates NbKAS1 expression levels with and without transgenic expression of WRI1 and 14-3-3κ. FIG. 10E graphically illustrates AtWRI1 expression levels with and without transgenic expression of WRI1 and 14-3-3κ. FIG. 10F graphically illustrates NbDGAT1 expression levels with and without transgenic expression of WRI1 and 14-3-3κ. Quantitative real-time PCR (qRT-PCR) analysis is shown of transcript accumulation in *N. benthamiana* transient expression of 1) 14-3-3κ, 2) AtWRI1, and 3) co-expression of AtWRI1 and 14-3-3κ. Results are shown as mean+SE (n=3). Symbols "*" and "**" indicate significant differences (P<0.05 and P<0.01 respectively, one-way ANOVA) between AtWRI1 and co-expression of AtWRI1 and 14-3-3κ.

Figure 11A:
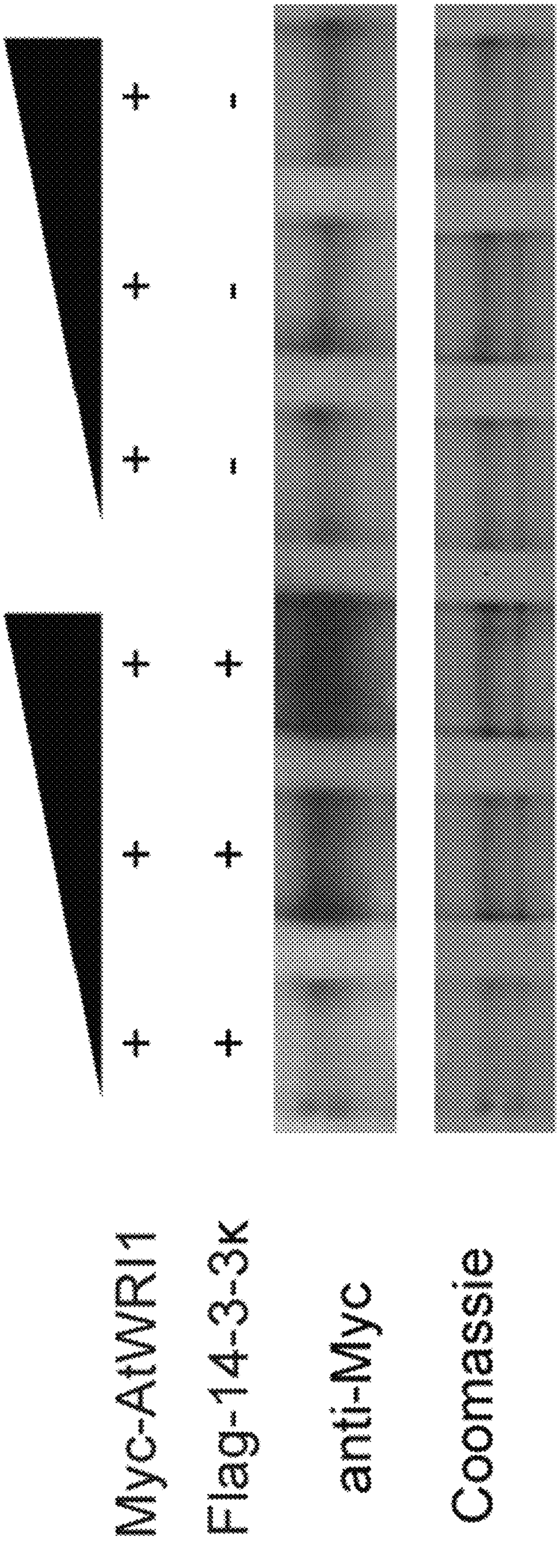
Figure 11B:
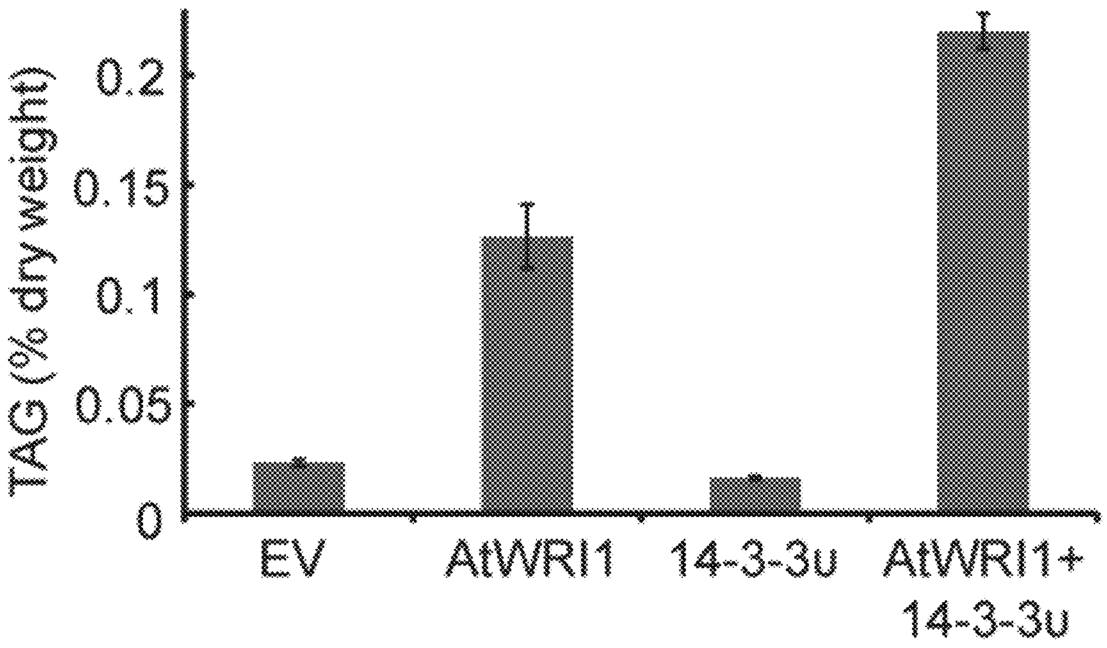
Figure 11C:
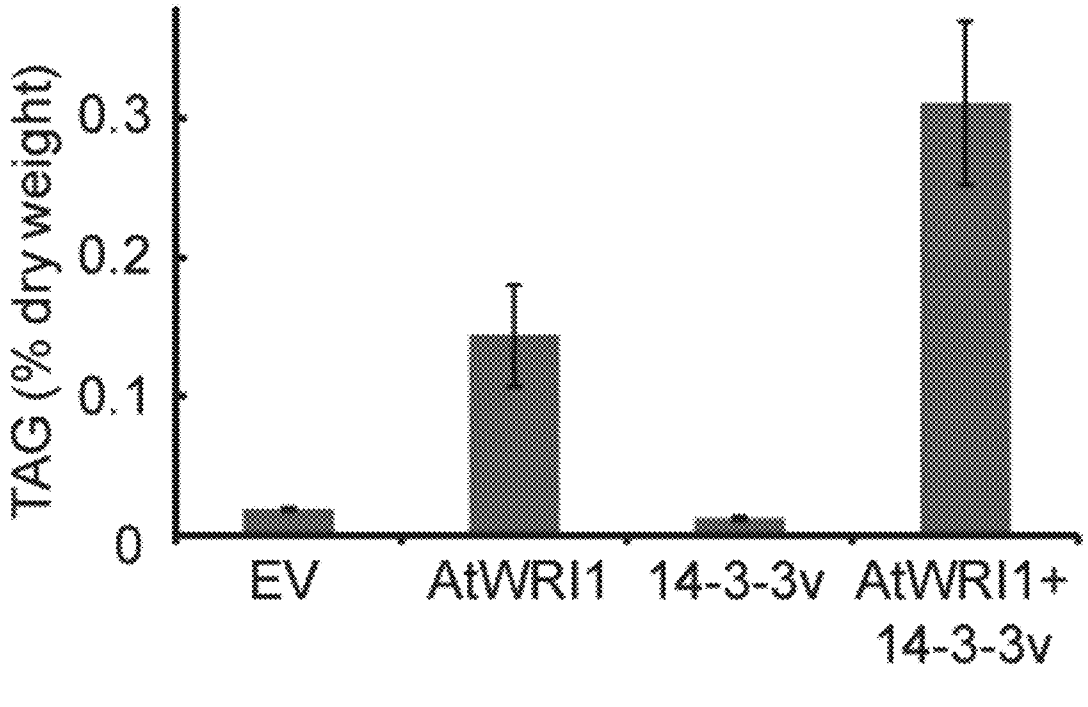
Figure 11D:
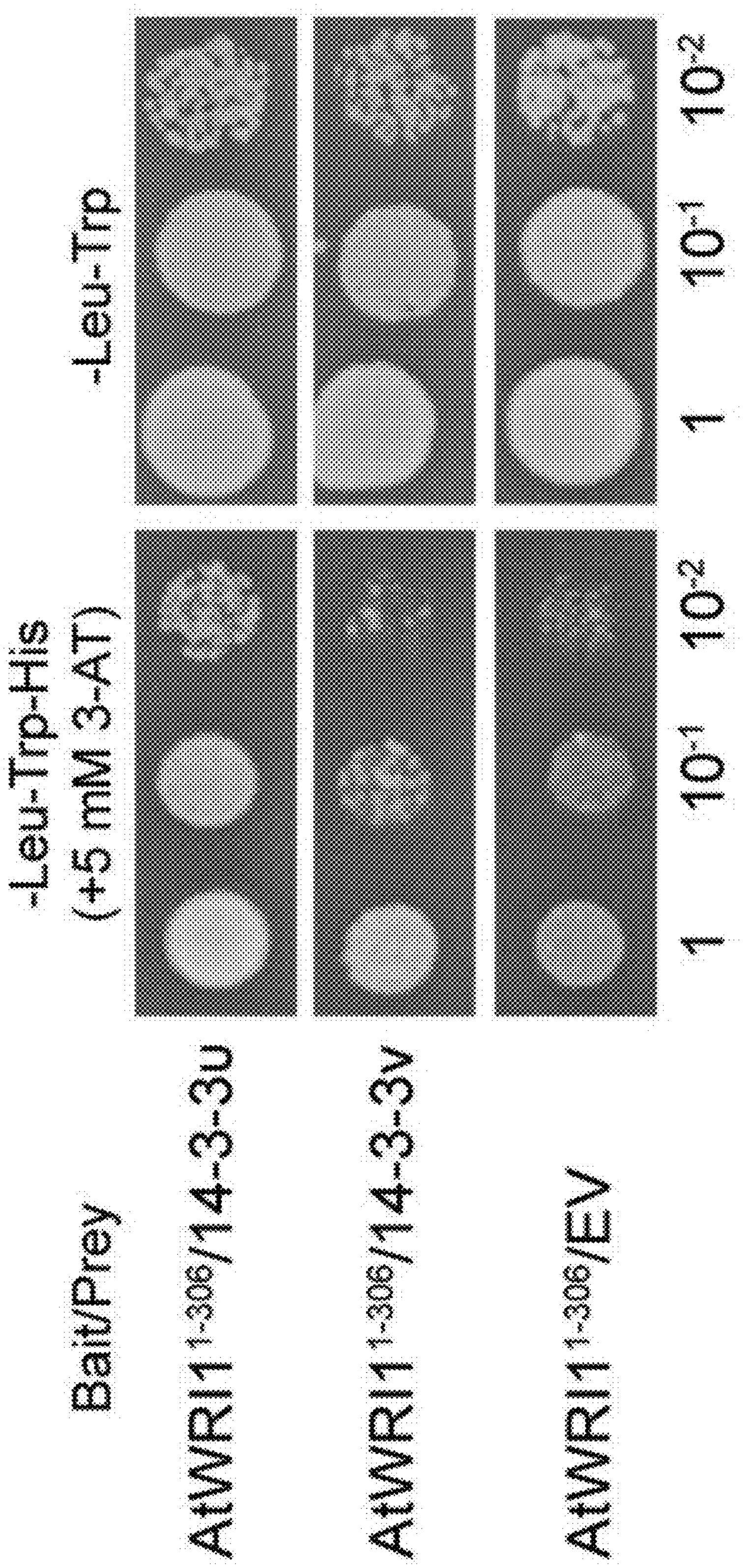

FIG. 11A-11D illustrates that several 14-3-3 isoforms enhance the stability of AtWRI1. FIG. 11A shows a Western blot illustrating AtWRI1 protein abundance following *N. benthamiana* transient expression of cDNAs encoding: 1. Myc-AtWRI1, 2. co-expression of Myc-AtWRI1 and Flag-14-3-3κ. Each protein sample was loaded in three lanes with amount of 2.5, 3.5 and 5 μg protein, respectively. FIG. 11B-11C graphically illustrate that two 14-3-3 isoforms can also enhance AtWRI1-mediated oil biosynthesis. FIG. 11B graphically illustrates TAG content as measured in *N. benthamiana* leaves transiently co-expressing AtWRI1 and 14-3-3υ encoding cDNAs. Results are shown as mean±SE (EV (n=2); other samples (n=3)). FIG. 11C graphically illustrates TAG content was measured in *N. benthamiana* leaves transiently co-expressing AtWRI1 and 14-3-3ν cDNAs. Results are shown as mean±SE (EV and 14-3-3ν (n=2); other samples (n=4)). Empty vector (EV) was used as a control. FIG. 11D illustrates interaction between AtWRI1 and two 14-3-3 isoforms (14-3-3υ and 14-3-3ν) as detected by Y2H assays. Empty vector (EV) was used as a control.

Figure 12A:
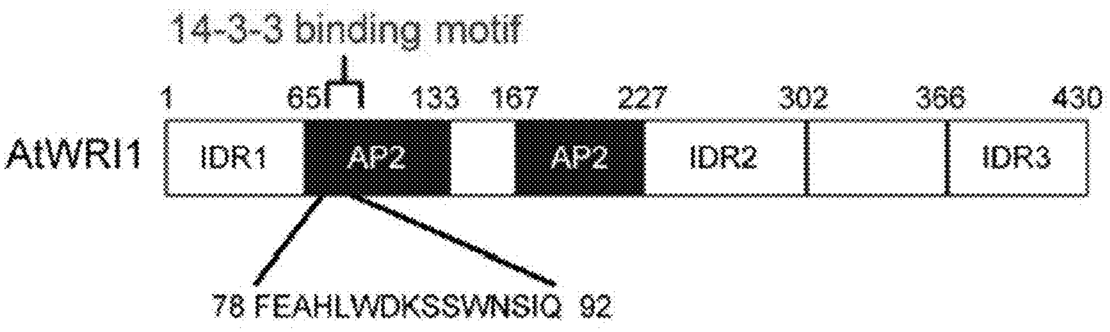
Figure 12B:
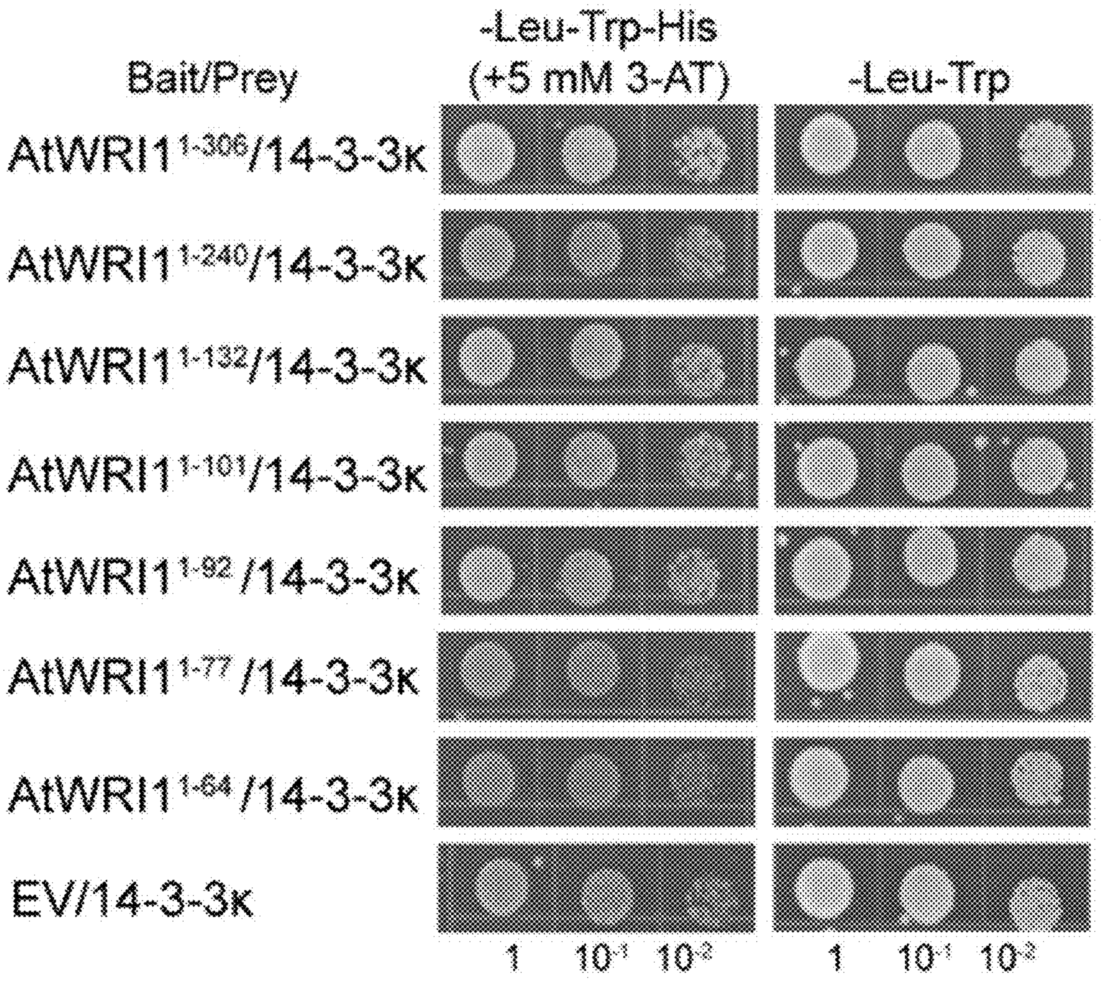
Figure 12C:
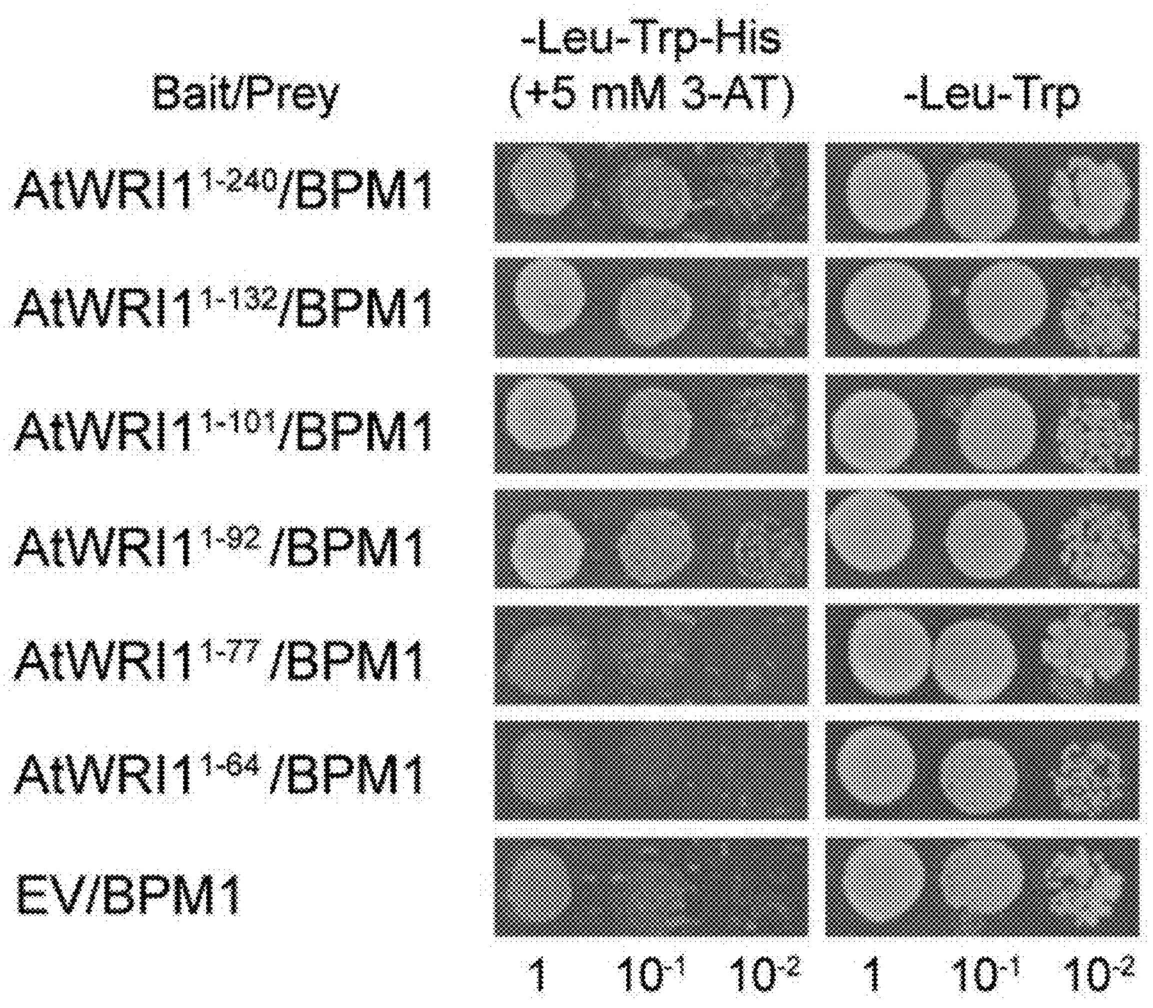

FIG. 12A-12C illustrate some of the properties of the 14-3-3 binding motif in AtWRI1. FIG. 12A is a schematic representation of AtWRI1, showing where the binding motif for 14-3-3 proteins is located in the WRI1 protein. The 14-3-3 binding motif has the following sequence: FEAHLWDKSSWNSIQ (SEQ ID NO:77). FIG. 12B illustrates interaction between 14-3-3κ and AtWRI1 truncated variants as determined by Y2H assay. FIG. 12C illustrates results of mapping of the binding region within AtWRI1 for the E3 ligase bridge protein BPM1 by Y2H assay. Interactions between BPM1 and truncated variants of AtWRI1 were tested in an Y2H experiment. EV was used as a negative control.

Figure 13:
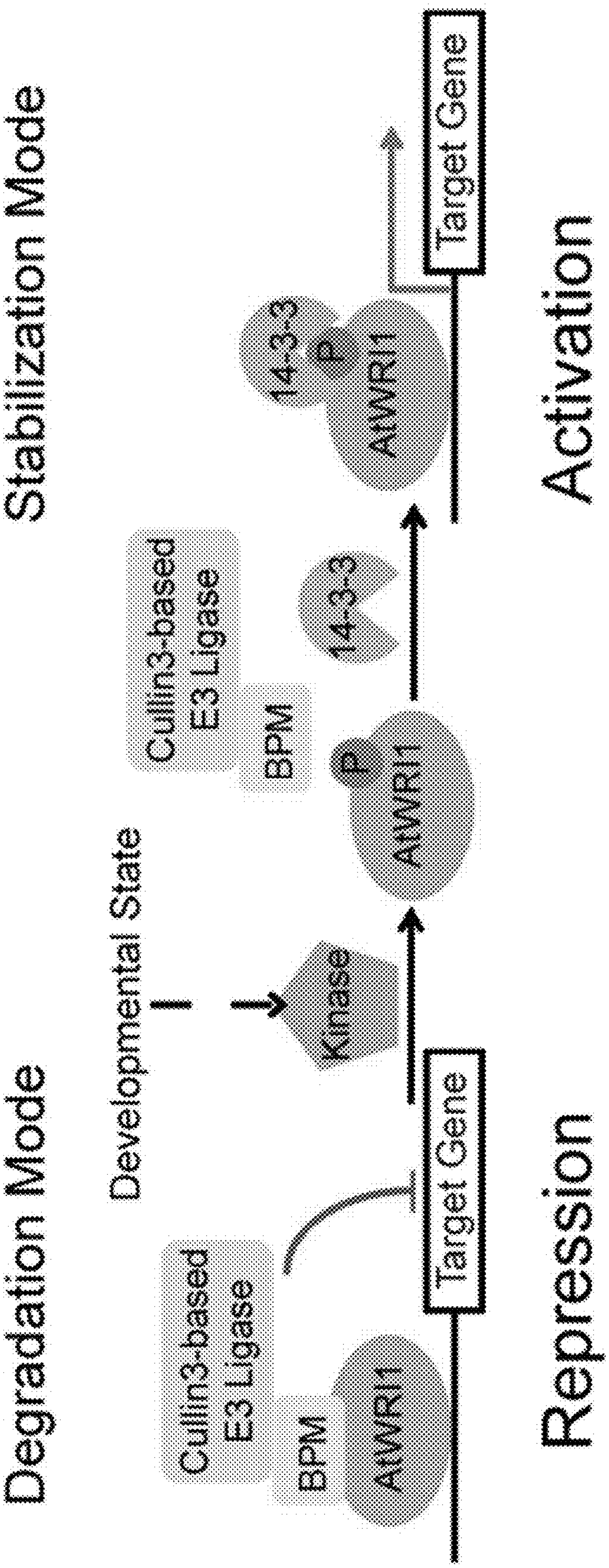

FIG. 13 is a schematic diagram illustrating how 14-3-3 polypeptides may effect on AtWRI1 stability. Phosphorylation of AtWRI1 may create the docking site(s) for the binding of 14-3-3 protein. Phosphorylation of WRI1 may be dependent on the developmental state of the embryo. The interaction of 14-3-3 and AtWRI1 may result in either 1) the blocking of E3 ligase-BPMs binding to AtWRI1 and/or 2) the detachment of the E3 ligase-BPMs from AtWRI1. As a result, the AtWRI1-14-3-3 protein complex displays increased stability and enhanced transcriptional activity.

DETAILED DESCRIPTION

The invention relates to plants, plant cells, and seeds that express heterologous 14-3-3 and/or WRI1 proteins. Such plants, plant cells, and seeds can have heterologous nucleic acids encoding such 14-3-3 and/or WRI1 proteins. Plants and seeds that include 14-3-3 and WRI1 expression cassettes or expression vectors produce more oil in their seeds and tissues than corresponding native (wild type) plants. Accordingly, the invention also relates to methods of generating and using such plants, plant cells, seeds, or seedlings, for example, to generate oil.

Wrinkled

One useful function for the WRINKLED1 (WRI1) transcription factor is to increase the accumulation of triacylglycerols (TAGs) in plants and their seeds. Overexpression of WRI1 is thought to up-regulate a set of genes involved in fatty acid (FA) synthesis including, for example, genes for a subunit of pyruvate kinase (Pl-PKβ1), acetyl-CoA carboxylase (BCCP2), acyl carrier protein (ACP1), and ketoacyl-acyl carrier protein synthase (KAS1). WRI1 can bind to upstream sequences in such genes and may have a number of upstream binding sites. For example, workers have observed that seven different WRI1 binding sites share a sequence [CnTnG](n)$_7$[CG], where n is any nucleotide; this sequence has been designated the AW-box (Maeo et al., *The Plant Journal* 60: 476-487 (2009)). WRI1 facilitates synthesis of plant carbons into oil by activating genes involved in oil synthesis.

As described herein, WRI1 is a transcription factor that can increase the synthesis of proteins involved in oil synthesis. Modification of plants to express increased levels of stabilized WRI1 transcription factors can further increase the oil content of seeds and non-seed tissues (e.g., leaves, stalks and roots) in a variety of transgenic plants. Plants can be generated as described herein to include WRI1 nucleic acids that encode stabilized WRI transcription factors. Plants are especially desirable when the WRI1 nucleic acids are operably linked to control sequences capable of WRI1 expression in a multitude of plant tissues, or in selected tissues and during selected parts of the plant life cycle to optimize the synthesis of oil. Such control sequences are typically heterologous to the coding region of the WRI1 nucleic acids.

One example of an amino acid sequence for a WRI1 (WRI1) sequence from *Arabidopsis thaliana* is available as accession number AAP80382.1 (GI: 32364685), and is reproduced below as SEQ ID NO: 1.

1 MKKRLTTSTC SSSPSSSVSS STTTSSPIQS EAPRPKRAKR
41 AKKSSPSGDK SHNPTSPAST RRSSIYRGVT RHRWTGRFEA
81 HLWDKSSWNS IQNKKGKQVY LGAYDSEEAA AHTYDLAALK
121 YWGPDTILNF PAETYTKELE EMQRVTKEEY LASLRRQSSG
161 FSRGVSKYRG VARHHHNGRW EARIGRVFGN KYLYLGTYNT
201 QEEAAAAYDM AAIEYRGANA VTNFDISNYI DRLKKKGVFP
241 FPVNQANHQE GILVEAKQEV ETREAKEEPR EEVKQQYVEE
281 PPQEEEEKEE EKAEQQEAEI VGYSEEAAVV NCCIDSSTIM
301 EMDRCGDNNE LAWNFCMMDT GFSPFLTDQN LANENPIEYP
361 ELFNELAFED NIDFMFDDGK HECLNLENLD CCVVGRESPP
401 SSSSPLSCLS TDSASSTTTT TTSVSCNYLV

A nucleic acid sequence for the above *Arabidopsis thaliana* WRI1 protein is available as accession number AY254038.2 (GI: 51859605), and is reproduced below as SEQ ID NO:2.

1 AAACCACTCT GCTTCCTCTT CCTCTGAGAA ATCAAATCAC
41 TCACACTCCA AAAAAAAATC TAAACTTTCT CAGAGTTTAA
81 TGAAGAAGCG CTTAACCACT TCCACTTGTT CTTCTTCTCC
121 ATCTTCCTCT GTTTCTTCTT CTACTACTAC TTCCTCTCCT
161 ATTCAGTCGG AGGCTCCAAG GCCTAAACGA GCCAAAAGGG
201 CTAAGAAATC TTCTCCTTCT GGTGATAAAT CTCATAACCC
241 GACAAGCCCT GCTTCTACCC GACGCAGCTC TATCTACAGA

281 GGAGTCACTA GACATAGATG GACTGGGAGA TTCGAGGCTC
301 ATCTTTGGGA CAAAAGCTCT TGGAATTCGA TTCAGAACAA
361 GAAAGGCAAA CAAGTTTATC TGGGAGCATA TGACAGTGAA
401 GAAGCAGCAG CACATACGTA CGATCTGGCT GCTCTCAAGT
421 ACTGGGGACC CGACACCATC TTGAATTTTC CGGCAGAGAC
481 GTACACAAAG GAATTGGAAG AAATGCAGAG AGTGACAAAG
521 GAAGAATATT TGGCTTCTCT CCGCCGCCAG AGCAGTGGTT
581 TCTCCAGAGG CGTCTCTAAA TATCGCGGCG TCGCTAGGCA
601 TCACCACAAC GGAAGATGGG AGGCTCGGAT CGGAAGAGTG
641 TTTGGGAACA AGTACTTGTA CCTCGGCACC TATAATACGC
681 AGGAGGAAGC TGCTGCAGCA TATGACATGG CTGCGATTGA
721 GTATCGAGGC GCAAACGCGG TTACTAATTT CGACATTAGT
761 AATTACATTG ACCGGTTAAA GAAGAAAGGT GTTTTCCCGT
801 TCCCTGTGAA CCAAGCTAAC CATCAAGAGG GTATTCTTGT
841 TGAAGCCAAA CAAGAAGTTG AAACGAGAGA AGCGAAGGAA
881 GAGCCTAGAG AAGAAGTGAA ACAACAGTAC GTGGAAGAAC
921 CACCGCAAGA AGAAGAAGAG AAGGAAGAAG AGAAAGCAGA
961 GCAACAAGAA GCAGAGATTG TAGGATATTC AGAAGAAGCA
1001 GCAGTGGTCA ATTGCTGCAT AGACTCTTCA ACCATAATGG
1041 AAATGGATCG TTGTGGGGAC AACAATGAGC TGGCTTGGAA
1081 CTTCTGTATG ATGGATACAG GGTTTTCTCC GTTTTTGACT
1121 GATCAGAATC TCGCGAATGA GAATCCCATA GAGTATCCGG
1141 AGCTATTCAA TGAGTTAGCA TTTGAGGACA ACATCGACTT
1201 CATGTTCGAT GATGGGAAGC ACGAGTGCTT GAACTTGGAA
1241 AATCTGGATT GTTGCGTGGT GGGAAGAGAG AGCCCACCCT
1281 CTTCTTCTTC ACCATTGTCT TGCTTATCTA CTGACTCTGC
1321 TTCATCAACA ACAACAACAA CAACCTCGGT TTCTTGTAAC
1361 TATTTGGTCT GAGAGAGAGA GCTTTGCCTT CTAGTTTGAA
1401 TTTCTATTTC TTCCGCTTCT TCTTCTTTTT TTTCTTTTGT
1441 TGGGTTCTGC TTAGGGTTTG TATTTCAGTT TCAGGGCTTG
1481 TTCGTTGGTT CTGAATAATC AATGTCTTTG CCCCTTTTCT
1501 AATGGGTACC TGAAGGGCGA

A PEST domain that has an amino acid sequence enriched in proline (P), glutamic acid (E), serine (S), and threonine (T)) is associated with intrinsically disordered regions (IDRs). As described herein, removal of the C-terminal PEST domain or mutations in putative phosphorylation sites with such C-terminal PEST domains results in a more stable WRINKLED transcription factors and increased oil biosynthesis by plants expressing such deleted or mutated WRINKLED transcription factors.

The PEST domain of the *Arabidopsis thaliana* protein with SEQ ID NO: 1 can have deletions or mutations in the following PEST sequence (SEQ ID NO:3).

396 RESPP SSSSPLSCLS TDSASSTTTT TTSVSC-NYLV.

For example, expression of a C-terminally truncated *Arabidopsis thaliana* WRI1 protein or an *Arabidopsis thaliana* WRI1 protein with at least four mutations at any of positions 398, 401, 402, 407, 415, 416, 420, 421, 422, and/or 423 increases the content of triacylglycerol in plant tissues such as leaves and seeds. Hence, one aspect of the invention is a mutant WRI1 protein that includes a mutation (substitution, insertion, or deletion) in the following sequence (SEQ ID NO: 4):

396 REXPP XXSSPLXCLS TDSAXXTTTX XXXVSC-NYLV.

where at least four of the X residues in the SEQ ID NO:4 sequence is a substitution, insertion, or deletion compared to the wild type sequence (SEQ ID NO:3). The X residues are not acidic amino acids such as aspartic acid or glutamic acid. However, the X residue can be a small amino acid or a hydrophobic amino acid. For example, the X residues can each separately be alanine, glycine, valine, leucine, isoleucine, methionine, or any mixture thereof. As illustrated herein, WRI1 proteins with an alanine instead of a serine or a threonine at each of positions 398, 401, 402, and 407 have increased stability and, when expressed in plant cells, the cells produce more triacylglycerols than do wild type plants that do not express such a mutant WRI1 protein.

Another aspect of the invention is a mutant WRI1 protein with a truncation at the C terminus of at least 5, or at least 7, or at least 10, or at least 13, or at least 15, or at least 17, or at least 20, or at least 25, or at least 30, or at least 35, or at least 40, or at least 45 amino acids. For example, such deletions can be within the SEQ ID NO:3 portion of the WRI1 protein. Such mutant WRI1 proteins can be expressed in plant tissues to increase the oil/fatty acid/TAG content of those tissues.

Other types of WRI1 proteins also have utility for increasing the oil/fatty acid/TAG content of plant tissues.

For example, an amino acid sequence for a WRI1 sequence from *Brassica napus* is available as accession number ADO16346.1 (GI: 308193634). This *Brassica napus* WRI1 sequence is reproduced below as SEQ ID NO:5.

1 MKRPLTTSPS TSSSTSSSAC ILPTQPETPR PKRAKRAKKS
41 SIPTDVKPQN PTSPASTRRS SIYRGVTRHR WTGRYEAHLW
81 DKSSWNSIQN KKGKQVYLGA YDSEEAAAHT YDIAALKYWG
121 PDTILNFPAE TYTKELEEMQ RCTKEEYLAS LRRQSSGFSR
161 GVSKYRGVAR HHHNGRWEAR IGRVFGNKYL YLGTYNTQEE
201 AAAAYDMAAI EYRGANAVTN FDISNYIDRL KKKGVFPFPV
241 SQANHQEAVL AEAKQEVEAK EEPTEEVKQC VEKEEPQEAK
281 EEKTEKKQQQ QEVEEAVVTC CIDSSESNEL AWDFCMMDSG

301 FAPFLTDSNL SSENPIEYPE LFNEMGFEDN IDF-MFEEGKQ

361 DCLSLENLDC CDGVVVVGRE SPTSLSSSPL SCLSTDSASS

401 TTTTTITSVS CNYSV

A nucleic acid sequence for the above *Brassica napus* WRI1 protein is available as accession number HM370542.1 (GI: 308193633), and is reproduced below as SEQ ID NO:6.

1 ATGAAGAGAC CCTTAACCAC TTCTCCTTCT ACCTCCTCTT

41 CTACTTCTTC TTCGGCTTGT ATACTTCCGA CTCAACCAGA

61 GACTCCAAGG CCCAAACGAG CCAAAAGGGC TAAGAAATCT

121 TCTATTCCTA CTGATGTTAA ACCACAGAAT CCCACCAGTC

161 CTGCCTCCAC CAGACGCAGC TCTATCTACA GAGGAGTCAC

201 TAGACATAGA TGGACAGGGA GATACGAGGC TCATCTATGG

241 GACAAAAGCT CGTGGAATTC GATTCAGAAC AAGAAAGGCA

281 AACAAGTTTA TCTGGGAGCA TATGACAGCG AGGAAGCAGC

321 AGCGCATACG TACGATCTAG CTGCTCTCAA GTACTGGGGT

361 CCCGACACCA TCTTGAACTT TCCGGCTGAG ACGTACACAA

401 AGGAGTTGGA GGAGATGCAG AGATGTACAA AGGAAGAGTA

441 TTTGGCTTCT CTCCGCCGCC AGAGCAGTGG TTTCTCTAGA

481 GGCGTCTCTA AATATCGCGG CGTCGCCAGG CATCACCATA

521 ACGGAAGATG GGAAGCTAGG ATTGGAAGGG TGTTTGGAAA

541 CAAGTACTTG TACCTCGGCA CTTATAATAC GCAGGAGGAA

601 GCTGCAGCTG CATATGACAT GGCGGCTATA GAGTACAGAG

641 GCGCAAACGC AGTGACCAAC TTCGACATTA GTAACTACAT

681 CGACCGGTTA AAGAAAAAAG GTGTCTTCCC ATTCCCTGTG

721 AGCCAAGCCA ATCATCAAGA AGCTGTTCTT GCTGAAGCCA

761 AACAAGAAGT GGAAGCTAAA GAAGAGCCTA CAGAAGAAGT

801 GAAGCAGTGT GTCGAAAAAG AAGAAC-CGCA AGAAGCTAAA

841 GAAGAGAAGA CTGAGAAAAA ACAACAA-CAA CAAGAAGTGG

881 AGGAGGCGGT GGTCACTTGC TGCATTGATT CTTCGGAGAG

921 CAATGAGCTG GCTTGGGACT TCTGTATGAT GGATTCAGGG

961 TTTGCTCCGT TTTTGACGGA TTCAAATCTC TCGAGTGAGA

1001 ATCCCATTGA GTATCCTGAG CTTTTCAATG AGATGGGGTT

1041 TGAGGATAAC ATTGACTTCA TGTTCGAGGA AGGGAAGCAA

1081 GACTGCTTGA GCTTGGAGAA TCTGGATTGT TGCGATGGTG

1121 TTGTTGTGGT GGGAAGAGAG AGC-CCAACTT CATTGTCGTC

1161 TTCACCGTTG TCTTGCTTGT CTACTGACTC TGCTTCATCA

1201 ACAACAACAA CAACAATAAC CTCTGTTTCT TGTAACTATT

1241 CTGTCTGA

Expression of a C-terminally truncated *Brassica napus* WRI1 protein or an *Brassica napus* WRI1 protein with a mutation (e.g., substitution, insertion, or deletion) at four or more of positions 381, 383, 384, 386, 387, 388, 391, 399, 400, 401, 402, 403, 404, 405, 407, or 408 can increase the content of triacylglycerol in plant tissues such as leaves and seeds. Hence, one aspect of the invention is a mutant WRI1 protein that includes a mutation (substitution, insertion, or deletion) in the following sequence (SEQ ID NO: 7):

379 RE SPTSLSSSPL SCLSTDSASS TTTTTITSVS CNYSV

For example, expression of a C-terminally truncated *Brassica napus* WRI1 protein or a *Brassica napus* WRI1 protein with at least four mutations (substitution, insertion, or deletion) at any of positions 381, 383, 384, 386, 387, 388, 391, 399, 400, 401, 402, 403, 404, 405, 407, and/or 408 can increase the content of triacylglycerol in plant tissues such as leaves and seeds. Hence, another aspect of the invention is a mutant WRI1 protein that includes the following sequence (SEQ ID NO: 8):

RE XPXXLXXXPL XCLSTDSAXX XXXXXIXXVS CNYSV where at least four of the X residues in the SEQ ID NO:8 sequence is a substitution, insertion, or deletion compared to the wild type sequence (SEQ ID NO:7). The X residues are not acidic amino acids such as aspartic acid or glutamic acid. However, the X residue can be a small amino acid or a hydrophobic amino acid. For example, the X residues can each separately be alanine, glycine, valine, leucine, isoleucine, methionine, or any mixture thereof.

Another aspect of the invention is a mutant WRI1 protein with a truncation at the C terminus of the SEQ ID NO:5 (or from the SEQ ID NO:7) sequence of at least 4, or at least 5, or at least 7, or at least 10, or at least 13, or at least 15, or at least 17, or at least 20, or at least 25, or at least 30, or at least 35, or at least 40, or at least 45 amino acids. Such mutant WRI1 proteins can be expressed in plant tissues to increase the oil/fatty acid/TAG content of those tissues.

Another example of an amino acid sequence for a WRINKLED1 (WRI1) sequence from *Brassica napus* is available as accession number ABDI6282.1 (GI: 87042570), and is reproduced below as SEQ ID NO:9.

1 MKRPLTTSPS SSSSTSSSAC ILPTQSETPR PKRAKRAKKS

41 SLRSDVKPQN PTSPASTRRS SIYRGVTRHR WTGRYEAHLW

81 DKSSWNSIQN KKGKQVYLGA YDSEEAAAHT YDLAALKYWG

121 PNTILNFPVE TYTKELEEMQ RCTKEEYLAS LRRQSSGFSR

161 GVSKYRGVAR HHHNGRWEAR IGRVFGNKYL YLGTYNTQEE

201 AAAAYDMAAI EYRGANAVTN FDIGNYIDRL KKKGVFPFPV

241 SQANHQEAVL AETKQEVEAK EEPTEEVKQC VEKEEAKEEK

281 TEKKQQQEVE EAVITCCIDS SESNELAWDF CMMDSGFAPF

321 LTDSNLSSEN PIEYPELFNE MGFEDNIDFM FEEGKQDCLS

361 LENLDCCDGV VVVGRESPTS LSSSPLSCLS TDSASSTTTT

401 ATTVTSVSWN YSV

A nucleic acid sequence for the above *Brassica napus* WRI1 protein is available as accession number DQ370141.1 (GI: 87042569), and is reproduced below as SEQ ID NO:10.

1 ATGAAGAGAC CCTTAACCAC TTCTCCTTCT TCCTCCTCTT
41 CTACTTCTTC TTCGGCCTGT ATACTTCCGA CTCAATCAGA
61 GACTCCAAGG CCCAAACGAG CCAAAAGGGC TAAGAAATCT
121 TCTCTGCGTT CTGATGTTAA ACCACAGAAT CCCACCAGTC
161 CTGCCTCCAC CAGACGCAGC TCTATCTACA GAGGAGTCAC
181 TAGACATAGA TGGACAGGGA GATACGAAGC TCATCTATGG
241 GACAAAAGCT CGTGGAATTC GATTCAGAAC AAGAAAGGCA
281 AACAAGTTTA TCTGGGAGCA TATGACAGCG AGGAAGCAGC
321 AGCACATACG TACGATCTAG CTGCTCTCAA GTACTGGGGT
361 CCCAACACCA TCTTGAACTT TCCGGTTGAG ACGTACACAA
401 AGGAGCTGGA GGAGATGCAG AGATGTACAA AGGAAGAGTA
441 TTTGGCTTCT CTCCGCCGCC AGAGCAGTGG TTTCTCTAGA
481 GGCGTCTCTA AATATCGCGG CGTCGCCAGG CATCACCATA
521 ATGGAAGATG GGAAGCTCGG ATTGGAAGGG TGTTTGGAAA
541 CAAGTACTTG TACCTCGGCA CCTATAATAC GCAGGAGGAA
601 GCTGCAGCTG CATATGACAT GGCGGCTATA GACTACAGAG
641 GTGCAAACGC AGTGACCAAC TTCGACATTG GTAACTACAT
681 CGACCGGTTA AAGAAAAAAG GTGTCTTCCC GTTCCCCGTG
721 AGCCAAGCTA ATCATCAAGA AGCTGTTCTT GCTGAAACCA
761 AACAAGAAGT GGAAGCTAAA GAAGAGCCTA CAGAAGAAGT
801 GAAGCAGTGT GTCGAAAAAG AAGAAGCTAA AGAAGAGAAG
841 ACTGAGAAAA AACAACAACA AGAAGTG-GAG GAGGCGGTGA
881 TCACTTGCTG CATTGATTCT TCAGAGAGCA ATGAGCTGGC
921 TTGGGACTTC TGTATGATGG ATTCAGGGTT TGCTCCGTTT
961 TTGACTGATT CAAATCTCTC GAGTGAGAAT CCCATTGAGT
1001 ATCCTGAGCT TTTCAATGAG ATGGGTTTTG AGGATAACAT
1041 TGACTTCATG TTCGAGGAAG GGAAGC-AAGA CTGCTTGAGC
1081 TTGGAGAATC TTGATTGTTG CGATGGTGTT GTTGTGGTGG
1121 GAAGAGAGAG CCCAACTTCA TTGTCGTCTT CTCCGTTGTC
1141 CTGCTTGTCT ACTGACTCTG CTTCATCAAC AACAACAACA
1201 GCAACAACAG TAACCTCTGT TTCTTGGAAC TATTCTGTCT
1241 GA

Expression of a C-terminally truncated *Brassica napus* WRI1 protein or a *Brassica napus* WRI1 protein with a mutation at four or more of positions 381, 383, 384, 385, 387, 388, 391, 394, 399, 400, 401, 402, 403, 404, 406, 407, 409, and/or 410 can increase the content of triacylglycerol in plant tissues such as leaves and seeds. Hence, one aspect of the invention is a mutant WRI1 protein that includes a mutation (substitution, insertion, or deletion) in the following sequence (SEQ ID NO: 11):

379 RE SPTSLSSSPL SCLSTDSASS TTTTATTVTS VSWN

For example, expression of a C-terminally truncated *Brassica napus* WRI1 protein or a *Brassica napus* WRI1 protein with at least four mutations at any of positions 381, 383, 384, 385, 387, 388, 391, 394, 399, 400, 401, 402, 403, 404, 406, 407, 409, and/or 410 can increase the content of triacylglycerol in plant tissues such as leaves and seeds. Hence, another aspect of the invention is a mutant WRI1 protein that includes the following sequence (SEQ ID NO: 12):

379 RE XPXXLXSSPL XCLXTDSAXX XXXX-AXXVXX VSWN where at least four of the X residues in the SEQ ID NO: 12 sequence is a substitution, insertion, or deletion compared to the wild type sequence (SEQ ID NO: 11). The X residues are not acidic amino acids such as aspartic acid or glutamic acid. However, the X residue can be a small amino acid or a hydrophobic amino acid. For example, the X residues can each separately be alanine, glycine, valine, leucine, isoleucine, methionine, or any mixture thereof.

Another aspect of the invention is a mutant WRI1 protein with a truncation at the C terminus of the SEQ ID NO:9 (or from the SEQ ID NO:11) sequence of at least 4, or at least 5, or at least 7, or at least 10, or at least 13, or at least 15, or at least 17, or at least 20, or at least 25, or at least 30, or at least 35, or at least 40, or at least 45 amino acids. Such mutant WRI1 proteins can be expressed in plant tissues to increase the oil/fatty acid/TAG content of those tissues.

Other *Brassica napus* amino acid and cDNA WRI1 sequences are available as accession numbers ABD72476.1 (GI: 89357185) and DQ402050.1 (GI: 89357184), respectively.

An example of an amino acid sequence for a WRI1 sequence from *Zea mays* is available as accession number ACG32367.1 (GI: 195621074), and reproduced below as SEQ ID NO: 13.

1 MERSQRQSPP PPSPSSSSSS VSADTVLVPP GKRRRAATAK
41 AGAEPNKRIR KDPAAAAAGK RSSVYRGVTR HRWTGRFEAH
81 LWDKHCLAAL HNKKKGRQVY LGAYDSEEAA ARAYDLAALK
121 YWGPETLLNF PVEDYSSEMP EMEAVSREEY LASLRRRSSG
161 FSRGVSKYRG VARHHHNGRW EARIGRVFGN KYLYLGTFDT
201 QEEAAKAYDL AAIEYRGVNA VTNFDISCYL DHPLFLAQLQ
241 QEPQVVPALN QEPQPDQSET GTTEQEPESS EAKTPDGSAE
281 PDENAVPDDT AEPLSTVDDS IEEGLWSPCM DYELDTMSRP
321 NFGSSINLSE WFADADFDCN IGCLFDGCSA ADEGSKDGVG
361 LADFSLFEAG DVQLKDVLSD MEEGIQPPAM ISVCN

A nucleic acid sequence for the above *Zea mays* WRI1 protein sequence is available as accession number EU960249.1 (GI: 195621073), and is reproduced below as SEQ ID NO: 14.

1 CTCCCCCGCC TCGCCGCCAG TCAGATTCAC CACCGGCTCC
41 CCTGCACAAC CGCGTCCGCG CTGCACCACC ACCGTTCATC
81 GAGGAGGAGG GGGGACGGAG ACCACGGACA TGGAGAGATC
121 TCAACGGCAG TCTCCTCCGC CACCGTCGCC GTCCTCCTCC
161 TCGTCCTCCG TCTCCGCGGA CACCGTCCTC GTCCCTCCCG
201 GAAAGAGGCG GAGGGCGGCG ACGGC-CAAGG CCGGCGCCGA
241 GCCTAATAAG AGGATCCGCA AGGACCCCGC CGCCGCCGCC
281 GCGGGGAAGA GGAGCTCCGT CTACAGGGGA GTCACCAGGC
321 ACAGGTGGAC GGGCAGGTTC GAGGCGCATC TCTGGGACAA
361 GCACTGCCTC GCCGCGCTCC ACAACAAGAA GAAAGGCAGG
401 CAAGTCTACC TGGGGGCGTA TGACAGCGAG GAGGCAGCTG
441 CTCGTGCCTA TGACCTCGCA GCTCTCAAGT ACTGGGGTCC
481 TGAGACTCTG CTCAACTTCC CTGTGGAGGA TTACTCCAGC
521 GAGATGCCGG AGATGGAGGC CGTTTCCCGG GAGGAGTACC
561 TGGCCTCCCT CCGCCGCAGG AGCAGCGGCT TCTCCAGGGG
601 CGTCTCCAAG TACAGAGGCG TCGCCAGGCA TCACCACAAC
641 GGGAGGTGGG AGGCACGGAT TGGGCGAGTC TTTGGGAACA
681 AGTACCTCTA CTTGGGAACA TTTGACACTC AAGAAGAGGC
721 AGCCAAGGCC TATGACCTTG CGGCCATTGA ATACCGTGGC
761 GTCAATGCTG TAACCAACTT CGACATCAGC TGCTACCTGG
801 ACCACCCGCT GTTCCTGGCA CAGCTCCAAC AGGAGCCACA
841 GGTGGTGCCG GCACTCAACC AAGAACCTCA ACCTGATCAG
881 AGCGAAACCG GAACTACAGA GCAAGAG-CCG GAGTCAAGCG
921 AAGCCAAGAC ACCGGATGGC AGTGCAGAAC CCGATGAGAA
961 CGCGGTGCCT GACGACACCG CGGAGCCCCT CAGCACAGTC
1001 GACGACAGCA TCGAAGAGGG CTTGTG-GAGC CCTTGCATGG
1041 ATTACGAGCT AGACACCATG TCGAGACCAA ACTTTGGCAG
1081 CTCAATCAAT CTGAGCGAGT GGTTCGCTGA CGCAGACTTC
1121 GACTGCAACA TCGGGTGCCT GTTCGATGGG TGTTCTGCGG
1161 CTGACGAAGG AAGCAAGGAT GGTGTAG-GTC TGGCAGATTT
1201 CAGTCTGTTT GAGGCAGGTG ATGTCCAGCT GAAGGATGTT
1241 CTTTCGGATA TGGAAGAGGG GATACAACCT CCAGCGATGA
1281 TCAGTGTGTG CAACTAATTC TGGAACCCGA GGAGGTTTTC
1321 GCTTTCCAGG TGTCCTGTCT TGGGTAATCC TTGATCTGTC
1361 TAATGCCACA GTGCCACTGC ACCAGAGCAG CTGAGAACTT
1401 TCTTGTAGAA AGCCCATGGC AGTTTGGCGT TAGACAAGTG
1441 TGTCGATGTT CTTTAATTCT TTGAATTTGC CCCTAGGCTG
1481 CTTGGCTAAC GTTAAGGGTT TGTCATTGTC TCACTTAGCC
1521 TAGATTCAAC TAATCACATC CTGAATCTGA AAAAAAAAAA
1561 CAAAAAAAAA AAAAAA

Expression of an internally deleted *Zea mays* WRI1 protein or a *Zea mays* WRI1 protein with a mutation at four or more of amino acid positions 358, 360, 362, 363, 369, 370, 374, 378, 395, 395, 400, 407, 416, 418, and/or 419 can increase the content of triacylglycerol in plant tissues such as leaves and seeds. Hence, one aspect of the invention is a mutant WRI1 protein that includes a mutation (substitution, insertion, or deletion) in the following sequence (SEQ ID NO: 15):

232 HPLFLAQLQ
241 QEPQVVPALN QEPQPDQSET GTTEQEPESS EAKTPDGSAE
281 PDENAVPDDT AEPLSTVDDS IEEGLWSPCM DYELDTMSR

For example, expression of an internally deleted *Zea mays* WRI1 protein or a *Zea mays* WRI1 protein with a mutation at four or more of the following positions 358, 360, 362, 363, 369, 370, 374, 378, 395, 395, 400, 407, 416, 418, and/or 419 can increase the content of triacylglycerol in plant tissues. Hence, another aspect of the invention is a mutant WRI1 protein that includes a mutation (substitution, insertion, or deletion) in the following sequence (SEQ ID NO: 16):

232 HPLFLAQLQ
241 QEPQWPALN QEPQPDQXEX GXXEQEPEXX EAKXPDGXAE
281 PDENAVPDDX AEPLXXVDDX IEEGLWXPCM DYELDXMXR where at least four of the X residues in the SEQ ID NO: 16 sequence is a substitution, insertion, or deletion compared to the wild type sequence (SEQ ID NO:15). The X residues are not acidic amino acids such as aspartic acid or glutamic acid. However, the X residue can be a small amino acid or a hydrophobic amino acid. For example, the X residues can each separately be alanine, glycine, valine, leucine, isoleucine, methionine, or any mixture thereof.

Another aspect of the invention is a mutant WRI1 protein with a deletion within the SEQ ID NO: 15 portion of the WRI1 protein of at least 3, or at least 4, or at least 5, or at least 6, or at least 7, or at least 8, or at least 10, or at least 13, or at least 15, or at least 17, or at least 20, or at least 25, or at least 30, or at least 35, or at least 40, or at least 45 amino acids. Such mutant WRI1 proteins can be expressed in plant tissues to increase the oil/fatty acid/TAG content of those tissues.

Another example of an amino acid sequence for a WRI1 sequence from *Zea mays* is available as accession number NP_001131733.1 (GI: 212721372), and reproduced below as SEQ ID NO: 17.

1 MTMERSQPQH QQSPPSPSSS SSCVSADTVL VPPGKRRRRA
41 ATAKANKRAR KDPSDPPPAA GKRSSVYRGV TRHRWTGRFE
81 AHLWDKHCLA ALHNKKKGRQ VYLGAYDGEE AAARAYDLAA
121 LKYWGPEALL NFPVEDYSSE MPEMEAASRE EYLASLRRRS
161 SGFSRGVSKY RGVARHHHNG RWEARIGRVL GNKYLYLGTF
201 DTQEEAAKAY DLAAIEYRGA NAVTNFDISC YLDHPLFLAQ
241 LQQEQPQVVP ALDQEPQADQ REPETTAQEP VSSQAKTPAD
281 DNAEPDDIAE PLITVDNSVE ESLWSPCMDY ELDTMSRSNF
321 GSSINLSEWF TDADFDSDLG CLFDGRSAVD GGSKGGVGVA
361 DFSLFEAGDG QLKDVLSDME EGIQPPTIIS VCN

A nucleic acid sequence for the above *Zea mays* WRI1 protein sequence is available as accession number NM_001138261.1 (GI: 212721371), and is reproduced below as SEQ ID NO: 18.

1 CGTTCATGCA TGACCATGGA GAGATCTCAA CCGCAGCACC
41 AGCAGTCTCC TCCGTCGCCG TCGTCCTCCT CGTCCTGCGT
81 CTCCGCGGAC ACCGTCCTCG TCCCTCCGGG AAAGAGGCGG
121 CGGAGGGCGG CGACAGCCAA GGCCAATAAG AGGGCCCGCA
161 AGGACCCCTC TGATCCTCCT CCCGCCGCCG GGAAGAGGAG
201 CTCCGTATAC AGAGGAGTCA CCAGGCACAG GTGGACGGGC
241 AGGTTCGAGG CGCATCTCTG GGACAAGCAC TGCCTCGCCG
281 CGCTCCACAA CAAGAAGAAA GGCAGGCAAG TCTATCTGGG
321 GGCGTACGAC GGCGAGGAGG CAGCGGCTCG TGCCTATGAC
361 CTTGCAGCTC TCAAGTACTG GGGTCCTGAG GCTCTGCTCA
401 ACTTCCCTGT GGAGGATTAC TCCAGCGAGA TGCCGGAGAT
441 GGAGGCAGCG TCCCGGGAGG AGTACCTGGC CTCCCTCCGC
481 CGCAGGAGCA GCGGCTTCTC CAGGGGGGTC TCCAAGTACA
521 GAGGCGTCGC CAGGCATCAC CACAACGGGA GATGGGAGGC
561 ACGGATCGGG CGAGTTTTAG GGAACAAGTA CCTCTACTTG
601 GGAACATTCG ACACTCAAGA AGAGGCAGCC AAGGCCTATG
641 ATCTTGCGGC CATCGAATAC CGAGGTGCCA ATGCTGTAAC
681 CAACTTCGAC ATCAGCTGCT ACCTGGACCA CCCACTGTTC
721 CTGGCGCAGC TCCAGCAGGA GCAGCCACAG GTGGTGCCAG
761 CGCTCGACCA AGAACCTCAG GCTGATCAGA GAGAACCTGA
801 AACCACAGCC CAAGAGCCTG TGTCAAGCCA AGCCAAGACA
841 CCGGCGGATG ACAATGCAGA GCCTGATGAC ATCGCGGAGC
881 CCCTCATCAC GGTCGACAAC AGCGTCGAGG AGAGCTTATG
921 GAGTCCTTGC ATGGATTATG AGCTAGACAC CATGTCGAGA
961 TCTAACTTTG GCAGCTCGAT CAACCTGAGC GAGTGGTTCA
1001 CTGACGCAGA CTTCGACAGC GACTTGGGAT GCCTGTTCGA
1041 CGGGCGCTCT GCAGTTGATG GAGGAAGCAA GGGTGGCGTA
1081 GGTGTGGCGG ATTTCAGTTT GTTTGAAGCA GGTGATGGTC
1121 AGCTGAAGGA TGTTCTTTCG GATATGGAAG AGGGGATACA
1161 ACCTCCAACG ATAATCAGTG TGTGCAATTG ATTCTGAGAC
1201 CTATGCGTGG CGTGCGACAA GTGTCCTGTC TTTGGGTATA
1241 CTTGGTTTGT CCAATGCCAC GGTGCCACTG CTGCGAGTCA
1281 GCTGAACTTC TTGTAGAAAG CACATGGCAG CTTGGCATTA
1321 GACAAGTGTG TTGGTGTTCC TTAATTCTTT GGATATGCTT
1361 TAGGCATTGA CTAACCTTAA GGGTTCGTCA CTGTCTCGCT
1401 TAGCTTAGAT TAGACTAATC ACATCCTTGA ATCTGAAGTA
1441 GTTGTGCAGT ATCACAGTTT CACATGGCAA TTCTGCCAAT
1481 GCAGCATAGA TTTGTTCGTT TGAACAGCTG TAACTGTAAC
1521 CCTATAGCTC CAGATTAAGG AACAGTTTGT TTTTCATCCA
1561 T

Expression of an internally deleted *Zea mays* WRI1 protein or a *Zea mays* WRI1 protein with a mutation at four or more of positions 265, 266, 272, 273, 277, 294, 298, 302, 305, 314, and/or 316 can increase the content of triacylglycerol in plant tissues such as leaves and seeds. Hence, one aspect of the invention is a mutant WRI1 protein that includes a mutation (substitution, insertion, or deletion) in the following sequence (SEQ ID NO: 19):

261 REPETTAQEP VSSQAKTPAD
281 DNAEPDDIAE PLITVDNSVE ESLWSPCMDY ELDTMSR

For example, expression of an internally deleted *Zea mays* WRI1 protein or a *Zea mays* WRI1 protein with a mutation at four or more of positions 265, 266, 272, 273, 277, 294, 298, 302, 305, 314, and/or 316 can increase the content of triacylglycerol in plant tissues. Hence, another aspect of the invention is a mutant WRI1 protein that includes the following sequence (SEQ ID NO: 20):

261 REPEXXAQEP VXXQAKXPAD
281 DNAEPDDIAE PLIXVDNXVE EXLWXPCMDY ELDXMXR where at least four of the X residues in the SEQ ID NO:20 sequence is a substitution, insertion, or deletion compared to the wild type sequence (SEQ ID NO:19). The X residues are not acidic amino acids such as aspartic acid or glutamic acid. However, the X residue can be a small amino acid or a hydrophobic amino acid. For example, the X residues can each separately be alanine, glycine, valine, leucine, isoleucine, methionine, or any mixture thereof.

Another aspect of the invention is a mutant WRI1 protein with a deletion within the SEQ ID NO: 19 portion of the WRI1 protein of at least 3, or at least 4, or at least 5, or at least 6, or at least 7, or at least 8, or at least 10, or at least 13, or at least 15, or at least 17, or at least 20, or at least 25, or at least 30, or at least 35, or at least 40, or at least 45 amino acids. Such mutant WRI1 proteins can be expressed in plant tissues to increase the oil/fatty acid/TAG content of those tissues.

An example of an amino acid sequence for a WRI1 sequence from *Elaeis guineensis* (palm oil) is available as accession number XP_010922928.1 (GI: 743789536), and reproduced below as SEQ ID NO:21.

1 MTLMKNSPPS TPLPPISPSS SASPSSYAPL SSPN-MIPLNK
41 CKKSKPKHKK AKNSDESSRR RSSIYRGVTR HRGTGRYEAH
81 LWDKHWQHPV QNKKGRQVYL GAFTDELDAA RAHDLAALKL
121 WGPETILNFP VEMYREEYKE MQTMSKEEVL ASVRRRSNGF
161 ARGTSKYRGV ARHHKNGRWE ARLSQDVGCK YIYLGTYATQ
201 EEAAQAYDLA ALVHKGPNIV TNFASSVYKH RLQPFMQLLV
241 KPETEPAQED LGVLQMEATE TIDQTMPNYD LPEISWTFDI
281 DHDLGAYPLL DVPIEDDQHD ILNDLNFEGN IEHLFEEFET
321 FGGNESGSDG FSASKGA

A nucleic acid sequence for the above *Elaeis guineensis* WRI1 protein sequence is available as accession number XM_010924626.1 (GI: 743789535), and is reproduced below as SEQ ID NO:22.

1 AGAGAGAGAG AGATTCCAAC ACAGGGCAGC TGAGATTGAG
41 CACAAGGCGC CGTGGAAACC ACGAGTTCCA TTGGCAACAT
81 GGGAAACCTG GTGGCCAAGT GTAGAGCTCT CTCACACAAA
121 CCCATGCGGC CAACTTGCAG ACCCTCGAGT CATTTGGACT
161 CTTCCAAGCT CACCAGCCGT AGGGTTTTTT GACAAGAGGG
201 ACCTCCAGTA AACGTTAAAC AAACTCGCAG CTCCCACCTT
241 TGGATCCATT CCATCGCTTC AACGGTGGGT TAGAAGCCTC
281 CGCGCCAAAT GCACGAGTGC TCAACAGCAC GCTCCCCTAA
321 TTTTTCTCTC TCCACCTCCT CACTTCTCTA TATATAATCC
361 TCTCTTTGGT GAACCACCAT CAACCAAACC AACGGTATAG
401 TATACGTAGG AAATAATCCC TTTCTAGAAC ATGACTCTCA
441 TGAAGAAATC TCCTCCCTCT ACTCCTCTCC CACCAATATC
481 GCCTTCCTCT TCCGCTTCAC CATCCAGCTA TGCACCCCTT
521 TCTTCTCCTA ATATGATCCC TCTTAACAAG TGCAAGAAGT
561 CGAAGCCAAA ACATAAGAAA GCTAAGAACT CAGATGAAAG
601 CAGTAGGAGA AGAAGCTCTA TCTACAGAGG AGTCACGAGG
641 CACCGAGGGA CTGGGAGATA TGAAGCTCAC CTGTGGGACA
681 AGCACTGGCA GCATCCGGTC CAGAACAAGA AAGGCAGGCA
721 AGTTTACTTG GGAGCCTTTA CTGATGAGTT GGACGCAGCA
761 CGAGCTCATG ACTTGGCTGC CCTTAAGCTC TGGGGTCCAG
801 AGACAATTTT AAACTTCCCT GTGGAAATGT ATAGAGAAGA
841 GTACAAGGAG ATGCAAACCA TGTCAAAGGA AGAGGTGCTG
881 GCTTCGGTTA GGCGCAGGAG CAACGGCTTT GCCAGGGGTA
921 CCTCTAAGTA CCGTGGGGTG GCCAGGCATC ACAAAAACGG
961 CCGGTGGGAG GCCAGGCTTA GCCAGGACGT TGGCTGCAAG
1001 TACATCTACT TGGGAACATA CGCAACTCAA GAGGAGGCTG
1041 CCCAAGCTTA TGATTTAGCT GCTCTAGTAC ACAAAGGGCC
1081 AAATATAGTG ACCAACTTTG CTAGCAGTGT CTATAAGCAT
1121 CGCCTACAGC CATTCATGCA GCTATTAGTG AAGCCTGAGA
1161 CGGAGCCAGC ACAAGAAGAC CTGGGG-GTTA TGCAAATGGA
1201 AGCAACCGAG ACAATCGATC AGACCATGCC AAATTACGAC
1241 CTGCCGGAGA TCTCATGGAC CTTCGACATA GACCATGACT
1281 TAGGTGCATA TCCTCTCCTT GATGTCCCAA TTGAGGATGA
1321 TCAACATGAC ATCTTGAATG ATCTCAATTT CGAGGGGAAC
1361 ATTGAGCACC TCTTTGAAGA GTTTGAGACC TTCGGAGGCA
1401 ATGAGAGTGG AAGTGATGGT TTCAGTGCAA GCAAAGGTGC
1441 CTAGCAGAGG AAAGTGGTTT GAAGATG-GAG GACATGGCAT
1481 CTAAAGCGAA CTGAGCCTCC TGGCCTCTTC AAAGTAGTGT
1521 CTGCTTTTTA GAAATCTTGG TGGGTCGATT TGAGTTAGGA
1561 GCCCGATACT TCTATCAGGG GATATGTTTA GCTACAATTC
1601 TAGTTTTTTT TTCTTTTTTT TTTTTCAGCC GGAAGTCTGG
1641 TACTTCTGTT GAATATTATG ATGTGCTTCT TGCTTAGTTG
1681 TTCCTGTTCT TCTCCCTTTT AGAGTTCAGC ATATTTATGT
1721 TTTGATGTAA TGGGGAATGT TGGCAGACAG CTTGATATAT
1761 GGTTATTTCA TTCTCCATTA AA

Expression of an internally deleted *Elaeis guineensis* WRI1 protein or an *Elaeis* guieensis WRI1 protein with a mutation at four or more of the following positions 244, 259, 261, 265, 275, and/or 277 can increase the content of triacylglycerol in plant tissues such as leaves and seeds. Hence, one aspect of the invention is a mutant WRI1 protein that includes a mutation (e.g., a substitution, insertion, or deletion) in the following sequence (SEQ ID NO:23):

241 KPETEPAQED LGVLQMEATE TIDQTMPNYD LPEISWTFDI DH

For example, expression of an internally deleted *Elaeis guineensis* WRI1 protein or an *Elaeis guineensis* WRI1 protein with a mutation at four or more of positions 244, 259, 261, 265, 275, and/or 277 can increase the content of triacylglycerol in plant tissues. Hence, another aspect of the invention is a mutant WRI1 protein that includes the following sequence (SEQ ID NO: 24):

241 KPEXEPAQED LGVLQMEAXE XIDQXMPNYD LPEIXWXFDI DH where at least four of the X residues in the SEQ ID NO:24 sequence is a substitution, insertion, or deletion compared to the wild type sequence (SEQ ID NO:23). The X residues are not acidic amino acids such as aspartic acid or glutamic acid. However, the X residue can be a small amino acid or a hydrophobic amino acid. For example, the X residues can each separately be alanine, glycine, valine, leucine, isoleucine, methionine, and any mixture thereof.

Another aspect of the invention is a mutant WRI1 protein with a deletion within the SEQ ID NO:23 portion of the WRI1 protein of at least 3, or at least 4, or at least 5, or at least 6, or at least 7, or at least 8, or at least 10, or at least 13, or at least 15, or at least 17, or at least 20, or at least 25, or at least 30, or at least 35, or at least 40, or at least 45 amino acids. Such mutant WRI1 proteins can be expressed in plant tissues to increase the oil/fatty acid/TAG content of those tissues.

An example of an amino acid sequence for a WRI1 sequence from *Glycine max* (soybean) is available as accession number XP_006596987.1 (GI: 571513961), and reproduced below as SEQ ID NO:25.

1 MKRSPASSCS SSTSSVGFEA PIEKRRPKHP RRNNLKSQKC
41 KQNQTTTGGR RSSIYRGVTR HRWTGRFEAH LWDKSSWNNI
81 QSKKGRQGAY DTEESAARTY DLAALKYWGK DATLNFPIET
121 YTKELEEMDK VSREEYLASL RRQSSGFSRG LSKYRGVARH
161 HHNGRWEARI GRVCGNKYLY LGTYKTQEEA AVAYDMAAIE
201 YRGVNAVTNF DISNYMDKIK KKNDQTQQQQ TEAQTETVPN
241 SSDSEEVEVE QQTTTITTPP PSENLHMPPQ QHQVQYTPHV
281 SPREEESSSL ITIMDHVLEQ DLPWSFMYTG LSQFQDPNLA
321 FCKGDDDLVG MFDSAGFEED IDFLFSTQPG DETESDVNNM
361 SAVLDSVECG DTNGAGGSMM HVDNKQKIVS FASSPSSTTT
401 VSCDYALDL

A nucleic acid sequence for the above *Glycine max* WRI1 protein sequence is available as accession number XM_006596924.1 (GI: 571513960), and is reproduced below as SEQ ID NO:26.

1 AGTGTTGCTC AAATTCAAGC CACTTAATTA GCCATGGTTG
41 ATTGATCAAG TTAAATTCCA ACCCAAGGTT AAATCATTAC
81 TCCCTTCTCA TCCTTCCCAA CCCCAACCCC CAGAAATATT
121 ACAGATTCAA TTGCTTAATT AAATACTATT TTCCCCTCCT
161 TCTATAATAC CCTCCAAAAT CTTTTTCCTT CTTCATTCTC
201 CCTTTCTCTA TGTTTTGGCA AACCACTTTA GGTAACCAGA
241 TTACTACTAC TATTGCTTCA TATACAAAGA TGCTATCGTA
281 AAAAAGAGAG AAACTTGGGA AGTGGGAACA CATTCAAAAT
321 CCTTGTTTTT CTTTTTGGTC TAATTTTTCA TCTCAAAACA
361 CACACCCATT GAGTATTTTT CATTTTTTTG TTCTTTTGGG
401 ACAAAAAAGG TGGGTGTTGT TGGCATTATT GAAGATAGAG
441 GCCCCCAAAA TGAAGAGGTC TCCAGCATCT TCTTGTTCAT
481 CATCTACTTC CTCTGTTGGG TTTGAAGCTC CCATTGAAAA
521 AAGAAGGCCT AAGCATCCAA GGAGGAATAA TTTGAAGTCA
561 CAAAAATGCA AGCAGAACCA AACCACCACT GGTGGCAGAA
601 GAAGCTCTAT CTATAGAGGA GTTACAAGGC ATAGGTGGAC
641 AGGGAGGTTT GAAGCTCACC TATGGGATAA GAGCTCTTGG
681 AACAACATTC AGAGCAAGAA GGGTCGACAA GGGGCATATG
721 ATACTGAAGA ATCTGCAGCC CGTACCTATG ACCTTGCAGC
761 CCTTAAATAC TGGGGAAAAG ATGCAACCCT GAATTTCCCG
801 ATAGAAACTT ATACCAAGGA GCTCGAGGAA ATGGACAAGG
841 TTTCAAGAGA AGAATATTTG GCTTCTTTGC GGCGCCAAAG
881 CAGTGGCTTT TCTAGAGGCC TGTCTAAGTA CCGTGGGGTT
921 GCTAGGCATC ATCATAATGG TCGCTGGGAA GCACGAATTG
961 GAAGAGTATG CGGAAACAAG TACCTCTACT TGGGGACATA
1001 TAAAACTCAA GAGGAGGCAG CAGTGGCATA TGACATGGCA
1041 GCAATAGAGT ACCGTGGAGT CAATGCAGTG ACCAATTTTG
1081 ACATAAGCAA CTACATGGAC AAAATAAAGA AGAAAAATGA
1121 CCAAACCCAA CAACAACAAA CAGAAGCACA AACGGAAACA
1161 GTTCCTAACT CCTCTGACTC TGAAGAAGTA GAAGTAGAAC
1201 AACAGACAAC AACAATAACC ACACCACCCC CATCTGAAAA
1241 TCTGCACATG CCACCACAGC AGCACCAAGT TCAATACACC
1281 CCCCATGTCT CTCCAAGGGA AGAAGAATCA TCATCACTGA
1321 TCACAATTAT GGACCATGTG CTTGAGCAGG ATCTGCCATG
1361 GAGCTTCATG TACACTGGCT TGTCTCAGTT TCAAGATCCA
1401 AACTTGGCTT TCTGCAAAGG TGATGATGAC TTGGTGGGCA
1441 TGTTTGATAG TGCAGGGTTT GAGGAAGACA TTGATTTTCT
1481 GTTCAGCACT CAACCTGGTG ATGAGACTGA GAGTGATGTC
1521 AACAATATGA GCGCAGTTTT GGATAGTGTT GAGTGTGGAG

1561 ACACAAATGG GGCTGGTGGA AGCATGATGC ATGTGGATAA
1601 CAAGCAGAAG ATAGTATCAT TTGCTTCTTC ACCATCATCT
1641 ACAACTACAG TTTCTTGTGA CTATGCTCTA GATCTATGAT
1681 CTCTTCAGAA GGGTGATGGA TGACCTACAT GGAATGGAAC
1721 CTTGTGTAGA TTATTATTGG GTTTGTTATG CATGTTGTTG
1761 GGGTTTGTTG TGATAGGTTG GTGGATGGGT GTGACTTGTG
1801 AAAATGTTCA TTGGTTTTAG GATTTTCCTT TCATCCATAC
1841 TCCGTTGTCG AAAGAAGAAA ATGTTCATTT TAGACTTGGA
1881 TTTTAGTATA AAAAAAAAGG AGAAAAAACC AAAAATGTGA
1921 TTTGGGTGCA AACAATGTTT TGTTTTTCTT TTTACTTTTG
1961 GGGTAAGGAG ATGAAGAGAG GGGAA-ATTTA AACCATTCCT
2001 ATTCTTGGGG GATAATGCAG TATAAATTAA GATCAGACTG
2041 TTTTTAGCAT ATGGAGTGCA AACTGCAAAG GCCAAGTTTC
2081 CTTTGTTTAA ACAATTTAGG CTTTCTTTTC CTTTGCCTAT
2121 TTTTTTTTTA TTTTTTTTTT TGTATTGGGG CATAGCAGTT
2161 AGTGTTGTGT TGAGATCTGA AATCTGATCT CTGGTTTGGT
2201 TTGTTC

Expression of an internally deleted *Glycine max* WRI1 protein or an *Glycine max* WRI1 protein with a mutation at four or more of the following positions 353, 355, 361, 366, 372, 378, 390, 393, 394, 396, 397, 398, 399, 400 and/or 402 can increase the content of triacylglycerol in plant tissues such as leaves and seeds. Hence, one aspect of the invention is a mutant WRI1 protein that includes a mutation (e.g., a substitution, insertion, or deletion) in the following sequence (SEQ ID NO:27):

351 DETESDVNNM
361 SAVLDSVECG DTNGAGGSMM HVDNKQKIVS FASSPSSTTT
401 VSCDYALDL

For example, expression of an internally deleted *Glycine max* WRI1 protein or a *Glycine max* WRI1 protein with a mutation at four or more of positions 353, 355, 361, 366, 372, 378, 390, 393, 394, 396, 397, 398, 399, 400 and/or 402 can increase the content of triacylglycerol in plant tissues. Hence, another aspect of the invention is a mutant WRI1 protein that includes the following sequence (SEQ ID NO: 28):

351 DEXEXDVNNM
361 XAVLDXVECG DXNGAGGXMM HVDNKQKIVX FAXXPXXXXX
401 VXCDYALDL where at least four of the X residues in the SEQ ID NO:28 sequence is a substitution, insertion, or deletion compared to the wild type sequence (SEQ ID NO:27). The X residues are not acidic amino acids such as aspartic acid or glutamic acid. However, the X residue can be a small amino acid or a hydrophobic amino acid. For example, the X residues can each separately be alanine, glycine, valine, leucine, isoleucine, methionine, and any mixture thereof.

Another aspect of the invention is a mutant WRI1 protein with a deletion within the SEQ ID NO:27 portion of the WRI1 protein of at least 3, or at least 4, or at least 5, or at least 6, or at least 7, or at least 8, or at least 10, or at least 13, or at least 15, or at least 17, or at least 20, or at least 25, or at least 30, or at least 35, or at least 40, or at least 45 amino acids. Such mutant WRI1 proteins can be expressed in plant tissues to increase the oil/fatty acid/TAG content of those tissues.

Any of the nucleic acids encoding wild type or mutant WRI1 proteins can have an ATG start codon, either naturally or as an added codon at the 5' end of the coding region.

Sequences related to the WRI1 sequences provided herein can also be used in the methods and plants provided herein. For example, the following protein sequences exhibit sequence identity to the *Brassica napus* WRI amino acid sequence with SEQ ID NO:5.

| Accession | Description | Sequence Identity |
|---|---|---|
| ADO16346.1 | WRINKLED1 1 [Brassica napus] | 100% |
| ABD16282.1 | AP2/EREBP transcription factor [Brassica napus] >gb\|ABD72476.1\| AP2/EREBP transcriptional factor WRI1 [Brassica napus] | 94% |
| AAT44955.1 | putative AP2/EREBP transcription factor [Arabidopsis thaliana] | 93% |
| CAB81797.1 | aintegumaenta-like protein [Arabidopsis thaliana] | 91% |
| XP_002876251.1 | hypothetical protein ARALYDRAFT_485830 [Arabidopsis lyrata subsp. lyrata] >gb\|EFH52510.1\| hypothetical protein ARALYDRAFT_485830 [Arabidopsis lyrata subsp. lyrata] | 82% |
| NP_001030857.1 | ethylene-responsive transcription factor WRI1 [Arabidopsis thaliana] >sp\|Q6X5Y6.1\|WRI1_ARATH RecName: Full=Ethylene-responsive transcription factor WRI1; AltName: Full=Protein ACTIVATOR OF SPORAMIN::LUC 1; AltName: Full=Protein WRINKLED1 >gb\|AAP80382.1\| WRINKLED1 [Arabidopsis thaliana] >gb\|AAX11223.1\| activator of sporamin LUC 1 [Arabidopsis thaliana] >gb\|AEE79215.1\| ethylene-responsive transcription factor WRI1 [Arabidopsis thaliana] | 81% |
| NP_191000.3 | ethylene-responsive transcription factor WRI1 [Arabidopsis thaliana] >gb\|AEE79213.1\| ethylene-responsive transcription factor WRI1 [Arabidopsis thaliana] | 81% |
| XP_002966660.1 | hypothetical protein SELMODRAFT_85823 [Selaginella moellendorffii] >gb\|EFJ32687.1\| hypothetical protein SELMODRAFT_85823 [Selaginella moellendorffii] | 80% |
| XP_002528384.1 | conserved hypothetical protein [Ricinus communis] >gb\|EEF33977.1\| conserved hypothetical protein [Ricinus communis] | 80% |
| NP_001061917.1 | Os08g0442400 [Oryza sativa Japonica Group] >dbj\|BAF23831.1\| Os08g0442400 [Oryza sativa Japonica Group] >dbj\|BAG97826.1\| unnamed protein product [Oryza sativa Japonica Group] >gb\|ADX60232.1\| AP2-EREBP transcription factor [Oryza sativa Japonica Group] | 78% |
| EEC83647.1 | hypothetical protein OsI_29392 [Oryza sativa Indica Group] | 78% |
| NP_974430.1 | ethylene-responsive transcription factor WRI1 [Arabidopsis thaliana] >gb\|AEE79214.1\| ethylene-responsive transcription factor WRI1 [Arabidopsis thaliana] | 78% |
| XP_003530370.1 | PREDICTED: ethylene-responsive transcription factor WRI1-like [Glycine max] | 78% |
| XP_002989385.1 | hypothetical protein SELMODRAFT_129793 [Selaginella moellendorffii] >gb\|EFJ09476.1\| hypothetical protein SELMODRAFT_129793 [Selaginella moellendorffii] | 78% |

-continued

| Accession | Description | Sequence Identity |
|---|---|---|
| XP_003561189.1 | PREDICTED: AP2-like ethylene-responsive transcription factor ANT-like [Brachypodium distachyon] | 77% |
| ABL85061.1 | hypothetical protein 57h21.37 [Brachypodium sylvaticum] | 77% |
| XP_002323836.1 | AP2 domain-containing transcription factor [Populus trichocarpa] >gb\|EEF03969.1\| AP2 domain-containing transcription factor [Populus trichocarpa] | 77% |
| XP_002437819.1 | hypothetical protein SORBIDRAFT_10g003160 [Sorghum bicolor] >gb\|EER89186.1\| hypothetical protein SORBIDRAFT_10g003160 [Sorghum bicolor] | 77% |
| EAZ35820.1 | hypothetical protein OsJ_20113 [Oryza sativa Japonica Group] | 77% |
| BAD68417.1 | AP2 DNA-binding domain protein-like [Oryza sativa Japonica Group] >dbj\|BAD68772.1\| AP2 DNA-binding domain protein-like [Oryza sativa Japonica Group] | 77% |
| EAY99657.1 | hypothetical protein OsI_21635 [Oryza sativa Indica Group] | 77% |
| XP_002517474.1 | conserved hypothetical protein [Ricinus communis] >gb\|EEF45016.1\| conserved hypothetical protein [Ricinus communis] | 77% |
| XP003567050.1 | PREDICTED: uncharacterized protein LOC100825100 [Brachypodium distachyon] | 77% |
| BAD10030.1 | AP2/EREBP transcription factor-like protein [Oryza sativa Japonica Group] | 77% |
| XP_003525949.1 | PREDICTED: AP2-like ethylene-responsive transcription factor At1g16060-like [Glycine max] | 76% |
| CBI36586.3 | unnamed protein product [Vitis vinifera] | 76% |
| NP_001077849.1 | AP2-like ethylene-responsive transcription factor [Arabidopsis thaliana] >gb\|AEE36289.1\| AP2-like ethylene-responsive transcription factor [Arabidopsis thaliana] | 76% |
| CBI25261.3 | unnamed protein product [Vitis vinifera] | 76% |
| XP_002889265.1 | hypothetical protein ARALYDRAFT_477146 [Arabidopsis lyrata subsp. lyrata] >gb\|EFH65524.1\| hypothetical protein ARALYDRAFT_477146 [Arabidopsis lyrata subsp. lyrata] | 76% |
| XP_002441444.1 | hypothetical protein SORBIDRAFT_09g026800 [Sorghum bicolor] >gb\|EES19874.1\| hypothetical protein SORBIDRAFT_09g026800 [Sorghum bicolor] | 76% |
| XP_001779615.1 | predicted protein [Physcomitrella patens subsp. patens] >gb\|EDQ55609.1\| predicted protein [Physcomitrella patens subsp. patens] | 76% |
| XP_002460236.1 | hypothetical protein SORBIDRAFT_02g025080 [Sorghum bicolor] >gb\|EER96757.1\| hypothetical protein SORBIDRAFT_02g025080 [Sorghum bicolor] | 75% |
| XP_003533548.1 | PREDICTED: ethylene-responsive transcription factor WRI1-like [Glycine max] | 75% |
| XP_002272159.1 | PREDICTED: AP2-like ethylene-responsive transcription factor At1g16060-like [Vitis vinifera] | 75% |
| XP_002297679.1 | AP2 domain-containing transcription factor [Populus trichocarpa] >gb\|EEE82484.1\| AP2 domain-containing transcription factor [Populus trichocarpa] | 75% |
| XP_003578142.1 | PREDICTED: AP2-like ethylene-responsive transcription factor At1g16060-like [Brachypodium distachyon] | 75% |
| XP_002273046.2 | PREDICTED: AP2-like ethylene-responsive transcription factor Atig16060 [Vitis vinifera] | 75% |
| XP_003553203.1 | PREDICTED: AP2-like ethylene-responsive transcription factor ANT-like [Glycine max] | 75% |
| XP_003530686.1 | PREDICTED: AP2-like ethylene-responsive transcription factor At1g16060-like [Glycine max] | 75% |
| XP_002325111.1 | AP2 domain-containing transcription factor [Populus trichocarpa] >gb\|EEF03676.1\| AP2 domain-containing transcription factor [Populus trichocarpa] | 74% |
| XP_002315794.1 | AP2 domain-containing transcription factor [Populus trichocarpa] >gb\|EEF01965.1\| AP2 domain-containing transcription factor [Populus trichocarpa] | 74% |
| NP_001063215.1 | Os09g0423800 [Oryza sativa Japonica Group] >dbj\|BAF25129.1\| Os09g0423800 [Oryza sativa Japonica Group] | 74% |
| EAZ09147.1 | hypothetical protein OsI_31417 [Oryza sativa Indica Group] | 74% |
| NP_001146338.1 | uncharacterized protein LOC100279914 [Zea mays] >gb\|ACL53718.1\| unknown [Zea mays] | 74% |
| ACF84637.1 | unknown [Zea mays] | 74% |
| EEE69730.1 | hypothetical protein OsJ_29415 [Oryza sativa Japonica Group] | 74% |
| XP_003524030.1 | PREDICTED: AP2-like ethylene-responsive transcription factor At1g16060-like [Glycine max] | 74% |
| CBI22161.3 | unnamed protein product [Vitis vinifera] | 74% |
| XP_002303866.1 | AP2 domain-containing transcription factor [Populus trichocarpa] >gb\|EEE78845.1\| AP2 domain-containing transcription factor [Populus trichocarpa] | 74% |
| XP_003519167.1 | PREDICTED: AP2-like ethylene-responsive transcription factor At1g16060-like [Glycine max] | 73% |
| XP_003550676.1 | PREDICTED: AP2-like ethylene-responsive transcription factor At1g16060-like [Glycine max] | 73% |
| AAW78366.1 | transcription factor AP2D4 [Oryza sativa Japonica Group] | 72% |
| EEC79593.1 | hypothetical protein OsI_20775 [Oryza sativa Indica Group] | 72% |
| XP_003610261.1 | AP2 domain-containing transcription factor [Medicago truncatula] >gb\|AES92458.1\| AP2 domain-containing transcription factor [Medicago truncatula] | 72% |
| AAW78369.1 | transcription factor AP2D14 [Oryza sativa Japonica Group] | 71% |
| CAE00853.1 | AP2-1 protein [Oryza sativa Japonica Group] | 70% |
| BAJ33872.1 | unnamed protein product [Thellungiella halophila] | 70% |

14-3-3

Plant 14-3-3 proteins are phosphopeptide-binding proteins, belonging to a large family of proteins involved in numerous physiological processes including primary metabolism, although little is known about the function of 14-3-3s in plant lipid metabolism. As described herein, 14-3-3 proteins are able to interact with WRI1, both in yeast and plant cells. Transient co-expression of 14-3-3- and WRI1 led to increased oil biosynthesis in *Nicotiana benthamiana* leaves. Stable transgenic plants overproducing a 14-3-3 protein also displayed increased seed oil content. Co-production of a 14-3-3 protein with WRI1 enhanced and stabilized the transcriptional activity of WRI1. The 14-3-3 binding site was identified in one of the two AP2 domains of WRI1. Such 14-3-3 binding sites can also interfere with and inhibit interaction of WRI1 with an E3 ligase linker protein to protect WRI1 from degradation.

One example of an *Arabidopsis thaliana* 14-3-3 protein sequence is shown below as SEQ ID NO:67

1 MENEQSTHVH FASLSSSSER YNETFEEIKK AMKKSVQLKA

41 ELSAKERNLV SVGYKNVISA RRASLEILSS IVQKEESKGN

81 EENVKKLKNY RNKVEDELAK ICNDILSVIN KQLIPSSTTV
121 DSSVLFYNML ADFSSNAESK EATDQSLDAY KRLVWYQQFQ
161 LYMTLNWTSV FLNSPESAYQ LAKQAFDDAI NEFDNLTERE
201 EVIFLFPYLP PLMIDR

A cDNA sequence that encodes the SEQ ID NO:67 protein can have the following sequence (SEQ ID NO:68).

1 TTCTTCTCCA AGCATCTATT GTTTAAGAGA GAAAAAGAAG
41 AAAAGCCATG GAGAATGAAC AATCAACGCA CGTTCACTTC
81 GCGAGTCTCT CTTCGTCAAG CGAGCGCTAC AATGAAACAT
121 TTGAAGAGAT AAAGAAAGCG ATGAAGAAAA GTGTTCAGCT
151 TAAAGCGGAG CTATCAGCAA AGGAGAGAAA TCTTGTATCA
201 GTGGGGTACA AGAATGTGAT TAGCGCAAGG AGAGCTTCAT
241 TGGAAATACT ATCATCCATT GTGCAAAAGG AAGAGTCAAA
281 AGGAAATGAG GAAAATGTCA AGAAGCTTAA GAATTATCGA
321 AACAAGGTTG AAGATGAGCT TGCCAAAATT TGTAATGACA
361 TCCTGTCCGT CATCAATAAG CAACTCATTC CATCGTCTAC
401 CACTGTGGAC TCCTCTGTTC TTTTCTACAA TATGCTGGCA
441 GACTTCAGTT CTAATGCTGA AAGCAAGGAA GCTACTGATC
481 AGTCTCTTGA TGCATATAAG AGACTGGTTT GGTACCAACA
521 GTTCCAGCTA TACATGACTT TGAATTGGAC TTCTGTTTTC
561 TTAAACTCTC CTGAAAGTGC ATACCAATTG GCAAAGCAAG
601 CGTTCGATGA TGCAATTAAT GAATTTGACA ACCTCACAGA
641 AAGAGAGGAG GTAATCTTTT TATTTCCCTA TCTGCCTCCT
681 CTGATGATAG ATAGATAGTT TCCTTTGGAA TCAATATAAG
721 CCATTTTTGT GAAATTTTGT TAGTTCTTGT ACTGTTATGA
761 GGAGCCTAAA CTTTGATTCG AATGTTAATG CTTGGGAACA
801 TATTTACGGC TTTGTGGATC TTTCATTGCT TAAACGCCAA
841 GTTGTTGAAT TCAAGCAAAT TTTGTTGCAA GAAACCAATT
861 AGCATACT

One example of an *Arabidopsis thaliana* 14-3-3kappa protein sequence is shown below as SEQ ID NO:69.

1 MATTLSRDQY VYMAKLAEQA ERYEEMVQFM EQLVSGATPA
41 GELTVEERNL LSVAYKNVIG SLRAAWRIVS SIEQKEESRK
81 NEEHVSLVKD YRSKVETELS SICSGILRLL DSHLIPSATA
121 SESKVFYLKM KGDYHRYLAE FKSGDERKTA AEDTMIAYKA
161 AQDVAVADLA PTHPIRLGLA LNFSVFYYEI LNSSEKACSM
201 AKQAFEEAIA ELDTLGEESY KDSTLIMQLL RDNLTLWTSD
241 MQVCPILYFH IQLHHQKLAY

A cDNA sequence that encodes the SEQ ID NO:69 *Arabidopsis thaliana* 14-3-3kappa protein can have the following sequence (SEQ ID NO:70).

1 ACGTGGGTTT CACGCTGTTA ATCCTTATTT CAACTAACGA
41 CGTCGTTTAT CAGAGTGTGT TAATCACGCG CGAGTGAAGA
81 GAATTTCCTT TTACAGCTCA TTATGACTCG GCTTTGAAGC
121 TTTTTATTCT TCTTCTCAAT TTCTTTTTTT CTTCCAGAAA
161 TTTCCTCCGA TTTCAAAATT TTCCGGTGAA ATCGAAAAAA
201 AAAGCGAGAT CTTCTTCTCT AATGGCGACG ACCTTAAGCA
241 GAGATCAATA TGTCTACATG GCGAAGCTCG CCGAGCAAGC
281 CGAGCGTTAC GAAGAGATGG TTCAATTCAT GGAACAGCTC
321 GTAAGTGGAG CTACACCGGC CGGTGAGCTG ACCGTAGAAG
361 AGAGGAATCT TCTCTCGGTC GCGTATAAGA ACGTGATTGG
401 ATCTCTTCGT GCGGCATGGA GAATCGTGTC TTCGATTGAG
441 CAAAAGGAAG AGAGCAGGAA GAAC-GAAGAA CACGTGTCGC
481 TTGTTAAGGA TTACAGATCT AAAGTTGAGA CTGAGCTTTC
521 TTCGATCTGT TCTGGGATTC TCAGGTTACT TGATTCGCAT
561 CTAATTCCTT CAGCTACTGC CAGTGAGTCT AAGGTTTTTT
601 ACCTGAAGAT GAAAGGAGAT TATCATCGTT ATTTGGCTGA
641 GTTTAAATCT GGTGATGAGA GGAAAACTGC TGCTGAAGAT
681 ACTATGATCG CTTACAAAGC TGCTCAGGAC GTTGCAGTTG
721 CTGATCTAGC ACCTACACAT CCGATCAGGC TTGGTTTGGC
761 TCTTAACTTC TCAGTGTTTT ACTACGAGAT TCTCAACTCT
801 TCAGAGAAAG CTTGTAGCAT GGCGAAACAG GCTTTTGAAG
841 AAGCCATTGC TGAGCTGGAC ACATTGGGAG AGGAGTCATA
881 CAAGGACAGT ACTCTCATCA TGCAGTTGCT AAGGGACAAT
921 CTAACCCTTT GGACCTCCGA TATGCAGGTT TGCCCAATTC
961 TATACTTTCA TATTCAATTG CATCATCAGA AACTCGCATA
1001 TTGATAGTCT TATAAGATTA TTCGGATAAT AACACCCCAA
1041 AACTCAATGA TCGACTGCTT TATTCAGGAG CAGATGGATG
1081 AGGCCTGAAG GTCTAATGGA AGAAAA-GACG GTTATGTAAT
1121 GTACCTGCAA CCGTAACCGA AAATCTGAGT TCAACCTCCT
1161 TTGCTGTAAA ACTTGTCGAA AAGAAAAGTT TGTTTTTTTA
1201 TGACAGATTA TGTGCACAGC TTTGGTGTTA TCTSCTGCTC
1241 TGTATCAACT CT

Proteins that are related to the 14-3-3 protein shown above can also be expressed with WRI1 to enhance oil production in a variety of plant types. For example, a 14-3-3-related protein from *Arabidopsis thaliana*, called hypothetical protein T16E15.9 (NCBI accession no. G86355 (GI: 25288846)) shares significant sequence identity with the SEQ ID NO:67 protein as illustrated by the following sequence comparison.

| Score | Expect | Method | Identities | Positives | Gaps |
|---|---|---|---|---|---|
| 422 bits(1086) | 2e-150 | Compositional matrix adjust. | 215/241(89%) | 216/241(89%) | 25/241(10%) |

```
Query   1  MENEQSTHVHFASLSSSSERYNETFEEIKKAMKKSVQLKAELSAKERNLVSVGYKNVISA   60
           MENEQSTHVHFASLSSSSERYNETFEEIKKAMKKSVQLKAELSAKERNLVSVGYKNVISA
Sbjct   1  MENEQSTHVHFASLSSSSERYNETFEEIKKAMKKSVQLKAELSAKERNLVSVGYKNVISA   60

Query  61  RRASLEILSSIVQKEESKGNEENVKKLKNYRNKVEDELAKICNDILSVINKQLIPSSTTV  120
           RRASLEILSSIVQKEESKGNEENVKKLKNYRNKVEDELAKICNDILSVINKQLIPSSTTV
Sbjct  61  RRASLEILSSIVQKEESKGNEENVKKLKNYRNKVEDELAKICNDILSVINKQLIPSSTTV  120

Query 121  DSSVLFYNMLADFSSNAESKEATDQSLDAYKRLVWYQQFQLYMTLNWTSVFLNSPESAYQ  180
           DSSVLFYNMLADFSSNAESKFATDQSLDAYKRLVWYQQFQLYMTLNWTSVFLNSPESAYQ
Sbjct 121  DSSVLFYNKLADESSNAESKEATDQSLDAYKRLVWYQQFQLYMTLNWTSVFLNSPESAYQ  180

Query 181  LAKQAFDDAINEFD-------------------------NLTEREEVIFLFPYLPPLMID  215
           LAKQAFDDAINEFD                         +LTEREEVIFLFPYLFPLMID
Sbjct 181  LAKQAFDDAINEFDISDESNKDMTLIIQLLRDNLNMWTLDLTEREEVIFLEPYLPPLMID  240

Query 216  R  216
           R
Sbjct 241  R  241
```

This 14-3-3 related protein has the following sequence, shown below as SEQ ID NO:71.

1 MENEQSTHVH FASLSSSSER YNETFEEIKK AMKKSVQLKA
41 ELSAKERNLV SVGYKNVISA RRASLEILSS IVQKEESKGN
81 EENVKKLKNY RNKVEDELAK ICNDILSVIN KQLIPSSTTV
121 DSSVLFYNML ADFSSNAESK EATDQSLDAY KRLVWYQQFQ
161 LYMTLNWTSV FLNSPESAYQ LAKQAFDDAI NEFDISDESN
201 KDMTLIIQLL RDNLNMWTLD LTEREEVIFL FPYLPPLMID
241 R

A 14-3-3 related protein from *Brassica napus*, called BnaAnng29600D (NCBI accession no. CDY69181.1 (GI: 674861508)) shares significant sequence identity with the SEQ ID NO:67 protein as illustrated by the following sequence comparison.

1 METEREKHVY LAKLSEQTER YDEMVEAMKK VAQLDVELTV
41 EERNLVSVGY KNVIGARRAS WRILSSIEQK EESKGNEENV
81 KRIQNYRKKV EDELAKVCND ILSVIDKHLI PSSTAVESTV
121 FFYKMKGDYY RYLAEFSSGA ERKEAADQSL EAYKAAVAAA
161 ETGLAPTHPV RLGLALNFSV FYYEILNSPE SACQLAKQAF
201 DDAIAELDSL NEESYKDSTL IMQLLRDNLT LWTSDLPEEG
241 DERAKGDEPQ EEV

A genomic sequence for the 14-3-3 related protein, called BnaAnng29600D (NCBI accession no. CDY69181.1 (GI: 674861508)), is available as NCBI accession no. LK038808.1 (GI: 674861506).

Another 14-3-3 related protein from *Brassica napus*, called 14-3-3-like protein GFI4 epsilon (NCBI accession no. XP_009145353.1 (GI: 685309464)) also shares significant sequence identity with the SEQ ID NO:67 protein as illustrated by the following sequence comparison.

| Score | Expect | Method | Identities | Positives | Gaps |
|---|---|---|---|---|---|
| 229 bits(585) | 3e-74 | Compositional matrix adjust. | 135/217(62%) | 154/217(70%) | 24/217(11%) |

```
Query   1  MENEQSTHVHFASLSSSSERYNETFEEIKKAMKKSVQLKAELSAKERNLVSVGYKNVISA   60
           ME E+  HV+ A LS  +ERY+E  E    AMKK  QL  EL+ +ERNLVSVGYKNVI A
Sbjct   1  METEREKHVYLAKLSEQTERYDEMVE----AMKKVAQLDVELTVEERNLVSVGYKNVIGA   56

Query  61  RRASLEILSSIVQKEESKGNEENVKKLKNYRNKVEDELAKICNDILSVINKQLIPSSTTV  120
           RRAS  ILSSI QKEESKGNEENVK+++NYR KVEDELAK+CNDILSVI+K LIPSST V
Sbjct  57  RRASWRILSSIEQKEESKGNEENVKRIQNYRKKVEDELAKVCNDILSVIDKHLIPSSTAV  116

Query 121  DSSVLFYNM-------LADFSSNAESKEATDQSLDAYKR--------LVWYQQFQLYMTL  165
           +S+V FY M       LA+FSS AE KEA DQSL+AYK         L      +L + L
Sbjct 117  ESTVFFYKMKGDYYRYLAEFSSGAERKEAADQSLEAYKAAVAAAETGLAPTHPVRLGLAL  176

Query 166  NWTSVF----LNSPESAYQLAKQAFDDAINEFDNLTE  198
           N+ SVF    LNSPESA QLAKQAFDDAI E D+L E
Sbjct 177  NF-SVFYYEILNSPESACQLAKQAFDDAIAELDSLNE  212
```

This 14-3-3 related protein, called BnaAnng29600D (NCBI accession no. CDY69181.1 (GI: 674861508)), has the following sequence, shown below as SEQ ID NO:72.

| Score | Expect | Method | Identities | Positives | Gaps |
|---|---|---|---|---|---|
| 229 bits(585) | 4e-74 | Compositional matrix adjust. | 135/217(62%) | 154/217(70%) | 24/217(11%) |

```
Query   1  MENEQSTHVHFASLSSSSERYNETFEEIKKAMKKSVQLKAELSAKERNLVSVGYKNVISA   60
           ME E+  HV+ A LS  +ERY+E  E    AMKK  QL  EL+ +ERNLVSVGYKNVI A
Sbjct   1  METEREKHVYLAKLSEQTERYDEMVE----AMKKVAQLDVELTVEERNLVSVGYKNVIGA   56

Query  61  RRASLEILSSIVQKEESKGNEENVKKLKNYRNKVEDELAKICNDILSVINKQLIPSSTTV  120
           RRAS  ILSSI QKEESKGNEENVK+++NYR KVEDELAK+CNDILSVI+K LIPSST V
Sbjct  57  RRASWRILSSIEQKEESKGNEENVKRIQNYRKKVEDELAKVCNDILSVIDKHLIPSSTAV  116

Query 121  DSSVLFYNM-------LADFSSNAESKEATDQSLDAYKR--------LVWYQQFQLYMTL  165
           +S+V FY M       LA+FSS AE KEA DQSL+AYK         L      +L + L
Sbjct 117  ESTVFFYKMKGDYYRYLAEFSSGAERKEAADQSLEAYKKAAVAAAETGLAPTHPVRLGLAL  176

Query 166  NWTSVF----LNSPESAYQLAKQAFDDAINEFDNLTE  198
           N+ SVF    LNSPESA QLAKQAFDDAI E D+L E
Sbjct 177  NF-SVFYYEILNSPESACQLAKQAFDDAIAELDSLNE  212
```

This 14-3-3 related protein, called 14-3-3-like protein GFI4 epsilon (NCBI accession no. XP_009145353.1 (GI: 685309464)), has the following sequence (SEQ ID NO:73).

1 METEREKHVY LAKLSEQTER YDEMVEAMKK VAQLDVELTV

41 EERNLVSVGY KNVIGARRAS WRILSSIEQK EESKGNEENV

61 KRIQNYRKKV EDELAKVCND ILSVIDKHLI PSSTAVESTV

121 FFYKMKGDYY RYLAEFSSGA ERKEAADQSL EAYKAAVAAA

161 ETGLAPTHPV RLGLALNFSV FYYEILNSPE SACQLAKQAF

201 DDAIAELDSL NEESYKDSTL IMQLLRDNLT LWTSDLPEEG

241 DERAKGDEPQ EEN

A cDNA encoding the 14-3-3 related protein, called 14-3-3-like protein GF14 epsilon (NCBI accession no. XP_009145353.1 (GI: 685309464)), has the following sequence (SEQ ID NO:74).

1 CATCAAACCA TCCTAGGGTT ACCACTAATC CCAAAAATCA

41 AATCGAGCGT CCAGAGAGAA GAAAGAAGAA GAAGCATCCA

81 TGGAGACTGA GAGGGAAAAG CATGTTTACT TGGCCAAGCT

121 CTCTGAGCAA ACCGAGCGAT ACGATGAGAT GGTTGAGGCG

161 ATGAAGAAAG TAGCTCAGCT TGATGTGGAG CTCACGGTAG

201 AGGAGAGGAA CCTTGTGTCT GTAGGGTACA AGAACGTGAT

241 TGGGGCAAGG AGAGCTTCGT GGAGAATACT ATCATCCATC

281 GAGCAGAAGG AAGAGTCCAA GGGGAAC-GAG GAGAATGTCA

321 AGAGGATTCA GAACTATCGA AAGAAAGTTG AAGACGAGCT

361 TGCTAAAGTT TGTAATGACA TCTTGTCTGT CATCGATAAA

401 CATCTCATTC CGTCGTCTAC TGCTGTGGAG TCCACTGTGT

441 TTTTCTACAA AATGAAAGGA GATTATTATC GATATCTGGC

481 AGAGTTCAGT TCTGGTGCTG AACGCAAGGA AGCCGCAGAT

521 CAGTCTCTTG AGGCATATAA GGCTGCTGTT GCTGCTGCGG

561 AGACTGGATT GGCACCAACA CATCCAGTTA GACTCGGCTT

601 GGCGTTGAAC TTTTCTGTTT TCTACTATGA GATCTTAAAC

641 TCTCCTGAAA GCGCATGTCA ATTGGCTAAG CAAGCATTCG

681 ACGATGCAAT AGCTGAACTT GACAGCCTGA ACGAGGAATC

721 ATACAAGGAC AGCACTCTTA TCATGCAGCT ACTTAGAGAC

761 AATCTCACCT TGTGGACTTC AGACCTCCCT GAGGAAGGAG

801 ACGAGCGAGC CAAAGGTGAT GAGCCTCAGG AAGAGAACTG

841 AAGTCCTGAC TCCTCTGTGA GATGAGAAAC AACTCTTGAT

881 GCAAGCCTCG TTTGCTCTAG ATTGTGTATT TTTTTTTTTA

921 TTTTGTCTTT GTTGATGATG TTTTCAGATC TTTGACGTAC

961 TGCACTTGAA CACTGCGTAT CTTCAACTCT TATCACTTAT

1001 TAGTTTGCTT CTTTGTTGTT GAA

A 14-3-3 related protein from *Glycine max* called 14-3-3-like protein GF14 iota (NCBI accession no. XP_006605542.1 (GI: 571563852)) shares significant sequence identity with the SEQ ID NO:67 protein as illustrated by the following sequence comparison.

| Score | Expect | Method | Identities | Positives | Gaps |
|---|---|---|---|---|---|
| 192 bits(487) | 9e-61 | Compositional matrix adjust. | 110/216(51%) | 144/216(66%) | 24/216(11%) |

```
Query   2  ENEQSTHVHFASLSSSSERYNETFEEIKKAMKKSVQLKAELSAKERNLVSVGYKNVISAR   61
           E E+ T V+ A LS  +ERY    EE+ + MK   +L  EL+ +ERNL+SVGYKNVI AR
Sbjct   4  EKERETQVYLAKLSEQAERY----EEMVECMKTIAKLDLELTVEERNLLSVGYKNVIGAR   59
```

-continued

```
Query  62  RASLEILSSIVQKEESKGNEENVKKLKNYRNKVEDELAKICNDILSVINKQLIPSSTTVD  121
           RAS  I+SSI QKEESKGNE N K +KNYR KVE+EL+KIC+DILS+I++ L+PSST+ +
Sbjct  60  RASWRIMSSIEQKEESKGNESNAKLIKNYRQKVEEELSKICSDILSIIDQHLVPSSTSGE  119

Query 122  SSVLFYNM-------LADFSSNAESKEATDQSLDAYK--------RLVWYQQFQLYMTLN  166
           ++V +Y M       LA+F ++ + KEA +QSL  Y+            L      +L + LN
Sbjct 120  ATVFYYKMKGDYYRYLAEFKTDQDRKEAAEQSLKGYEAALATASTELPSTHPIRLGLALN  179

Query 167  WTSVF----LNSPESAYQLAKQAFDDAINEFDNLTE  198
           + SVF    LNSPE A  LAKQAFD+AI E D L+E
Sbjct 180  F-SVFYYEILNSPERACHLAKQAFDEAIAELDTLSE  214
```

This 14-3-3 related protein from *Glycine max*, called 14-3-3-like protein GF14 iota (NCBI accession no. XP_006605542.1 (GI: 571563852)), has the following sequence (SEQ ID NO:75).

1 MSTEKERETQ VYLAKLSEQA ERYEEMVECM KTIAKLDLEL

41 TVEERNLLSV GYKNVIGARR ASWRIMSSIE QKEESKGNES

81 NAKLIKNYRQ KVEEELSKIC SDILSIIDQH LVPSSTSGEA

121 TVFYYKMKGD YYRYLAEFKT DQDRKEAAEQ SLKGYEAALA

161 TASTELPSTH PIRLGLALNF SVFYYEILNS PER-ACHLAKQ

201 AFDEAIAELD TLSEESYKDS TLIMQLLRDN LTLWTSDLPE

241 DGGDEIKTEE AKPAETSEHS

A cDNA encoding the 14-3-3 related protein from *Glycine max*, called 14-3-3-like protein GF14 iota (NCBI accession no. XP_006605542.1 (GI: 571563852)), has the following sequence (SEQ ID NO:76).

1 CTCATAAGCT TCTTTTTTAA TTTTTCTTTA ATTCAATTTA

41 GTTTTCTCTG ATACAACAAT AATACAACAA CAATGTCCAC

81 AGAGAAGGAG AGAGAGACCC AAGTTTACTT GGCCAAGCTC

121 TCTGAGCAAG CCGAGAGATA TGAAGAGATG GTTGAATGCA

161 TGAAGACAAT TGCAAAACTT GATCTAGAAC TAACTGTTGA

201 AGAGAGGAAC CTGCTCTCAG TGGGATATAA GAATGTGATT

241 GGTGCAAGAA GAGCCTCTTG GCGCATTATG TCATCAATTG

281 AACAAAAGGA AGAGTCTAAA GGAAATGAAA GCAATGCAAA

321 ACTGATAAAG AATTATCGTC AAAAGGTTGA AGAGGAACTC

361 TCAAAGATTT GCAGTGACAT TCTCAGCATT ATTGACCAGC

401 ATCTTGTTCC TTCTTCCACC TCAGGAGAAG CCACCGTTTT

441 CTACTATAAG ATGAAAGGTG ACTATTATCG ATATTTAGCC

481 GAGTTCAAGA CCGATCAGGA TAGAAAGGAG GCTGCTGAGC

521 AATCACTAAA GGGATATGAG GCTGCTTTAG CTACAGCAAG

561 CACAGAGCTT CCATCAACAC ATCCAATCCG TCTTGGACTT

601 GCGCTCAACT TCTCAGTCTT CTATTATGAG ATACTGAACT

641 CTCCTGAAAG GGCCTGTCAT TTGGCTAAGC AAGCTTTCGA

681 TGAGGCAATT GCAGAGTTAG ACACCTTGAG TGAAGAGTCA

721 TACAAGGACA GCACTTTGAT CATGCAGCTG CTGAGAGACA

761 ATCTCACTCT CTGGACCTCT GATTTACCTG AGGATGGAGG

801 TGACGAAATT AAAACAGAAG AAGCCAAACC TGCTGAAACT

841 TCTGAGCACT CATAGTATAC GATTGCCCCT GGAGCAGTGA

881 AGTCCATTTG GACCAGAAAA TGCAAATTAT GGTCACTTCA

921 TAGTTGTGCT CTCGTTACAT CTAGAAAAGT TCAACCTACG

961 GCTTATATTA GTTACCAATT TTTTTTTCTA TATACTTCAT

1001 ATATTTTAAG TAAAGGGGTC AATTGAAGTA ACGGATAATT

1041 TACATATTTT ACTTAAAAGC ATCTCTTCTC ATTATTGATT

1081 ACTTTTGAA

Variants and Homologs

Additional related WRI1 and 14-3-3 sequences can also be targeted or employed in the methods, seeds, plant cells, and plants described herein, including those with about at least 40% sequence identity, or at least 50% sequence identity, or at least 60% sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NOs: 1-31, 59, 60, 61, 62, 63, 64, 65, 67, 69-75. In some cases, the transcription factor nucleic acid and amino acid sequences are not identical to a wild type sequence. Instead the transcription factor nucleic acid and amino acid sequences have at least one, or at least two, or at least three, or at least four nucleotide or amino acid substitutions (replacements), deletions, or insertions compared to the corresponding wild type transcription factor nucleic acid or amino acid sequence.

Related WRI1 and/or 14-3-3 sequences can be isolated from a variety of plant types such as alfalfa (e.g., forage legume alfalfa), algae, avocado, barley, broccoli, Brussels sprouts, cabbage, canola, cassava, cauliflower, cole vegetables, collards, crucifers, grain legumes, grasses (e.g., forage grasses), jatropa, kale, kohlrabi, maize, miscanthus, mustards, nut sedge, oats, oil firewood trees, oilseeds, potato, radish, rapeseed, rice, rutabaga, sorghum, sugar beets, sugarcane, sunflower, switchgrass, tobacco, tomato, turnips, and wheat. In some embodiments, the plant is a

*Brassicaceae* or other *Solanaceae* species. In some embodiments, the plant is not a species of *Arabidopsis*, for example, in some embodiments, the plant is not *Arabidopsis thaliana*.

As described herein, nucleic acids encoding a 14-3-3 protein and a WRI1 transcription factor are useful for expressing such proteins in plants. Such mutant PEST domains can include any with at least at least 50% sequence identity, or at least 600' sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity to any of SEQ ID NO:3, 4, 7, 8, 11, 12, 15, 16, 19, 20, 23, 24, 27, 28, 59, 61, 63, 68, 70, and/or 76.

If desired, the proteins with any of SEQ ID NOs: 1-31, 59, 60, 61, 62, 63, 64, 65, 67, 69-75 can have one or more amino acid substitution, deletion, or insertion compared to its corresponding wild type amino acid sequence.

Nucleic acids with at least 50% sequence identity to those described herein can readily be identified, isolated and used to facilitate production of increased oil content in plants. Such nucleic acids can encode or hybridize to WRI1 nucleic acids, or fragments thereof. These related nucleic acids can be used to increase the expression of WRI1 in plants. Any of the nucleic acids encoding wild type or mutant 14-3-3 and WRI1 proteins can have an ATG start codon, either naturally or as an added codon at the 5' end of the coding region.

For example, related nucleic acids can be isolated and identified by mutation of the SEQ ID NO:2, SEQ ID NO:6, SEQ ID NO: 10, SEQ ID NO: 14, SEQ ID NO:18, SEQ ID NO:22, and/or SEQ ID NO:26 cDNA sequences and/or by hybridization to DNA and/or RNA isolated from other plant species using the SEQ ID NO:2, SEQ ID NO:6, SEQ ID NO:10, SEQ ID NO:14, SEQ ID NO:18, SEQ ID NO:22, and/or SEQ ID NO:26 nucleic acids as probes. Sequences of the WRI1 transcription factors (e.g., SEQ ID NO: 1, 5, 9, 13, 17, 21, 25, 29, 30, 31, 62, and/or 64) and sequences of 14-3-3 proteins (e.g., SEQ ID NOs: 67, 69-75) can also be examined and used a basis for designing alternative 14-3-3 or WRI1 proteins and nucleic acids.

In some embodiments, the WRINKLED1 nucleic acids described herein include any nucleic acid that can selectively hybridize to a nucleic acid with any of the SEQ ID NO:2, SEQ ID NO:6, SEQ ID NO: 10, SEQ ID NO: 14, SEQ ID NO: 18, SEQ ID NO:22, and/or SEQ ID NO:26, SEQ ID NO:68, SEQ ID NO:70, or SEQ ID NO: 76 cDNA sequences.

Alternatively, the WRI1 and/or 14-3-3 nucleic acids (e.g., SEQ ID NO:2, 6, 10, 14, 18, 22, 26, 68, 70, and/or 76) can be examined and used a basis for designing additional nucleic acids (e.g., having optimized codons or selected mutant WRI1 transcription factors and/or selected mutant 14-3-3 proteins) that function in selected plant species.

The term "selectively hybridize" includes hybridization, under stringent hybridization conditions, of a nucleic acid sequence to a specified nucleic acid target sequence (e.g., SEQ ID NO:2, 6, 10, 14, 18, 22, 26, 68, 70, and/or 76) to a detectably greater degree (e.g., at least 2-fold over background) than its hybridization to non-target nucleic acid sequences. Such selective hybridization substantially excludes non-target nucleic acids.

Related WRI1 nucleic acids sequences typically have about at least 40% sequence identity, or at least 50% sequence identity, or at least 60% sequence identity, or at least 70% sequence identity, or at least 80% sequence identity, or at least 85% sequence identity, or at least 90% sequence identity, or at least 95% sequence identity, or at least 97% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NO:2, 6, 10, 14, 18, 22, 26, 68, 70, and/or 76. In some embodiments, a selectively hybridizing sequence has about at least about 80% sequence identity or complementarity with any of SEQ ID NO: 2, 6, 10, 14, 18, 22, 26, 68, 70, and/or 76. The WRI1 and/or 14-3-3 nucleic acids employed in the expression vectors, transgenes, plants, plant cells, plant seeds and methods described herein can also have less than 100%, or less than 99.5%, or less than 99% sequence identity (or complementarity) with any of SEQ ID NO: 2, 6, 10, 14, 18, 22, 26, 68, 70, and/or 76. In other words, the WRI1 and/or 14-3-3 nucleic acids employed in the expression vectors, transgenes, plants, plant cells, plant seeds and methods described herein can also not include a wild type sequence. However, use of wild type WRI1 and/or 14-3-3 nucleic acids in the expression vectors, transgenes, plants, plant cells, plant seeds and methods described herein can also be useful.

In some embodiments, the nucleic acids used in the methods and plants provided herein can include fragments of WRI1 or 14-3-3 nucleic acids. For example, the nucleic acids of the invention include those with about 500 of the same nucleotides as any of the SEQ ID NO: 2, 6, 10, 14, 18, 22, 26, 68, 70, and/or 76 sequences, or about 700 of the same nucleotides as any of the SEQ ID NO: 2, 6, 10, 14, 18, 22, 26, 68, 70, and/or 76 sequences, or about 900 of the same nucleotides as any of the 2, 6, 10, 14, 18, 22, 26, 68, 70, and/or 76 sequences, or about 1000 of the same nucleotides as any of the SEQ ID NO: 2, 6, 10, 14, 18, 22, 26, 68, 70, and/or 76 sequences, or about 1200 of the same nucleotides as any of the SEQ ID NO: 2, 6, 10, 14, 18, 22, 26, 68, 70, and/or 76 sequences, or about 1250 of the same nucleotides as any of the SEQ ID NO: 2, 6, 10, 14, 18, 22, 26, 68, 70, and/or 76 sequences, or about 1300 of the same nucleotides as any of the SEQ ID NO:2, 6, 10, 14, 18, 22, and/or 26 sequences. The identical nucleotides can be distributed throughout the nucleic acid, and need not be contiguous but are present in homologous positions.

For example, the nucleic acid sequence of a WRI1 and/or 14-3-3 nucleic acids can be optimized for expression in a particular plant species by altering selected codons to encode the same amino acid but use nucleotide codons that are more easily 'read' by the transcription/translation machinery of a selected plant species.

Note that if a value of a variable that is necessarily an integer (e.g., the number of nucleotides or amino acids in a nucleic acid or protein), is described as a range, such as 80-99% sequence identity, what is meant is that the value can be any integer between 80 and 99 inclusive, i.e., 80, 81, 82, 83, 84, 85, 86, 87, 88, 89, 90, 91, 92, 93, 94, 95, 96, 97, 98 or 99, or any range between 80 and 99 inclusive, e.g., 81-99%, 81-98%, 82-99%, etc. Moreover, if a specifically recited percent sequence identity indicates that a partial nucleotide or amino acid is present (in a nucleic acid or polypeptide) the percent sequence identity is rounded up or down so that a complete nucleotide or amino acid is present.

In some embodiments, a related nucleic acid hybridizes to at least one of the nucleic acids described herein under "stringent conditions" or "stringent hybridization conditions." The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be hybridized that have up to 100% complementarity to the probe (homologous probing). Alternatively, stringency conditions can be adjusted to allow some mismatching in sequences so that lower degrees of sequence similarity are detected (heterologous probing).

A probe for identifying and/or isolating a related nucleic acid can be approximately 15-500 nucleotides in length, but can vary greatly in length from about 17 nucleotides to equal to the entire length of the target sequence. In some embodiments, the probe is about 10-50 nucleotides in length, or about 15-50 nucleotides in length, or about 16-45 nucleotides in length, or about 18-25 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution. Hence, high stringency conditions include can be achieved simply by employing a wash in 0.1×SSC at 60 to 65° C.

For DNA-DNA hybrids, the $T_m$ can be approximated from the equation of Meinkoth and Wahl (Anal. Biochem. 138: 267-84 (1984)):

$$T_m = 81.5° \text{ C.} + 16.6(\log M) + 0.41(\%\ GC) - 0.61(\%\ \text{formamide}) - 500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to any of the SEQ ID NO: 2, 6, 10, 14, 18, 22, 26, 68, 70, and/or 76 sequences.

Those of skill in the art also understand how to vary the hybridization and/or wash solutions to isolate desirable nucleic acids. For example, if the desired degree of mismatching results in a $T_m$ of less than 45° C. (aqueous solution) or 32 OC (formamide solution) it is preferred to increase the SSC concentration so that a higher temperature can be used.

An extensive guide to the hybridization of nucleic acids is found in Tijssen, Laboratory Techniques in Biochemistry and Molecular Biology-Hybridization with Nucleic Acid Probes, part 1, chapter 2, "Overview of principles of hybridization and the strategy of nucleic acid probe assays," Elsevier, N.Y. (1993); and in Current Protocols in Molecular Biology, chapter 2, Ausubel, et al., eds, Greene Publishing and Wiley-Interscience, New York (1995).

Unless otherwise stated, in the present application, high stringency is defined as a wash in 0.1×SSC, 0.1% SDS at 65° C. High stringency hybridization can include hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., followed by a wash in 0.1×SSC, 0.1% SDS at 65° C.

The following terms are used to describe the sequence relationships between two or more nucleic acids or nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. The reference sequence can be a nucleic acid sequence (e.g., any of the SEQ ID NO: 2, 6, 10, 14, 18, 22, 26, 68, 70, and/or 76 cDNA sequences) or an amino acid sequence (e.g., any of the SEQ ID NO:1, 5, 9, 13, 17, 21, 25, 67, 69-74, 75 or 77 amino acid sequences). A reference sequence may be a subset or the entirety of a specified sequence. For example, a reference sequence may be a segment of a full-length cDNA or of a genomic DNA sequence, or the complete cDNA or complete genomic DNA sequence, or a domain of a polypeptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 16 contiguous nucleotides in length, and optionally can be 18, 20, 30, 40, 50, 100 or more nucleotides. For amino acid sequences, the comparison window is at least about 15 amino acids, and can optionally be 20, 30, 40, 50, 100 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may permit optimal alignment of compared sequences; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. An example of a good program to use for optimal global alignment of multiple sequences is PileUp (Feng and Doolittle, (1987) J. Mol. Evol., 25:351-60, which is similar to the method described by Higgins and Sharp, (1989) CABIOS 5:151-53 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or more.

GAP presents one member of the family of best alignments. There may be many members of this family. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (C.sub.1-ayerie and States, (1993) Comput. Chem. 17:191-201) low-complexity filters can be employed alone or in combination.

The terms “substantial identity” indicates that a related nucleic acid comprises a sequence with between 55-100% sequence identity to a reference sequence, with at least 55% sequence identity, or at least 60%, or at least 70%, or at least 80%, or at least 90% or at least 95% sequence identity or any percentage of range between 55-100% sequence identity relative to the reference sequence over a specified comparison window. Optimal alignment may be ascertained or conducted using the homology alignment algorithm of Needleman and Wunsch, supra.

An indication that two polypeptide sequences are substantially identical is that both polypeptides have similar activities. For example, when the polypeptide is related to WRI1, that polypeptide can act as a transcription factor by binding to the same or similar upstream regions of genes normally under the regulatory control of WRI1. For example, transcription factors related to the WRI1 can be identified and/or characterized in assays that involve binding of a test protein (i.e., a potential transcription factor related to a WRI1 factor) to a promoter or regulatory sequence that is bound by a WRI1 factor with any of the sequences recited herein.

For example, when the polypeptide is related to 14-3-3, that polypeptide can stabilize WRI1 proteins and/or increase the oil content of plants, and plant seeds relative to plant and seeds that have only a WRI1 transgene (e.g., not a combination of WRI1 and 14-3-3 transgenes).

The related WRI1 and 14-3-3 polypeptide can be identified, evaluated or characterized in assays for observing increased (or decreased) expression a set of genes involved in fatty acid (FA) synthesis including, for example, genes for a subunit of pyruvate kinase (PI-PKβ1), acetyl-CoA carboxylase (BCCP2), acyl carrier protein (ACP1), ketoacyl-acyl carrier protein synthase (KAS1), and combinations thereof.

In some embodiments, a WRI1 and/or 14-3-3 protein with a sequence related to any of SEQ ID NO:1, 5, 9, 13, 17, 21, 25, 67, 69-74, or 75 sequence may not have exactly the same level of activity as the WRI1 or 14-3-3 protein with a SEQ ID NO: 1, 5, 9, 13, 17, 21, 25, 67, 69-74, or 75. Instead, the substantially identical polypeptide may exhibit greater or lesser levels of activity than the WRI1 transcription factor or a 14-3-3 protein with a SEQ ID NO: 1, 5, 9, 13, 17, 21, 25, 67, 69-74, or 75 sequence, as measured by assays available in the art. For example, the substantially identical polypeptide may have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the activity of the WRI1 transcription factor or 14-3-3 protein with a SEQ ID NO: 1, 5, 9, 13, 17, 21, 25, 67, 69-74, or 75 sequence, when measured by similar assay procedures.

Alternatively, substantial identity is present when second polypeptide is immunologically reactive with antibodies raised against the first polypeptide (e.g., a polypeptide with SEQ ID NO: 1, 5, 9, 13, 17, 21, 25, 67, 69-74, or 75 sequence). Thus, a polypeptide is substantially identical to a first polypeptide, for example, where the two polypeptides differ only by a conservative substitution. In addition, a polypeptide can be substantially identical to a first polypeptide when they differ by a non-conservative change if the epitope that the antibody recognizes is substantially identical. Polypeptides that are "substantially similar" share sequences as noted above except that some residue positions, which are not identical, may differ by conservative amino acid changes.

The WRI1 and/or 14-3-3 polypeptides can include at least the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 112, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, or 199 N-terminal amino acid residues of a the SEQ ID NO: 1, 5, 9, 13, 17, 21, 25, 67, 69-74, or 75 sequence.

Transgenic Plants

In order to engineer plants with increased vegetative tissue oil content that, one of skill in the art can introduce nucleic acids encoding the WRI1 and/or 14-3-3 proteins described herein into the plants to promote the production of oils.

For example, one of skill in the art can generate genetically-modified plants that contain nucleic acids encoding WRI1 and/or 14-3-3 proteins within their somatic and/or germ cells. Such genetic modification can be accomplished by procedures available in the art. For example, one of skill in the art can prepare an expression cassette or expression vector that can express one or more encoded WRI1 and/or 14-3-3 proteins. Plant cells can be transformed by the expression cassette or expression vector, and whole plants (and their seeds) can be generated from the plant cells that were successfully transformed with the WRI1 and/or 14-3-3 nucleic acids. Some procedures for making such genetically modified plants and their seeds are described below.

Promoters:

The WRI1 and/or 14-3-3 nucleic acids can be operably linked to a promoter, which provides for expression of an mRNA expressed from the WRI1 and/or 14-3-3 nucleic acids. The promoter can be a promoter functional in plants and/or seeds, and/or it can be a promoter functional during plant growth and development or in a mature plant. The promoter can be a heterologous promoter. As used herein, "heterologous" when used in reference to a gene or nucleic acid refers to a gene or nucleic acid that has been manipulated in some way. For example, a heterologous promoter is a promoter that contains sequences that are not naturally linked to an associated coding region.

A WRI1 and/or 14-3-3 nucleic acid is operably linked to the promoter when it is located downstream from the promoter, thereby forming a key portion of an expression cassette. Any of the nucleic acids encoding wild type or mutant 14-3-3 and WRI1 proteins can have an ATG start codon, either naturally or as an added codon, for example between the promoter and the 5' end of the 14-3-3 and WRI1 coding region.

Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired. In some embodiments, the promoter is an inducible promoter and/or a tissue-specific promoter.

Examples of promoters that can be used include, but are not limited to, the CaMV 35S promoter (Odell et al., *Nature.* 313:810-812 (1985)), or others such as CaMV 19S (Lawton et al., *Plant Molecular Biology.* 9:315-324 (1987)), nos (Ebert et al., *Proc. Natl. Acad. Sci. USA.* 84:5745-5749 (1987)), Adh1 (Walker et al., *Proc. Natl. Acad Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)), the CCR (cinnamoyl CoA:NADP oxidoreductase, EC 1.2.1.44) promoter sequence isolated from *Lollium perenne*, (or a perennial ryegrass) and/or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan, *Proc. Natl. Acad Sci. LSA*. 83:3320-3324 (1985). Other promoters useful in the practice of the invention are known to those of skill in the art.

Alternatively, novel tissue specific promoter sequences may be employed in the practice of the present invention. cDNA clones from a particular tissue are isolated and those clones which are expressed specifically in that tissue are identified, for example, using Northern blotting. Preferably, the gene isolated is not present in a high copy number, but is relatively abundant in specific tissues. The promoter and control elements of corresponding genomic clones can then be localized using techniques well known to those of skill in the art.

For example, the promoter can be an inducible promoter. Such inducible promoters can be activated by agents such as chemicals, hormones, sugars, metabolites, or by the age or developmental stage of the plant. For example, the promoter can be an ethanol-inducible promoter, a sugar-inducible promoter, a senescence-induced promoter or any promoter activated in vegetative tissues of dicots and monocots. One example of a sugar-inducible promoter is a patatin B33 promoter. Such a patatin B33 promoter can, for example, be used in tuber crops such as cassava, potato, rutabaga, sugar beet, and the like. An example of a sequence for the patatin B33 promoter is as follows (SEQ ID NO:28).

1 aagcttatgt tgccatatag agtagtttgt gatggtatac
41 ttcataaact ttaacttatg ttaaatttgt aatgataaaa
81 tttttattgt aaattaaaaa ttacttataa aattgggcat
121 tataacatat gaaagacaaa ttgtgttaca tattttactt
161 ttgactttaa tatgaatatt tcaatttaaa tcattgtttt
201 attttctctt tctttttaca ggtataaaag gtgaaaattg
241 aagcaagatt gattgcaagc tatgtgtcac cacgttattg
281 atactttgga agaaattttt acttatatgt ctttgtttag
321 gagtaatatt tgatatgttt tagttagatt ttcttgtcat
361 ttatgcttta gtataatttt agttattttt attatatgat
401 catgggtgaa ttttgataca aatatttttg tcattaaata
441 aattaattta tcacaacttg attactttca gtgacaaaaa
481 atgtattgtc gtagtaccct tttttgttga atatgaataa
521 ttttttttat tttgtgacaa ttgtaattgt cactacttat
561 gataatattt agtgacatat atgtcgtcgg taaaagcaaa
601 cactttcagt gacaaaataa tagatttaat cacaaaatta
641 ttaacctttt ttataataat aaatttatcc ctaatttata
681 catttaagga caaagtattt tttttatata taaaaaatag
721 tctttagtga cgatcgtagt gttgagtcta gaaatcataa
761 tgttgaatct agaaaaatct catgcagtgt aaaataaacc
801 tcaaaaagga cgttcagtcc atagaggggg tgtatgtgac
841 accccaacct cagcaaaaga aaacctccct tcaacaagga
881 catttgcggt gctaaacaat ttcaagtctc atcacacata
921 tatttattat ataatactaa taaagaatag aaaaggaaag
961 gtaaacatca ttaaatcgtc tttgtatatt tttagtgaca
1001 actgattgac gaaatctttt tcgtcacaca aaatttttag
1041 tgacgaaaca tgatttatag atgatgaaat tatttgtccc
1081 tcataatcta atttgttgta gtgatcatta ctcctttgtt
1121 tgttttattt gtcatgttag tccattaaaa aaaaatatct
1161 ctcttcttat gtacgtgaat ggttggaacg gatctattat
1201 ataatactaa taaagaatag aaaaaggaaa gtgagtgagg
1241 ttcgagggag agaatctgtt taatatcaga gtcgatcatg
1281 tgtcaatttt atcgatatga ccctaacttc aactgagttt
1321 aaccaattcc gataaggcga gaaatatcat agtattgagt
1361 ctagaaaaat ctcatgtagt gtggggtaaa cctcagcaag
1401 gacgttgagt ccatagaggg ggtgtatgt gacaccccaa
1441 cctcagcaaa agaaaacctc ccctcaagaa ggacatttgc
1481 ggtgctaaac aatttcaagt ctcatcacac atatatatat
1521 attatataat actaataaat aatagaaaaa ggaaaggtaa
1561 acatcactaa cgacagttgc ggtgcaaact gagtgaggta
1601 ataaacatca ctaactttta ttggttatgt caaactcaaa
1641 gtaaaatttc tcaacttgtt tacgtgccta tatataccat
1681 gcttgttata tgctcaaagc accaacaaaa tttaaaaaca
1721 ctttgaacat ttgcaaaatg gcaactacta aaactttttt
1761 aattttattt tttatgatat tagcaactac tagttcaaca
1801 tgtgctaagt tggaagaaat ggttactgtt ctaagtattg
1841 atggaggtgg aattaaggga atcattccag ctatcattct
1881 cgaatttctt gaaggacaac ttcaggtatt gtaaaaatat
1921 tttttaatgt atgtgcgtaa gtgtgacact actactatag
1961 tcattctggg tacct A WRI1 and/or 14-3-3 nucleic acid can be combined with the promoter by standard methods to yield an expression cassette, for example, as described in Sambrook et al. (Molecular Cloning: A Laboratory Manual. Second Edition (Cold Spring Harbor, N.Y.: Cold Spring Harbor Press (1989); Molecular Cloning: A Laboratory Manual. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The WRI1 and/or 14-3-3 nucleic acids can be subcloned downstream from the promoter using restriction enzymes and positioned to ensure that the DNA is inserted in proper orientation with respect to the promoter so that the DNA can be expressed as sense RNA. Once the WRI1 and/or 14-3-3 nucleic acid is operably linked to a promoter, the expression cassette so formed can be subcloned into a plasmid or other vector (e.g., an expression vector).

In some embodiments, a cDNA clone encoding a selected WRI1 and/or 14-3-3 protein is isolated from vegetative tissue (e.g., stems, roots, and/or leaves). The cDNA clone encoding a selected WRI1 and/or 14-3-3 protein can be isolated from mature plants. In other embodiments, cDNA clones from other species (that encode a WRI1 and/or 14-3-3 protein) are isolated from selected plant tissues, or a nucleic acid encoding a mutant or modified WRI1 and/or 14-3-3 protein is prepared by available methods or as described herein. For example, the nucleic acid encoding a mutant or modified WRI1 and/or 14-3-3 protein can be any nucleic acid with a coding region that hybridizes, for example, to SEQ ID NO:2, 6, 10, 14, 18, 22, 26, 68, 70, or 76, and that has WRI1 transcription factor activity and 14-3-3 stabilization/oil production.

Using restriction endonucleases, the coding sequence for the selected WRI1 and/or 14-3-3 is subcloned downstream of the promoter in a 5' to 3' sense orientation.

Targeting Sequences:

Additionally, expression cassettes can be constructed and employed to target the WRI1 and/or 14-3-3 expression cassettes/vectors to an intracellular compartment within plant cells (e.g., the nucleus) or to direct the transcription factor to the extracellular environment (e.g., for collection and/or purification). This can generally be achieved by joining a DNA sequence encoding a transit or signal peptide sequence to the coding sequence of the WRI1 and/or 14-3-3 nucleic acid. The resultant transit, or signal, peptide will transport the protein to a particular intracellular, or extracellular destination, respectively, and can then be posttranslational removed. Transit peptides act by facilitating the transport of proteins through intracellular membranes, e.g., vacuole, vesicle, plastid and mitochondrial membranes, whereas signal peptides direct proteins through the extracellular membrane.

By facilitating transport of the protein into compartments inside or outside the cell, these sequences can increase the accumulation of a particular gene product in a particular location. For example, see U.S. Pat. No. 5,258,300.

3' Sequences:

When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research.* 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology.* 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the WRI1 and/or 14-3-3 nucleic acids by standard methods.

Selectable and Screenable Marker Sequences:

In order to improve identification of transformants, a selectable or screenable marker gene can be employed with the WRI1 and/or 14-3-3 nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Examples of proteins suitable for modification in this manner include extensin or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich wall proteins (Keller et al., *EMBO J.* 8:1309-1314 (1989)) could be modified by the addition of an antigenic site to create a screenable marker.

Possible selectable markers for use in connection with the present invention include, but are not limited to, a neo gene (Potrykus et al., *Mol. Gen. Genet.* 199:183-188 (1985)) which codes for kanamycin resistance and can be selected for using kanamycin, G418, and the like; a bar gene which codes for bialaphos resistance; a gene which encodes an altered EPSP synthase protein (Hinchee et al., *Bio/Technology.* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)), a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death. The success in using this selective system in conjunction with monocots was surprising because of the major difficulties that have been reported in transformation of cereals (Potrykus, *Trends Biotech.* 7:269-273 (1989)).

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* $18^{th}$ Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TRI 12, a K55 derivative that is r-g, b, Pl. Alternatively any genotype of maize can be utilized if the C1 and R alleles are introduced together.

The R gene regulatory regions may be employed in chimeric constructs in order to provide mechanisms for controlling the expression of chimeric genes. More diversity of phenotypic expression is known at the R locus than at any other locus (Coe et al., in *Corn and Corn Improvement*, eds. Sprague, G. F. & Dudley, J. W. (Am. Soc. Agron., Madison, Wis.), pp. 81-258 (1988)). It is contemplated that regulatory regions obtained from regions 5' to the structural R gene can be useful in directing the expression of genes, e.g., insect resistance, drought resistance, herbicide tolerance or other protein coding regions. In some embodiments, any of the various R gene family members may be successfully employed (e.g., P, S, Lc, etc.). However, one that can be used is Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Elements of the present disclosure are exemplified through the use of particular marker genes. However in light of this disclosure, numerous other possible selectable and/or screenable marker genes will be apparent to those of skill in the art in addition to the one set forth herein below. Therefore, it will be understood that the discussion provided herein is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Other Optional Sequences:

An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, such as antibiotic or herbicide resistance, unique multiple cloning sites providing for multiple sites to insert DNA sequences, and/or sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology.* 153:292 (1987)). This binary Ti vector can be replicated in prokaryotic bacteria such as *E. coli* and *Agrobacterium*. The *Agrobacterium* plasmid vectors can be used to transfer the expression cassette to dicot plant cells and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes:

Once the expression cassette is constructed and subcloned into a suitable plasmid, it can be screened for the ability to express the encoded WRI1 transcription factor(s) and/or 14-3-3 proteins by available methods. For example, the WRI protein can bind to upstream sequences in genes such as a subunit of pyruvate kinase (PI-PK81), acetyl-CoA carboxylase (BCCP2), acyl carrier protein (ACP1), and ketoacyl-acyl carrier protein synthase (KAS1). Binding assays to WRI1 binding sites with sequences such as $[CnTnG](n)_7$ [CG], where n is any nucleotide designated as the AW-box, can be employed to detect WRI1 expression. Expression of WRINKLED can also be detected by observing whether an expression cassette or vector encoding a WRINKLED protein can facilitate synthesis of plant carbons into oils (e.g., TCAs).

DNA Delivery of the DNA Molecules into Host Cells:

The WRINKLED nucleic acid can be introduced into a recipient cell to create a transformed cell by available methods. The frequency of occurrence of cells taking up exogenous (foreign) DNA can be low, and it is likely that not all recipient cells receiving DNA segments or sequences will result in a transformed cell wherein the DNA is stably integrated into the plant genome and/or expressed. Some may show only initial and transient gene expression. However, cells from virtually any dicot or monocot species can be stably transformed, and those cells can be regenerated into transgenic plants, for example, through the application of the techniques disclosed herein.

Another aspect of the invention is a plant species with increased vegetative tissue oil content, wherein the plant has an introduced WRI1 and/or 14-3-3 nucleic acid. The plant can be a monocotyledon or a dicotyledon. Another aspect of the invention includes plant cells (e.g., embryonic cells or other cell lines) that can regenerate fertile transgenic plants. Another aspect of the invention includes transgenic seeds from which transgenic plants can be grown. The plants, cells and seeds can be either monocotyledons or dicotyledons. The cell(s) may be in a suspension cell culture or may be in an intact plant part, such as an immature embryo, or in a specialized plant tissue, such as callus, such as Type I or Type II callus.

Examples of plants, seeds, and/or plant cells that can be modified as described herein to express the WRI1 transcription factors and/or 14-3-3 proteins include alfalfa (e.g., forage legume alfalfa), algae, avocado, barley, broccoli, Brussels sprouts, cabbage, canola, cassava, cauliflower, cole vegetables, collards, corn, crucifers, grain legumes, grasses (e.g., forage grasses), jatropa, kale, kohlrabi, maize, miscanthus, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and wheat. In some embodiments, the plant is a *Brassicaceae* or other *Solanaceae* species. In some embodiments, the plant or cell can be a maize plant or cell. In some embodiments, the plant is not a species of *Arabidopsis*, for example, in some embodiments the plant is not *Arabidopsis thaliana.*

Transformation of the cells of the plant tissue source can be conducted by any one of a number of methods known to those of skill in the art. Examples are: Transformation by direct DNA transfer into plant cells by electroporation (U.S. Pat. Nos. 5,384,253 and 5,472,869, Dekeyser et al., *The Plant Cell.* 2:591-602 (1990)); direct DNA transfer to plant cells by PEG precipitation (Hayashimoto et al., *Plant Physiol.* 93:857-863 (1990)); direct DNA transfer to plant cells by microprojectile bombardment (McCabe et al., *Bio/Technology.* 6:923-926 (1988); Gordon-Kamm et al., *The Plant Cell.* 2:603-618 (1990); U.S. Pat. Nos. 5,489,520; 5,538,877; and 5,538,880) and DNA transfer to plant cells via infection with *Agrobacterium. Methods such as microprojectile bombardment or electroporation can be carried out with "naked" DNA where the expression cassette may be simply carried on any E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227:1229-1231 (1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. Nos. 5,384,253; and 5,472,869). For example, embryogenic cell lines derived from immature *Zea mays* embryos can be transformed by accelerated particle treatment as described by Gordon-Kamm et al. (*The Plant Cell.* 2:603-618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA encoding the WRI1 and/or 14-3-3 protein for an effective period of time. This may range from a less than one second pulse of electricity for electroporation to a 2-3 day co-cultivation in the presence of plasmid-bearing *Agrobacterium* cells. Buffers and media used will also vary with the plant tissue source and transformation protocol. Many transformation protocols employ a feeder layer of suspended culture cells (e.g., tobacco or Black Mexican Sweet corn, for example) on the surface of solid media plates, separated by a sterile filter paper disk from the plant cells or tissues being transformed.

Electroporation:

Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment:

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic Black Mexican Sweet (BMS) cells are bombarded with intact cells of the bacteria *E. coli* or *Agrobacterium tume-*

*faciens* containing plasmids with the WRI1 and/or 14-3-3 nucleic acids engineered for expression in plants. Bacteria were inactivated by ethanol dehydration prior to bombardment. A low level of transient expression of the WRINKLED protein can be observed 24-48 hours following DNA delivery. In addition, stable transformants containing the WRINKLED nucleic acids are recovered following bombardment with either *E. coli* or *Agrobacterium tumefaciens* cells. It is contemplated that particles may contain DNA rather than be coated with DNA. Hence particles may increase the level of DNA delivery but are not, in and of themselves, necessary to introduce DNA into plant cells.

An advantage of microprojectile bombardment, in addition to it being an effective means of reproducibly stably transforming monocots, is that the isolation of protoplasts (Christou et al., *PNAS.* 84:3962-3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell.* 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension can be concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here-in one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize:

After effecting delivery of one or more WRINKLED nucleic acid(s) to recipient cells by any of the methods discussed above (e.g., in an expression vector), the transformed cells can be identified for further culturing and plant regeneration. As mentioned above, in order to improve the ability to identify transformants, one may desire to employ a selectable or screenable marker gene as, or in addition to, the WRI1 and/or 14-3-3 nucleic acids. In this case, one would then generally assay the potentially transformed cell population by exposing the cells to a selective agent or agents, or one would screen the cells for the desired marker gene trait. Alternatively, the introduced (e.g., transgenic) nucleic acids can be detected and/or characterized by use of a nucleic acid probe to detect the presence of an expression cassette and/or expressed RNA. The introduced nucleic acids can also be detected and/or evaluated by sequencing.

Selection:

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

For example, to use the bar-bialaphos or the EPSPS-glyphosate selective system, bombarded tissue is cultured for about 0-28 days on nonselective medium and subsequently transferred to medium containing from about 1-3 mg/I bialaphos or about 1-3 mM glyphosate, as appropriate. While ranges of about 1-3 mg/bialaphos or about 1-3 mM glyphosate can be employed, it is proposed that ranges of at least about 0.1-50 mg/l bialaphos or at least about 0.1-50 mM glyphosate may be useful. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In one example, embryogenic Type II callus of *Zea mays* L. can be selected with sub-lethal levels of bialaphos. Slowly growing tissue was subsequently screened for expression of the luciferase gene and transformants can be identified.

Regeneration and Seed Production:

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·$m^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that express the desired trait(s). In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the WRI1 and/or 14-3-3 nucleic acids into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced WRINKLED nucleic acids, the plant is self-pollinated at least once in order to produce a homozygous backcross converted inbred containing the WRI1 and/or 14-3-3 nucleic acids. Progeny of these plants are true breeding.

Alternatively, seed from transformed plants regenerated from transformed tissue cultures is grown in the field and self-pollinated to generate true breeding plants.

Seed from the fertile transgenic plants can be evaluated for the presence and/or expression of the WRI1 and/or 14-3-3 nucleic acids (or the WRI1 and/or 14-3-3 protein products). Transgenic plant and/or seed tissue can be analyzed for WRI1 and/or 14-3-3 expression using standard methods such as SDS polyacrylamide gel electrophoresis, liquid chromatography (e.g., HPLC) or other means of detecting a WRI1 and/or 14-3-3 protein.

Once a transgenic seed expressing the WRINKLED transcription factor, and having an increase in oil in the plant tissue is identified, the seed can be used to develop true breeding plants. The true breeding plants are used to develop a line of plants with an increase in the percent of oil in the plant tissues while still maintaining other desirable functional agronomic traits. Adding the trait of increased oil/decreased carbohydrate production to the plant can be accomplished by back-crossing with this trait and with plants that do not exhibit these traits and studying the pattern of inheritance in segregating generations.

Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of an increased percent of oil in the plant. The resulting progeny are then crossed back to the parent that expresses the increased oil/decreased carbohydrate trait. The progeny from this cross will also segregate so that some of the progeny carry the traits and some do not. This back-crossing is repeated until an inbred line with the desirable functional agronomic traits, and with expression of the trait involving an increase in oil and/or a decrease in carbohydrate in the vegetative tissues of the plant. Such expression of the increased percentage of oil or decreased percentage of carbohydrate in plant tissues can be expressed in a dominant fashion.

Subsequent to back-crossing, the new transgenic plants can be evaluated for an increase in the weight percent of oil (TAG) incorporated into vegetative tissues of the plant. This can be done, for example, by thin layer chromatography (TLC), gas chromatography, gas chromatography-flame ionization detector (GC-FID), electrospray ionization mass spectrometry (ESI-MS), mass spectroscopy, nuclear magnetic resonance (NMR), high pressure liquid chromatography (HPLC), and/or infrared spectral analysis of plant tissue or by other available methods of detecting and quantifying oils in harvested plant tissues. The new transgenic plants can also be evaluated for a battery of functional agronomic characteristics such as lodging, kernel hardness, yield, resistance to disease, resistance to insect pests, drought resistance, and/or herbicide resistance.

Plants that can be generated by these methods include but are not limited to oil and/or starch plants (canola, potatoes, cassava, lupins, rape, rapeseed, soybean, sunflower and cottonseed), forage plants (alfalfa, clover and fescue), grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and eucalyptus). Examples of plants and/or plant cells that can be modified as described herein include alfalfa (e.g., forage legume alfalfa), algae, avocado, barley, broccoli, Brussels sprouts, cabbage, canola, cassava, cauliflower, cole vegetables, collards, corn, crucifers, grain legumes, grasses (e.g., forage grasses), jatropa, kale, kohlrabi, maize, miscanthus, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and wheat. In some embodiments, the plant is a *Brassicaceae* or other *Solanaceae* species. In some embodiments, the plant or cell can be a maize plant or cell. In some embodiments, the plant is not a species of *Arabidopsis*, for example, in some embodiments, the plant is not *Arabidopsis thaliana.*

Determination of Stably Transformed Plant Tissues:

To confirm the presence of the WRI1 and/or 14-3-3 nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant. In some embodiments, the amount of oil in plant tissues is quantified. Such a quantified oil content can be compared to a control plant, for example, a control plant of the same species that has not be modified to express the WRI1 transcription factor and/or the 14-3-3 protein.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from the introduced WRI1 and/or 14-3-3 nucleic acids. RT-PCR also be used to reverse transcribe expressed RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

Southern blotting, northern blotting and PCR may be used to detect the WRI1 and/or 14-3-3 nucleic acid in question. Expression may also be evaluated by specifically identifying the presence or absence of protein products of the introduced WRI1 and/or 14-3-3 nucleic acids, by assessing the level of WRI1 and/or 14-3-3 mRNA and/or protein expressed, or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to confirm the identity of the WRI1 and/or 14-3-3 protein expressed such as evaluation by nucleic acid or amino acid sequencing following purification. The Examples of this application also provide assay procedures for detecting WRI1 and/or 14-3-3 activity. Other procedures may be additionally used.

The expression of a WRI1 and/or 14-3-3 gene product can also be determined by evaluating the phenotypic results of its expression. These assays also may take many forms including but not limited to analyzing changes in the chemical composition, morphology, or physiological properties of the plant. Chemical composition of plant tissues may be altered by expression of the WRI1 and/or 14-3-3 protein(s).

Cultivation

Seeds, seedlings and plants containing WRI1 and/or 14-3-3 nucleic acids can be grown in any medium which supports plant growth such as a commercial media, soil or water (hydroponically). The medium can be supplemented with a source of sugar (sugar source), such as carbohydrate or sugar. Such supplementation can increase the oil content of seedlings and plants containing WRI1 and/or 14-3-3 nucleic acids.

As used herein, a source of sugar or a sugar source includes a material that contains or releases sugar. A material that releases sugar can be a material that is digested by agents in the environment that erodes under cultivation conditions, that is formulated for sustained release, or that is a polymer of sugar units. “Sugar” refers to sugars, e.g., fructose, sucrose, and glucose, and to sugar alcohols, e.g., sorbitol.

The medium for growth of plants can contain about 0.1% to about 10% sugar or a source of sugar. The medium for growth of plants can also contain about 0.2% to about 7%, or about 0.5% to about 6%, or about 1% to about 5%, or about 1.5% to about 4%, or about 2% to about 4%, of sugar or a source of sugar.

Kits

A kit is provided that can include a transgenic seed containing WRI1 and/or 14-3-3 nucleic acids, as well as instructions for cultivating the seeds, as well the use of any other material or reagent not included in the kit. The kit can also include a medium for growth of the seeds, or for grow of seedlings, or for induction of expression of the WRI1 and/or 14-3-3 nucleic acids to generate WRI1 transcription factors and/or 14-3-3 proteins. Such a medium can also include sugar or a source of sugar. The kit can also include fertilizer. Instructions can include text on when and how to induce expression of the WRI1 and/or 14-3-3. Variations that can be implemented can also be described in the instructions.

Any of the WRINKLED nucleic acids, polypeptides and/or related nucleic acids and/or polypeptides described herein can be included in a kit. In some embodiments, the kits can include a container that includes a nucleic acid, or a mixture of nucleic acids. Such a nucleic acid or mixture of nucleic acids can be used, for example, to transform plant cells and/or generate transgenic plants. The nucleic acid(s) can encode a WRI1 transcription factor and/or the 14-3-3 protein.

The kits can also include more than one container. For example, the kits can include two or more containers, where one container includes a WRI1 and/or 14-3-3 nucleic acid, and another container includes other nucleic acids of interest, or other components for transformation of plant cells. For example, the kit can include a container with a WRI1 and/or 14-3-3 nucleic acid, where the WRI1 and/or 14-3-3 nucleic acid can be part of an expression cassette or an expression vector.

The kits may also include one or more containers of buffers, such as buffers to dilute or stabilize the WRI1 and/or 14-3-3 nucleic acids, or transcription buffers, or hybridization buffers, or buffers for measuring WRINKLED activity or compounds for manipulating the nucleic acids, and/or components for isolating the resultant expression cassette that may be integrated into a plant genome.

The components of the kits may be packaged either in aqueous media or in lyophilized form. The containers can be vials, test tubes, flasks, bottles, syringes or other container means, into which a component may be placed, and suitably aliquoted.

Where there is more than one component in the kit, the kit also will generally contain a second, third or other additional container into which the additional components may be separately placed. However, various combinations of components may also be included in one container. The kits of the present invention also will typically include a means for containing the nucleic acids, and any other reagent containers in close confinement for commercial sale. Such containers may include injection or blow-molded plastic packages into which the desired vials are retained.

When the components of the kit are provided in one and/or more liquid solutions, the liquid solution is an aqueous solution, for example, a sterile aqueous solution. The nucleic acids can also be provided as an alcohol precipitate or as dried powder(s). When reagents and/or components are provided as a dry powder, the powder can be reconstituted by the addition of a suitable solvent. It is envisioned that the solvent may also be provided in another container.

In some embodiments, nucleic acids are provided in dried form or suspended in an appropriate buffer or solvent. It is contemplated that 0.1, 1, 5, 10, 20, 30, 40, 50, 60, 70, 80, 90, 100, 120, 120, 130, 140, 150, 160, 170, 180, 190, 200, 300, 400, 500, 600, 700, 800, 900, 1000 μg or nucleic acid can be provided in kits of the invention.

The kits can also include a means for containing the vials in close confinement for commercial sale, such as, e.g., injection and/or blow-molded plastic containers into which the desired vials are retained.

Such kits may also include components that preserve or maintain the nucleic acids or that protect against their degradation. Such components may be DNAse-free or RNAse free. The kits may include containers of DNase or RNase inhibitors. Such kits generally will comprise, in suitable means, distinct containers for each individual reagent or solution.

A kit will also include instructions for employing the kit components as well the use of any other reagent not included in the kit. Instructions may include variations that can be implemented.

Definitions

As used herein, "isolated" means a nucleic acid or polypeptide has been removed from its natural or native cell. Thus, the nucleic acid or polypeptide can be physically isolated from the cell, or the nucleic acid or polypeptide can be present or maintained in another cell where it is not naturally present or synthesized. The isolated nucleic acid or the isolated polypeptide can also be a nucleic acid or protein that is modified but has been introduced into a cell where it is or was naturally present. Thus, a modified isolated nucleic acid or an isolated polypeptide expressed from a modified isolated nucleic acid can be present in a cell along with a wild copy of the (unmodified) natural nucleic acid and along with wild type copies of the (natural) polypeptide.

As used herein, a "native" nucleic acid or polypeptide means a DNA, RNA or amino acid sequence or segment that has not been manipulated in vitro, i.e., has not been isolated, purified, mutated, and/or amplified.

The term "transgenic" when used in reference to a plant or leaf or vegetative tissue or seed for example a "transgenic plant," transgenic leaf," "transgenic vegetative tissue," "transgenic seed," or a "transgenic host cell" refers to a plant or leaf or tissue or seed that contains at least one heterologous or foreign gene in one or more of its cells.

The term "transgenic plant material" refers broadly to a plant, a plant structure, a plant tissue, a plant seed or a plant cell that contains at least one heterologous gene in one or more of its cells.

The term "transgene" refers to a foreign gene that is placed into an organism or host cell by the process of transfection. The term "foreign nucleic acid" or refers to any nucleic acid (e.g., encoding a promoter or coding region) that is introduced into the genome of an organism or tissue of an organism or a host cell by experimental manipulations, such as those described herein, and may include nucleic acid sequences found in that organism so long as the introduced gene does not reside in the same location, as does the naturally occurring gene.

The term "host cell" refers to any cell capable of replicating and/or transcribing and/or translating a heterologous nucleic acid. Thus, a "host cell" refers to any eukaryotic or prokaryotic cell (e.g., plant cells, algal cells, bacterial cells, yeast cells, *E. coli*, insect cells, etc.), whether located in vilro or in vivo. For example, a host cell may be located in a transgenic plant, or located in a plant part or part of a plant tissue or in cell culture.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

As used herein, the term "plant" is used in its broadest sense. It includes, but is not limited to, any species of grass (e.g. turf grass), ornamental or decorative, crop or cereal, fodder or forage, fruit or vegetable, fruit plant or vegetable plant, herb plant, woody plant, flower plant or tree. It is not meant to limit a plant to any particular structure. It also refers to a unicellular plant (e.g. microalga) and a plurality of plant cells that are largely differentiated into a colony (e.g. volvox) or a structure that is present at any stage of a plant's development. Such structures include, but are not limited to, a seed, a tiller, a sprig, a stolen, a plug, a rhizome, a shoot, a stem, a leaf, a flower petal, a fruit, et cetera.

The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, a leaf and a cell. Plant parts may comprise one or more of a tiller, plug, rhizome, sprig, stolen, meristem, crown, and the like. In some instances the plant part can include vegetative tissues of the plant.

Vegetative tissues or vegetative plant parts do not include plant seeds, and instead include non-seed tissues or parts of a plant. The vegetative tissues can include reproductive tissues of a plant, but not the mature seeds.

The term "seed" refers to a ripened ovule, consisting of the embryo and a casing.

The term "propagation" refers to the process of producing new plants, either by vegetative means involving the rooting or grafting of pieces of a plant, or by sowing seeds. The terms "vegetative propagation" and "asexual reproduction" refer to the ability of plants to reproduce without sexual reproduction, by producing new plants from existing vegetative structures that are clones, i.e., plants that are identical in all attributes to the mother plant and to one another. For example, the division of a clump, rooting of proliferations, or cutting of mature crowns can produce a new plant.

The term "heterologous" when used in reference to a nucleic acid refers to a nucleic acid that has been manipulated in some way. For example, a heterologous nucleic acid includes a nucleic acid from one species introduced into another species. A heterologous nucleic acid also includes a nucleic acid native to an organism that has been altered in some way (e.g., mutated, added in multiple copies, linked to a non-native promoter or enhancer sequence, etc.). Heterologous nucleic acids can include cDNA forms of a nucleic acid; the cDNA may be expressed in either a sense (to produce mRNA) or anti-sense orientation (to produce an anti-sense RNA transcript that is complementary to the mRNA transcript). For example, heterologous nucleic acids can be distinguished from endogenous plant nucleic acids in that the heterologous nucleic acids are typically joined to nucleic acids comprising regulatory elements such as promoters that are not found naturally associated with the natural gene for the protein encoded by the heterologous gene. Heterologous nucleic acids can also be distinguished from endogenous plant nucleic acids in that the heterologous nucleic acids are in an unnatural chromosomal location, or are associated with portions of the chromosome not found in nature (e.g., the heterologous nucleic acids are expressed in tissues where the gene is not normally expressed).

The term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination," "in operable order," and "operably linked" refer to the linkage of nucleic acid sequences in such a manner that a nucleic acid molecule capable of directing the transcription of a coding region (e.g., gene) and/or the synthesis of a desired protein molecule is produced. The term also refers to the linkage of amino acid sequences in such a manner so that a functional protein is produced.

Transcriptional control signals in eukaryotes comprise "promoter" and "enhancer" elements. Promoters and enhancers consist of short arrays of DNA sequences that interact specifically with cellular proteins involved in transcription (see, for e.g., Maniatis, et al. (1987) Science 236:1237; herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al. (1987), supra; herein incorporated by reference).

The terms "promoter element," "promoter," or "promoter sequence" refer to a DNA sequence that is located at the 5' end of the coding region of a DNA polymer. The location of most promoters known in nature is 5' to the transcribed region. The promoter functions as a switch, activating the expression of a gene. If the gene is activated, it is said to be transcribed, or is participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length. Promoters may be tissue specific or cell specific.

The term "tissue specific" as it applies to a promoter refers to a promoter that is capable of directing selective expression of a nucleic acid of interest to a specific type of tissue (e.g., vegetative tissues) in the relative absence of expression of the same nucleic acid of interest in a different type of tissue (e.g., seeds). Tissue specificity of a promoter may be evaluated by, for example, operably linking a reporter gene and/or a reporter gene expressing a reporter molecule, to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter that is capable of directing selective expression of a nucleic acid of interest in a specific type of cell in the relative absence of expression of the same nucleic acid of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody that is specific for the polypeptide product encoded by the nucleic acid of interest whose expression is controlled by the promoter. A labeled (e.g., peroxidase conjugated) secondary antibody that is specific for the primary antibody is allowed to bind to the sectioned tissue and specific binding detected (e.g., with avidin/biotin) by microscopy.

Promoters may be "constitutive" or "inducible." The term "constitutive" when made in reference to a promoter means that the promoter is capable of directing transcription of an operably linked nucleic acid in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098; herein incorporated by reference), and ubi3 promoters (see e.g., Garbarino and Belknap, Plant Mol. Biol. 24:119-127 (1994); herein incorporated by reference). Such promoters have been used successfully to direct the expression of heterologous nucleic acid sequences in transformed plant tissue.

In contrast, an "inducible" promoter is one that is capable of directing a level of transcription of an operably linked nucleic acid in the presence of a stimulus (e.g., heat shock, chemicals, light, etc.) that is different from the level of transcription of the operably linked nucleic acid in the absence of the stimulus.

The term "vector" refers to nucleic acid molecules that transfer DNA segment(s). Transfer can be into a cell, cell to cell, et cetera. The term "vehicle" is sometimes used interchangeably with "vector." The vector can, for example, be a plasmid. But the vector need not be plasmid.

The following non-limiting Examples illustrate how aspects of the invention have been developed and can be made and used.

Example 1: Materials and Methods

This Example illustrates some methods that can be employed to make and use the invention.

Plant Materials

*Arabidopsis* (*Arabidopsis thaliana*) wild type (Columbia-2 ecotype) and wri1-1 were used in this study. *Arabidopsis* and *N. benthamiana* plants were grown in a growth chamber on potting mix at 22° C. with a 16 h light (100-150 μmol m-2 s-1 illumination)/8 h dark photoperiod cycle (Ma et al. *PloS one,* 8, e68887 (2013)). *Arabidopsis* transformation, plant growth on plates, seed surface sterilization, and transgenic seedling selection followed methods previously described (Ma et al. *PloS one,* 8, e68887 (2013)).

Bioinformatics Analysis

Amino acid composition of AtWRI1 was analyzed by Composition Profiler (Vacic et al., *BMC Bioinformatics,* 8, 211 (2007)). Intrinsically disordered regions were predicted using PONDR-VL3 (Radivojac et al. *Pac Symp Biocomput,* 216-227 (2003)), PONDR-FIT (Xue et al. *Biochim Biophys Acta,* 1804, 996-1010 (2010)) and RONN (Yang et al. *Bioinformatics,* 21, 3369-3376 (2005)). PEST Domain analysis was performed by ePESTfind. Phosphorylation prediction was performed by NetPhos 2.0 (Blom et al. *J Mol Biol,* 294, 1351-1362 (1999)) and DISPHOS1.3 (lakoucheva et al. *Nucleic Acids Res,* 32, 1037-1049 (2004)).

Plasmid Construction

Coding sequence of AtWRI1 (including truncated AtWRI1 variants or site-directed AtWRI1 mutants) were amplified by PCR and subcloned into pENTR4 vector (Life Technologies) to obtain entry constructs. A wild type AtWRI1 with the following amino acid sequence (SEQ ID NO: 29) was employed as a basis for several of the experiments described herein.

1 MKKRLTTSTC SSSPSSSVSS STTTSSPIQS EAPRPKRAKR
41 AKKSSPSGDK SHNPTSPAST RRSSIYRGVT RHRWTGRFEA
81 HLWDKSSWNS IQNKKGKQVY LGAYDSEEAA AHTYDLAALK
121 YWGPDTILNF PAETYTKELE EMQRVTKEEY LASLRRQSSG
161 FSRGVSKYRG VARHHHNGRW EARIGRVFGN KYLYLGTYNT
201 QEEAAAAYDM AAIEYRGANA VTNFDISNYI DRLKKKGVFP
241 FPVNQANHQE GILVEAKQEV ETREAKEEPR EEVKQQYVEE
281 PPQEEEEKEE EKAEQQEAEI VGYSEEAAVV NCCIDSSTIM
321 EMDRCGDNNE LAWNFCMMDT GFSPFLTDQN LANENPIEYP
361 ELFNELAFED NIDFMFDDGK HECLNLENLD CCWGRESPP
401 SSSSPLSCLS TDSASSTTTT TTSVSCNYLV

A fragment of AtWRI1 was first synthesized with mutations (Integrated DNA Technologies). The following mutant AtWRI1 were generated: $AtWRI1^{S398A/S401A/S402A/S407A/S415A/S416A/T420A/T421A/T422A/S423A}$ (referred to as $AtWRI1^{PEST/AA}$; SEQ ID NO:30):

1 MKKRLTTSTC SSSPSSSVSS STTTSSPIQS EAPRPKRAKR
41 AKKSSPSGDK SHNPTSPAST RRSSIYRGVT RHRWTGRFEA
81 HLWDKSSWNS IQNKKGKQVY LGAYDSEEAA AHTYDLAALK
121 YWGPDTILNF PAETYTKELE EMQRVTKEEY LASLRRQSSG
161 FSRGVSKYRG VARHHHNGRW EARIGRVFGN KYLYLGTYNT
201 QEEAAAAYDM AAIEYRGANA VTNFDISNYI DRLKKKGVFP
241 FPVNQANHQE GILVEAKQEV ETREAKEEPR EEVKQQYVEE
281 PPQEEEEKEE EKAEQQEAEI VGYSEEAAVV NCCIDSSTIM
321 EMDRCGDNNE LAWNFCMMDT GFSPFLTDQN LANENPIEYP
361 ELFNELAFED NIDFMFDDGK HECLNLENLD CCVVGREAPP
401 AASSPLACLS TDSAAATTTA AAAVSCNYLV;

$AtWRI1^{S98D/S401D/S402D/S407D/S415D/S416D/T420D/T421D/T422D/S423D}$ (referred to as $AtWRI1^{PEST/DD}$; SEQ ID NO:31):

1 MKKRLTTSTC SSSPSSSVSS STTTSSPIQS EAPRPKRAKR
41 AKKSSPSGDK SHNPTSPAST RRSSIYRGVT RHRWTGRFEA
81 HLWDKSSWNS IQNKKGKQVY LGAYDSEEAA AHTYDLAALK

121 YWGPDTILNF PAETYTKELE EMQRVTKEEY LASLRRQSSG
161 FSRGVSKYRG VARHHHNGRW EARIGRVFGN KYLYLGTYNT
201 QEEAAAAYDM AAIEYRGANA VTNFDISNYI DRLKKKGVFP
241 FPVNQANHQE GILVEAKQEV ETREAKEEPR EEVKQQYVEE
281 PPQEEEEKEE EKAEQQEAEI VGYSEEAAVV NCCIDSSTIM
321 EMDRCGDNNE LAWNFCMMDT GFSPFLTDQN LANENPIEYP
361 ELFNELAFED NIDFMFDDGK HECLNLENLD CCVVGREDPP
401 DDSSPLDCLS TDSADDTTTD DDDVSCNYLV

PCR was performed to amplify the full length AtWRI1$^{PEST/AA}$ and AtWRI1$^{PEST/DD}$. Entry constructs were introduced into destination vectors (BiFC vectors, and pEarleyGate binary vectors) through LR reactions (Life Technologies). The BTB/POZ and MATH domain-containing (BPM) 1 (BPM1) entry construct was obtained from *Arabidopsis* Biological Resource Center (ABRC; Cat. No.: U24902). A list of the primers employed is shown below.

| Primer Name SEQ ID NO: | Sequence 5' to 3' |
|---|---|
| AtWRI1-FW NO: 32 | 5'-AATGGATCCGGACAATGAAGAAGCGCTTA |
| AtWRI1-RV NO: 33 | 5'-TCCCTCGAGTCAGACCAAATAGTT |
| AtWRI1$^{PEST/AA}$-FW NO: 34 | 5'-GTAGGATATTCAGAAGAAGCAGCA |
| AtWRI1$^{PEST/AA}$-RV NO: 35 | 5'-TGCTGCTTCTTCTGAATATCCTAC |
| AtWRI1$^{4SA}$-FW NO: 36 | 5'-GCAGCATCTTCACCATTGGCATGCTTAT CTACTGACTCTG |
| AtWRI1$^{4SA}$-RV NO: 37 | 5'-AGAGTCAGTAGATAAGCATGCCAATGGT GAAGATGCTGC |
| AtWRI1$^{4SD}$-FW NO: 38 | 5'-GTGGTGGGAAGAGAGGACCCACCCGACGAC TCTTCACCATTGGACTGCTTATCTACTGAC |
| AtWRI1$^{4SD}$-RV NO: 39 | 5'-GTCAGTAGATAAGCAGTCCAATGGTGAAGA GTCGTCGGGTGGGTCCTCTCTTCCCACCAC |
| AtWRI1$^{1-302}$-RV NO: 40 | 5'-TCCCTCGAGTCATCCTACAATCTCTGCT |
| AtWRI1$^{1-366}$-RV NO: 41 | 5'-TATGCGGCCGCTCATAACTCATTGAATAGC TCCGGATAC |
| AtWRI1$^{1-397}$-RV NO: 42 | 5'-TCCCTCGAGTCACTCTCTTCCCACCACGCA A |
| AtWRI1$^{1-306}$RV NO: 43 | 5'-TGACTCGAGTCATTCTTCTGAATATCC |
| AtWRI1$^{307-430}$-FW NO: 44 | 5'-GCAGGATCCATATGGCAGCAGTGGT |
| AtWRI1$^{307-397}$-RV NO: 45 | 5'-GTACTCGAGTCACTCTCTTCCCACCAC |
| AtWRI1$^{307-368}$-RV NO: 46 | 5'-GTACTCGAGTCAAAATGCTAACTCATT |
| AtWRI1$^{368-430}$-FW NO: 47 | 5'-AATGGATCCGGACAATGTTTGAGGACAACA TCGACTT |

-continued

| Primer Name SEQ ID NO: | Sequence 5' to 3' |
|---|---|
| AtWRI1$^{P3A}$-FW NO: 48 | 5'-TGGTGGGAAGAGAGAGCGCAGCATCTTCT TCTTCAGCATTGTCTTGCTTATCTACTG |
| AtWRI1$^{P3A}$-RV NO: 49 | 5'-CAGTAGATAAGCAAGACAATGCTGAAGAA GAAGATGCTGCGCTCTCTCTTCCCACCA |
| AtWRI1$^{P3L}$-FW NO: 50 | 5'-TGGTGGGAAGAGAGAGCTTGTTGTCTTCT TCTTCATTGTTGTCTTGCTTATCTACTG-3' |
| AtWRI1$^{P3L}$-RV NO: 51 | 5'-CAGTAGATAAGCAAGACAACAATGAAGAAG AAGACAACAAGCTCTCTCTTCCCACCA-3' |

Transient Expression in *N. benthamiana*

*Agrobacterium tumefaciens*-mediated transient expression in *N. benthamiana* leaves was performed as described previously with slight modification (Vanhercke el al. *FEBS Lett,* 587, 364-369 (2013)). In brief, *A. tumefaciens* overnight cultures were centrifuged and re-suspended in MMA buffer (containing 10 mM MES (pH 5.6), 10 mM $MgCl_2$, and 100 μM acetosyringone) to a concentration of 1.2 $OD_{600}$, and incubated at room temperature for at least 3 hrs. The cell culture was diluted to 0.4 $OD_{600}$ prior to infiltration. Five- to seven-week-old *N. benthamiana* plants were usually chosen for the experiments.

Confocal microscopy and bimolecular fluorescence complementation (BiFC) assays used 35S:YFP-AtWRI1 (including truncated AtWRI1 variants and AtWRI1 site-directed mutants fused to yellow fluorescent protein (YFP)) were generated through GATEWAY system. For BiFC experiments, 35S:nYFP-AtWRI1 (including truncated AtWRI variants) and 35S:cYFP-BPM1 were similarly assembled. Constructs were transformed into *A. tumefaciens* (GV3101 strain). For BiFC experiments to test protein-protein interaction, *A. tumefaciens* harboring each nYFP and cYFP fusion construct was prepared (each culture was re-suspended to 1.2 $OD_{600}$ in MMA buffer) and adjusted to 0.4 $OD_{600}$, prior to injection into plant leaves. Healthy leaves of *N. benthamiana* plants were infiltrated by bacterial suspensions with a 1-mL blunt-end syringe. Plants were returned to growth chambers and YFP fluorescence signals were captured by a confocal microscope 2 to 3 d after bacterial infiltration. YFP fluorescence signal intensity was analyzed using ImageJ software.

Quantitative Real-Time PCR (qRT-PCR)

RNA extraction and cDNA synthesis followed the methods described by Ma el al. (*PloS one,* 8, e68887 (2013)). qRT-PCR was performed using the SYBR Green PCR Core Reagents mix (Life Technologies) according to the manufacturer's manual. The expression level of WRI1 target gene was normalized to PP2A gene (internal standard). qRT-PCR primers (YFP) were:

FW: 5'-AGGGCTATGTGCAGGAGAGA-3' (SEQ ID NO: 52);

RV: 5'-CTTGTGGCCGAGAATGTTTC-3' (SEQ ID NO:53).

The qRT-PCR primers (AtWRI1) were:

FW: 5'-AGAGCAGTGGTTTCTCCAGAGG-3' (SEQ ID NO:54);

RV: 5'-TTCCGTTGTGGTGATGCCTAGC-3' (SEQ ID NO:55).

The primers for the PP2A gene that were used for qRT-PCR

FW: 5'-GACCCTGATGTTGATGTTCGCT-3' (SEQ ID NO:56);

RV: 5'-GAGGGATTTGAAGAGAGATTTC-3' (SEQ ID NO:57)

were described previously (Liu et al. *PloS one,* 7, e46451 (2012)).

Yeast Transactivation Assay

The transactivation activity of AtWRI1 variants were evaluated by β-Galactosidase (β-Gal) activity. Both colony-lift filter assay and liquid culture assay were performed according to the Yeast Protocols Handbook (Clonetech). 5-bromo-4-chloro-3-indolyl-1-D-galactopyranoside (X-GAL) was used as the substrate for the colony-lift filter assay and o-nitrophenyl-β-D-galactopyranoside (ONPG) was chosen as the substrate for the liquid culture assay.

Cell-Free Degradation Assay

AtWRI1-WT and its variants were subcloned into pDESTI 5 vector to obtain N-terminal GST tag fused recombinant proteins. Recombinant proteins were expressed in *E. coli* BL21 (DE3) and induced by 1 mM IPTG at room temperature for 3 h. Protein extraction and purification were as described by Kong et al. (*Proc Natl Acad Sci USA,* 109, E2091-2097 (2012)). Purified proteins were dialyzed against 20 mM Tris-HCl (pH 8.0), 100 mM NaCl, and 10% glycerol. Protein concentration was measured by Bio-Rad protein assay kit (Bio-Rad). The cell-free degradation assay was performed as previously described by Liu and Stone (*J Biol Chem,* 288, 20267-20279 (2013); and Wang et al. *Plant Cell,* 21, 2378-2390 (2009)) with slight modifications. Seven-day-old *Arabidopsis* seedlings were harvested and ground into fine powder in liquid nitrogen. Total protein was extracted using extraction buffer containing 25 mM Tris-HCl pH 8.0, 10 mM NaCl, 10 mM MgCI2, 5 mM DTT and protease inhibitor cocktail (Roche) and centrifuged at 18000 g at 4° C. for 20 min. The supernatant was collected as total protein extract and protein concentration was determined by Bio-Rad protein assay kit (Bio-Rad). In the degradation assay, 3 μg recombinant protein was mixed with 500 μg total protein extract and 10 mM ATP with or without 10 μM MG132 in a total volume of 300 μL. 50 μL of the reaction mixture was sampled at time points of 0, 30, 60, 120, 240, and 360 min. 10 μL of 6×SDS loading buffer was added and the samples were heated at 95° C. for 5 min to stop the reaction. After SDS-PAGE, recombinant proteins were detected by Western blots using anti-GST-HRP conjugate (Thermo fisher) at 1:2000 dilution followed by chemiluminescence detection using ChemiDoc™ System (Bio-Rad). The band density was analyzed by ImageJ software.

Lipid Analysis

For lipid analysis in *N. benthamiana* plants, leaves were harvested 5 d after bacterial infiltration (transient expression) and frozen in liquid nitrogen. Frozen leaves were lyophilized prior to lipid analysis. Lipid analysis followed methods described previously by Hara and Radin (*Anal Biochem,* 90, 420-426 (1978)) and by Li et al. (*Phytochemistry,* 67, 904-915 (2006)), with slight modification. In brief, lyophilized leaves (20-30 mg) were first incubated in 2 mL preheated isopropanol at 90° C. for 10 min. After cooling to room temperature, leaves were ground by a glass pestle followed by adding 3 mL hexane and vortexing strongly. 2.5 mL 15% (w/v) sodium sulfate was added, again vortexing strongly. After centrifugation, the upper phase was collected and the lower phase re-extracted with hexane:isopropanol (7:2; v/v). The combined upper phases were dried under a stream of nitrogen gas and dissolved in chloroform. Lipid extracts were separated on a thin-layer chromatography (TLC) plate using hexane:diethylether: acetic acid (70:30:1, v/v/v). The TLC plate was sprayed with primuline solution and lipid bands were visualized under UV light. TAG bands, identified by co-migration with standards, were scraped and transferred into a glass tube for transmethylation and analysis by GC. For lipid analysis of *Arabidopsis* seeds, lipid analysis followed methods described by Ma et al. (*PloS one,* 8, e68887 (2013)).

Example 2: AtWRI1 Protein Shows Hallmarks of Intrinsic Disorder

To identify intrinsically disordered regions in the AtWRI1 protein, the amino acid composition of AtWRI1 was analyzed using Composition Profiler. Disordered proteins often display amino acid compositional bias (Romero et al. *Proteins,* 42, 38-48 (2001); Valsecchi et al., *Molecular bioSystems,* 9, 2282-2295 (2013)) with an abundance of polar residues and depletion of hydrophobic amino acids (Dyson and Wright *Nat Rev Mol Cell Biol,* 6, 197-208 (2005)). The AtWRI1 protein is enriched in polar amino acids (Ser (S), Thr (T), Tyr (Y), Cys (C), Asn (N)), while hydrophobic amino acids (Leu (L), Phe (F), lie (1), Val (V), Met (M)) are depleted (FIG. 1E). These results indicated that AtWRI1 may be intrinsically disordered. A protein disorder predictor (PONDR VL3) indicated that the AtWRI1 protein has a disorder value of 53% (predicted by PONDR VL3) compared to an average of 23% for all *Arabidopsis* proteins. The protein disorder of several AtWRI1 orthologs including BnWRI1 (*B. napus*), EgWRI1 (oil palm), ZmWRI1a and ZmWRI1b (*Z. mays*) was also compared. These WRI1 orthologs consistently displayed a high level of disorder (BnWRI1 (62%), ZmWRI1a (57%), ZmWRI1b (49%) and EgWRI1 (52%) (predicted by PONDR VL3) (FIG. 1F). Taken together, these data show that AtWRI1 proteins have the typical hallmarks of intrinsic disorder.

Example 3: Identification of Intrinsically Disordered Regions (IDRs) in AtWRI1

Figure 1A:
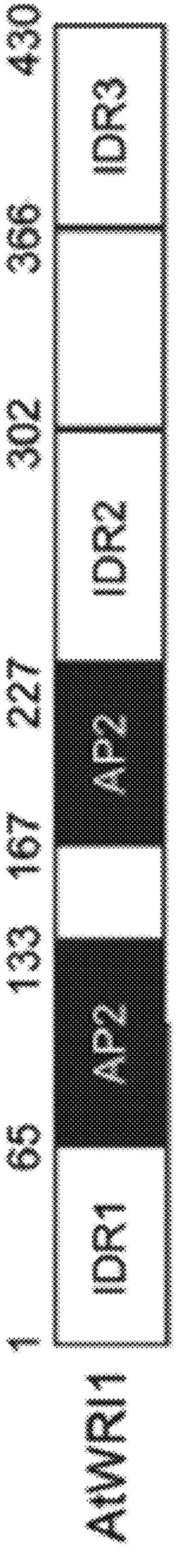
Figure 1B:
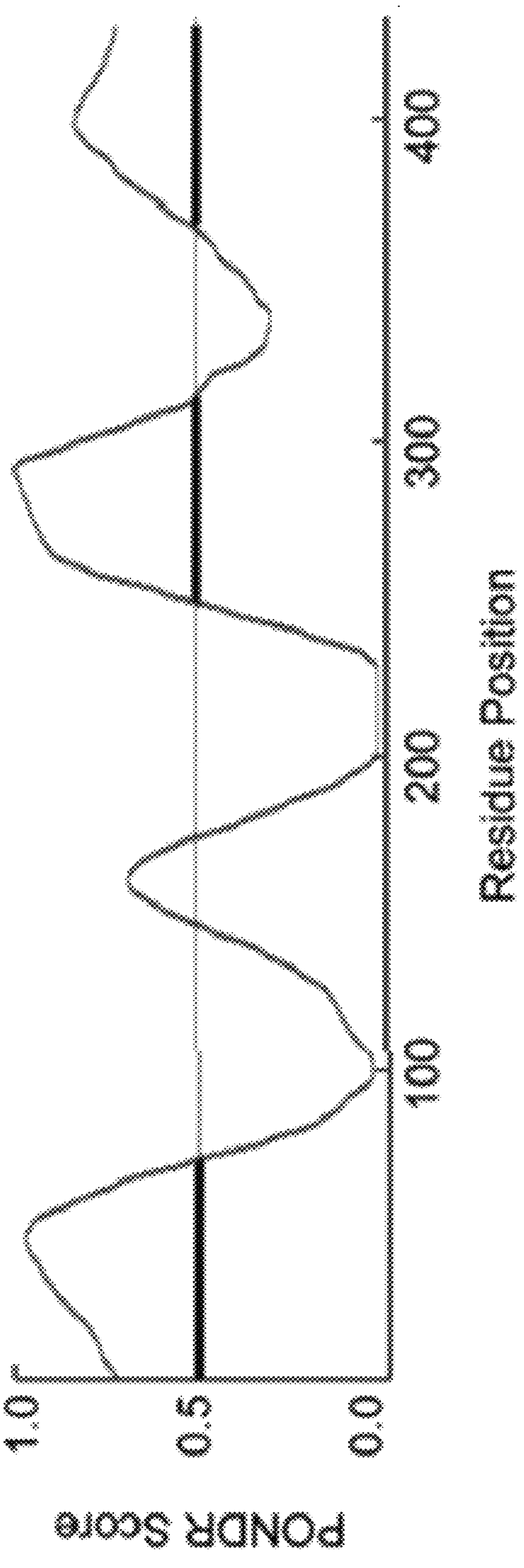
Figure 1C:
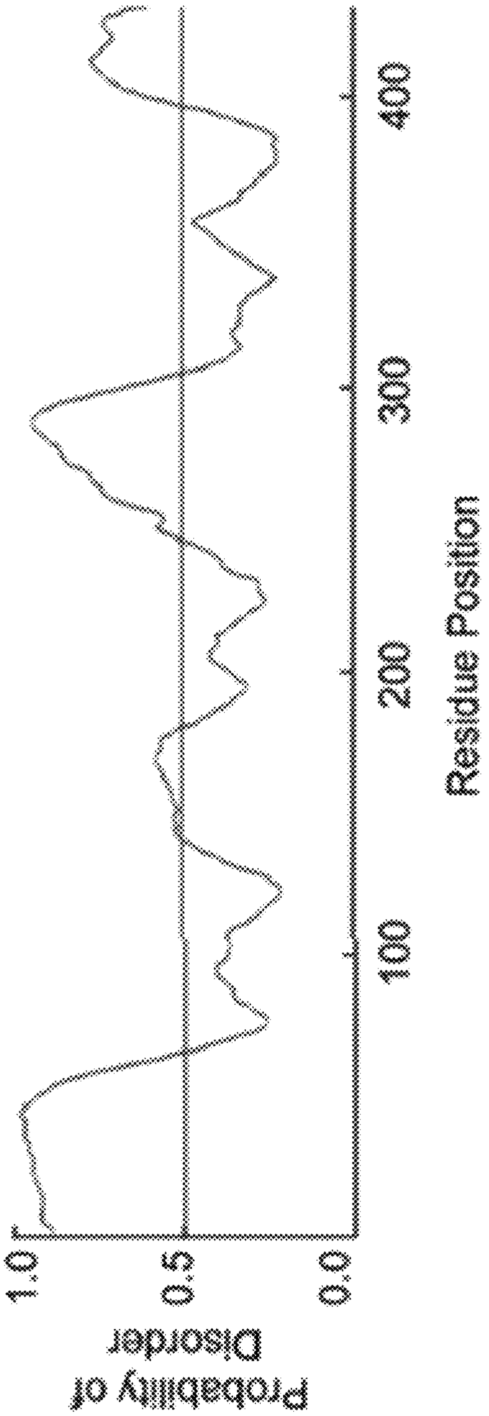
Figure 1D:
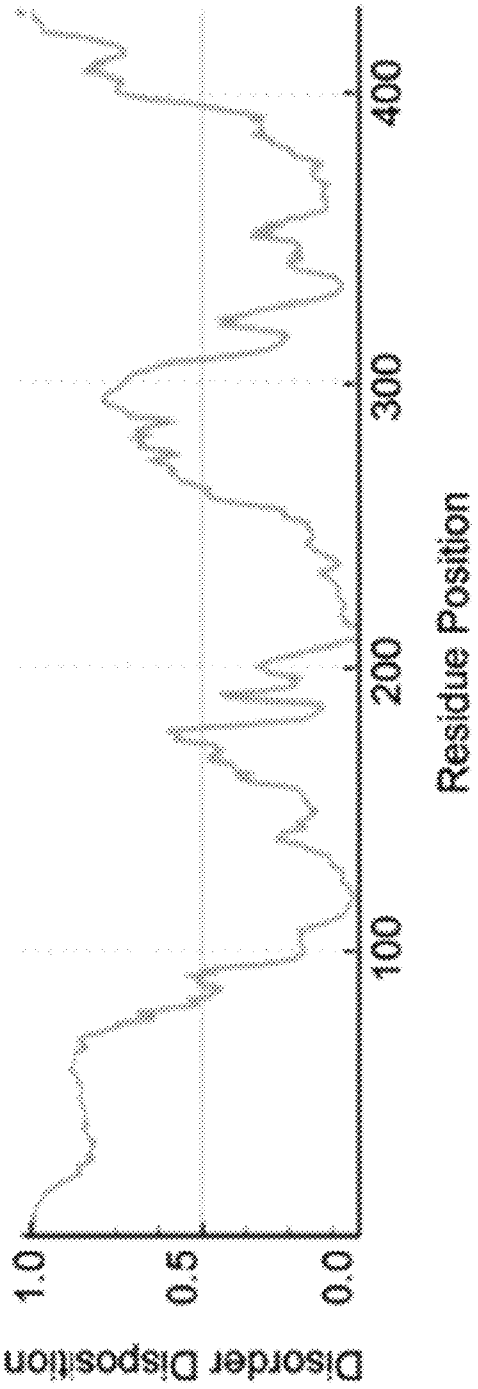

Additional in silico analyses were performed using three IDR prediction algorithms to identify the major IDRs in AtWRI1. A total of three major IDRs were consistently predicted in AtWRI1 by the three algorithms (FIG. 1A-ID). One disordered domain ($AtWRI1^{IDR1}$; also referred to as IDR1) was close to the N-terminus and the other two disordered domains ($AtWRI1^{IRD2}$ and $AtWRI1^{IDR3}$) were in the C-terminal region of AtWRI1 (FIGS. 1A-ID and 1G). The IDR1 region was located between amino acid positions 1 and 83. The $AtWRI1^{IDR2}$ region (also referred to as IDR2) was located between amino acid positions 249 and 313, while the $AtWRI1^{IDR3}$) region (also referred to as IDR3, was located between amino acid positions 368-430. It should be noted that the different algorithms predicted slight variations in IDR placement (FIG. 1G).

Example 4: IDR3 Domain of AtWRI1 Determines Stability of AtWRI1

The IDR1 and IDR2 regions flank the already well-characterized and functionally-critical AP2 domains. For these experiments, the inventors decided to focus on the analysis of the less characterized C-terminus with its IDR domain ($AtWRI1^{IDR3}$).

Figures 2A, 2B:
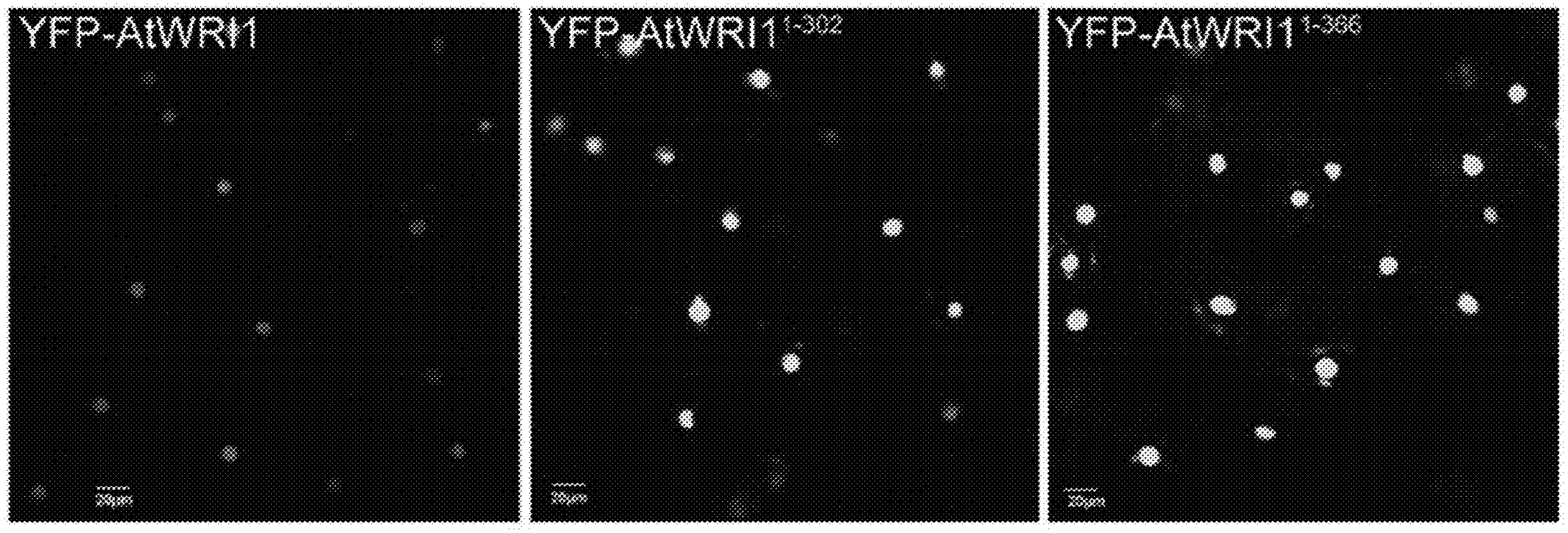
FIG. 2A-2C shows that the C-terminal portion of AtWRI1 regulates protein stability.
Figure 2C:
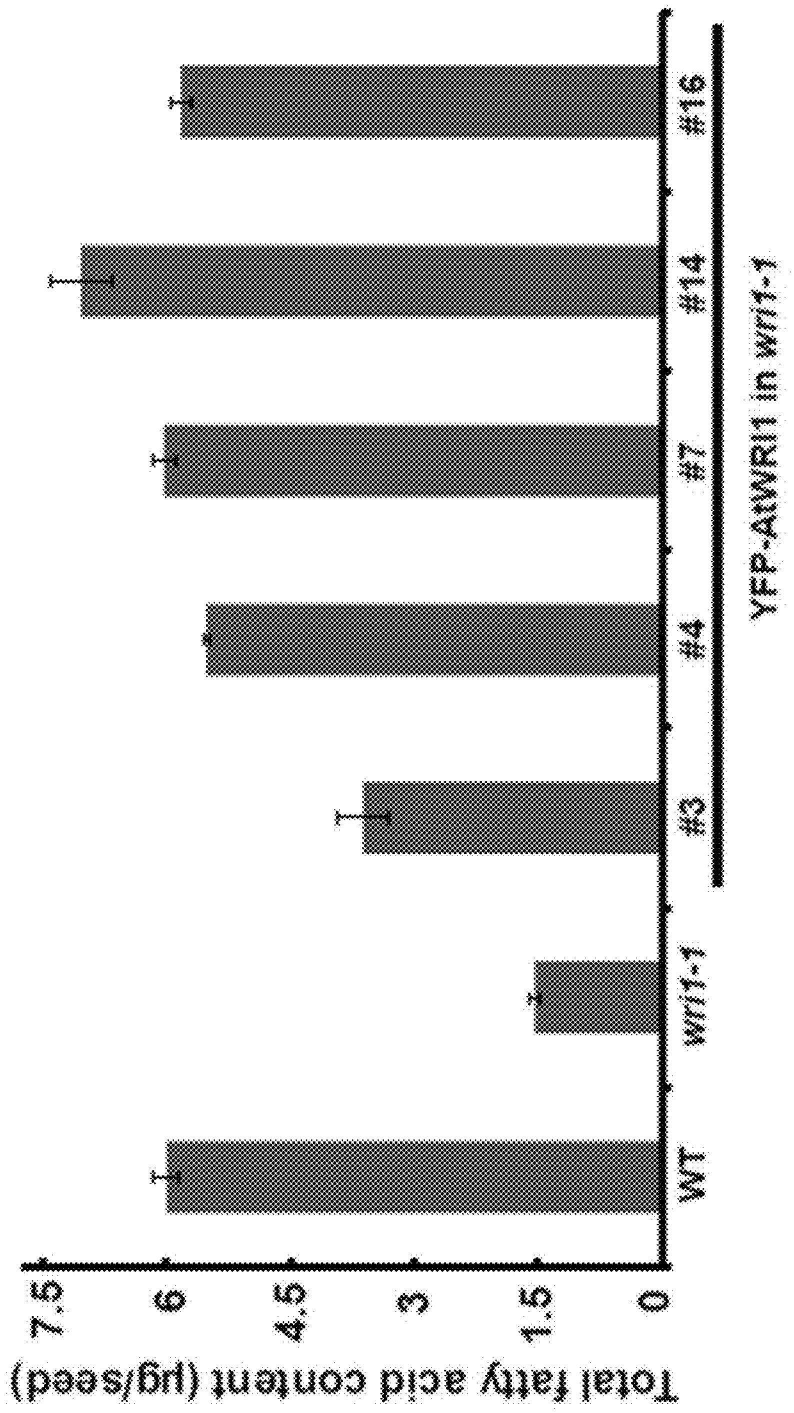

In order to investigate the function of $AtWRI1^{IDR3}$, two truncated AtWRI1 variants were generated with IDR3 removed ($AtWRI1^{1-302}$ and $AtWRI1^{1-366}$ having the first 302 and 366 amino acids, respectively). Yellow fluorescent protein (YFP) was fused at the N-terminus of each AtWRI1 variant. These YFP fusions are functional as demonstrated by complementation of the xri1-1 mutation (which expresses a defective WRINKLED transcription factor). For example, as shown in FIG. 2C, the fatty acid content of seeds from AtWRI1$^{1-302}$ and AtWRI1$^{1-366}$ transformed plant lines have greater levels of fatty acids than seeds with the wri1-1 mutation. The fatty acid content of seeds expressing the YFP-AtWRI1 wild-type (WT) construct) is also shown in FIG. 2C.

AtWRI1-WT and AtWRI1 C-terminally truncated variants were transiently produced in *N. benthamiana* leaves. These experiments indicated an approximately 3-fold increase in YFP fluorescence signal intensity of AtWRI1$^{1-302}$ and AtWRI1$^{1-366}$ compared to AtWRI1 (FIG. 2A-2B). These results therefore provided a first clue that AtWRI1$^{IDR3}$ plays a role in mediating the degradation of AtWRI1. It is unlikely that the increased YFP fluorescence detected in FIG. 2 resulted from YFP released from AtWRI1 because YFP-AtWRI1 fluorescence was nuclear localized, and predominant nuclear localization was not observed in transformations with YFP alone (results not shown).

Example 5: AtWRI1$^{IDR3}$ is not Required for WRI1 Interaction with the E3 Ligase Linker Protein This Example describes results showing that wild type and variant AtWRI1 proteins interact with the BPM1 protein.

Recently, AtWRI1 was shown to be subject to 26S proteasome mediated degradation by interaction with BTB/POZ-MATH (BPM) proteins (Chen et al. *Plant Cell,* 25, 2253-2264 (2013)). When BPM proteins complex with transcription factors such as WRINKLED, the transcription factor is destabilized. However, the domain(s) of AtWRI1 responsible for the interaction between AtWRI1 and BPM proteins remain unknown. Because removal of IDR3 of AtWRI1 (AtWRI1$^{\Delta 367-430}$) led to increased YFP fluorescence intensity (FIG. 2), the inventors hypothesized that IDR3 of AtWRI1 might be a domain facilitating interaction of AtWRI1 with BPMs.

A bimolecular fluorescence complementation (BiFC) assay was used to investigate the interaction between AtWRI1 and a BPM protein (BPM1). AtWRI1 and BPM1 were subcloned to BiFC vectors which generated nYFP-AtWRI1 and cYFP-BPM1 (half N-terminus of YFP and half C-terminus of YFP, respectively). The BiFC assay was performed following transient expression of the constructs in *N. benthamiana* leaves.

The YFP signal was strong in the nucleus of epidermal cells when nYFP-AtWRI1 and cYFP-BPM1 were co-produced. No YFP fluorescence signal was observed when nYFP-AtWRI1 and cYFP-BPM1 were produced individually. These results indicate that AtWRI1 and BPM1 interacted in planta.

A fluorescence signal was still detected when nYFP-AtWRI1$^{1-366}$ (removal of IDR3) and cYFP-BPM1 were co-produced in the BiFC assay. These results show that IDR3 of AtWRI1 was not essential for the interaction between AtWRI1 and BPM1 protein. Accordingly, the major domain of AtWRI1 and BPM1 interaction does not reside in amino acids 367-430 of AtWRI1.

Example 6: AtWRI1$^{IDR3}$ Contains One PEST Domain

This Example illustrates that the AtWRI1$^{IDR3}$ region contains a PEST domain.

Given that AtWRI1$^{IDR3}$ is not essential for interaction with BPMs, the inventors investigated other functions of AtWRI1$^{IDR3}$ that may mediate AtWRI1 stability. A PEST domain (amino acid sequence enriched in proline (P), glutamic acid (E), serine (S), and threonine (T)) is considered a proteolytic signal (Rechsteiner and Rogers, *Trends Biochem Sci,* 21, 267-271 (1996): Rogers et al. *Science,* 234, 364-368 (1986)) and PEST domains are often found to be associated with IDRs (Singh et al. *Proteins,* 62, 309-315 (2006)). In silico analysis revealed that AtWRI1 had two PEST domains, one at about amino acid positions 4-34 (RLTTSTC SSSPSSSVSS STTTSSPIQS EAPR, SEQ ID NO:58), and the other at about amino acid positions 395-430 (RESPP SSSSPLSCLS TDSASSTTTT TTSVSCNYLV, SEQ ID NO:59).

Notably, both PEST domains are located in IDRs of AtWRI1 (IDR1 and IDR3 respectively). Given the fact that AtWRI1$^{\Delta IDR3}$ resulted in an increase of YFP fluorescence (FIG. 2), the C-terminal PEST domain AtWRI1$^{396-430}$ which is located in IDR3 may be involved in AtWRI1 protein degradation.

Example 7: The Transactivation Domain (TAD) of AtWRI1 does not Include the IDR3-PEST Domain This Example shows that the transactivation domain (TAD) of AtWRI1 does not include the IDR3-PEST region.

Previously it was shown that deletion of the C-terminal 170 amino acids of AtWRI1 (AtWRI1$^{\Delta 621-430}$) results in the abolishment of transactivation activity (Masaki et al. *Plant & cell physiology,* 46, 547-556 (2005)). Removing the PEST domain in AtWRI1$^{IDR3}$ to increase AtWRI1 protein stability may adversely affect the transactivation domain (TAD) of WRI1, also located in the C-terminal portion of the protein.

Experiments were performed to ascertain whether the entire AtWRI1$^{261-430}$ domain functions as a TAD or if the TAD of AtWRI1 can be further narrowed down within the C-terminus, and is not overlapping with the PEST domain. To address this question, the inventors used a GAL4-based One-Hybrid System. As shown in FIG. 3, there was no transactivation activity of AtWRI1$^{1-306}$ carrying a deletion of the C-terminal 124 amino acids.

Therefore, smaller regions within the AtWRI1 C-terminal end (AtWRI1$^{307-430}$) were tested to identify the putative TAD. The amino acid composition of AtWRI1 indicates that residues 307 to 430 of AtWRI1 are enriched in acidic amino acids (FIG. 3A), which are also common to TADs. The AtWRI1$^{307-430}$ deletion mutant maintained strong transactivation activity (FIG. 3B). Importantly, AtWRI1$^{307-397}$ displayed a similar transcriptional activity compared to wild-type AtWRI1, which indicates that the last 33 residues of AtWRI1 (AtWRI1$^{398-430}$) are not required for the AtWRI1 transactivation activity (FIG. 3B). However, deletion of either AtWRI1$^{307-368}$ or AtWRI1$^{369-430}$ showed a strongly reduced transcriptional activity (FIG. 3B). Taken together, these data indicate that the TAD for AtWRI1 is encompassed by AtWRI1$^{307-397}$ and does not overlap with the IDR3-PEST domain.

Example 8: AtWRI1 Degradation In Vitro is Slowed by Removal of IDR3-PEST Domain This Example describes experiments showing that removal of the C-terminal PEST domain increases the stability of the AtWRI1 protein.

To further identify the residues involved in determining the stability of the AtWRI1 protein and to investigate the AtWRI1 degradation mechanism in vitro, recombinant *E. coli*—was employed to produce the AtWRI1$^{1-397}$ protein without the IDR3-PEST domain, and the wild type AtWRI1 protein. These protein preparations were incubated in a cell-free system with total protein extracted from *Arabidopsis* WT seedlings (in the presence or absence of the 26S proteasome inhibitor MG132).

The *E. coli*-produced AtWRI1 protein degraded with incubation of the total protein extract (FIGS. 4A and 4B). AtWRI1 protein degradation decreased following the addition of the MG132 proteasome inhibitor into the *Arabidopsis* WT crude protein extracts. These results indicate that AtWRI1 degradation in cell-free assay displayed 26S proteasome dependence. Importantly, AtWRI1$^{1-397}$ displayed less degradation compared to AtWRI1 WT at five of six time points assayed in the cell-free assay (FIGS. 4A and 4B), indicating increased stability of AtWRI1$^{1-397}$. Taken together, the biochemical evidence indicates that the IDR3-PEST domain in AtWRI1 is critical for the stability of AtWRI1.

Example 9: AtWRI1$^{1-397}$ Enhances Oil Accumulation

This Example shows that deletion of the C-terminal IDR3-PEST domain of AtWRI1 increases oil production in seeds.

The sequence of the AtWRI1$^{1-397}$ protein is provided below (SEQ ID NO:65).

1 MKKRLTTSTC SSSPSSSVSS STTTSSPIQS EAPRPKRAKR
41 AKKSSPSGDK SHNPTSPAST RRSSIYRGVT RHRWTGRFEA
81 HLWDKSSWNS IQNKKGKQVY LGAYDSEEAA AHTYDLAALK
121 YWGPDTILNF PAETYTKELE EMQRVTKEEY LASLRRQSSG
161 FSRGVSKYRG VARHHHNGRW EARIGRVFGN KYLYLGTYNT
201 QEEAAAAYDM AAIEYRGANA VTNFDISNYI DRLKKKGVFP
241 FPVNQANHQE GILVEAKQEV ETREAKEEPR EEVKQQYVEE
281 PPQEEEEKEE EKAEQQEAEI VGYSEEAAVV NCCIDSSTIM
321 EMDRCGDNNE LAWNFCMMDT GFSPFLTDQN LANENPIEYP
361 ELFNELAFED NIDFMFDDGK HECLNLENLD CCVVGRE

The inventors generated an YFP-AtWRI1$^{1-397}$ plant expression construct that did not include the IDR3-PEST domain to further characterize the function of the C-terminal region of AtWRI1. When the YFP-AtWRI1$^{1-397}$ protein is transiently expressed in *N. benthamiana* assays the YFP fluorescence intensity was increased. qRT-PCR indicated that there was no noticeable difference in transcript levels between YFP-AtWRI1 and YFP-AtWRI1$^{1-397}$ and therefore the increased fluorescence intensity was not the result of differences in transcript stability.

Comparison of triacylglycerol (TAG) accumulation following YFP-AtWRI1 and YFP-AtWRI1$^{1-397}$ transient production in *N. benthamiana* leaves showed that the TAG content in the presence of YFP-AtWRI1$^{1-397}$ was approximately 2 fold higher than in leaves expressing YFP-AtWRI1 (FIG. 4C). Thus, YFP-AtWRI1$^{1-397}$ expression resulted in enhanced fluorescence intensity and in increased oil biosynthesis in the *N. benthamiana* transient assay.

Example 10: Removal of Phosphorylation Sites in the IDR3-PEST Domain Enhances WRI1 Stability This Example describes experiments evaluating the stability of AtWRI1 with and without the predicted phosphorylation sites in the IDR3-PEST domain.

At present there is no direct experimental evidence for phosphorylation of AtWRI1. To investigate the possible involvement of phosphorylation in AtWRI1 stability, putative phosphorylation sites (Ser/Thr/Tyr (S/T/Y)) of AtWRI1 were identified using NetPhos 2.0 as being those that are underlined and in bold in SEQ ID NO:60 sequence shown below.

397 ESPPSSSSPLSCLSTDSASSTTTTTTSVSCNYLV 430

Notably, abundant phosphorylation sites were predicted in AtWRI1$^{IDR3}$ and all were localized in the PEST domain.

Using an indirect but readily feasible approach to investigate a potential role of phosphorylation, a multi-point mutant was generated in which all predicted AtWRI1 PEST phosphorylation sites (AtWRI1$^{S398A/S401A/S402A/S407A/S415A/S416A/T420A/F421A/422A/S423A}$, abbreviated AtWRI1$^{PEST/AA}$; SEQID NO:30) were substituted with alanine (A)). The PEST domain of this AtWRI$^{PEST/AA}$ transcription factor has the following sequence (SEQ ID NO:61).

397 EAPP
401 AASSPLACLS TDSAAATTTA AAAVSCNYLV

The signal intensity in the YFP-AtWRI1$^{PEST/AA}$ was stronger compared to YFP-AtWRI1 in transient expression assays (FIG. 4D), consistent with increased stability of AtWRI1$^{PEST/AA}$. Furthermore, AtWRI1$^{PEST/AA}$ enhanced oil biosynthesis in transient expression assays (FIG. 4E). Stable transgenic wri1-1 plants expressing 35S:AtWRI1 and 35S:AtWRI1$^{PEST/AA}$ were also generated. As shown in FIG. 5, the fatty acid content in seeds of 35S:AIWRI1$^{PEST/AA}$/wri1-1 transgenic lines (#7 and #9) was higher than 35S:AtWRI1/wri1-1 transgenic lines. Taken together, these results indicate that phosphorylation site mutations in the PEST domain of AtWRI1$^{IDR3}$ lead to increased AtWRI stability and increased oil biosynthesis in planta.

Example 11: Phosphorylation Mimics of the IDR3-PEST Domain do not Enhance AtWRI1 Stability or Oil Accumulation To further explore the role of phosphorylation in AtWRI1 stability, the inventors generated a phosphorylation mimic mutant of AtWRI1 (AtWRI1$^{S398D/S401D/S402D/S407D/S415D/S416D/T420D/T421D/T422D/S423D}$; (with the simplified designation "AtWRI1$^{PEST/DD}$"; SEQ ID NO:31)) by substituting all putative phosphorylation sites in AtWRI1$^{PEST}$ with Asp (D).

Yellow fluorescent protein (YFP) fluorescence and oil production induced by YFP-AtWRI1$^{PEST/DD}$ were examined in *N. benthamiana* leaves. In contrast to the alanine substitutions, YFP-AtWRI1$^{PEST/DD}$ did not cause an increase in the fluorescence signal (FIG. 4F). Furthermore, TAG production due to the presence of YFP-AtWRI1$^{PEST/DD}$ was not increased as was observed for YFP-AtWRI1 (FIG. 4G). These data indicate that phosphorylation at the C-terminal PEST domain in AtWRI1 may be critical for function or stability of AtWRI1.

DISPHOS 1.3 and NetPhos 2.0 (disorder-enhanced phosphorylation sites prediction programs) was employed to narrow down the residue(s) in the PEST domain affecting AtWRI1 stability. DISPHOS 1.3 and NetPhos 2.0 showed different predictions of phosphorylation sites in the IDR3-PEST domain of AtWRI1. However, four residues (S398/S401/S402/S407) were consistently predicted by both programs—these four are identified in bold and by underlining in the SEQ ID NO:60 below.

397 ESPPSSSSPLSCLSTDSASSTTTTTTSVSCNYLV 430 NetPhos 2.0

397 ESPPSSSSPLSCLSTDSASSTTTTTTSVSCNYLV 430 DISPHOS1.3

An additional putative phosphorylation site mutant of AtWRI1 ($AtWRI1^{S398A/S401A/S402A/S407A}$ ($AtWRI1^{4SA}$)) Was generated that had the following sequence (SEQ ID NO:62).

1 MKKRLTTSTC SSSPSSSVSS STTTSSPIQS EAPRPKRAKR
41 AKKSSPSGDK SHNPTSPAST RRSSIYRGVT RHRWTGRFEA
81 HLWDKSSWNS IQNKKGKQVY LGAYDSEEAA AHTYDLAALK
121 YWGPDTILNF PAETYTKELE EMQRVTKEEY LASLRRQSSG
161 FSRGVSKYRG VARHHHNGRW EARIGRVFGN KYLYLGTYNT
201 QEEAAAAYDM AAIEYRGANA VTNFDISNYI DRLKKKGVFP
241 FPVNQANHQE GILVEAKQEV ETREAKEEPR EEVKQQYVEE
281 PPQEEEEKEE EKAEQQEAEI VGYSEEAAW NCCIDSSTIM
321 EMDRCGDNNE LAWNFCMMDT GFSPFLTDQN LANENPIEYP
361 ELFNELAFED NIDFMFDDGK HECLNLENLD CCVVGREAPP
401 AASSPLACLS TDSASSTTTT TTSVSCNYLV

The PEST domain of this $AtWRI1^{4SA}$ transcription factor therefore has the following sequence (SEQ ID NO:63).

397 EAPP AASSPLACLS TDSASSTTTT TTSVSCNYLV

In addition, a phosphorylation mimic mutant of AtWRI1 ($AtWRI1^{S398D/S401D/S402D/S407D}$($AtWRI1^{4SD}$) was generated by substituting the four consensus predicted phosphorylation sites in the IDR3-PEST domain of AtWRI1 with Asp (D). The sequence of the $AtWRI1^{4SD}$ protein is provided below (SEQ ID NO:64).

1 MKKRLTTSTC SSSPSSSVSS STTTSSPIQS EAPRPKRAKR
41 AKKSSPSGDK SHNPTSPAST RRSSIYRGVT RHRWTGRFEA
81 HLWDKSSWNS IQNKKGKQVY LGAYDSEEAA AHTYDLAALK
121 YWGPDTILNF PAETYTKELE EMQRVTKEEY LASLRRQSSG
161 FSRGVSKYRG VARHHHNGRW EARIGRVFGN KYLYLGTYNT
201 QEEAAAAYDM AAIEYRGANA VTNFDISNYI DRLKKKGVFP
241 FPVNQANHQE GILVEAKQEV ETREAKEEPR EEVKQQYVEE
281 PPQEEEEKEE EKAEQQEAEI VGYSEEAAVV NCCIDSSTIM
321 EMDRCGDNNE LAWNFCMMDT GFSPFLTDQN LANENPIEYP
361 ELFNELAFED NIDFMFDDGK HECLNLENLD CCVVGREDPP
401 DDSSPLDCLS TDSASSTTTT TTSVSCNYLV

Transient expression assays indicated that $AtWRI1^{4SA}$ was able to increase AtWRI1 stability (increased YFP signal intensity) and did produce increased TAG biosynthesis in planta (FIG. 6A-6B). In contrast, the phosphorylation mimic mutant $AtWRI1^{4SD}$ failed to either increase stability or elevate TAG production (FIG. 6A-6B). Taken together, these results show that $AtWRI1^{4SA}$ is sufficient to generate a more stable AtWRI1 protein and that phosphorylation at Ser-398, 401, 402 and 407 in AtWRI1 contributes to the degradation of AtWRI1.

Hence WRINKLED transcription factors with mutations in PEST domains such as the following can increase oil production in plants, plant cells, and plant seeds.

EAPP AASSPLACLS TDSASSTTTT TTSVSCNYLV (SEQ ID NO:63).

Identification of a PEST domain in $AtWRI1^{IDR3}$ and its mutational analysis therefore shows that the PEST domain is at the core of IDR3, and it mediates the degradation of AtWRI1. The PEST domain does not overlap the TAD.

Example 11: IDR3-PEST Proline Residues do not Contribute to AtWRI1 Stability

AtWRI1 mutants with alanine or leucine at positions 399, 400, and 405 instead of proline ($AtWRI1^{P399A/P400A/P405A}$ ($AtWRI1^{P3A}$) and $AtWRI1^{P399L/P400L/P405L}$ ($AtWRI1^{P3L}$)) were generated. The functions of these mutants were analyzed in transient assays. FIG. 6 shows that neither $AtWRI1^{P3A}$ nor $AtWRI1^{P3L}$ led to an increase in TAG biosynthesis compared to AtWRI1. These results show that proline residues in the AtWRI1 IDR3-PEST domain were not essential for determining AtWRI1 stability.

Example 12: Construction of WRI1 and 14-3-3K Transgenes and Assays Therefor

This Example describes some of the expression cassettes and assays for WRI1 and 14-3-3κ.

Plasmid Construction

Growth conditions and methods for *Arabidopsis* (*A. thaliana*) and *N. benthamiana* plants were as described (Ma et al. 2013). *Arabidopsis* transformation and transgenic seedling selection was done as previously described (Ma et al. *PloS one* 8: e68887 (2013)).

The coding sequences of AtWRI1 (including truncated AIWRI1 variants) and 14-3-3 isoforms were amplified by PCR and introduced into the pENTR4 vector (Life Technologies). Entry constructs were combined with destination vectors (yeast-two-hybrid (Y2H) vectors, BiFC vectors, and pEarlygate binary vectors) through LR reactions (Life Technologies) as described by Ma et al. (*The Plant journal,* 83, 864-874 (2015)). Entry constructs of 14-3-3κ, 14-3-3λ, 14-3-3ν and BPM1 were obtained from the *Arabidopsis* Biological Resource Center (ABRC). A list of the primers used for plasmid construction is given in Table 1.

TABLE 1

Primers for WRI1 and 14-3-3

| Primer Name | Sequence 5' to 3' | SEQ ID NO: |
|---|---|---|
| AtWRI1-FW | AATGGATCCGGACAATGAAGAAGCGCTTA | 78 |
| AtWRI1-RV | TCCCTCGAGTCAGACCAAATAGTT | 79 |
| AtWRI1 1-64-RV | TCCCTCGAGTCAAGAGCTGCGTCGGGTAGAAGC | 80 |
| AtWRI1 1-77-RV | TCCCTCGAGTCATCTCCCAGTCCATCTATGTCTAGTGAC | 81 |

TABLE 1-continued

| Primers for WRI1 and 14-3-3 | | |
|---|---|---|
| Primer Name | Sequence 5' to 3' | SEQ ID NO: |
| AtWRI1 1-92-RV | TCCCTCGAGTCACTGAATCGAATTCCAAGA GCTTTT | 82 |
| AtWRI1 1-101-RV | TCCCTCGAGTCACAGATAAACTTGTTTGCC TTTCTTGT | 83 |
| AtWRI1 1-132-RV | TCCCTCGAGTCATGCCGGAAAATTCAAGAT GGTGTCGG | 84 |
| AtWRI1 1-240-RV | TAACTCGAGTTACGGGAAAACACC | 88 |
| AtWRI1 1-306-RV | TGACTCGAGTCATTCTTCTGAATATCC | 89 |
| 14-3-3u-FW | ACTGGATCCGGACAATGTCTTCTGATTCGTCC | 90 |
| 14-3-3u-RV | TATCTCGAGTCACTGCGAAGGTGGTGG | 91 |

Y2H Assay

The Y2H transactivation activity of AtWRI1 variants was evaluated by 3-galactosidase (β-Gal) activity, and as described in the foregoing Examples. Both colony-lift filter assay and liquid culture assay were performed according to the Yeast Protocols Handbook (Clonetech). 5-bromo-4-chloro-3-indolyl-β-D-galactopyranoside (X-GAL) was used as the substrate for the colony-lift filter assay and o-nitrophenyl-β-D-galactopyranoside (ONPG) was chosen as the substrate for the liquid culture assay.

Transient Expression in *N. benthamiana*

*Agrobacterium tumefaciens*-mediated transient expression in *N. benthamiana* was done as previously described (Ma et al. 2015).

Subcellular Localization and BiFC Experiments

The subcellular localization and BiFC experiments, were done as previously described (Ma et al. 2015).

Quantitative Real-Time PCR (qRT-PCR)

RNA extraction, cDNA synthesis and qRT-PCR experiments were done as previously (Ma et al. 2013). The primers used for AIWRI1 and NbPP2A were as described in (Ma et al. 2015).

*Arabidopsis* sequences were used to search against the *Nicotiana benthamiana* database (see website at benthgenome.qut.edu.au/). The qRT-PCR primers were designed by Primer-Blast (Ye et al. 2012). The primers used for qRT-PCR are summarized in Table 2.

TABLE 2

| Primers for qRT-PCR | | |
|---|---|---|
| Primer Name | Sequence 5' to 3' | SEQ ID NO: |
| NbBCCP2-FW | TTTCAGTGTCCCTTGTCGCA | 92 |
| NbBCCP2-RV | TCAAGGAAACGGAGACGTGG | 93 |
| NbACP1-FW | TCAGGTGCATTTGAAGGGCT | 94 |
| NbACP1-RV | CTGGTTTAGCCGCACACiGTA | 95 |
| NbPKPβ1-FW | A TTGTCCATCCCACCCCAAC | 96 |
| NbPKPβ1-RV | AACAGCATCAGCACCCTCTC | 97 |
| NbKAS1-FW | TGGTCACAACTCTGTCGTCG | 98 |
| NbKAS1-RV | TCTCGCCGCACCTTGTTTAT | 99 |
| NbDGAT1-FW | CGGCCAATCCCTTAACGACT | 100 |
| NbDGAT1-RV | CTCTGTGTGGTGCiTGCTGAT | 101 |
| AtWRI1-FW | AGAGCAGTGGTTTCTCC.AGAGG | 102 |
| AtWRI1-RV | TTCCGTTGTGGTGATGCCTAGC | 103 |
| NbPP2A-FW | GACCCTGATGTTGATGTTCGCT | 104 |
| NbPP2A-RV | GAGGGATTTGAAGAGAGATTTC | 105 |

Protein Extraction and Western Blotting

Three days after bacterial infiltration, infiltrated *N. benthamiana* leaves were harvested and ground into fine powder in liquid nitrogen. Crude nuclear protein extracts were isolated from *N. benthamiana* using CelLytic PN Isolation/Extraction Kit (Sigma) according to the manufacturer's instructions. The Myc-AtWRI1 protein was detected by western blotting using an anti-myc primary antibody (Santa Cruz Biotechnology) at 1:200 dilution and anti-mouse IgG at 1:2000 dilution. The western blotting procedure followed the methods described in (Ma et al. 2015).

Fatty Acid Analysis

Lipid analysis in *N. benthamiana* and *Arabidopsis* were done as previously described (Ma et al. 2013, Ma et al. 2015).

Example 13: AtWRI1 is a 14-3-3 Client

To examine the interaction between AtWRI1 and 14-3-3s, we performed yeast-two-hybrid (Y2H) assays. AtWRI1 showed physical interaction with 14-3-3K and 14-3-3λ isoforms in this assay (FIG. 8).

Based on data obtained by microarray analysis (Winter et al. PloS one 2: e718 (2007)), both 14-3-3κ and 14-3-3λ are ubiquitously expressed during the majority of plant developmental stages including seed development, when AtWRI1 is most highly expressed (data not shown). These overlapping expression profiles provide in planta biological context for an interaction between AtWRI1 and a 14-3-3 protein.

Example 14: AtWRI1 and 14-3-3s are Expressed in Cellular Nuclei

Previous studies indicated that some 14-3-3 isoforms have a broad subcellular distribution, including the nucleus (Bihn et al. *Plant Journal* 12: 1439-1445 (1997); Carrasco et al. *PloS one:* 9 (2014); Paul et al. *Frontiers in plant science* 3: 190 (2012); Paul et al. *Molecular biology of the cell* 16: 1735-1743 (2005)) while AtWRI1 is active exclusively in the nucleus (Chen et al. *Plant Cell* 25: 2253-2264 (2013); Ma et al 2015). To further gain corroboration of the relevance of AtWRI1 and 14-3-3 protein interaction in planta, the location of AtWRI1 and 14-3-3 proteins was probed in plant cells. AtWRI1-CFP, YFP-14-3-3K, and YFP-14-3-3, were transiently produced in *N. benthamiana* leaves. AtWRI1-CFP was found to be present in the nucleus and YFP-14-3-3κ (or YFP-14-3-3)) in both the nucleus and the cytoplasm. Therefore, AtWRI1 and 14-3-3s have the potential to interact in the nucleus of plant cells.

Example 15: AtWRI1 and 14-3-3 Proteins Interact in Planta

In order to validate the interaction between AtWRI1 and 14-3-3 proteins, the interaction between AtWRI1 and 14-3-3s in planta was tested through a bimolecular fluorescence complementation (BiFC) assay. cDNAs encoding AtWRI1 and two 14-3-3 isoforms (14-3-3K and 14-3-3)) were introduced into BiFC vectors enabling protein fusions to the N-terminal half of YFP and C-terminal half of YFP (nYFP-AtWRI1 and cYFP-14-3-3s, respectively). nYFP-AtWRI1 and cYFP-14-3-3s were transiently co-produced in *N. benthamiana* leaves and strong YFP fluorescence signals were detected in the nucleus (data not shown). No fluorescence was observed when nYFP-AtWRI1 or cYFP-14-3-3s were produced alone (data not shown). Therefore, AtWRI1 and 14-3-3 proteins can interact in planta in the nucleus.

Example 16: 14-3-3 Enhances AtWRI1-Induced Triacylglycerol (TAG) Biosynthesis

In order to determine if 14-3-3 proteins affect the activity of AtWRI1 on genes encoding enzymes required for oil biosynthesis, AtWRI1- and 14-3-3-encoding cDNAs were transiently co-expressed in *N. benthamiana* leaves.

Co-production of 14-3-3κ or 14-3-3λ and AtWRI1 proteins led to increased TAG content compared to production of AtWRI1 alone (FIG. 9C). Transient production of 14-3-3κ or 14-3-3λ proteins alone did not lead to the activation of TAG biosynthesis (FIG. 9C), which indicated that the increase in oil biosynthesis attributed to 14-3-3κ was AtWRI1-dependent.

Since the expression level of WRI1 is very low in plant leaves, these results indicate that the increased oil content through co-production of 14-3-3s and AtWRI1 (FIG. 9C) may be due to the interaction of the 14-3-3 protein with AtWRI1.

Example 17: Overexpression of 14-3-3K and 14-3-32 Increases Seed Oil Content

Stable transgenic plants were generated that overexpress 14-3-3κ and 14-3-3λ cDNAs. As shown in FIG. 9A-9B, transgenic plants overproducing 14-3-3 isoforms displayed increased seed oil content compared to WT. Thus, the analysis of oil content in 14-3-3s transgenic seeds further indicated that 14-3-3κ and 14-3-3λ enhance AtWRI1-mediated plant oil biosynthesis.

Example 18: 14-3-3 Enhanced AtWRI1 Transcriptional Activity

This Example describes the effects of 14-3-3s on AtWRI1 transcriptional activity. Transient expression of AtWRI1 in *N. benthamiana* leaves activated the expression of AtWRI1 target genes including BCCP2, ACP1, PKPβ1 and KAS1 (FIG. 10). Notably, co-production of 14-3-3K with AtWRI1 resulted in an increased expression of AtWRI1 target genes compared to AtWRI1 alone (FIG. 10). 14-3-3K production had no effect on the expression of either AtWRI1 or DGAT1 (a non-AtWRI1 target gene) (FIG. 10). Therefore, the effect was specific for known AtWRI1 targets.

Example 19: 14-3-3 Increases AtWRI1 Stability

In mammalian cells, 14-3-3s have been found to increase the stability of their clients through their direct interaction (Oh et al. 2013, Yang el al. 2003). As indicated in FIG. 10, 14-3-3 did not increase AtWRI1 transcript levels.

To understand the effect of the interaction between 14-3-3s and AtWRI1 on AtWRI1-regulated oil biosynthesis, tests were performed to ascertain whether 14-3-3 affected AtWRI1 protein stability, using the *N. benthamiana* transient expression system. Western blot analysis indicated that co-production of Flag-14-3-3u increased the protein level of Myc-AtWRI1 compared to Myc-AtWRI1 alone (FIG. 11A).

Hence, these results indicate that the 14-3-3 protein may stabilize AtWRI1, which provides a molecular mechanism for the effects of 14-3-3s on AtWRI1 transcriptional activity and WRI1-dependent TAG biosynthesis.

Example 20: Redundancy of 14-3-3s

This Example describes tests to ascertain whether various 14-3-3 isoforms can affect AtWRI1-mediated oil biosynthesis.

Two 14-3-3 isoforms (14-3-3u and 14-3-3ν) both exhibited expression in developing embryos of *Arabidopsis* (data not shown). Interestingly, coproduction of two additional 14-3-3 isoforms (14-3-3υ and 14-3-3ν) led to enhanced AtWRI1-mediated oil biosynthesis (FIG. 11B-11C). Further Y2H assays indicated that AtWRI1 interacted with 14-3-3υ and 14-3-3ν (FIG. 11D). Thus, several different 14-3-3 isoforms can enhance AtWRI1-regulated oil biosynthesis.

Example 21: Characterization of the 14-3-3 Binding Motif in AtWRI1

This Example describes experiments to further delineate the molecular basis of the interaction between 14-3-3 and AtWRI1.

Y2H assays were used to probe the interaction between 14-3-3κ and truncated AtWRI1 variants (FIG. 12A). As shown in FIG. 12B, AtWRI1$^{1-64}$ and AtWRI1$^{1-77}$ did not interact to the same extent with 14-3-3κ as AtWRI1$^{1-92}$ and other truncated AtWRI1 variants. These results indicated that the region of AtWRI$^{178-92}$, which falls within the first AP2 domain of AtWRI1, was important for the interaction between 14-3-3 and AtWRI1.

Example 22: The 14-3-3 Binding and E3 Ligase Linker Motifs of WRI1 Overlap

The inventors' previous results indicate that the C-terminal IDR3 domain of AtWRI1 is not the domain for the interaction with the E3 ligase linker BPM protein (Chen et al. *Plant Cell,* 25, 2253-2264 (2013)). The inventors now hypothesize that the interaction between 14-3-3 and AtWRI1 might interfere with the interaction between AtWRI1 and BPMs, given that 14-3-3 seemed to increase the stability of AtWRI1 and its transcriptional activity. To test this hypothesis, Y2H assays were performed on truncated AtWRI1 proteins.

FIG. 12C illustrates results of mapping of the binding region within AtWRI1 for the E3 ligase bridge protein BPM1 by Y2H assay. As shown in FIG. 12C, the AtWRI1 1-77 truncated protein had no interaction with BPM1, while interaction was exhibited for AtWRI1$^{1-92}$. Thus, the 14-3-3 binding motif in AtWRI1 (AtWRI1$^{78-92}$) appears to overlap with that for BPM.

Hence, the foregoing Examples provide evidence that 14-3-3 proteins can stabilize the AtWRI1 protein and enhances its transcriptional activity (FIGS. 10-11). Deletion assays indicate that the 14-3-3 binding motif in AtWRI1 overlaps with the WRI1 interaction domain for the E3 ligase bridge protein BPM1 (FIG. 12A-12C).

Data described herein also show that 14-3-3 binding motif is present in the first AP2 domain of AtWRI1. The inventors have previously identified "99VYL101" in the first AP2 domain in AtWRI1 as a set of residues that may be involved in interaction of AtWRI1 with other biological molecules (Ma et al. 2013). The application illustrates that AtWRI178-92 (FEAHLWDKSSWNSIQ, SEQ ID NO:77) acts as the core 14-3-3 binding motif which is also located in the first AP2 domain ofAtWRIL. The AP2 domain is a conserved feature of all plant AP2 transcription factors.

Phosphorylation of AtWRI1 may have a dual function (see, e.g., FIG. 13). The inventors hypothesize that phosphorylation of AtWRI1 may create a binding site for a 14-3-3 protein as a step during early plant embryo development, which facilitates the stabilization of the AtWRI1 protein. The inventors further hypothesize that phosphorylation of AtWRI1 at the C-terminal IDR3-PEST can serve as a mechanism during late stage of plant embryo development, when the activity of WRI1 needs to be down-regulated perhaps by degradation of AtWRI1 protein. The phosphorylation of AtWRI1 at the 14-3-3 binding motif and C-terminal IDR3-PEST motif could provide a protein kinase-based fine-tuning mechanism which takes cues from relevant signal transduction pathways during embryo development and seed maturation.

FIG. 13 is a proposed model illustrating the modulation of WRI1 activity and oil biosynthesis by the interaction with 14-3-3. Interaction of AtWRI1 and the cullin3-based E3 ligase linker (BPM) leads to the degradation of AtWRI1 and as a result maintains the AtWRI1 protein at low levels. Developmentally regulated phosphorylation of AtWRI1 by creates a 14-3-3 binding site that causes the detachment of the E3 ligase from the AtWRI1 protein or that prevents the E3 ligase from interacting with AtWRI1. Hence, the AtWRI1-14-3-3 protein complex displays increased stability and enhanced transcriptional activity.

These features provide strategies for increasing oil content in plant cells for use in a variety of ways, including for example, generating energy-rich foods and forage, and as a source of oil for biofuels.

REFERENCES

Baud, S., Mendoza, M. S., To, A., Harscoet, E., Lepiniec, L. and Dubreucq, B. (2007) WRINKLED1 specifies the regulatory action of LEAFY COTYLEDON2 towards fatty acid metabolism during seed maturation in *Arabidopsis. Plant J,* 50, 825-838.

Blom, N., Gammeltoft, S. and Brunak, S. (1999) Sequence and structure-based prediction of eukaryotic protein phosphorylation sites. *J Mol Biol,* 294, 1351-1362.

Cernac, A. and Benning, C. (2004) WRINKLED1 encodes an AP2/EREB domain protein involved in the control of storage compound biosynthesis in *Arabidopsis. Plant J,* 40, 575-585.

Chen, L, Lee, J. H., Weber, H., Tohge, T., Witt, S., Roje, S., Fernie, A. R. and Hellmann, H. (2013) *Arabidopsis* BPM Proteins Function as Substrate Adaptors to a CULLIN3-Based E3 Ligase to Affect Fatty Acid Metabolism in Plants. *Plant Cell,* 25, 2253-2264.

Duek, P. D., Elmer, M. V., van Oosten, V. R. and Fankhauser, C. (2004) The degradation of HFR1, a putative bHLH class transcription factor involved in light signaling, is regulated by phosphorylation and requires COP1. *Curr Biol,* 14, 2296-2301.

Dunker, A. K., Brown, C. J., Lawson, J. D., lakoucheva, L. M. and Obradovic, Z. (2002) Intrinsic disorder and protein function. *Biochemistry,* 41, 6573-6582.

Dyson, H. J. and Wright, P. E. (2005) Intrinsically unstructured proteins and their functions. *Nat Rev Mol Cell Biol,* 6, 197-208.

Evrard, A., Kumar, M., Lecourieux, D., Lucks, J., von Koskull-Doring, P. and Hirt, H. (2013) Regulation of the heat stress response in *Arabidopsis* by MPK6-targeted phosphorylation of the heat stress factor HsfA2. *PeerJ,* 1, e59.

Focks, N. and Benning, C. (1998) wrinkledl: A novel, low-seed-oil mutant of *Arabidopsis* with a deficiency in the seed-specific regulation of carbohydrate metabolism. *Plant Physiol,* 118, 91-101.

Gao, J. and Xu, D. (2012) Correlation between posttranslational modification and intrinsic disorder in protein. *Pac Symp Biocomput,* 94-103.

Garcia-Alai, M. M., Gallo, M., Salame, M., Wetzler, D. E., McBride, A. A., Paci, M., Cicero, D. O. and de Prat-Gay, G. (2006) Molecular basis for phosphorylation-dependent, PEST-mediated protein turnover. *Structure,* 14, 309-319

Hara, A. and Radin, N. S. (1978) Lipid extraction of tissues with a low-toxicity solvent. *AnalBiochem,* 90, 420-426.

Hardtke, C. S., Gobda, K., Osterlund, M. T., Oyama, T., Okada, K. and Deng, X. W. (2000) HY5 stability and activity in *arabidopsis* is regulated by phosphorylation in its COP1 binding domain. *EMBO J,* 19, 4997-5006.

Iakoucheva, L. M., Radivojac, P., Brown, CJ., O'Connor, T. R., Sikes, J. G., Obradovic, Z. and Dunker, A. K. (2004) The importance of intrinsic disorder for protein phosphorylation. *Nucleic Acids Res,* 32, 1037-1049.

Kjaersgaard, T., Jensen, M. K., Christiansen, M. W., Gregersen, P., Kragelund, B. B. and Skriver, K. (2011) Senescence-associated barley NAC (NAM, ATAF1,2, CUC) transcription factor interacts with radical-induced cell death 1 through a disordered regulatory domain. *J Biol Chem,* 286, 35418-35429.

Kong, Q., Pattanaik, S., Feller, A., Werkman, J. R., Chai, C., Wang, Y., Grotewold, E. and Yuan, L. (2012) Regulatory switch enforced by basic helix-loop-helix and ACT-domain mediated dimerizations of the maize transcription factor R. *Proc Natl Acad Sci USA,* 109, E2091-2097.

Kragelund, B. B., Jensen, M. K. and Skriver, K. (2012) Order by disorder in plant signaling. *Trends in plani science,* 17, 625-632.

Kurotani, A, Tokmakov, A. A., Kuroda, Y., Fukami, Y., Shinozaki, K. and Sakurai, T. (2014) Correlations between predicted protein disorder and post-translational modifications in plants. *Bioinformatics.*

Li, Y., Beisson, F., Pollard, M. and Ohlrogge, J. (2006) Oil content of *Arabidopsis* seeds: the influence of seed anatomy, light and plant-to-plant variation. *Phytochemistry,* 67, 904-915.

Lindemose, S., O'Shea, C., Jensen, M. K. and Skriver, K. (2013) Structure, function and networks of transcription factors involved in abiotic stress responses. *Int J Mol Sci,* 14, 5842-5878.

Liu, D., Shi, L, Han, C., Yu, J., Li, D. and Zhang, Y. (2012) Validation of reference genes for gene expression studies in virus-infected *Nicotiana benthamiana* using quantitative real-time PCR. *PloS one,* 7, e46451.

Liu, H. and Stone, S. L. (2013) Cytoplasmic degradation of the *Arabidopsis* transcription factor abscisic acid insensitive 5 is mediated by the RING-type E3 ligase KEEP ON GOING. *J Biol Chem,* 288, 20267-20279.

Liu, J., Hua, W., Zhan, G., Wei, F., Wang, X., Liu, G. and Wang, H. (2010) Increasing seed mass and oil content in transgenic *Arabidopsis* by the overexpression of wri1-like gene from *Brassica napus. Plant Physiol Biochem,* 48, 9-15.

Liu, J., Perumal, N. B., Oldfield, C. J., Su, E. W., Uversky, V. N. and Dunker, A. K. (2006) Intrinsic disorder in transcription factors. *Biochemistry,* 45, 6873-6888.

Liu, Z. P., Galindo, R L. and Wasserman, S. A. (1997) A role for CKII phosphorylation of the cactus PEST domain in dorsoventral patterning of the *Drosophila* embryo. *Genes Dev,* 11, 3413-3422.

Lu, Q. S., Paz, J. D., Pathmanathan, A., Chin, R. S., Tsai, A. Y. and Gazzarrini, S. (2010) The C-terminal domain of FUSCA3 negatively regulates mRNA and protein levels, and mediates sensitivity to the hormones abscisic acid and gibberellic acid in *Arabidopsis. Plant J,* 64, 100-113.

Ma, W., Kong, Q., Arondel, V., Kilaru, A., Bates, P. D., Thrower, N. A., Benning, C. and Ohblrogge, J. B. (2013) Wrinkled 1, a ubiquitous regulator in oil accumulating tissues from *Arabidopsis* embryos to oil palm mesocarp. *PloS one,* 8, e68887.

Ma, W., Kong, Q., Grix, M., Mantyla, J. J., Yang, Y., Benning, C. and Ohilrogge, J. B. (2015) Deletion of a C-terminal intrinsically disordered region of WRINKLED1 affects its stability and enhances oil accumulation in *Arabidopsis. The Plant Journal,* 83, 864-874.

Maeo, K., Tokuda, T., Ayame, A., Mitsui, N., Kawai, T., Tsukagoshi, H., Ishiguro, S. and Nakamura, K. (2009) An AP2-type transcription factor, WRINKLED1, of *Arabidopsis thaliana* binds to the AW-box sequence conserved among proximal upstream regions of genes involved in fatty acid synthesis. *Plant J,* 60, 476-487.

Marchive C, N. K., To A, Lepiniec L & and Baud S (2014) Transcriptional regulation of fatty acid production in higher plants: Molecular bases and biotechnological outcomes. *Eur J Lipid Sci Technol,* 116, 1332-1343.

Marin, M., Thallmair, V. and Ott, T. (2012) The intrinsically disordered N-terminal region of AtREMI 0.3 remorin protein mediates protein-protein interactions. *J Biol Chem,* 287, 39982-39991.

Masaki, T., Mitsui, N., Tsukagoshi, H., Nishii, T., Morikami, A. and Nakamura, K. (2005) ACTIVATOR of Spomin:: LUC1/WRINKLED1 of *Arabidopsis thaliana* transactivates sugar-inducible promoters. *Plant & cell physiology,* 46, 547-556.

Meyer, R. D., Srinivasan, S., Singh, A. J., Mahoney, J. E., Gharahassanlou, K. R. and Rahimi, N. (2011) PEST motif serine and tyrosine phosphorylation controls vascular endothelial growth factor receptor 2 stability and downregulation. *Mol Cell Biol,* 31, 2010-2025.

Mitchell, P. J. and Tjian, R. (1989) Transcriptional regulation in mammalian cells by sequence-specific DNA binding proteins. *Science,* 245, 371-378.

Miura, K., Ohta, M., Nakazawa, M., Ono, M. and Hasegawa, P. M. (2011) ICEl Ser403 is necessary for protein stabilization and regulation of cold signaling and tolerance. *Plant J,* 67, 269-279.

Mizoi, J., Ohori, T., Moriwaki, T., Kidokoro, S., Todaka, D., Maruyama, K., Kusakabe, K., Osakabe, Y., Shinozaki, K. and Yamaguchi-Shinozaki, K. (2013) GmDREB2A; 2, a canonical DEHYDRATION-RESPONSIVE ELEMENT-BINDING PROTEIN2-type transcription factor in soybean, is posttranslationally regulated and mediates dehydration-responsive element-dependent gene expression. *Plant Physiol,* 161, 346-361.

Oldfield, C. J., Cheng, Y., Cortese, M. S., Brown, C. J., Uversky, V. N. and Dunker, A. K. (2005) Comparing and combining predictors of mostly disordered proteins. *Biochemistry,* 44, 1989-2000.

Pazos, F., Pietrosemoli, N., Garcia-Martin, J. A. and Solano, R. (2013) Protein intrinsic disorder in plants. *Frontiers in plant science,* 4, 363.

Pouvreau, B., Baud, S., Vernoud, V., Morin, V., Py, C., Gendrot, G., Pichon, J. P., Rouster, J., Paul, W. and Rogowsky, P. M. (2011) Duplicate maize Wrinkled1 transcription factors activate target genes involved in seed oil biosynthesis. *Plant Physiol,* 156, 674-686.

Radivojac, P., Obradovic, Z., Brown, C. J. and Dunker, A. K. (2003) Prediction of boundaries between intrinsically ordered and disordered protein regions. *Pac Symp Biocomput,* 216-227.

Rechsteiner, M. and Rogers, S. W. (1996) PEST sequences and regulation by proteolysis. *Trends Biochem Sci,* 21, 267-271.

Rogers, S., Wells, R. and Rechsteiner, M. (1986) Amino acid sequences common to rapidly degraded proteins: the PEST hypothesis. *Science,* 234, 364-368.

Romero, P., Obradovic, Z., Li, X., Garner, E. C., Brown, C. J. and Dunker, A. K. (2001) Sequence complexity of disordered protein. *Proteins,* 42, 38-48.

Ruuska, S. A., Girke, T., Benning, C. and Ohlrogge, J. B. (2002) Contrapuntal networks of gene expression during *Arabidopsis* seed filling. *Plant Cell,* 14, 1191-1206.

Sakuma, Y., Maruyama, K., Osakabe, Y., Qin, F., Seki, M., Shinozaki, K. and Yamaguchi-Shinozaki, K. (2006a) Functional analysis of an *Arabidopsis* transcription factor, DREB2A, involved in drought-responsive gene expression. *Plant Cell,* 18, 1292-1309.

Sakuma, Y., Maruyama, K., Qin, F., Osakabe, Y., Shinozaki, K. and Yamaguchi-Shinozaki, K. (2006b) Dual function of an *Arabidopsis* transcription factor DREB2A in water-stress-responsive and heat-stress-responsive gene expression. *Proc Natl Acad Sci USA,* 103, 18822-18827.

Salmeron, A., Janzen, J., Soneji, Y., Bump, N., Kamens, J., Allen, H. and Ley, S. C. (2001) Direct phosphorylation of NF-kappaB 1 p105 by the IkappaB kinase complex on serine 927 is essential for signal-induced p105 proteolysis. *J Biol Chem,* 276, 22215-22222.

Sanjaya, Durrett, T. P., Weise, S. E. and Benning, C. (2011) Increasing the energy density of vegetative tissues by diverting carbon from starch to oil biosynthesis in transgenic *Arabidopsis. Plant biotechnology journal,* 9, 874-883.

Shen, B., Allen, W. B., Zheng, P., Li, C., Glassman, K., Ranch, J., Nubel, D. and Tarczynski, M. C. (2010) Expression of ZmLEC1 and ZmWRI1 increases seed oil production in maize. *Plant Physiol,* 153, 980-987.

Singh, G. P., Ganapathi, M., Sandhu, K. S. and Dash, D. (2006) Intrinsic unstructuredness and abundance of PEST motifs in eukaryotic proteomes. *Proteins,* 62, 309-315.

Sirichandra, C., Davanture, M., Turk, B. E., Zivy, M., Valot, B., Leung, J., and Merlot, S. (2010) The *Arabidopsis* ABA-activated kinase OSTI phosphorylates the bZIP transcription factor ABF3 and creates a 14-3-3 binding site involved in its turnover. *PloS one,* 5, e13935.

Tsai, A. Y. and Gazzarrini, S. (2012) AKIN10 and FUSCA3 interact to control lateral organ development and phase transitions in *Arabidopsis. Plant J,* 69, 809-821.

Vacic, V., Uversky, V. N., Dunker, A. K. and Lonardi, S. (2007) Composition Profiler: a tool for discovery and visualization of amino acid composition differences. *BMC Bioinformatics,* 8, 211.

Valsecchi, I., Guittard-Crilat, E., Maldiney, R., Habricot, Y., Lignon, S., Lebrun, R L, Miginiac, E., Ruelland, E., Jeannette, E. and Lebreton, S. (2013a) The intrinsically disordered C-terminal region of *Arabidopsis thaliana* TCP8 transcription factor acts both as a transactivation and self-assembly domain. *Molecular bioSystems,* 9, 2282-2295.

Valsecchi, I., Guittard-Crilat, E., Maldiney, R., Habricot, Y., Lignon, S., Lebrun, R., Miginiac, E., Ruelland, E., Jeannette, E. and Lebreton, S. (2013b) The intrinsically disordered C-terminal region of *Arabidopsis thaliana* TCP8 transcription factor acts both as a transactivation and self-assembly domain. *Mol Biosyst,* 9, 2282-2295.

Vanhercke, T., El Tahchy, A., Shrestha, P., Zhou, X. R., Singh, S. P. and Petrie, J. R. (2013) Synergistic effect of WRI1 and DGAT1 coexpression on triacylglycerol biosynthesis in plants. *FEBS Left,* 587, 364-369.
Wang, F., Zhu, D., Huang, X., Li, S., Gong, Y., Yao, Q., Fu, X., Fan, L M. and Deng, X. W. (2009) Biochemical insights on degradation of *Arabidopsis* DELLA proteins gained from a cell-free assay system. *Plant Cell,* 21, 2378-2390.
Ward, J. J., Sodhi, J. S., McGuffin, L. J., Buxton, B. F. and Jones, D. T. (2004) Prediction and functional analysis of native disorder in proteins from the three kingdoms of life. *J Mol Biol,* 337, 635-645.
Wu, XL, Liu, Z. H., Hu, Z. H. and Huang, R. Z. (2014) BnWRI1 coordinates fatty acid biosynthesis and photosynthesis pathways during oil accumulation in rapeseed. *J Integr Plant Biol,* 56, 582-593.
Xue, B., Dunbrack, R. L, Williams, R. W., Dunker, A. K. and Uversky, V. N. (2010) PONDR-FIT: a meta-predictor of intrinsically disordered amino acids. *Biochim Biophys Acta,* 1804, 996-1010.
Yamaguchi, M., Ohtani, M., Mitsuda, N., Kubo, M., Ohme-Takagi, M., Fukuda, H. and Demura, T. (2010) VND-INTERACTING2, a NAC domain transcription factor, negatively regulates xylem vessel formation in *Arabidopsis. Plant Cell,* 22, 1249-1263.
Yang, Z. R., Thomson, R., McNeil, P. and Esnouf, R. M. (2005) RONN: the bio-basis function neural network technique applied to the detection of natively disordered regions in proteins. *Bioinformatics,* 21, 3369-3376.
Yin, Y., Wang, Z. Y., Mora-Garcia, S., Li, J., Yoshida, S., Asami, T. and Chory, J. (2002) BES 1 accumulates in the nucleus in response to brassinosteroids to regulate gene expression and promote stem elongation. *Cell,* 109, 181-191.
Zhai, Q., Yan, L., Tan, D., Chen, R., Sun, J., Gao, L., Dong, M. Q., Wang, Y. and Li, C. (2013) Phosphorylation-coupled proteolysis of the transcription factor MYC2 is important for jasmonate-signaled plant immunity. *PLoS genetics,* 9, e1003422.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements summarize and describe aspects of the invention.

Statements:

1. A transcription factor with at least 90% amino acid sequence identity to any of SEQ ID NOs: 1, 3, 4, 5, 7, 8, 9, 11, 12, 13, 15, 16, 17, 19, 20, 21, 23, 24, 25, 27, 28, 29, 30, 31, 59, 60, 61, 62, or 63, wherein the transcription factor has at least one amino acid substitution, amino acid deletion, or amino acid insertion compared to a corresponding wild type (or native) amino acid sequence.
2. The transcription factor comprising a PEST domain having at least 90% amino acid sequence identity to any of SEQ ID NOs:3, 4, 7, 8, 11, 12, 15, 16, 19, 20, 23, 24, 27, 28, 59, 60, 61 or 63, wherein the PEST domain has at least one amino acid substitution, amino acid deletion, or amino acid insertion compared to a corresponding wild type (or native) PEST amino acid sequence.
3. The transcription factor of statement 1 or 2, comprising a mutant PEST domain comprising any of SEQ ID NOs:3, 4, 7, 8, 11, 12, 15, 16, 19, 20, 23, 24, 27, 28, 59, 61, or 63, wherein the PEST domain has at least four of amino acid substitution, amino acid deletion, or amino acid insertion compared to a corresponding wild type (or native) PEST amino acid sequence.
4. The transcription factor of any of statements 1-3, comprising a mutant PEST domain comprising any of SEQ ID NOs: 4, 8, 12, 16, 20, 24, or 28, wherein each X is a small amino acid or a hydrophobic amino acid.
5. The transcription factor of any of statements 1-4, comprising a mutant PEST domain comprising any of SEQ ID NOs: 4, 8, 12, 16, 20, 24, or 28, wherein each X is not an acidic amino acid, serine, or threonine.
6. The transcription factor of any of statements 1-5, comprising a mutant PEST domain comprising any of SEQ ID NOs: 4, 8, 12, 16, 20, 24, or 28, wherein each X is separately alanine, glycine, valine, leucine, isoleucine, methionine, or any mixture thereof.
7. A 14-3-3 protein or a 14-3-3-related protein with at least 70%, or at least 80%, or at least 90%, or at least 95%, or at least 97% sequence identity to any of SEQ ID NO: 67, 69-74, or 75.
8. The 14-3-3 protein or a 14-3-3-related protein with at least one amino acid replacement, deletion, or insertion in any of SEQ ID NO: 67, 69-74, or 75.
9. A nucleic acid encoding the transcription factor and/or the 14-3-3 protein of any of statements 1-8.
10. An expression cassette or expression vector encoding the transcription factor and/or the 14-3-3 protein of any of statements 1-8.
11. The expression cassette or expression vector of statement 10, further comprising a promoter operably linked to a nucleic acid segment that encodes the transcription factor, and/or promoter operably linked to a nucleic acid segment that encodes the 14-3-3 protein.
12. The expression cassette or expression vector of statement 10 or 11, wherein the promoter is a constitutive or an inducible promoter.
13. The expression cassette or expression vector of any of statements 10-12, wherein the promoter is a developmentally regulated promoter.
14. The expression cassette or expression vector of any of statements 10-13, wherein the promoter is a poplar xylem-specific secondary cell wall specific cellulose synthase 8 promoter, cauliflower mosaic virus promoter, Z10 promoter from a gene encoding a 10 kD zein protein, Z27 promoter from a gene encoding a 27 kD zein protein, pea rbcS gene, actin promoter from rice, CaMV 35S promoter, CaMV 19S, nos, Adh1, sucrose synthase, α-tubulin, ubiquitin, actin, cab, PEPCase, the CCR (cinnamoyl CoA:NADP oxidoreductase, EC 1.2.1.44) promoter sequence isolated from *Lollium perenne* (or a perennial ryegrass), promoter from an R gene complex, a seed-specific promoter, or a phaseolin promoter.
15. A plant cell comprising the transcription factor and/or the 14-3-3 protein of any of statements 1-8.
16. A plant cell comprising the nucleic acid of statement 9.
17. A plant cell comprising the expression cassette or expression vector of any of statements 10-14.
18. The plant cell of any of statements 15-17, wherein the plant cell is not an *Arabidopsis thaliana* plant cell.

19. The plant cell of any of statements 15-18, wherein the plant cell is a food plant cell, vegetable oil plant cell, seed oil plant cell, forage plant cell, or fodder plant cell.
20. The plant cell of any of statements 15-19, wherein the plant cell is of *Brassicaceae* or other *Solanaceae* species.
21. The plant cell of any of statements 15-20, wherein the plant cell is an alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseed, potato, radish, rapeseed, rice, rutabaga, sorghum, soybean, sugar beet, sugarcane, switchgrass, tobacco, tomato, turnips, or wheat plant cell.
22. A seed comprising the transcription factor and/or the 14-3-3 protein of any of statements 1-8.
23. A seed comprising the nucleic acid of statement 9.
24. A seed comprising the expression cassette or expression vector of any of statements 10-14.
25. The seed of any of statements 22-24, wherein the seed is not an *Arabidopsis thaliana* plant cell.
26. The seed of any of statements 22-25, wherein the seed is a food plant seed, vegetable oil plant seed, seed oil plant seed, forage plant seed, or fodder plant seed.
27. The seed of any of statements 22-26, wherein the seed is of *Brassicaceae* or other *Solanaceae* species.
28. The seed of any of statements 22-27, wherein the seed is an alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rapeseed, rice, rutabaga, sorghum, soybean, sugar beets, sugarcane, sunflower, switchgrass, tobacco, tomato, turnips, or wheat seed.
29. The seed of any of statements 22-28, wherein the seed has about 0.5% to about 40%, or about 0.5% to about 35%, or about 0.5% to about 30%, or about 0.5% to about 25%, or about 0.5% to about 20%, or about 1% to about 18%, or about 2% to about 15%, or about 3% to about 15%, or about 5% to about 15% oil content.
30. The seed of any of statements 22-29, wherein the seed has at least about 1.2-fold, at least about 1.5-fold, least about 2-fold, at least about 3-fold, at least about 4-fold, at least about 5-fold, at least about 7-fold, at least about 10-fold, at least about 12-fold, at least about 15-fold, more oil, as measured by percent oil per dry weight, than a seed of the same species that has not been modified to contain the nucleic acid, expression cassette, or expression vector.
31. A plant comprising the transcription factor and/or the 14-3-3 protein of any of statements 1-8.
32. A plant comprising the nucleic acid of statement 9.
33. A plant comprising the expression cassette or expression vector of any of statements 10-14.
34. The plant of any of statements 31-33, wherein the plant is not an *Arabidopsis thaliana* plant.
35. The plant of any of statements 31-34, wherein the plant is a food plant, vegetable oil plant, seed oil plant, forage plant, or fodder plant.
36. The plant of any of statements 31-35, wherein the plant is of *Brassicaceae* or other *Solanaceae* species.
37. The plant of any of statements 31-36, wherein the plant is an alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rapeseed, rice, rutabaga, sorghum, soybean, sugar beets, sugarcane, switchgrass, tobacco, tomato, turnips, or wheat plant.
38. The plant of any of statements 31-37, wherein the plant tissues of the plant have about 0.5% to about 40%, or about 0.5% to about 35%, or about 0.5% to about 30%, or about 0.5% to about 25%, or about 0.5% to about 20%, or about 1% to about 18%, or about 2% to about 15%, or about 3% to about 15%, or about 5% to about 15% oil content.
39. The plant of any of statements 31-38, wherein the seed has at least about 1.2-fold, at least about 1.5-fold, least about 2-fold, at least about 3-fold, at least about 4-fold, at least about 5-fold, at least about 7-fold, at least about 10-fold, at least about 12-fold, or at least about 15-fold, more oil in its plant tissues, as measured by percent oil per dry weight, than a plant of the same species that has not been modified to contain the nucleic acid, expression cassette, or expression vector.
40. A method of generating oil comprising isolating tissues or seeds from the plant of any of statements 31-39 and extracting oil from the tissues or seeds.
41. The method of statement 40, further comprising cultivating a seed comprising a nucleic acid encoding the transcription factor of any of statements 1-6 to generate the plant.
42. The method of statement 40 or 41, further comprising cultivating a seed comprising a nucleic acid encoding the transcription factor and/or 14-3-3 protein of any of statements 1-7, the nucleic acid of statement 8, or the expression cassette or expression vector of any of statements 9-13.
43. The method of any of statements 40-42, further comprising generating at least one line of plants comprising a nucleic acid encoding the transcription factor and/or 14-3-3 protein of any of statements 1-8, the nucleic acid of statement 9, or the expression cassette or expression vector of any of statements 10-14.
44. The method of statement 43, wherein the at least one line of plants is generated by transforming one or more plant cells with the nucleic acid encoding the transcription factor and/or 14-3-3 protein of any of statements 1-8, or the nucleic acid of statement 9, or the expression cassette or expression vector of any of statements 10-14 to generate one or more transgenic plant cells; generating one or more transgenic plants from the one or more transgenic plant cells; and clonally or vegetatively propagating at least one line of transgenic plants.
45. The method of any of statements 40-44, wherein the plant is not an *Arabidopsis thaliana* plant.
46. The method of any of statements 40-45, wherein the plant is a food plant, vegetable oil plant, seed oil plant, forage plant, or fodder plant.
47. The method of any of statements 40-46, wherein the plant is of *Brassicaceae* or other *Solanaceae* species.
48. The method of any of statements 40-47, wherein the plant is an alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rapeseed, rice, rutabaga, sorghum, soybean, sugar beets, sugarcane, sunflower, switchgrass, tobacco, tomato, turnips, or wheat plant.

49. A plant, plant cell, or seed comprising a heterologous WRINKLED1 transcription factor and a heterologous 14-3-3 protein.
50. A method comprising introducing the nucleic acid encoding the transcription factor and/or 14-3-3 protein of any of statements 1-8, or the nucleic acid of statement 9, or the expression cassette or expression vector of any of statements 10-14 to generate one or more transgenic plant cells; generating one or more transgenic plants from the one or more transgenic plant cells;

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms “a,” “an,” and “the” include plural reference unless the context clearly dictates otherwise. Thus, for example, a reference to “a seed” or “a plant” or “a promoter” includes a plurality of such seeds, plants or promoters, and so forth. In this document, the term “or” is used to refer to a nonexclusive or, such that “A or B” includes “A but not B,” “B but not A,” and “A and B,” unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed is:

1. A plant, plant cell, or seed comprising a heterologous WRINKLED1 (WRI1) transcription factor and a heterologous 14-3-3 protein.

2. The plant, plant cell, or seed of claim 1 comprising a heterologous WRI1 transcription factor comprising at least 90% amino acid sequence identity to any of SEQ ID NOs: 1-31, 59, 60, 61, 62, 63, 64, or 65.

3. The plant, plant cell, or seed of claim 1 comprising a heterologous 14-3-3 protein factor comprising at least 90% amino acid sequence identity to any of SEQ ID NOs: 67, 69-74 or 75.

4. The plant, plant cell, or seed of claim 1, wherein the plant, plant cell, or plant seed is a food, vegetable oil, seed oil, forage, or fodder plant, plant cell, or plant seed.

5. The plant, plant cell, or seed of claim 1, wherein the plant, plant cell, or plant seed has about 0.5% to about 40% oil content.

6. The plant, plant cell, or seed of claim 1, wherein the plant, plant cell, or plant seed is an alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rapeseed, rice, rutabaga, sorghum, soybean, sugar beets, sugarcane, sunflower, switchgrass, tobacco, tomato, turnips, or wheat plant, plant cell, or plant seed.

7. A nucleic acid encoding WRINKLED1 (WRI1) transcription factor and a heterologous 14-3-3 protein.

8. An expression system comprising a first expression cassette comprising a first promoter operably linked to a nucleic acid encoding a WRI1 transcription factor and a second expression cassette comprising a second promoter operably linked to a nucleic acid encoding a 14-3-3 protein.

9. The expression system of claim 8, wherein the first expression cassette encodes a WRI1 transcription factor comprising at least 90% amino acid sequence identity to any of SEQ ID NOs: 1-31, 59, 60, 61, 62, 63, 64, or 65.

10. The expression system of claim 8, wherein the second expression cassette encodes a 14-3-3 protein factor comprising at least 90% amino acid sequence identity to any of SEQ ID NOs: 67, 69-74 or 75.

11. The expression system of claim 8, wherein the first promoter or the second promoter, or both of the first promoter and the second promoter, is an inducible promoter, a tissue-specific promoter, or a developmentally regulated promoter.

12. A method of generating oil comprising isolating tissues, cells, or seeds from the plant of claim 1 and extracting oil from the plant tissues, cells, or seeds.

13. A method comprising introducing a heterologous nucleic acid encoding a WRINKLED1 (WRI1) transcription factor and a 14-3-3 protein, or an expression system comprising a first expression cassette comprising a first promoter operably linked to a nucleic acid encoding a WRI1 transcription factor and a second expression cassette comprising a second promoter operably linked to a nucleic acid encoding a 14-3-3 protein, to generate one or more transgenic plant cells; and generating one or more transgenic plants from the one or more transgenic plant cells.

14. The method of claim 13, wherein the WRI1 transcription factor comprises at least 90% amino acid sequence identity to any of SEQ ID NOs: 1-31, 59, 60, 61, 62, 63, 64, or 65.

15. The method of claim 13, wherein the 14-3-3 protein factor comprises at least 90% amino acid sequence identity to any of SEQ ID NOs: 67, 69-74 or 75.

16. The method of claim 13, wherein the first promoter or the second promoter, or both of the first promoter and the second promoter, is an inducible promoter, a tissue-specific promoter, or a developmentally regulated promoter.

17. The method of claim 13, wherein one or more of the transgenic plant cells or transgenic plants has about 0.5% to about 40% oil content.

18. The method of claim 13, further comprising collecting one or more transgenic seeds from at least one of the transgenic plant.

19. The method of claim 13, wherein one or more of the transgenic seeds has about 0.5% to about 40% oil content.

20. The method of claim 13, wherein the transgenic plant cell, or the transgenic plant is an alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rapeseed, rice, rutabaga, sorghum, soybean, sugar beets, sugarcane, sunflower, switchgrass, tobacco, tomato, turnips, or wheat plant, plant cell, or plant seed.

* * * * *

SEQUENCE LISTING

<160> NUMBER OF SEQ ID NOS: 146

<210> SEQ ID NO 1
<211> LENGTH: 430
<212> TYPE: PRT
<213> ORGANISM: Arabidopsis thaliana

<400> SEQUENCE: 1

Met Lys Lys Arg Leu Thr Thr Ser Thr Cys Ser Ser Ser Pro Ser Ser
1 5 10 15

Ser Val Ser Ser Ser Thr Thr Thr Ser Ser Pro Ile Gln Ser Glu Ala
20 25 30

Pro Arg Pro Lys Arg Ala Lys Arg Ala Lys Lys Ser Ser Pro Ser Gly
35 40 45

Asp Lys Ser His Asn Pro Thr Ser Pro Ala Ser Thr Arg Arg Ser Ser
50 55 60

Ile Tyr Arg Gly Val Thr Arg His Arg Trp Thr Gly Arg Phe Glu Ala
65 70 75 80

His Leu Trp Asp Lys Ser Ser Trp Asn Ser Ile Gln Asn Lys Lys Gly
85 90 95

Lys Gln Val Tyr Leu Gly Ala Tyr Asp Ser Glu Glu Ala Ala Ala His
100 105 110

-continued

```
Thr Tyr Asp Leu Ala Ala Leu Lys Tyr Trp Gly Pro Asp Thr Ile Leu
        115                 120                 125

Asn Phe Pro Ala Glu Thr Tyr Thr Lys Glu Leu Glu Glu Met Gln Arg
    130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190

Leu Tyr Leu Gly Thr Tyr Asn Thr Gln Glu Glu Ala Ala Ala Ala Tyr
        195                 200                 205

Asp Met Ala Ala Ile Glu Tyr Arg Gly Ala Asn Ala Val Thr Asn Phe
    210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Glu Pro Arg Glu Glu
            260                 265                 270

Val Lys Gln Gln Tyr Val Glu Glu Pro Pro Gln Glu Glu Glu Glu Lys
        275                 280                 285

Glu Glu Glu Lys Ala Glu Gln Gln Glu Ala Glu Ile Val Gly Tyr Ser
    290                 295                 300

Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
                325                 330                 335

Met Met Asp Thr Gly Phe Ser Pro Phe Leu Thr Asp Gln Asn Leu Ala
            340                 345                 350

Asn Glu Asn Pro Ile Glu Tyr Pro Glu Leu Phe Asn Glu Leu Ala Phe
        355                 360                 365

Glu Asp Asn Ile Asp Phe Met Phe Asp Asp Gly Lys His Glu Cys Leu
    370                 375                 380

Asn Leu Glu Asn Leu Asp Cys Cys Val Val Gly Arg Glu Ser Pro Pro
385                 390                 395                 400

Ser Ser Ser Ser Pro Leu Ser Cys Leu Ser Thr Asp Ser Ala Ser Ser
                405                 410                 415

Thr Thr Thr Thr Thr Thr Ser Val Ser Cys Asn Tyr Leu Val
            420                 425                 430
```

<210> SEQ ID NO 2
<211> LENGTH: 1540
<212> TYPE: DNA
<213> ORGANISM: Arabidopsis thaliana

<400> SEQUENCE: 2

```
aaaccactct gcttcctctt cctctgagaa atcaaatcac tcacactcca aaaaaaaatc      60

taaactttct cagagtttaa tgaagaagcg cttaaccact tccacttgtt cttcttctcc     120

atcttcctct gtttcttctt ctactactac ttcctctcct attcagtcgg aggctccaag     180

gcctaaacga gccaaaaggg ctaagaaatc ttctccttct ggtgataaat ctcataaccc     240

gacaagccct gcttctaccc gacgcagctc tatctacaga ggagtcacta gacatagatg     300

gactgggaga ttcgaggctc atctttggga caaaagctct tggaattcga ttcagaacaa     360
```

```
gaaaggcaaa caagtttatc tgggagcata tgacagtgaa gaagcagcag cacatacgta    420

cgatctggct gctctcaagt actggggacc cgacaccatc ttgaattttc cggcagagac    480

gtacacaaag gaattggaag aaatgcagag agtgacaaag gaagaatatt tggcttctct    540

ccgccgccag agcagtggtt tctccagagg cgtctctaaa tatcgcggcg tcgctaggca    600

tcaccacaac ggaagatggg aggctcggat cggaagagtg tttgggaaca agtacttgta    660

cctcggcacc tataatacgc aggaggaagc tgctgcagca tatgacatgg ctgcgattga    720

gtatcgaggc gcaaacgcgg ttactaattt cgacattagt aattacattg accggttaaa    780

gaagaaaggt gttttcccgt tccctgtgaa ccaagctaac catcaagagg gtattcttgt    840

tgaagccaaa caagaagttg aaacgagaga agcgaaggaa gagcctagag aagaagtgaa    900

acaacagtac gtggaagaac caccgcaaga agaagaagag aaggaagaag agaaagcaga    960

gcaacaagaa gcagagattg taggatattc agaagaagca gcagtggtca attgctgcat   1020

agactcttca accataatgg aaatggatcg ttgtggggac aacaatgagc tggcttggaa   1080

cttctgtatg atggatacag ggttttctcc gtttttgact gatcagaatc tcgcgaatga   1140

gaatcccata gagtatccgg agctattcaa tgagttagca tttgaggaca acatcgactt   1200

catgttcgat gatgggaagc acgagtgctt gaacttggaa aatctggatt gttgcgtggt   1260

gggaagagag agcccaccct cttcttcttc accattgtct tgcttatcta ctgactctgc   1320

ttcatcaaca acaacaacaa caacctcggt ttcttgtaac tatttggtct gagagagaga   1380

gctttgcctt ctagtttgaa tttctatttc ttccgcttct tcttcttttt tttcttttgt   1440

tgggttctgc ttagggtttg tatttcagtt tcagggcttg ttcgttggtt ctgaataatc   1500

aatgtctttg ccccttttct aatgggtacc tgaagggcga                         1540
```

<210> SEQ ID NO 3
<211> LENGTH: 35
<212> TYPE: PRT
<213> ORGANISM: Arabidopsis thaliana

<400> SEQUENCE: 3

```
Arg Glu Ser Pro Pro Ser Ser Ser Ser Pro Leu Ser Cys Leu Ser Thr
1               5                   10                  15

Asp Ser Ala Ser Ser Thr Thr Thr Thr Thr Thr Ser Val Ser Cys Asn
            20                  25                  30

Tyr Leu Val
        35
```

<210> SEQ ID NO 4
<211> LENGTH: 35
<212> TYPE: PRT
<213> ORGANISM: Artificial Sequence
<220> FEATURE:
<223> OTHER INFORMATION: A synthetic protein
<221> NAME/KEY: SITE
<222> LOCATION: 3,6,7,12,20,21,25,26,27,28
<223> OTHER INFORMATION: Xaa = is any amino acid

<400> SEQUENCE: 4

```
Arg Glu Xaa Pro Pro Xaa Xaa Ser Ser Pro Leu Xaa Cys Leu Ser Thr
1               5                   10                  15

Asp Ser Ala Xaa Xaa Thr Thr Thr Xaa Xaa Xaa Xaa Val Ser Cys Asn
            20                  25                  30

Tyr Leu Val
        35
```

<210> SEQ ID NO 5
<211> LENGTH: 415
<212> TYPE: PRT
<213> ORGANISM: Brassica napus

<400> SEQUENCE: 5

Met Lys Arg Pro Leu Thr Thr Ser Pro Ser Thr Ser Ser Ser Thr Ser
1               5                   10                  15

Ser Ser Ala Cys Ile Leu Pro Thr Gln Pro Glu Thr Pro Arg Pro Lys
            20                  25                  30

Arg Ala Lys Arg Ala Lys Lys Ser Ser Ile Pro Thr Asp Val Lys Pro
        35                  40                  45

Gln Asn Pro Thr Ser Pro Ala Ser Thr Arg Arg Ser Ser Ile Tyr Arg
    50                  55                  60

Gly Val Thr Arg His Arg Trp Thr Gly Arg Tyr Glu Ala His Leu Trp
65                  70                  75                  80

Asp Lys Ser Ser Trp Asn Ser Ile Gln Asn Lys Lys Gly Lys Gln Val
                85                  90                  95

Tyr Leu Gly Ala Tyr Asp Ser Glu Glu Ala Ala Ala His Thr Tyr Asp
            100                 105                 110

Leu Ala Ala Leu Lys Tyr Trp Gly Pro Asp Thr Ile Leu Asn Phe Pro
        115                 120                 125

Ala Glu Thr Tyr Thr Lys Glu Leu Glu Glu Met Gln Arg Cys Thr Lys
    130                 135                 140

Glu Glu Tyr Leu Ala Ser Leu Arg Arg Gln Ser Ser Gly Phe Ser Arg
145                 150                 155                 160

Gly Val Ser Lys Tyr Arg Gly Val Ala Arg His His His Asn Gly Arg
                165                 170                 175

Trp Glu Ala Arg Ile Gly Arg Val Phe Gly Asn Lys Tyr Leu Tyr Leu
            180                 185                 190

Gly Thr Tyr Asn Thr Gln Glu Glu Ala Ala Ala Ala Tyr Asp Met Ala
        195                 200                 205

Ala Ile Glu Tyr Arg Gly Ala Asn Ala Val Thr Asn Phe Asp Ile Ser
    210                 215                 220

Asn Tyr Ile Asp Arg Leu Lys Lys Lys Gly Val Phe Pro Phe Pro Val
225                 230                 235                 240

Ser Gln Ala Asn His Gln Glu Ala Val Leu Ala Glu Ala Lys Gln Glu
                245                 250                 255

Val Glu Ala Lys Glu Glu Pro Thr Glu Glu Val Lys Gln Cys Val Glu
            260                 265                 270

Lys Glu Glu Pro Gln Glu Ala Lys Glu Glu Lys Thr Glu Lys Lys Gln
        275                 280                 285

Gln Gln Gln Glu Val Glu Glu Ala Val Val Thr Cys Cys Ile Asp Ser
    290                 295                 300

Ser Glu Ser Asn Glu Leu Ala Trp Asp Phe Cys Met Met Asp Ser Gly
305                 310                 315                 320

Phe Ala Pro Phe Leu Thr Asp Ser Asn Leu Ser Ser Glu Asn Pro Ile
                325                 330                 335

Glu Tyr Pro Glu Leu Phe Asn Glu Met Gly Phe Glu Asp Asn Ile Asp
            340                 345                 350

Phe Met Phe Glu Glu Gly Lys Gln Asp Cys Leu Ser Leu Glu Asn Leu
        355                 360                 365

Asp Cys Cys Asp Gly Val Val Val Val Gly Arg Glu Ser Pro Thr Ser 370 375 380

Leu Ser Ser Ser Pro Leu Ser Cys Leu Ser Thr Asp Ser Ala Ser Ser
385 390 395 400

Thr Thr Thr Thr Thr Ile Thr Ser Val Ser Cys Asn Tyr Ser Val
405 410 415

<210> SEQ ID NO 6
<211> LENGTH: 1248
<212> TYPE: DNA
<213> ORGANISM: Brassica napus

<400> SEQUENCE: 6
atgaagagac ccttaaccac ttctccttct acctcctctt ctacttcttc ttcggcttgt 60
atacttccga ctcaaccaga gactccaagg cccaaacgag ccaaaagggc taagaaatct 120
tctattccta ctgatgttaa accacagaat cccaccagtc ctgcctccac cagacgcagc 180
tctatctaca gaggagtcac tagacataga tggacaggga gatacgaggc tcatctatgg 240
gacaaaagct cgtggaattc gattcagaac aagaaaggca aacaagttta tctgggagca 300
tatgacagcg aggaagcagc agcgcatacg tacgatctag ctgctctcaa gtactggggt 360
cccgacacca tcttgaactt tccggctgag acgtacacaa aggagttgga ggagatgcag 420
agatgtacaa aggaagagta tttggcttct ctccgccgcc agagcagtgg tttctctaga 480
ggcgtctcta aatatcgcgg cgtcgccagg catcaccata acggaagatg ggaagctagg 540
attggaaggg tgtttggaaa caagtacttg tacctcggca cttataatac gcaggaggaa 600
gctgcagctg catatgacat ggcggctata gagtacagag gcgcaaacgc agtgaccaac 660
ttcgacatta gtaactacat cgaccggtta aagaaaaaag gtgtcttccc attccctgtg 720
agccaagcca atcatcaaga agctgttctt gctgaagcca aacaagaagt ggaagctaaa 780
gaagagccta cagaagaagt gaagcagtgt gtcgaaaaag aagaaccgca agaagctaaa 840
gaagagaaga ctgagaaaaa acaacaacaa caagaagtgg aggaggcggt ggtcacttgc 900
tgcattgatt cttcggagag caatgagctg gcttgggact tctgtatgat ggattcaggg 960
tttgctccgt ttttgacgga ttcaaatctc tcgagtgaga atcccattga gtatcctgag 1020
cttttcaatg agatggggtt tgaggataac attgacttca tgttcgagga agggaagcaa 1080
gactgcttga gcttggagaa tctggattgt tgcgatggtg ttgttgtggt gggaagagag 1140
agcccaactt cattgtcgtc ttcaccgttg tcttgcttgt ctactgactc tgcttcatca 1200
acaacaacaa caacaataac ctctgtttct tgtaactatt ctgtctga 1248

<210> SEQ ID NO 7
<211> LENGTH: 37
<212> TYPE: PRT
<213> ORGANISM: Brassica napus

<400> SEQUENCE: 7

Arg Glu Ser Pro Thr Ser Leu Ser Ser Ser Pro Leu Ser Cys Leu Ser
1 5 10 15

Thr Asp Ser Ala Ser Ser Thr Thr Thr Thr Thr Ile Thr Ser Val Ser
20 25 30

Cys Asn Tyr Ser Val
35

<210> SEQ ID NO 8
<211> LENGTH: 37
<212> TYPE: PRT

```
<213> ORGANISM: Artificial Sequence
<220> FEATURE:
<223> OTHER INFORMATION: A synthetic protein
<221> NAME/KEY: SITE
<222> LOCATION: 3,5,6,8,9,10,13,21,22,23,24,25,26,27,29,30
<223> OTHER INFORMATION: Xaa = is any amino acid

<400> SEQUENCE: 8

Arg Glu Xaa Pro Xaa Xaa Leu Xaa Xaa Xaa Pro Leu Xaa Cys Leu Ser
1               5                   10                  15

Thr Asp Ser Ala Xaa Xaa Xaa Xaa Xaa Xaa Xaa Ile Xaa Xaa Val Ser
            20                  25                  30

Cys Asn Tyr Ser Val
        35


<210> SEQ ID NO 9
<211> LENGTH: 413
<212> TYPE: PRT
<213> ORGANISM: Brassica napus

<400> SEQUENCE: 9

Met Lys Arg Pro Leu Thr Thr Ser Pro Ser Ser Ser Ser Ser Thr Ser
1               5                   10                  15

Ser Ser Ala Cys Ile Leu Pro Thr Gln Ser Glu Thr Pro Arg Pro Lys
            20                  25                  30

Arg Ala Lys Arg Ala Lys Lys Ser Ser Leu Arg Ser Asp Val Lys Pro
        35                  40                  45

Gln Asn Pro Thr Ser Pro Ala Ser Thr Arg Arg Ser Ser Ile Tyr Arg
    50                  55                  60

Gly Val Thr Arg His Arg Trp Thr Gly Arg Tyr Glu Ala His Leu Trp
65                  70                  75                  80

Asp Lys Ser Ser Trp Asn Ser Ile Gln Asn Lys Lys Gly Lys Gln Val
                85                  90                  95

Tyr Leu Gly Ala Tyr Asp Ser Glu Glu Ala Ala Ala His Thr Tyr Asp
            100                 105                 110

Leu Ala Ala Leu Lys Tyr Trp Gly Pro Asn Thr Ile Leu Asn Phe Pro
        115                 120                 125

Val Glu Thr Tyr Thr Lys Glu Leu Glu Glu Met Gln Arg Cys Thr Lys
    130                 135                 140

Glu Glu Tyr Leu Ala Ser Leu Arg Arg Gln Ser Ser Gly Phe Ser Arg
145                 150                 155                 160

Gly Val Ser Lys Tyr Arg Gly Val Ala Arg His His His Asn Gly Arg
                165                 170                 175

Trp Glu Ala Arg Ile Gly Arg Val Phe Gly Asn Lys Tyr Leu Tyr Leu
            180                 185                 190

Gly Thr Tyr Asn Thr Gln Glu Glu Ala Ala Ala Ala Tyr Asp Met Ala
        195                 200                 205

Ala Ile Glu Tyr Arg Gly Ala Asn Ala Val Thr Asn Phe Asp Ile Gly
    210                 215                 220

Asn Tyr Ile Asp Arg Leu Lys Lys Lys Gly Val Phe Pro Phe Pro Val
225                 230                 235                 240

Ser Gln Ala Asn His Gln Glu Ala Val Leu Ala Glu Thr Lys Gln Glu
                245                 250                 255

Val Glu Ala Lys Glu Glu Pro Thr Glu Glu Val Lys Gln Cys Val Glu
            260                 265                 270

Lys Glu Glu Ala Lys Glu Glu Lys Thr Glu Lys Lys Gln Gln Gln Glu
        275                 280                 285
```

-continued

```
Val Glu Glu Ala Val Ile Thr Cys Cys Ile Asp Ser Ser Glu Ser Asn
    290                 295                 300

Glu Leu Ala Trp Asp Phe Cys Met Met Asp Ser Gly Phe Ala Pro Phe
305                 310                 315                 320

Leu Thr Asp Ser Asn Leu Ser Ser Glu Asn Pro Ile Glu Tyr Pro Glu
                325                 330                 335

Leu Phe Asn Glu Met Gly Phe Glu Asp Asn Ile Asp Phe Met Phe Glu
            340                 345                 350

Glu Gly Lys Gln Asp Cys Leu Ser Leu Glu Asn Leu Asp Cys Cys Asp
        355                 360                 365

Gly Val Val Val Val Gly Arg Glu Ser Pro Thr Ser Leu Ser Ser Ser
    370                 375                 380

Pro Leu Ser Cys Leu Ser Thr Asp Ser Ala Ser Ser Thr Thr Thr Thr
385                 390                 395                 400

Ala Thr Thr Val Thr Ser Val Ser Trp Asn Tyr Ser Val
                405                 410


<210> SEQ ID NO 10
<211> LENGTH: 1242
<212> TYPE: DNA
<213> ORGANISM: Brassica napus

<400> SEQUENCE: 10

atgaagagac ccttaaccac ttctccttct tcctcctctt ctacttcttc ttcggcctgt      60

atacttccga ctcaatcaga gactccaagg cccaaacgag ccaaaagggc taagaaatct     120

tctctgcgtt ctgatgttaa accacagaat cccaccagtc ctgcctccac cagacgcagc     180

tctatctaca gaggagtcac tagacataga tggacaggga gatacgaagc tcatctatgg     240

gacaaaagct cgtggaattc gattcagaac aagaaaggca aacaagttta tctgggagca     300

tatgacagcg aggaagcagc agcacatacg tacgatctag ctgctctcaa gtactggggt     360

cccaacacca tcttgaactt tccggttgag acgtacacaa aggagctgga ggagatgcag     420

agatgtacaa aggaagagta tttggcttct ctccgccgcc agagcagtgg tttctctaga     480

ggcgtctcta aatatcgcgg cgtcgccagg catcaccata atggaagatg ggaagctcgg     540

attggaaggg tgtttggaaa caagtacttg tacctcggca cctataatac gcaggaggaa     600

gctgcagctg catatgacat ggcggctata gagtacagag gtgcaaacgc agtgaccaac     660

ttcgacattg gtaactacat cgaccggtta aagaaaaaag gtgtcttccc gttccccgtg     720

agccaagcta atcatcaaga agctgttctt gctgaaacca aacaagaagt ggaagctaaa     780

gaagagccta cagaagaagt gaagcagtgt gtcgaaaaag aagaagctaa agaagagaag     840

actgagaaaa aacaacaaca agaagtggag gaggcggtga tcacttgctg cattgattct     900

tcagagagca atgagctggc ttgggacttc tgtatgatgg attcagggtt tgctccgttt     960

ttgactgatt caaatctctc gagtgagaat cccattgagt atcctgagct tttcaatgag    1020

atgggttttg aggataacat tgacttcatg ttcgaggaag ggaagcaaga ctgcttgagc    1080

ttggagaatc ttgattgttg cgatggtgtt gttgtggtgg gaagagagag cccaacttca    1140

ttgtcgtctt ctccgttgtc ctgcttgtct actgactctg cttcatcaac aacaacaaca    1200

gcaacaacag taacctctgt ttcttggaac tattctgtct ga                       1242


<210> SEQ ID NO 11
<211> LENGTH: 36
<212> TYPE: PRT
```

```
<213> ORGANISM: Brassica napus

<400> SEQUENCE: 11

Arg Glu Ser Pro Thr Ser Leu Ser Ser Ser Pro Leu Ser Cys Leu Ser
1               5                   10                  15

Thr Asp Ser Ala Ser Ser Thr Thr Thr Thr Ala Thr Thr Val Thr Ser
            20                  25                  30

Val Ser Trp Asn
        35


<210> SEQ ID NO 12
<211> LENGTH: 36
<212> TYPE: PRT
<213> ORGANISM: Artificial Sequence
<220> FEATURE:
<223> OTHER INFORMATION: A synthetic protein
<221> NAME/KEY: SITE
<222> LOCATION: 3,5,6,8,13,16,21,22,23,24,25,26,28,29,31,32
<223> OTHER INFORMATION: Xaa = is any amino acid

<400> SEQUENCE: 12

Arg Glu Xaa Pro Xaa Xaa Leu Xaa Ser Ser Pro Leu Xaa Cys Leu Xaa
1               5                   10                  15

Thr Asp Ser Ala Xaa Xaa Xaa Xaa Xaa Xaa Ala Xaa Xaa Val Xaa Xaa
            20                  25                  30

Val Ser Trp Asn
        35


<210> SEQ ID NO 13
<211> LENGTH: 395
<212> TYPE: PRT
<213> ORGANISM: Zea mays

<400> SEQUENCE: 13

Met Glu Arg Ser Gln Arg Gln Ser Pro Pro Pro Pro Ser Pro Ser Ser
1               5                   10                  15

Ser Ser Ser Ser Val Ser Ala Asp Thr Val Leu Val Pro Pro Gly Lys
            20                  25                  30

Arg Arg Arg Ala Ala Thr Ala Lys Ala Gly Ala Glu Pro Asn Lys Arg
        35                  40                  45

Ile Arg Lys Asp Pro Ala Ala Ala Ala Ala Gly Lys Arg Ser Ser Val
    50                  55                  60

Tyr Arg Gly Val Thr Arg His Arg Trp Thr Gly Arg Phe Glu Ala His
65                  70                  75                  80

Leu Trp Asp Lys His Cys Leu Ala Ala Leu His Asn Lys Lys Lys Gly
                85                  90                  95

Arg Gln Val Tyr Leu Gly Ala Tyr Asp Ser Glu Glu Ala Ala Ala Arg
            100                 105                 110

Ala Tyr Asp Leu Ala Ala Leu Lys Tyr Trp Gly Pro Glu Thr Leu Leu
        115                 120                 125

Asn Phe Pro Val Glu Asp Tyr Ser Ser Glu Met Pro Glu Met Glu Ala
    130                 135                 140

Val Ser Arg Glu Glu Tyr Leu Ala Ser Leu Arg Arg Arg Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190
```

-continued

```
Leu Tyr Leu Gly Thr Phe Asp Thr Gln Glu Glu Ala Ala Lys Ala Tyr
        195                 200                 205

Asp Leu Ala Ala Ile Glu Tyr Arg Gly Val Asn Ala Val Thr Asn Phe
    210                 215                 220

Asp Ile Ser Cys Tyr Leu Asp His Pro Leu Phe Leu Ala Gln Leu Gln
225                 230                 235                 240

Gln Glu Pro Gln Val Val Pro Ala Leu Asn Gln Glu Pro Gln Pro Asp
                245                 250                 255

Gln Ser Glu Thr Gly Thr Thr Glu Gln Glu Pro Glu Ser Ser Glu Ala
            260                 265                 270

Lys Thr Pro Asp Gly Ser Ala Glu Pro Asp Glu Asn Ala Val Pro Asp
        275                 280                 285

Asp Thr Ala Glu Pro Leu Ser Thr Val Asp Asp Ser Ile Glu Glu Gly
    290                 295                 300

Leu Trp Ser Pro Cys Met Asp Tyr Glu Leu Asp Thr Met Ser Arg Pro
305                 310                 315                 320

Asn Phe Gly Ser Ser Ile Asn Leu Ser Glu Trp Phe Ala Asp Ala Asp
                325                 330                 335

Phe Asp Cys Asn Ile Gly Cys Leu Phe Asp Gly Cys Ser Ala Ala Asp
            340                 345                 350

Glu Gly Ser Lys Asp Gly Val Gly Leu Ala Asp Phe Ser Leu Phe Glu
        355                 360                 365

Ala Gly Asp Val Gln Leu Lys Asp Val Leu Ser Asp Met Glu Glu Gly
    370                 375                 380

Ile Gln Pro Pro Ala Met Ile Ser Val Cys Asn
385                 390                 395
```

<210> SEQ ID NO 14
<211> LENGTH: 1576
<212> TYPE: DNA
<213> ORGANISM: Zea mays

<400> SEQUENCE: 14

```
ctcccccgcc tcgccgccag tcagattcac caccggctcc cctgcacaac cgcgtccgcg      60

ctgcaccacc accgttcatc gaggaggagg ggggacggag accacggaca tggagagatc     120

tcaacggcag tctcctccgc caccgtcgcc gtcctcctcc tcgtcctccg tctccgcgga     180

caccgtcctc gtccctcccg gaaagaggcg gagggcggcg acggccaagg ccggcgccga     240

gcctaataag aggatccgca aggaccccgc cgccgccgcc gcggggaaga ggagctccgt     300

ctacagggga gtcaccaggc acaggtggac gggcaggttc gaggcgcatc tctgggacaa     360

gcactgcctc gccgcgctcc acaacaagaa gaaaggcagg caagtctacc tgggggcgta     420

tgacagcgag gaggcagctg ctcgtgccta tgacctcgca gctctcaagt actggggtcc     480

tgagactctg ctcaacttcc ctgtggagga ttactccagc gagatgccgg agatggaggc     540

cgtttcccgg gaggagtacc tggcctccct ccgccgcagg agcagcggct tctccagggg     600

cgtctccaag tacagaggcg tcgccaggca tcaccacaac gggaggtggg aggcacggat     660

tgggcgagtc tttgggaaca agtacctcta cttgggaaca tttgacactc aagaagaggc     720

agccaaggcc tatgaccttg cggccattga ataccgtggc gtcaatgctg taaccaactt     780

cgacatcagc tgctacctgg accacccgct gttcctggca cagctccaac aggagccaca     840

ggtggtgccg gcactcaacc aagaacctca acctgatcag agcgaaaccg gaactacaga     900

gcaagagccg gagtcaagcg aagccaagac accggatggc agtgcagaac ccgatgagaa     960
```

```
cgcggtgcct gacgacaccg cggagcccct cagcacagtc gacgacagca tcgaagaggg   1020

cttgtggagc ccttgcatgg attacgagct agacaccatg tcgagaccaa actttggcag   1080

ctcaatcaat ctgagcgagt ggttcgctga cgcagacttc gactgcaaca tcgggtgcct   1140

gttcgatggg tgttctgcgg ctgacgaagg aagcaaggat ggtgtaggtc tggcagattt   1200

cagtctgttt gaggcaggtg atgtccagct gaaggatgtt ctttcggata tggaagaggg   1260

gatacaacct ccagcgatga tcagtgtgtg caactaattc tggaacccga ggaggttttc   1320

gctttccagg tgtcctgtct tgggtaatcc ttgatctgtc taatgccaca gtgccactgc   1380

accagagcag ctgagaactt tcttgtagaa agcccatggc agtttggcgt tagacaagtg   1440

tgtcgatgtt ctttaattct ttgaatttgc ccctaggctg cttggctaac gttaagggtt   1500

tgtcattgtc tcacttagcc tagattcaac taatcacatc ctgaatctga aaaaaaaaaa   1560

caaaaaaaaa aaaaaa                                                   1576


<210> SEQ ID NO 15
<211> LENGTH: 88
<212> TYPE: PRT
<213> ORGANISM: Zea mays

<400> SEQUENCE: 15

His Pro Leu Phe Leu Ala Gln Leu Gln Gln Glu Pro Gln Val Val Pro
1               5                   10                  15

Ala Leu Asn Gln Glu Pro Gln Pro Asp Gln Ser Glu Thr Gly Thr Thr
            20                  25                  30

Glu Gln Glu Pro Glu Ser Ser Glu Ala Lys Thr Pro Asp Gly Ser Ala
        35                  40                  45

Glu Pro Asp Glu Asn Ala Val Pro Asp Asp Thr Ala Glu Pro Leu Ser
    50                  55                  60

Thr Val Asp Asp Ser Ile Glu Glu Gly Leu Trp Ser Pro Cys Met Asp
65                  70                  75                  80

Tyr Glu Leu Asp Thr Met Ser Arg
                85


<210> SEQ ID NO 16
<211> LENGTH: 88
<212> TYPE: PRT
<213> ORGANISM: Artificial Sequence
<220> FEATURE:
<223> OTHER INFORMATION: A synthetic protein
<221> NAME/KEY: SITE
<222> LOCATION: 27,29,31,32,38,39,43,47,59,64,65,69,76,85,87
<223> OTHER INFORMATION: Xaa = is any amino acid

<400> SEQUENCE: 16

His Pro Leu Phe Leu Ala Gln Leu Gln Gln Glu Pro Gln Val Val Pro
1               5                   10                  15

Ala Leu Asn Gln Glu Pro Gln Pro Asp Gln Xaa Glu Xaa Gly Xaa Xaa
            20                  25                  30

Glu Gln Glu Pro Glu Xaa Xaa Glu Ala Lys Xaa Pro Asp Gly Xaa Ala
        35                  40                  45

Glu Pro Asp Glu Asn Ala Val Pro Asp Asp Xaa Ala Glu Pro Leu Xaa
    50                  55                  60

Xaa Val Asp Asp Xaa Ile Glu Glu Gly Leu Trp Xaa Pro Cys Met Asp
65                  70                  75                  80

Tyr Glu Leu Asp Xaa Met Xaa Arg
                85
```

<210> SEQ ID NO 17
<211> LENGTH: 393
<212> TYPE: PRT
<213> ORGANISM: Zea mays

<400> SEQUENCE: 17

```
Met Thr Met Glu Arg Ser Gln Pro Gln His Gln Gln Ser Pro Pro Ser
1               5                   10                  15

Pro Ser Ser Ser Ser Ser Cys Val Ser Ala Asp Thr Val Leu Val Pro
            20                  25                  30

Pro Gly Lys Arg Arg Arg Arg Ala Ala Thr Ala Lys Ala Asn Lys Arg
        35                  40                  45

Ala Arg Lys Asp Pro Ser Asp Pro Pro Pro Ala Ala Gly Lys Arg Ser
    50                  55                  60

Ser Val Tyr Arg Gly Val Thr Arg His Arg Trp Thr Gly Arg Phe Glu
65                  70                  75                  80

Ala His Leu Trp Asp Lys His Cys Leu Ala Ala Leu His Asn Lys Lys
                85                  90                  95

Lys Gly Arg Gln Val Tyr Leu Gly Ala Tyr Asp Gly Glu Glu Ala Ala
            100                 105                 110

Ala Arg Ala Tyr Asp Leu Ala Ala Leu Lys Tyr Trp Gly Pro Glu Ala
        115                 120                 125

Leu Leu Asn Phe Pro Val Glu Asp Tyr Ser Ser Glu Met Pro Glu Met
    130                 135                 140

Glu Ala Ala Ser Arg Glu Glu Tyr Leu Ala Ser Leu Arg Arg Arg Ser
145                 150                 155                 160

Ser Gly Phe Ser Arg Gly Val Ser Lys Tyr Arg Gly Val Ala Arg His
                165                 170                 175

His His Asn Gly Arg Trp Glu Ala Arg Ile Gly Arg Val Leu Gly Asn
            180                 185                 190

Lys Tyr Leu Tyr Leu Gly Thr Phe Asp Thr Gln Glu Glu Ala Ala Lys
        195                 200                 205

Ala Tyr Asp Leu Ala Ala Ile Glu Tyr Arg Gly Ala Asn Ala Val Thr
    210                 215                 220

Asn Phe Asp Ile Ser Cys Tyr Leu Asp His Pro Leu Phe Leu Ala Gln
225                 230                 235                 240

Leu Gln Gln Glu Gln Pro Gln Val Val Pro Ala Leu Asp Gln Glu Pro
                245                 250                 255

Gln Ala Asp Gln Arg Glu Pro Glu Thr Thr Ala Gln Glu Pro Val Ser
            260                 265                 270

Ser Gln Ala Lys Thr Pro Ala Asp Asp Asn Ala Glu Pro Asp Asp Ile
        275                 280                 285

Ala Glu Pro Leu Ile Thr Val Asp Asn Ser Val Glu Glu Ser Leu Trp
    290                 295                 300

Ser Pro Cys Met Asp Tyr Glu Leu Asp Thr Met Ser Arg Ser Asn Phe
305                 310                 315                 320

Gly Ser Ser Ile Asn Leu Ser Glu Trp Phe Thr Asp Ala Asp Phe Asp
                325                 330                 335

Ser Asp Leu Gly Cys Leu Phe Asp Gly Arg Ser Ala Val Asp Gly Gly
            340                 345                 350

Ser Lys Gly Gly Val Gly Val Ala Asp Phe Ser Leu Phe Glu Ala Gly
        355                 360                 365

Asp Gly Gln Leu Lys Asp Val Leu Ser Asp Met Glu Glu Gly Ile Gln
    370                 375                 380
```

Pro Pro Thr Ile Ile Ser Val Cys Asn
385 390

<210> SEQ ID NO 18
<211> LENGTH: 1561
<212> TYPE: DNA
<213> ORGANISM: Zea mays

<400> SEQUENCE: 18
cgttcatgca tgaccatgga gagatctcaa ccgcagcacc agcagtctcc tccgtcgccg 60
tcgtcctcct cgtcctgcgt ctccgcggac accgtcctcg tccctccggg aaagaggcgg 120
cggagggcgg cgacagccaa ggccaataag agggcccgca aggacccctc tgatcctcct 180
cccgccgccg ggaagaggag ctccgtatac agaggagtca ccaggcacag gtggacgggc 240
aggttcgagg cgcatctctg ggacaagcac tgcctcgccg cgctccacaa caagaagaaa 300
ggcaggcaag tctatctggg ggcgtacgac ggcgaggagg cagcggctcg tgcctatgac 360
cttgcagctc tcaagtactg ggtcctgag gctctgctca acttccctgt ggaggattac 420
tccagcgaga tgccggagat ggaggcagcg tcccgggagg agtacctggc ctccctccgc 480
cgcaggagca gcggcttctc caggggggtc tccaagtaca gaggcgtcgc caggcatcac 540
cacaacggga gatgggaggc acggatcggg cgagttttag ggaacaagta cctctacttg 600
ggaacattcg acactcaaga agaggcagcc aaggcctatg atcttgcggc catcgaatac 660
cgaggtgcca atgctgtaac caacttcgac atcagctgct acctggacca cccactgttc 720
ctggcgcagc tccagcagga gcagccacag gtggtgccag cgctcgacca agaacctcag 780
gctgatcaga gagaacctga aaccacagcc caagagcctg tgtcaagcca agccaagaca 840
ccggcggatg acaatgcaga gcctgatgac atcgcggagc ccctcatcac ggtcgacaac 900
agcgtcgagg agagcttatg gagtccttgc atggattatg agctagacac catgtcgaga 960
tctaactttg gcagctcgat caacctgagc gagtggttca ctgacgcaga cttcgacagc 1020
gacttgggat gcctgttcga cgggcgctct gcagttgatg gaggaagcaa gggtggcgta 1080
ggtgtggcgg atttcagttt gtttgaagca ggtgatggtc agctgaagga tgttctttcg 1140
gatatggaag aggggataca acctccaacg ataatcagtg tgtgcaattg attctgagac 1200
ctatgcgtgg cgtgcgacaa gtgtcctgtc tttgggtata cttggtttgt ccaatgccac 1260
ggtgccactg ctgcgagtca gctgaacttc ttgtagaaag cacatggcag cttggcatta 1320
gacaagtgtg ttggtgttcc ttaattcttt ggatatgctt taggcattga ctaaccttaa 1380
gggttcgtca ctgtctcgct tagcttagat tagactaatc acatccttga atctgaagta 1440
gttgtgcagt atcacagttt cacatggcaa ttctgccaat gcagcataga tttgttcgtt 1500
tgaacagctg taactgtaac cctatagctc cagattaagg aacagtttgt ttttcatcca 1560
t 1561

<210> SEQ ID NO 19
<211> LENGTH: 57
<212> TYPE: PRT
<213> ORGANISM: Zea mays

<400> SEQUENCE: 19

Arg Glu Pro Glu Thr Thr Ala Gln Glu Pro Val Ser Ser Gln Ala Lys
1 5 10 15

Thr Pro Ala Asp Asp Asn Ala Glu Pro Asp Asp Ile Ala Glu Pro Leu
20 25 30

```
Ile Thr Val Asp Asn Ser Val Glu Glu Ser Leu Trp Ser Pro Cys Met
        35                  40                  45

Asp Tyr Glu Leu Asp Thr Met Ser Arg
    50                  55


<210> SEQ ID NO 20
<211> LENGTH: 57
<212> TYPE: PRT
<213> ORGANISM: Artificial Sequence
<220> FEATURE:
<223> OTHER INFORMATION: A synthetic protein
<221> NAME/KEY: SITE
<222> LOCATION: 5,6,12,13,17,34,38,42,45,54,56
<223> OTHER INFORMATION: Xaa  = is any amino acid

<400> SEQUENCE: 20

Arg Glu Pro Glu Xaa Xaa Ala Gln Glu Pro Val Xaa Xaa Gln Ala Lys
1               5                   10                  15

Xaa Pro Ala Asp Asp Asn Ala Glu Pro Asp Asp Ile Ala Glu Pro Leu
            20                  25                  30

Ile Xaa Val Asp Asn Xaa Val Glu Glu Xaa Leu Trp Xaa Pro Cys Met
        35                  40                  45

Asp Tyr Glu Leu Asp Xaa Met Xaa Arg
    50                  55


<210> SEQ ID NO 21
<211> LENGTH: 337
<212> TYPE: PRT
<213> ORGANISM: Elaeis guineensis

<400> SEQUENCE: 21

Met Thr Leu Met Lys Asn Ser Pro Pro Ser Thr Pro Leu Pro Pro Ile
1               5                   10                  15

Ser Pro Ser Ser Ser Ala Ser Pro Ser Ser Tyr Ala Pro Leu Ser Ser
            20                  25                  30

Pro Asn Met Ile Pro Leu Asn Lys Cys Lys Lys Ser Lys Pro Lys His
        35                  40                  45

Lys Lys Ala Lys Asn Ser Asp Glu Ser Ser Arg Arg Arg Ser Ser Ile
    50                  55                  60

Tyr Arg Gly Val Thr Arg His Arg Gly Thr Gly Arg Tyr Glu Ala His
65                  70                  75                  80

Leu Trp Asp Lys His Trp Gln His Pro Val Gln Asn Lys Lys Gly Arg
                85                  90                  95

Gln Val Tyr Leu Gly Ala Phe Thr Asp Glu Leu Asp Ala Ala Arg Ala
            100                 105                 110

His Asp Leu Ala Ala Leu Lys Leu Trp Gly Pro Glu Thr Ile Leu Asn
        115                 120                 125

Phe Pro Val Glu Met Tyr Arg Glu Glu Tyr Lys Glu Met Gln Thr Met
    130                 135                 140

Ser Lys Glu Glu Val Leu Ala Ser Val Arg Arg Arg Ser Asn Gly Phe
145                 150                 155                 160

Ala Arg Gly Thr Ser Lys Tyr Arg Gly Val Ala Arg His His Lys Asn
                165                 170                 175

Gly Arg Trp Glu Ala Arg Leu Ser Gln Asp Val Gly Cys Lys Tyr Ile
            180                 185                 190

Tyr Leu Gly Thr Tyr Ala Thr Gln Glu Glu Ala Ala Gln Ala Tyr Asp
        195                 200                 205
```

-continued

```
Leu Ala Ala Leu Val His Lys Gly Pro Asn Ile Val Thr Asn Phe Ala
    210                 215                 220

Ser Ser Val Tyr Lys His Arg Leu Gln Pro Phe Met Gln Leu Leu Val
225                 230                 235                 240

Lys Pro Glu Thr Glu Pro Ala Gln Glu Asp Leu Gly Val Leu Gln Met
                245                 250                 255

Glu Ala Thr Glu Thr Ile Asp Gln Thr Met Pro Asn Tyr Asp Leu Pro
            260                 265                 270

Glu Ile Ser Trp Thr Phe Asp Ile Asp His Asp Leu Gly Ala Tyr Pro
        275                 280                 285

Leu Leu Asp Val Pro Ile Glu Asp Asp Gln His Asp Ile Leu Asn Asp
    290                 295                 300

Leu Asn Phe Glu Gly Asn Ile Glu His Leu Phe Glu Glu Phe Glu Thr
305                 310                 315                 320

Phe Gly Gly Asn Glu Ser Gly Ser Asp Gly Phe Ser Ala Ser Lys Gly
                325                 330                 335

Ala


<210> SEQ ID NO 22
<211> LENGTH: 1782
<212> TYPE: DNA
<213> ORGANISM: Elaeis guineensis

<400> SEQUENCE: 22

agagagagag agattccaac acagggcagc tgagattgag cacaaggcgc cgtggaaacc     60

acgagttcca ttggcaacat gggaaacctg gtggccaagt gtagagctct ctcacacaaa    120

cccatgcggc caacttgcag accctcgagt catttggact cttccaagct caccagccgt    180

agggtttttt gacaagaggg acctccagta aacgttaaac aaactcgcag ctcccacctt    240

tggatccatt ccatcgcttc aacggtgggt tagaagcctc cgcgccaaat gcacgagtgc    300

tcaacagcac gctcccctaa tttttctctc tccacctcct cacttctcta tatataatcc    360

tctctttggt gaaccaccat caaccaaacc aacggtatag tatacgtagg aaataatccc    420

tttctagaac atgactctca tgaagaaatc tcctccctct actcctctcc caccaatatc    480

gccttcctct tccgcttcac catccagcta tgcacccctt tcttctccta atatgatccc    540

tcttaacaag tgcaagaagt cgaagccaaa acataagaaa gctaagaact cagatgaaag    600

cagtaggaga agaagctcta tctacagagg agtcacgagg caccgaggga ctgggagata    660

tgaagctcac ctgtgggaca agcactggca gcatccggtc cagaacaaga aaggcaggca    720

agtttacttg ggagccttta ctgatgagtt ggacgcagca cgagctcatg acttggctgc    780

ccttaagctc tggggtccag agacaatttt aaacttccct gtggaaatgt atagagaaga    840

gtacaaggag atgcaaacca tgtcaaagga agaggtgctg gcttcggtta ggcgcaggag    900

caacggcttt gccaggggta cctctaagta ccgtggggtg gccaggcatc acaaaaacgg    960

ccggtgggag gccaggctta gccaggacgt tggctgcaag tacatctact tgggaacata   1020

cgcaactcaa gaggaggctg cccaagctta tgatttagct gctctagtac acaaagggcc   1080

aaatatagtg accaactttg ctagcagtgt ctataagcat cgcctacagc cattcatgca   1140

gctattagtg aagcctgaga cggagccagc acaagaagac ctgggggtta tgcaaatgga   1200

agcaaccgag acaatcgatc agaccatgcc aaattacgac ctgccggaga tctcatggac   1260

cttcgacata gaccatgact taggtgcata tcctctcctt gatgtcccaa ttgaggatga   1320

tcaacatgac atcttgaatg atctcaattt cgaggggaac attgagcacc tctttgaaga   1380
```

```
gtttgagacc ttcggaggca atgagagtgg aagtgatggt ttcagtgcaa gcaaaggtgc   1440

ctagcagagg aaagtggttt gaagatggag gacatggcat ctaaagcgaa ctgagcctcc   1500

tggcctcttc aaagtagtgt ctgcttttta gaaatcttgg tgggtcgatt tgagttagga   1560

gcccgatact tctatcaggg gatatgttta gctacaattc tagttttttt ttcttttttt   1620

tttttcagcc ggaagtctgg tacttctgtt gaatattatg atgtgcttct tgcttagttg   1680

ttcctgttct tctccctttt agagttcagc atatttatgt tttgatgtaa tggggaatgt   1740

tggcagacag cttgatatat ggttatttca ttctccatta aa                      1782


<210> SEQ ID NO 23
<211> LENGTH: 42
<212> TYPE: PRT
<213> ORGANISM: Elaeis guineensis

<400> SEQUENCE: 23

Lys Pro Glu Thr Glu Pro Ala Gln Glu Asp Leu Gly Val Leu Gln Met
1               5                   10                  15

Glu Ala Thr Glu Thr Ile Asp Gln Thr Met Pro Asn Tyr Asp Leu Pro
            20                  25                  30

Glu Ile Ser Trp Thr Phe Asp Ile Asp His
        35                  40


<210> SEQ ID NO 24
<211> LENGTH: 42
<212> TYPE: PRT
<213> ORGANISM: Artificial Sequence
<220> FEATURE:
<223> OTHER INFORMATION: A synthetic protein
<221> NAME/KEY: SITE
<222> LOCATION: 4,19,21,25,35,37
<223> OTHER INFORMATION: Xaa = is any amino acid

<400> SEQUENCE: 24

Lys Pro Glu Xaa Glu Pro Ala Gln Glu Asp Leu Gly Val Leu Gln Met
1               5                   10                  15

Glu Ala Xaa Glu Xaa Ile Asp Gln Xaa Met Pro Asn Tyr Asp Leu Pro
            20                  25                  30

Glu Ile Xaa Trp Xaa Phe Asp Ile Asp His
        35                  40


<210> SEQ ID NO 25
<211> LENGTH: 409
<212> TYPE: PRT
<213> ORGANISM: Glycine max

<400> SEQUENCE: 25

Met Lys Arg Ser Pro Ala Ser Ser Cys Ser Ser Ser Thr Ser Ser Val
1               5                   10                  15

Gly Phe Glu Ala Pro Ile Glu Lys Arg Arg Pro Lys His Pro Arg Arg
            20                  25                  30

Asn Asn Leu Lys Ser Gln Lys Cys Lys Gln Asn Gln Thr Thr Thr Gly
        35                  40                  45

Gly Arg Arg Ser Ser Ile Tyr Arg Gly Val Thr Arg His Arg Trp Thr
    50                  55                  60

Gly Arg Phe Glu Ala His Leu Trp Asp Lys Ser Ser Trp Asn Asn Ile
65                  70                  75                  80

Gln Ser Lys Lys Gly Arg Gln Gly Ala Tyr Asp Thr Glu Glu Ser Ala
                85                  90                  95
```

-continued

```
Ala Arg Thr Tyr Asp Leu Ala Ala Leu Lys Tyr Trp Gly Lys Asp Ala
            100                 105                 110

Thr Leu Asn Phe Pro Ile Glu Thr Tyr Thr Lys Glu Leu Glu Glu Met
        115                 120                 125

Asp Lys Val Ser Arg Glu Glu Tyr Leu Ala Ser Leu Arg Arg Gln Ser
    130                 135                 140

Ser Gly Phe Ser Arg Gly Leu Ser Lys Tyr Arg Gly Val Ala Arg His
145                 150                 155                 160

His His Asn Gly Arg Trp Glu Ala Arg Ile Gly Arg Val Cys Gly Asn
                165                 170                 175

Lys Tyr Leu Tyr Leu Gly Thr Tyr Lys Thr Gln Glu Glu Ala Ala Val
            180                 185                 190

Ala Tyr Asp Met Ala Ala Ile Glu Tyr Arg Gly Val Asn Ala Val Thr
        195                 200                 205

Asn Phe Asp Ile Ser Asn Tyr Met Asp Lys Ile Lys Lys Lys Asn Asp
    210                 215                 220

Gln Thr Gln Gln Gln Gln Thr Glu Ala Gln Thr Glu Thr Val Pro Asn
225                 230                 235                 240

Ser Ser Asp Ser Glu Glu Val Glu Val Glu Gln Gln Thr Thr Thr Ile
                245                 250                 255

Thr Thr Pro Pro Pro Ser Glu Asn Leu His Met Pro Pro Gln Gln His
            260                 265                 270

Gln Val Gln Tyr Thr Pro His Val Ser Pro Arg Glu Glu Glu Ser Ser
        275                 280                 285

Ser Leu Ile Thr Ile Met Asp His Val Leu Glu Gln Asp Leu Pro Trp
    290                 295                 300

Ser Phe Met Tyr Thr Gly Leu Ser Gln Phe Gln Asp Pro Asn Leu Ala
305                 310                 315                 320

Phe Cys Lys Gly Asp Asp Asp Leu Val Gly Met Phe Asp Ser Ala Gly
                325                 330                 335

Phe Glu Glu Asp Ile Asp Phe Leu Phe Ser Thr Gln Pro Gly Asp Glu
            340                 345                 350

Thr Glu Ser Asp Val Asn Asn Met Ser Ala Val Leu Asp Ser Val Glu
        355                 360                 365

Cys Gly Asp Thr Asn Gly Ala Gly Gly Ser Met Met His Val Asp Asn
    370                 375                 380

Lys Gln Lys Ile Val Ser Phe Ala Ser Ser Pro Ser Ser Thr Thr Thr
385                 390                 395                 400

Val Ser Cys Asp Tyr Ala Leu Asp Leu
                405
```

<210> SEQ ID NO 26
<211> LENGTH: 2206
<212> TYPE: DNA
<213> ORGANISM: Glycine max

<400> SEQUENCE: 26

```
agtgttgctc aaattcaagc cacttaatta gccatggttg attgatcaag ttaaattcca      60

acccaaggtt aaatcattac tcccttctca tccttcccaa ccccaacccc cagaaatatt     120

acagattcaa ttgcttaatt aaatactatt ttcccctcct tctataatac cctccaaaat     180

ctttttcctt cttcattctc cctttctcta tgttttggca aaccacttta ggtaaccaga     240

ttactactac tattgcttca tatacaaaga tgctatcgta aaaaagagag aaacttggga     300
```

-continued

```
agtgggaaca cattcaaaat ccttgttttt ctttttggtc taatttttca tctcaaaaca    360
cacacccatt gagtattttt catttttttg ttcttttggg acaaaaaagg tgggtgttgt    420
tggcattatt gaagatagag gcccccaaaa tgaagaggtc tccagcatct tcttgttcat    480
catctacttc ctctgttggg tttgaagctc ccattgaaaa aagaaggcct aagcatccaa    540
ggaggaataa tttgaagtca caaaaatgca agcagaacca aaccaccact ggtggcagaa    600
gaagctctat ctatagagga gttacaaggc ataggtggac agggaggttt gaagctcacc    660
tatgggataa gagctcttgg aacaacattc agagcaagaa gggtcgacaa ggggcatatg    720
atactgaaga atctgcagcc cgtacctatg accttgcagc ccttaaatac tggggaaaag    780
atgcaaccct gaatttcccg atagaaactt ataccaagga gctcgaggaa atggacaagg    840
tttcaagaga agaatatttg gcttctttgc ggcgccaaag cagtggcttt tctagaggcc    900
tgtctaagta ccgtggggtt gctaggcatc atcataatgg tcgctgggaa gcacgaattg    960
gaagagtatg cggaaacaag tacctctact tggggacata taaaactcaa gaggaggcag   1020
cagtggcata tgacatggca gcaatagagt accgtggagt caatgcagtg accaattttg   1080
acataagcaa ctacatggac aaaataaaga agaaaaatga ccaaacccaa caacaacaaa   1140
cagaagcaca aacggaaaca gttcctaact cctctgactc tgaagaagta gaagtagaac   1200
aacagacaac aacaataacc acaccacccc catctgaaaa tctgcacatg ccaccacagc   1260
agcaccaagt tcaatacacc ccccatgtct ctccaaggga agaagaatca tcatcactga   1320
tcacaattat ggaccatgtg cttgagcagg atctgccatg gagcttcatg tacactggct   1380
tgtctcagtt tcaagatcca aacttggctt tctgcaaagg tgatgatgac ttggtgggca   1440
tgtttgatag tgcagggttt gaggaagaca ttgattttct gttcagcact caacctggtg   1500
atgagactga gagtgatgtc aacaatatga gcgcagtttt ggatagtgtt gagtgtggag   1560
acacaaatgg ggctggtgga agcatgatgc atgtggataa caagcagaag atagtatcat   1620
ttgcttcttc accatcatct acaactacag tttcttgtga ctatgctcta gatctatgat   1680
ctcttcagaa gggtgatgga tgacctacat ggaatggaac cttgtgtaga ttattattgg   1740
gtttgttatg catgttgttg gggtttgttg tgataggttg gtggatgggt gtgacttgtg   1800
aaaatgttca ttggttttag gattttcctt tcatccatac tccgttgtcg aaagaagaaa   1860
atgttcattt tagacttgga ttttagtata aaaaaaaagg agaaaaaacc aaaaatgtga   1920
tttgggtgca aacaatgttt tgtttttctt tttacttttg gggtaaggag atgaagagag   1980
gggaaattta aaccattcct attcttgggg gataatgcag tataaattaa gatcagactg   2040
tttttagcat atggagtgca aactgcaaag gccaagtttc ctttgtttaa acaatttagg   2100
ctttcttttc ctttgcctat ttttttttta tttttttttt tgtattgggg catagcagtt   2160
agtgttgtgt tgagatctga aatctgatct ctggtttggt ttgttc                 2206
```

<210> SEQ ID NO 27
<211> LENGTH: 59
<212> TYPE: PRT
<213> ORGANISM: Glycine max

<400> SEQUENCE: 27

```
Asp Glu Thr Glu Ser Asp Val Asn Asn Met Ser Ala Val Leu Asp Ser
1               5                   10                  15

Val Glu Cys Gly Asp Thr Asn Gly Ala Gly Gly Ser Met Met His Val
            20                  25                  30

Asp Asn Lys Gln Lys Ile Val Ser Phe Ala Ser Ser Pro Ser Ser Thr
```

```
                35                  40                  45
Thr Thr Val Ser Cys Asp Tyr Ala Leu Asp Leu
    50                  55

<210> SEQ ID NO 28
<211> LENGTH: 59
<212> TYPE: PRT
<213> ORGANISM: Artificial Sequence
<220> FEATURE:
<223> OTHER INFORMATION: A synthetic protein
<221> NAME/KEY: SITE
<222> LOCATION: 3,5,11,16,22,28,40,43,44,46,47,48,49,50,52
<223> OTHER INFORMATION: Xaa = is any amino acid

<400> SEQUENCE: 28

Asp Glu Xaa Glu Xaa Asp Val Asn Asn Met Xaa Ala Val Leu Asp Xaa
1               5                   10                  15

Val Glu Cys Gly Asp Xaa Asn Gly Ala Gly Gly Xaa Met Met His Val
                20                  25                  30

Asp Asn Lys Gln Lys Ile Val Xaa Phe Ala Xaa Xaa Pro Xaa Xaa Xaa
                35                  40                  45

Xaa Xaa Val Xaa Cys Asp Tyr Ala Leu Asp Leu
    50                  55

<210> SEQ ID NO 29
<211> LENGTH: 430
<212> TYPE: PRT
<213> ORGANISM: Arabidopsis thaliana

<400> SEQUENCE: 29

Met Lys Lys Arg Leu Thr Thr Ser Thr Cys Ser Ser Ser Pro Ser Ser
1               5                   10                  15

Ser Val Ser Ser Ser Thr Thr Thr Ser Ser Pro Ile Gln Ser Glu Ala
                20                  25                  30

Pro Arg Pro Lys Arg Ala Lys Arg Ala Lys Lys Ser Ser Pro Ser Gly
                35                  40                  45

Asp Lys Ser His Asn Pro Thr Ser Pro Ala Ser Thr Arg Arg Ser Ser
    50                  55                  60

Ile Tyr Arg Gly Val Thr Arg His Arg Trp Thr Gly Arg Phe Glu Ala
65              70                  75                  80

His Leu Trp Asp Lys Ser Ser Trp Asn Ser Ile Gln Asn Lys Lys Gly
                85                  90                  95

Lys Gln Val Tyr Leu Gly Ala Tyr Asp Ser Glu Glu Ala Ala Ala His
                100                 105                 110

Thr Tyr Asp Leu Ala Ala Leu Lys Tyr Trp Gly Pro Asp Thr Ile Leu
                115                 120                 125

Asn Phe Pro Ala Glu Thr Tyr Thr Lys Glu Leu Glu Glu Met Gln Arg
                130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
                180                 185                 190

Leu Tyr Leu Gly Thr Tyr Asn Thr Gln Glu Glu Ala Ala Ala Ala Tyr
                195                 200                 205

Asp Met Ala Ala Ile Glu Tyr Arg Gly Ala Asn Ala Val Thr Asn Phe
                210                 215                 220
```

Asp Ile Ser Asn Tyr Ile Asp Arg Leu Lys Lys Lys Gly Val Phe Pro
225 230 235 240

Phe Pro Val Asn Gln Ala Asn His Gln Glu Gly Ile Leu Val Glu Ala
245 250 255

Lys Gln Glu Val Glu Thr Arg Glu Ala Lys Glu Glu Pro Arg Glu Glu
260 265 270

Val Lys Gln Gln Tyr Val Glu Glu Pro Pro Gln Glu Glu Glu Glu Lys
275 280 285

Glu Glu Glu Lys Ala Glu Gln Gln Glu Ala Glu Ile Val Gly Tyr Ser
290 295 300

Glu Glu Ala Ala Val Val Asn Cys Cys Ile Asp Ser Ser Thr Ile Met
305 310 315 320

Glu Met Asp Arg Cys Gly Asp Asn Asn Glu Leu Ala Trp Asn Phe Cys
325 330 335

Met Met Asp Thr Gly Phe Ser Pro Phe Leu Thr Asp Gln Asn Leu Ala
340 345 350

Asn Glu Asn Pro Ile Glu Tyr Pro Glu Leu Phe Asn Glu Leu Ala Phe
355 360 365

Glu Asp Asn Ile Asp Phe Met Phe Asp Asp Gly Lys His Glu Cys Leu
370 375 380

Asn Leu Glu Asn Leu Asp Cys Cys Val Val Gly Arg Glu Ser Pro Pro
385 390 395 400

Ser Ser Ser Ser Pro Leu Ser Cys Leu Ser Thr Asp Ser Ala Ser Ser
405 410 415

Thr Thr Thr Thr Thr Thr Ser Val Ser Cys Asn Tyr Leu Val
420 425 430

<210> SEQ ID NO 30
<211> LENGTH: 430
<212> TYPE: PRT
<213> ORGANISM: Artificial Sequence
<220> FEATURE:
<223> OTHER INFORMATION: A synthetic protein

<400> SEQUENCE: 30

Met Lys Lys Arg Leu Thr Thr Ser Thr Cys Ser Ser Ser Pro Ser Ser
1 5 10 15

Ser Val Ser Ser Ser Thr Thr Thr Ser Ser Pro Ile Gln Ser Glu Ala
20 25 30

Pro Arg Pro Lys Arg Ala Lys Arg Ala Lys Lys Ser Ser Pro Ser Gly
35 40 45

Asp Lys Ser His Asn Pro Thr Ser Pro Ala Ser Thr Arg Arg Ser Ser
50 55 60

Ile Tyr Arg Gly Val Thr Arg His Arg Trp Thr Gly Arg Phe Glu Ala
65 70 75 80

His Leu Trp Asp Lys Ser Ser Trp Asn Ser Ile Gln Asn Lys Lys Gly
85 90 95

Lys Gln Val Tyr Leu Gly Ala Tyr Asp Ser Glu Glu Ala Ala Ala His
100 105 110

Thr Tyr Asp Leu Ala Ala Leu Lys Tyr Trp Gly Pro Asp Thr Ile Leu
115 120 125

Asn Phe Pro Ala Glu Thr Tyr Thr Lys Glu Leu Glu Glu Met Gln Arg
130 135 140

Val Thr Lys Glu Glu Tyr Leu Ala Ser Leu Arg Arg Gln Ser Ser Gly
145 150 155 160

Phe Ser Arg Gly Val Ser Lys Tyr Arg Gly Val Ala Arg His His His
165 170 175

Asn Gly Arg Trp Glu Ala Arg Ile Gly Arg Val Phe Gly Asn Lys Tyr
180 185 190

Leu Tyr Leu Gly Thr Tyr Asn Thr Gln Glu Glu Ala Ala Ala Tyr
195 200 205

Asp Met Ala Ala Ile Glu Tyr Arg Gly Ala Asn Ala Val Thr Asn Phe
210 215 220

Asp Ile Ser Asn Tyr Ile Asp Arg Leu Lys Lys Lys Gly Val Phe Pro
225 230 235 240

Phe Pro Val Asn Gln Ala Asn His Gln Glu Gly Ile Leu Val Glu Ala
245 250 255

Lys Gln Glu Val Glu Thr Arg Glu Ala Lys Glu Glu Pro Arg Glu Glu
260 265 270

Val Lys Gln Gln Tyr Val Glu Glu Pro Pro Gln Glu Glu Glu Glu Lys
275 280 285

Glu Glu Glu Lys Ala Glu Gln Gln Glu Ala Glu Ile Val Gly Tyr Ser
290 295 300

Glu Glu Ala Ala Val Val Asn Cys Cys Ile Asp Ser Ser Thr Ile Met
305 310 315 320

Glu Met Asp Arg Cys Gly Asp Asn Asn Glu Leu Ala Trp Asn Phe Cys
325 330 335

Met Met Asp Thr Gly Phe Ser Pro Phe Leu Thr Asp Gln Asn Leu Ala
340 345 350

Asn Glu Asn Pro Ile Glu Tyr Pro Glu Leu Phe Asn Glu Leu Ala Phe
355 360 365

Glu Asp Asn Ile Asp Phe Met Phe Asp Asp Gly Lys His Glu Cys Leu
370 375 380

Asn Leu Glu Asn Leu Asp Cys Cys Val Val Gly Arg Glu Ala Pro Pro
385 390 395 400

Ala Ala Ser Ser Pro Leu Ala Cys Leu Ser Thr Asp Ser Ala Ala Ala
405 410 415

Thr Thr Thr Ala Ala Ala Ala Val Ser Cys Asn Tyr Leu Val
420 425 430

<210> SEQ ID NO 31
<211> LENGTH: 430
<212> TYPE: PRT
<213> ORGANISM: Artificial Sequence
<220> FEATURE:
<223> OTHER INFORMATION: A synthetic protein

<400> SEQUENCE: 31

Met Lys Lys Arg Leu Thr Thr Ser Thr Cys Ser Ser Ser Pro Ser Ser
1 5 10 15

Ser Val Ser Ser Ser Thr Thr Thr Ser Ser Pro Ile Gln Ser Glu Ala
20 25 30

Pro Arg Pro Lys Arg Ala Lys Arg Ala Lys Lys Ser Ser Pro Ser Gly
35 40 45

Asp Lys Ser His Asn Pro Thr Ser Pro Ala Ser Thr Arg Arg Ser Ser
50 55 60

Ile Tyr Arg Gly Val Thr Arg His Arg Trp Thr Gly Arg Phe Glu Ala
65 70 75 80

His Leu Trp Asp Lys Ser Ser Trp Asn Ser Ile Gln Asn Lys Lys Gly
85 90 95

```
Lys Gln Val Tyr Leu Gly Ala Tyr Asp Ser Glu Glu Ala Ala Ala His
            100                 105                 110

Thr Tyr Asp Leu Ala Ala Leu Lys Tyr Trp Gly Pro Asp Thr Ile Leu
        115                 120                 125

Asn Phe Pro Ala Glu Thr Tyr Thr Lys Glu Leu Glu Glu Met Gln Arg
    130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190

Leu Tyr Leu Gly Thr Tyr Asn Thr Gln Glu Glu Ala Ala Ala Ala Tyr
        195                 200                 205

Asp Met Ala Ala Ile Glu Tyr Arg Gly Ala Asn Ala Val Thr Asn Phe
    210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Glu Pro Arg Glu Glu
            260                 265                 270

Val Lys Gln Gln Tyr Val Glu Glu Pro Pro Gln Glu Glu Glu Glu Lys
        275                 280                 285

Glu Glu Glu Lys Ala Glu Gln Gln Glu Ala Glu Ile Val Gly Tyr Ser
    290                 295                 300

Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
                325                 330                 335

Met Met Asp Thr Gly Phe Ser Pro Phe Leu Thr Asp Gln Asn Leu Ala
            340                 345                 350

Asn Glu Asn Pro Ile Glu Tyr Pro Glu Leu Phe Asn Glu Leu Ala Phe
        355                 360                 365

Glu Asp Asn Ile Asp Phe Met Phe Asp Asp Gly Lys His Glu Cys Leu
    370                 375                 380

Asn Leu Glu Asn Leu Asp Cys Cys Val Val Gly Arg Glu Asp Pro Pro
385                 390                 395                 400

Asp Asp Ser Ser Pro Leu Asp Cys Leu Ser Thr Asp Ser Ala Asp Asp
                405                 410                 415

Thr Thr Thr Asp Asp Asp Asp Val Ser Cys Asn Tyr Leu Val
            420                 425                 430
```

<210> SEQ ID NO 32
<211> LENGTH: 29
<212> TYPE: DNA
<213> ORGANISM: Artificial Sequence
<220> FEATURE:
<223> OTHER INFORMATION: A synthetic primer

<400> SEQUENCE: 32
aatggatccg gacaatgaag aagcgctta 29

<210> SEQ ID NO 33
<211> LENGTH: 24

<212> TYPE: DNA
<213> ORGANISM: Artificial Sequence
<220> FEATURE:
<223> OTHER INFORMATION: A synthetic primer

<400> SEQUENCE: 33
tccctcgagt cagaccaaat agtt 24

<210> SEQ ID NO 34
<211> LENGTH: 24
<212> TYPE: DNA
<213> ORGANISM: Artificial Sequence
<220> FEATURE:
<223> OTHER INFORMATION: A synthetic primer

<400> SEQUENCE: 34
gtaggatatt cagaagaagc agca 24

<210> SEQ ID NO 35
<211> LENGTH: 24
<212> TYPE: DNA
<213> ORGANISM: Artificial Sequence
<220> FEATURE:
<223> OTHER INFORMATION: A synthetic primer

<400> SEQUENCE: 35
tgctgcttct tctgaatatc ctac 24

<210> SEQ ID NO 36
<211> LENGTH: 40
<212> TYPE: DNA
<213> ORGANISM: Artificial Sequence
<220> FEATURE:
<223> OTHER INFORMATION: A synthetic primer

<400> SEQUENCE: 36
gcagcatctt caccattggc atgcttatct actgactctg 40

<210> SEQ ID NO 37
<211> LENGTH: 39
<212> TYPE: DNA
<213> ORGANISM: Artificial Sequence
<220> FEATURE:
<223> OTHER INFORMATION: A synthetic primer

<400> SEQUENCE: 37
agagtcagta gataagcatg ccaatggtga agatgctgc 39

<210> SEQ ID NO 38
<211> LENGTH: 60
<212> TYPE: DNA
<213> ORGANISM: Artificial Sequence
<220> FEATURE:
<223> OTHER INFORMATION: A synthetic primer

<400> SEQUENCE: 38
gtggtgggaa gagaggaccc acccgacgac tcttcaccat tggactgctt atctactgac 60

<210> SEQ ID NO 39
<211> LENGTH: 60
<212> TYPE: DNA
<213> ORGANISM: Artificial Sequence
<220> FEATURE:
<223> OTHER INFORMATION: A synthetic primer

<400> SEQUENCE: 39

-continued gtcagtagat aagcagtcca atggtgaaga gtcgtcgggt gggtcctctc ttcccaccac 60

<210> SEQ ID NO 40
<211> LENGTH: 28
<212> TYPE: DNA
<213> ORGANISM: Artificial Sequence
<220> FEATURE:
<223> OTHER INFORMATION: A synthetic primer

<400> SEQUENCE: 40
tccctcgagt catcctacaa tctctgct 28

<210> SEQ ID NO 41
<211> LENGTH: 39
<212> TYPE: DNA
<213> ORGANISM: Artificial Sequence
<220> FEATURE:
<223> OTHER INFORMATION: A synthetic primer

<400> SEQUENCE: 41
tatgcggccg ctcataactc attgaatagc tccggatac 39

<210> SEQ ID NO 42
<211> LENGTH: 31
<212> TYPE: DNA
<213> ORGANISM: Artificial Sequence
<220> FEATURE:
<223> OTHER INFORMATION: A synthetic primer

<400> SEQUENCE: 42
tccctcgagt cactctcttc ccaccacgca a 31

<210> SEQ ID NO 43
<211> LENGTH: 27
<212> TYPE: DNA
<213> ORGANISM: Artificial Sequence
<220> FEATURE:
<223> OTHER INFORMATION: A synthetic primer

<400> SEQUENCE: 43
tgactcgagt cattcttctg aatatcc 27

<210> SEQ ID NO 44
<211> LENGTH: 25
<212> TYPE: DNA
<213> ORGANISM: Artificial Sequence
<220> FEATURE:
<223> OTHER INFORMATION: A synthetic primer

<400> SEQUENCE: 44
gcaggatcca tatggcagca gtggt 25

<210> SEQ ID NO 45
<211> LENGTH: 27
<212> TYPE: DNA
<213> ORGANISM: Artificial Sequence
<220> FEATURE:
<223> OTHER INFORMATION: A synthetic primer

<400> SEQUENCE: 45
gtactcgagt cactctcttc ccaccac 27

<210> SEQ ID NO 46
<211> LENGTH: 27
<212> TYPE: DNA
<213> ORGANISM: Artificial Sequence
<220> FEATURE:
<223> OTHER INFORMATION: A synthetic primer

<400> SEQUENCE: 46
gtactcgagt caaaatgcta actcatt 27

<210> SEQ ID NO 47
<211> LENGTH: 37
<212> TYPE: DNA
<213> ORGANISM: Artificial Sequence
<220> FEATURE:
<223> OTHER INFORMATION: A synthetic primer

<400> SEQUENCE: 47
aatggatccg gacaatgttt gaggacaaca tcgactt 37

<210> SEQ ID NO 48
<211> LENGTH: 57
<212> TYPE: DNA
<213> ORGANISM: Artificial Sequence
<220> FEATURE:
<223> OTHER INFORMATION: A synthetic primer

<400> SEQUENCE: 48
tggtgggaag agagagcgca gcatcttctt cttcagcatt gtcttgctta tctactg 57

<210> SEQ ID NO 49
<211> LENGTH: 57
<212> TYPE: DNA
<213> ORGANISM: Artificial Sequence
<220> FEATURE:
<223> OTHER INFORMATION: A synthetic primer

<400> SEQUENCE: 49
cagtagataa gcaagacaat gctgaagaag aagatgctgc gctctctctt cccacca 57

<210> SEQ ID NO 50
<211> LENGTH: 56
<212> TYPE: DNA
<213> ORGANISM: Artificial Sequence
<220> FEATURE:
<223> OTHER INFORMATION: A synthetic primer

<400> SEQUENCE: 50
tggtgggaag agagagcttg ttgtcttctt cttcattgtt gtcttgctta tctact 56

<210> SEQ ID NO 51
<211> LENGTH: 57
<212> TYPE: DNA
<213> ORGANISM: Artificial Sequence
<220> FEATURE:
<223> OTHER INFORMATION: A synthetic primer

<400> SEQUENCE: 51
cagtagataa gcaagacaac aatgaagaag aagacaacaa gctctctctt cccacca 57

<210> SEQ ID NO 52
<211> LENGTH: 20
<212> TYPE: DNA
<213> ORGANISM: Artificial Sequence
<220> FEATURE:
<223> OTHER INFORMATION: A synthetic primer

<400> SEQUENCE: 52
agggctatgt gcaggagaga 20

-continued

<210> SEQ ID NO 53
<211> LENGTH: 20
<212> TYPE: DNA
<213> ORGANISM: Artificial Sequence
<220> FEATURE:
<223> OTHER INFORMATION: A synthetic primer

<400> SEQUENCE: 53
cttgtggccg agaatgtttc 20

<210> SEQ ID NO 54
<211> LENGTH: 22
<212> TYPE: DNA
<213> ORGANISM: Artificial Sequence
<220> FEATURE:
<223> OTHER INFORMATION: A synthetic primer

<400> SEQUENCE: 54
agagcagtgg tttctccaga gg 22

<210> SEQ ID NO 55
<211> LENGTH: 22
<212> TYPE: DNA
<213> ORGANISM: Artificial Sequence
<220> FEATURE:
<223> OTHER INFORMATION: A synthetic primer

<400> SEQUENCE: 55
ttccgttgtg gtgatgccta gc 22

<210> SEQ ID NO 56
<211> LENGTH: 22
<212> TYPE: DNA
<213> ORGANISM: Artificial Sequence
<220> FEATURE:
<223> OTHER INFORMATION: A synthetic primer

<400> SEQUENCE: 56
gaccctgatg ttgatgttcg ct 22

<210> SEQ ID NO 57
<211> LENGTH: 22
<212> TYPE: DNA
<213> ORGANISM: Artificial Sequence
<220> FEATURE:
<223> OTHER INFORMATION: A synthetic primer

<400> SEQUENCE: 57
gagggatttg aagagagatt tc 22

<210> SEQ ID NO 58
<211> LENGTH: 31
<212> TYPE: PRT
<213> ORGANISM: Arabidopsis thaliana

<400> SEQUENCE: 58

```
Arg Leu Thr Thr Ser Thr Cys Ser Ser Ser Pro Ser Ser Ser Val Ser
1               5                   10                  15

Ser Ser Thr Thr Thr Ser Ser Pro Ile Gln Ser Glu Ala Pro Arg
            20                  25                  30
```

<210> SEQ ID NO 59
<211> LENGTH: 35
<212> TYPE: PRT
<213> ORGANISM: Arabidopsis thaliana

<400> SEQUENCE: 59

Arg Glu Ser Pro Pro Ser Ser Ser Ser Pro Leu Ser Cys Leu Ser Thr
1 5 10 15

Asp Ser Ala Ser Ser Thr Thr Thr Thr Thr Thr Ser Val Ser Cys Asn
20 25 30

Tyr Leu Val
35

<210> SEQ ID NO 60
<211> LENGTH: 34
<212> TYPE: PRT
<213> ORGANISM: Arabidopsis thaliana

<400> SEQUENCE: 60

Glu Ser Pro Pro Ser Ser Ser Ser Pro Leu Ser Cys Leu Ser Thr Asp
1 5 10 15

Ser Ala Ser Ser Thr Thr Thr Thr Thr Thr Ser Val Ser Cys Asn Tyr
20 25 30

Leu Val

<210> SEQ ID NO 61
<211> LENGTH: 34
<212> TYPE: PRT
<213> ORGANISM: Arabidopsis thaliana

<400> SEQUENCE: 61

Glu Ala Pro Pro Ala Ala Ser Ser Pro Leu Ala Cys Leu Ser Thr Asp
1 5 10 15

Ser Ala Ala Ala Thr Thr Thr Ala Ala Ala Ala Val Ser Cys Asn Tyr
20 25 30

Leu Val

<210> SEQ ID NO 62
<211> LENGTH: 430
<212> TYPE: PRT
<213> ORGANISM: Artificial Sequence
<220> FEATURE:
<223> OTHER INFORMATION: A synthetic protein

<400> SEQUENCE: 62

Met Lys Lys Arg Leu Thr Thr Ser Thr Cys Ser Ser Ser Pro Ser Ser
1 5 10 15

Ser Val Ser Ser Ser Thr Thr Thr Ser Ser Pro Ile Gln Ser Glu Ala
20 25 30

Pro Arg Pro Lys Arg Ala Lys Arg Ala Lys Lys Ser Ser Pro Ser Gly
35 40 45

Asp Lys Ser His Asn Pro Thr Ser Pro Ala Ser Thr Arg Arg Ser Ser
50 55 60

Ile Tyr Arg Gly Val Thr Arg His Arg Trp Thr Gly Arg Phe Glu Ala
65 70 75 80

His Leu Trp Asp Lys Ser Ser Trp Asn Ser Ile Gln Asn Lys Lys Gly
85 90 95

Lys Gln Val Tyr Leu Gly Ala Tyr Asp Ser Glu Glu Ala Ala Ala His
100 105 110

Thr Tyr Asp Leu Ala Ala Leu Lys Tyr Trp Gly Pro Asp Thr Ile Leu
115 120 125

Asn Phe Pro Ala Glu Thr Tyr Thr Lys Glu Leu Glu Glu Met Gln Arg

```
    130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190

Leu Tyr Leu Gly Thr Tyr Asn Thr Gln Glu Glu Ala Ala Ala Ala Tyr
        195                 200                 205

Asp Met Ala Ala Ile Glu Tyr Arg Gly Ala Asn Ala Val Thr Asn Phe
    210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Glu Pro Arg Glu Glu
            260                 265                 270

Val Lys Gln Gln Tyr Val Glu Glu Pro Pro Gln Glu Glu Glu Glu Lys
        275                 280                 285

Glu Glu Glu Lys Ala Glu Gln Gln Glu Ala Glu Ile Val Gly Tyr Ser
    290                 295                 300

Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
                325                 330                 335

Met Met Asp Thr Gly Phe Ser Pro Phe Leu Thr Asp Gln Asn Leu Ala
            340                 345                 350

Asn Glu Asn Pro Ile Glu Tyr Pro Glu Leu Phe Asn Glu Leu Ala Phe
        355                 360                 365

Glu Asp Asn Ile Asp Phe Met Phe Asp Asp Gly Lys His Glu Cys Leu
    370                 375                 380

Asn Leu Glu Asn Leu Asp Cys Cys Val Val Gly Arg Glu Ala Pro Pro
385                 390                 395                 400

Ala Ala Ser Ser Pro Leu Ala Cys Leu Ser Thr Asp Ser Ala Ser Ser
                405                 410                 415

Thr Thr Thr Thr Thr Thr Ser Val Ser Cys Asn Tyr Leu Val
            420                 425                 430
```

<210> SEQ ID NO 63
<211> LENGTH: 34
<212> TYPE: PRT
<213> ORGANISM: Artificial Sequence
<220> FEATURE:
<223> OTHER INFORMATION: A synthetic protein

<400> SEQUENCE: 63

```
Glu Ala Pro Pro Ala Ala Ser Ser Pro Leu Ala Cys Leu Ser Thr Asp
1               5                   10                  15

Ser Ala Ser Ser Thr Thr Thr Thr Thr Thr Ser Val Ser Cys Asn Tyr
            20                  25                  30

Leu Val
```

<210> SEQ ID NO 64
<211> LENGTH: 430
<212> TYPE: PRT
<213> ORGANISM: Artificial Sequence

```
<220> FEATURE:
<223> OTHER INFORMATION: A synthetic protein

<400> SEQUENCE: 64

Met Lys Lys Arg Leu Thr Thr Ser Thr Cys Ser Ser Ser Pro Ser Ser
1               5                   10                  15

Ser Val Ser Ser Ser Thr Thr Thr Ser Ser Pro Ile Gln Ser Glu Ala
            20                  25                  30

Pro Arg Pro Lys Arg Ala Lys Arg Ala Lys Lys Ser Ser Pro Ser Gly
        35                  40                  45

Asp Lys Ser His Asn Pro Thr Ser Pro Ala Ser Thr Arg Arg Ser Ser
    50                  55                  60

Ile Tyr Arg Gly Val Thr Arg His Arg Trp Thr Gly Arg Phe Glu Ala
65                  70                  75                  80

His Leu Trp Asp Lys Ser Ser Trp Asn Ser Ile Gln Asn Lys Lys Gly
                85                  90                  95

Lys Gln Val Tyr Leu Gly Ala Tyr Asp Ser Glu Glu Ala Ala Ala His
            100                 105                 110

Thr Tyr Asp Leu Ala Ala Leu Lys Tyr Trp Gly Pro Asp Thr Ile Leu
        115                 120                 125

Asn Phe Pro Ala Glu Thr Tyr Thr Lys Glu Leu Glu Glu Met Gln Arg
    130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190

Leu Tyr Leu Gly Thr Tyr Asn Thr Gln Glu Glu Ala Ala Ala Ala Tyr
        195                 200                 205

Asp Met Ala Ala Ile Glu Tyr Arg Gly Ala Asn Ala Val Thr Asn Phe
    210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Glu Pro Arg Glu Glu
            260                 265                 270

Val Lys Gln Gln Tyr Val Glu Glu Pro Pro Gln Glu Glu Glu Glu Lys
        275                 280                 285

Glu Glu Glu Lys Ala Glu Gln Gln Glu Ala Glu Ile Val Gly Tyr Ser
    290                 295                 300

Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
                325                 330                 335

Met Met Asp Thr Gly Phe Ser Pro Phe Leu Thr Asp Gln Asn Leu Ala
            340                 345                 350

Asn Glu Asn Pro Ile Glu Tyr Pro Glu Leu Phe Asn Glu Leu Ala Phe
        355                 360                 365

Glu Asp Asn Ile Asp Phe Met Phe Asp Asp Gly Lys His Glu Cys Leu
    370                 375                 380

Asn Leu Glu Asn Leu Asp Cys Cys Val Val Gly Arg Glu Asp Pro Pro
385                 390                 395                 400
```

```
Asp Asp Ser Ser Pro Leu Asp Cys Leu Ser Thr Asp Ser Ala Ser Ser
                405                 410                 415

Thr Thr Thr Thr Thr Thr Ser Val Ser Cys Asn Tyr Leu Val
            420                 425                 430


<210> SEQ ID NO 65
<211> LENGTH: 124
<212> TYPE: PRT
<213> ORGANISM: Arabidopsis thaliana

<400> SEQUENCE: 65

Ala Ala Val Val Asn Cys Cys Ile Asp Ser Ser Thr Ile Met Glu Met
1               5                   10                  15

Asp Arg Cys Gly Asp Asn Asn Glu Leu Ala Trp Asn Phe Cys Met Met
            20                  25                  30

Asp Thr Gly Phe Ser Pro Phe Leu Thr Asp Gln Asn Leu Ala Asn Glu
        35                  40                  45

Asn Pro Ile Glu Tyr Pro Glu Leu Phe Asn Glu Leu Ala Phe Glu Asp
    50                  55                  60

Asn Ile Asp Phe Met Phe Asp Asp Gly Lys His Glu Cys Leu Asn Leu
65                  70                  75                  80

Glu Asn Leu Asp Cys Cys Val Val Gly Arg Glu Ser Pro Pro Ser Ser
                85                  90                  95

Ser Ser Pro Leu Ser Cys Leu Ser Thr Asp Ser Ala Ser Ser Thr Thr
            100                 105                 110

Thr Thr Thr Thr Ser Val Ser Cys Asn Tyr Leu Val
        115                 120


<210> SEQ ID NO 66

<400> SEQUENCE: 66

000


<210> SEQ ID NO 67
<211> LENGTH: 216
<212> TYPE: PRT
<213> ORGANISM: Arabidopsis thaliana

<400> SEQUENCE: 67

Met Glu Asn Glu Gln Ser Thr His Val His Phe Ala Ser Leu Ser Ser
1               5                   10                  15

Ser Ser Glu Arg Tyr Asn Glu Thr Phe Glu Glu Ile Lys Lys Ala Met
            20                  25                  30

Lys Lys Ser Val Gln Leu Lys Ala Glu Leu Ser Ala Lys Glu Arg Asn
        35                  40                  45

Leu Val Ser Val Gly Tyr Lys Asn Val Ile Ser Ala Arg Arg Ala Ser
    50                  55                  60

Leu Glu Ile Leu Ser Ser Ile Val Gln Lys Glu Glu Ser Lys Gly Asn
65                  70                  75                  80

Glu Glu Asn Val Lys Lys Leu Lys Asn Tyr Arg Asn Lys Val Glu Asp
                85                  90                  95

Glu Leu Ala Lys Ile Cys Asn Asp Ile Leu Ser Val Ile Asn Lys Gln
            100                 105                 110

Leu Ile Pro Ser Ser Thr Thr Val Asp Ser Ser Val Leu Phe Tyr Asn
        115                 120                 125

Met Leu Ala Asp Phe Ser Ser Asn Ala Glu Ser Lys Glu Ala Thr Asp
```

```
    130                 135                 140

Gln Ser Leu Asp Ala Tyr Lys Arg Leu Val Trp Tyr Gln Gln Phe Gln
145                 150                 155                 160

Leu Tyr Met Thr Leu Asn Trp Thr Ser Val Phe Leu Asn Ser Pro Glu
                165                 170                 175

Ser Ala Tyr Gln Leu Ala Lys Gln Ala Phe Asp Asp Ala Ile Asn Glu
            180                 185                 190

Phe Asp Asn Leu Thr Glu Arg Glu Glu Val Ile Phe Leu Phe Pro Tyr
        195                 200                 205

Leu Pro Pro Leu Met Ile Asp Arg
    210                 215


<210> SEQ ID NO 68
<211> LENGTH: 888
<212> TYPE: DNA
<213> ORGANISM: Arabidopsis thaliana

<400> SEQUENCE: 68

ttcttctcca agcatctatt gtttaagaga gaaaaagaag aaaagccatg gagaatgaac      60

aatcaacgca cgttcacttc gcgagtctct cttcgtcaag cgagcgctac aatgaaacat     120

ttgaagagat aaagaaagcg atgaagaaaa gtgttcagct taaagcggag ctatcagcaa     180

aggagagaaa tcttgtatca gtggggtaca agaatgtgat tagcgcaagg agagcttcat     240

tggaaatact atcatccatt gtgcaaaagg aagagtcaaa aggaaatgag gaaaatgtca     300

agaagcttaa gaattatcga aacaaggttg aagatgagct tgccaaaatt tgtaatgaca     360

tcctgtccgt catcaataag caactcattc catcgtctac cactgtggac tcctctgttc     420

ttttctacaa tatgctggca gacttcagtt ctaatgctga aagcaaggaa gctactgatc     480

agtctcttga tgcatataag agactggttt ggtaccaaca gttccagcta tacatgactt     540

tgaattggac ttctgttttc ttaaactctc ctgaaagtgc ataccaattg gcaaagcaag     600

cgttcgatga tgcaattaat gaatttgaca acctcacaga aagagaggag gtaatctttt     660

tatttcccta tctgcctcct ctgatgatag atagatagtt tcctttggaa tcaatataag     720

ccatttttgt gaaattttgt tagttcttgt actgttatga ggagcctaaa ctttgattcg     780

aatgttaatg cttgggaaca tatttacggc tttgtggatc tttcattgct taaacgccaa     840

gttgttgaat tcaagcaaat tttgttgcaa gaaaccaatt agcatact                  888


<210> SEQ ID NO 69
<211> LENGTH: 260
<212> TYPE: PRT
<213> ORGANISM: Arabidopsis thaliana

<400> SEQUENCE: 69

Met Ala Thr Thr Leu Ser Arg Asp Gln Tyr Val Tyr Met Ala Lys Leu
1               5                   10                  15

Ala Glu Gln Ala Glu Arg Tyr Glu Glu Met Val Gln Phe Met Glu Gln
            20                  25                  30

Leu Val Ser Gly Ala Thr Pro Ala Gly Glu Leu Thr Val Glu Glu Arg
        35                  40                  45

Asn Leu Leu Ser Val Ala Tyr Lys Asn Val Ile Gly Ser Leu Arg Ala
    50                  55                  60

Ala Trp Arg Ile Val Ser Ser Ile Glu Gln Lys Glu Glu Ser Arg Lys
65                  70                  75                  80

Asn Glu Glu His Val Ser Leu Val Lys Asp Tyr Arg Ser Lys Val Glu
```

```
                85                  90                  95

Thr Glu Leu Ser Ser Ile Cys Ser Gly Ile Leu Arg Leu Leu Asp Ser
            100                 105                 110

His Leu Ile Pro Ser Ala Thr Ala Ser Glu Ser Lys Val Phe Tyr Leu
        115                 120                 125

Lys Met Lys Gly Asp Tyr His Arg Tyr Leu Ala Glu Phe Lys Ser Gly
    130                 135                 140

Asp Glu Arg Lys Thr Ala Ala Glu Asp Thr Met Ile Ala Tyr Lys Ala
145                 150                 155                 160

Ala Gln Asp Val Ala Val Ala Asp Leu Ala Pro Thr His Pro Ile Arg
                165                 170                 175

Leu Gly Leu Ala Leu Asn Phe Ser Val Phe Tyr Tyr Glu Ile Leu Asn
            180                 185                 190

Ser Ser Glu Lys Ala Cys Ser Met Ala Lys Gln Ala Phe Glu Glu Ala
        195                 200                 205

Ile Ala Glu Leu Asp Thr Leu Gly Glu Glu Ser Tyr Lys Asp Ser Thr
    210                 215                 220

Leu Ile Met Gln Leu Leu Arg Asp Asn Leu Thr Leu Trp Thr Ser Asp
225                 230                 235                 240

Met Gln Val Cys Pro Ile Leu Tyr Phe His Ile Gln Leu His His Gln
                245                 250                 255

Lys Leu Ala Tyr
            260


<210> SEQ ID NO 70
<211> LENGTH: 1252
<212> TYPE: DNA
<213> ORGANISM: Arabidopsis thaliana

<400> SEQUENCE: 70

acgtgggttt cacgctgtta atccttattt caactaacga cgtcgtttat cagagtgtgt     60

taatcacgcg cgagtgaaga gaatttcctt ttacagctca ttatgactcg gctttgaagc    120

tttttattct tcttctcaat ttcttttttt cttccagaaa tttcctccga tttcaaaatt    180

ttccggtgaa atcgaaaaaa aaagcgagat cttcttctct aatggcgacg accttaagca    240

gagatcaata tgtctacatg gcgaagctcg ccgagcaagc cgagcgttac gaagagatgg    300

ttcaattcat ggaacagctc gtaagtggag ctacaccggc cggtgagctg accgtagaag    360

agaggaatct tctctcggtc gcgtataaga acgtgattgg atctcttcgt gcggcatgga    420

gaatcgtgtc ttcgattgag caaaaggaag agagcaggaa gaacgaagaa cacgtgtcgc    480

ttgttaagga ttacagatct aaagttgaga ctgagctttc ttcgatctgt tctgggattc    540

tcaggttact tgattcgcat ctaattcctt cagctactgc cagtgagtct aaggtttttt    600

acctgaagat gaaaggagat tatcatcgtt atttggctga gtttaaatct ggtgatgaga    660

ggaaaactgc tgctgaagat actatgatcg cttacaaagc tgctcaggac gttgcagttg    720

ctgatctagc acctacacat ccgatcaggc ttggtttggc tcttaacttc tcagtgtttt    780

actacgagat tctcaactct tcagagaaag cttgtagcat ggcgaaacag gcttttgaag    840

aagccattgc tgagctggac acattgggag aggagtcata caaggacagt actctcatca    900

tgcagttgct aagggacaat ctaacccttt ggacctccga tatgcaggtt tgcccaattc    960

tatactttca tattcaattg catcatcaga aactcgcata ttgatagtct tataagatta   1020

ttcggataat aacaccccaa aactcaatga tcgactgctt tattcaggag cagatggatg   1080
```

```
aggcctgaag gtctaatgga agaaaagacg gttatgtaat gtacctgcaa ccgtaaccga   1140

aaatctgagt tcaacctcct ttgctgtaaa acttgtcgaa aagaaaagtt tgttttttta   1200

tgacagatta tgtgcacagc tttggtgtta tctgctgctc tgtatcaact ct           1252
```

```
<210> SEQ ID NO 71
<211> LENGTH: 241
<212> TYPE: PRT
<213> ORGANISM: Arabidopsis thaliana

<400> SEQUENCE: 71

Met Glu Asn Glu Gln Ser Thr His Val His Phe Ala Ser Leu Ser Ser
1               5                   10                  15

Ser Ser Glu Arg Tyr Asn Glu Thr Phe Glu Glu Ile Lys Lys Ala Met
            20                  25                  30

Lys Lys Ser Val Gln Leu Lys Ala Glu Leu Ser Ala Lys Glu Arg Asn
        35                  40                  45

Leu Val Ser Val Gly Tyr Lys Asn Val Ile Ser Ala Arg Arg Ala Ser
    50                  55                  60

Leu Glu Ile Leu Ser Ser Ile Val Gln Lys Glu Glu Ser Lys Gly Asn
65                  70                  75                  80

Glu Glu Asn Val Lys Lys Leu Lys Asn Tyr Arg Asn Lys Val Glu Asp
                85                  90                  95

Glu Leu Ala Lys Ile Cys Asn Asp Ile Leu Ser Val Ile Asn Lys Gln
            100                 105                 110

Leu Ile Pro Ser Ser Thr Thr Val Asp Ser Ser Val Leu Phe Tyr Asn
        115                 120                 125

Met Leu Ala Asp Phe Ser Ser Asn Ala Glu Ser Lys Glu Ala Thr Asp
    130                 135                 140

Gln Ser Leu Asp Ala Tyr Lys Arg Leu Val Trp Tyr Gln Gln Phe Gln
145                 150                 155                 160

Leu Tyr Met Thr Leu Asn Trp Thr Ser Val Phe Leu Asn Ser Pro Glu
                165                 170                 175

Ser Ala Tyr Gln Leu Ala Lys Gln Ala Phe Asp Asp Ala Ile Asn Glu
            180                 185                 190

Phe Asp Ile Ser Asp Glu Ser Asn Lys Asp Met Thr Leu Ile Ile Gln
        195                 200                 205

Leu Leu Arg Asp Asn Leu Asn Met Trp Thr Leu Asp Leu Thr Glu Arg
    210                 215                 220

Glu Glu Val Ile Phe Leu Phe Pro Tyr Leu Pro Pro Leu Met Ile Asp
225                 230                 235                 240

Arg
```

```
<210> SEQ ID NO 72
<211> LENGTH: 253
<212> TYPE: PRT
<213> ORGANISM: Arabidopsis thaliana

<400> SEQUENCE: 72

Met Glu Thr Glu Arg Glu Lys His Val Tyr Leu Ala Lys Leu Ser Glu
1               5                   10                  15

Gln Thr Glu Arg Tyr Asp Glu Met Val Glu Ala Met Lys Lys Val Ala
            20                  25                  30

Gln Leu Asp Val Glu Leu Thr Val Glu Glu Arg Asn Leu Val Ser Val
        35                  40                  45

Gly Tyr Lys Asn Val Ile Gly Ala Arg Arg Ala Ser Trp Arg Ile Leu
```

```
    50                  55                  60

Ser Ser Ile Glu Gln Lys Glu Glu Ser Lys Gly Asn Glu Glu Asn Val
65                  70                  75                  80

Lys Arg Ile Gln Asn Tyr Arg Lys Lys Val Glu Asp Glu Leu Ala Lys
                85                  90                  95

Val Cys Asn Asp Ile Leu Ser Val Ile Asp Lys His Leu Ile Pro Ser
            100                 105                 110

Ser Thr Ala Val Glu Ser Thr Val Phe Phe Tyr Lys Met Lys Gly Asp
        115                 120                 125

Tyr Tyr Arg Tyr Leu Ala Glu Phe Ser Ser Gly Ala Glu Arg Lys Glu
    130                 135                 140

Ala Ala Asp Gln Ser Leu Glu Ala Tyr Lys Ala Ala Val Ala Ala Ala
145                 150                 155                 160

Glu Thr Gly Leu Ala Pro Thr His Pro Val Arg Leu Gly Leu Ala Leu
                165                 170                 175

Asn Phe Ser Val Phe Tyr Tyr Glu Ile Leu Asn Ser Pro Glu Ser Ala
            180                 185                 190

Cys Gln Leu Ala Lys Gln Ala Phe Asp Asp Ala Ile Ala Glu Leu Asp
        195                 200                 205

Ser Leu Asn Glu Glu Ser Tyr Lys Asp Ser Thr Leu Ile Met Gln Leu
    210                 215                 220

Leu Arg Asp Asn Leu Thr Leu Trp Thr Ser Asp Leu Pro Glu Glu Gly
225                 230                 235                 240

Asp Glu Arg Ala Lys Gly Asp Glu Pro Gln Glu Glu Val
                245                 250


<210> SEQ ID NO 73
<211> LENGTH: 253
<212> TYPE: PRT
<213> ORGANISM: Arabidopsis thaliana

<400> SEQUENCE: 73

Met Glu Thr Glu Arg Glu Lys His Val Tyr Leu Ala Lys Leu Ser Glu
1               5                   10                  15

Gln Thr Glu Arg Tyr Asp Glu Met Val Glu Ala Met Lys Lys Val Ala
            20                  25                  30

Gln Leu Asp Val Glu Leu Thr Val Glu Glu Arg Asn Leu Val Ser Val
        35                  40                  45

Gly Tyr Lys Asn Val Ile Gly Ala Arg Arg Ala Ser Trp Arg Ile Leu
    50                  55                  60

Ser Ser Ile Glu Gln Lys Glu Glu Ser Lys Gly Asn Glu Glu Asn Val
65                  70                  75                  80

Lys Arg Ile Gln Asn Tyr Arg Lys Lys Val Glu Asp Glu Leu Ala Lys
                85                  90                  95

Val Cys Asn Asp Ile Leu Ser Val Ile Asp Lys His Leu Ile Pro Ser
            100                 105                 110

Ser Thr Ala Val Glu Ser Thr Val Phe Phe Tyr Lys Met Lys Gly Asp
        115                 120                 125

Tyr Tyr Arg Tyr Leu Ala Glu Phe Ser Ser Gly Ala Glu Arg Lys Glu
    130                 135                 140

Ala Ala Asp Gln Ser Leu Glu Ala Tyr Lys Ala Ala Val Ala Ala Ala
145                 150                 155                 160

Glu Thr Gly Leu Ala Pro Thr His Pro Val Arg Leu Gly Leu Ala Leu
                165                 170                 175
```

```
Asn Phe Ser Val Phe Tyr Tyr Glu Ile Leu Asn Ser Pro Glu Ser Ala
            180                 185                 190

Cys Gln Leu Ala Lys Gln Ala Phe Asp Asp Ala Ile Ala Glu Leu Asp
        195                 200                 205

Ser Leu Asn Glu Glu Ser Tyr Lys Asp Ser Thr Leu Ile Met Gln Leu
    210                 215                 220

Leu Arg Asp Asn Leu Thr Leu Trp Thr Ser Asp Leu Pro Glu Glu Gly
225                 230                 235                 240

Asp Glu Arg Ala Lys Gly Asp Glu Pro Gln Glu Glu Asn
                245                 250


<210> SEQ ID NO 74
<211> LENGTH: 1023
<212> TYPE: DNA
<213> ORGANISM: Arabidopsis thaliana

<400> SEQUENCE: 74

catcaaacca tcctagggtt accactaatc ccaaaaatca aatcgagcgt ccagagagaa      60

gaaagaagaa gaagcatcca tggagactga gagggaaaag catgtttact tggccaagct     120

ctctgagcaa accgagcgat acgatgagat ggttgaggcg atgaagaaag tagctcagct     180

tgatgtggag ctcacggtag aggagaggaa ccttgtgtct gtagggtaca agaacgtgat     240

tggggcaagg agagcttcgt ggagaatact atcatccatc gagcagaagg aagagtccaa     300

ggggaacgag gagaatgtca agaggattca gaactatcga aagaaagttg aagacgagct     360

tgctaaagtt tgtaatgaca tcttgtctgt catcgataaa catctcattc cgtcgtctac     420

tgctgtggag tccactgtgt ttttctacaa aatgaaagga gattattatc gatatctggc     480

agagttcagt tctggtgctg aacgcaagga agccgcagat cagtctcttg aggcatataa     540

ggctgctgtt gctgctgcgg agactggatt ggcaccaaca catccagtta gactcggctt     600

ggcgttgaac ttttctgttt tctactatga gatcttaaac tctcctgaaa gcgcatgtca     660

attggctaag caagcattcg acgatgcaat agctgaactt gacagcctga acgaggaatc     720

atacaaggac agcactctta tcatgcagct acttagagac aatctcacct tgtggacttc     780

agacctccct gaggaaggag acgagcgagc caaaggtgat gagcctcagg aagagaactg     840

aagtcctgac tcctctgtga gatgagaaac aactcttgat gcaagcctcg tttgctctag     900

attgtgtatt ttttttttta ttttgtcttt gttgatgatg ttttcagatc tttgacgtac     960

tgcacttgaa cactgcgtat cttcaactct tatcacttat tagtttgctt ctttgttgtt    1020

gaa                                                                  1023


<210> SEQ ID NO 75
<211> LENGTH: 260
<212> TYPE: PRT
<213> ORGANISM: Arabidopsis thaliana

<400> SEQUENCE: 75

Met Ser Thr Glu Lys Glu Arg Glu Thr Gln Val Tyr Leu Ala Lys Leu
1               5                   10                  15

Ser Glu Gln Ala Glu Arg Tyr Glu Glu Met Val Glu Cys Met Lys Thr
            20                  25                  30

Ile Ala Lys Leu Asp Leu Glu Leu Thr Val Glu Glu Arg Asn Leu Leu
        35                  40                  45

Ser Val Gly Tyr Lys Asn Val Ile Gly Ala Arg Arg Ala Ser Trp Arg
    50                  55                  60
```

-continued

```
Ile Met Ser Ser Ile Glu Gln Lys Glu Glu Ser Lys Gly Asn Glu Ser
65                  70                  75                  80

Asn Ala Lys Leu Ile Lys Asn Tyr Arg Gln Lys Val Glu Glu Glu Leu
                85                  90                  95

Ser Lys Ile Cys Ser Asp Ile Leu Ser Ile Ile Asp Gln His Leu Val
            100                 105                 110

Pro Ser Ser Thr Ser Gly Glu Ala Thr Val Phe Tyr Tyr Lys Met Lys
        115                 120                 125

Gly Asp Tyr Tyr Arg Tyr Leu Ala Glu Phe Lys Thr Asp Gln Asp Arg
    130                 135                 140

Lys Glu Ala Ala Glu Gln Ser Leu Lys Gly Tyr Glu Ala Ala Leu Ala
145                 150                 155                 160

Thr Ala Ser Thr Glu Leu Pro Ser Thr His Pro Ile Arg Leu Gly Leu
                165                 170                 175

Ala Leu Asn Phe Ser Val Phe Tyr Tyr Glu Ile Leu Asn Ser Pro Glu
            180                 185                 190

Arg Ala Cys His Leu Ala Lys Gln Ala Phe Asp Glu Ala Ile Ala Glu
        195                 200                 205

Leu Asp Thr Leu Ser Glu Glu Ser Tyr Lys Asp Ser Thr Leu Ile Met
    210                 215                 220

Gln Leu Leu Arg Asp Asn Leu Thr Leu Trp Thr Ser Asp Leu Pro Glu
225                 230                 235                 240

Asp Gly Gly Asp Glu Ile Lys Thr Glu Glu Ala Lys Pro Ala Glu Thr
                245                 250                 255

Ser Glu His Ser
            260


<210> SEQ ID NO 76
<211> LENGTH: 1089
<212> TYPE: DNA
<213> ORGANISM: Glycine max

<400> SEQUENCE: 76

ctcataagct tcttttttaa tttttcttta attcaattta gttttctctg atacaacaat     60

aatacaacaa caatgtccac agagaaggag agagagaccc aagtttactt ggccaagctc    120

tctgagcaag ccgagagata tgaagagatg gttgaatgca tgaagacaat tgcaaaactt    180

gatctagaac taactgttga agagaggaac ctgctctcag tgggatataa gaatgtgatt    240

ggtgcaagaa gagcctcttg gcgcattatg tcatcaattg aacaaaagga agagtctaaa    300

ggaaatgaaa gcaatgcaaa actgataaag aattatcgtc aaaaggttga agaggaactc    360

tcaaagattt gcagtgacat tctcagcatt attgaccagc atcttgttcc ttcttccacc    420

tcaggagaag ccaccgtttt ctactataag atgaaaggtg actattatcg atatttagcc    480

gagttcaaga ccgatcagga tagaaaggag gctgctgagc aatcactaaa gggatatgag    540

gctgctttag ctacagcaag cacagagctt ccatcaacac atccaatccg tcttggactt    600

gcgctcaact tctcagtctt ctattatgag atactgaact ctcctgaaag ggcctgtcat    660

ttggctaagc aagctttcga tgaggcaatt gcagagttag acaccttgag tgaagagtca    720

tacaaggaca gcactttgat catgcagctg ctgagagaca atctcactct ctggacctct    780

gatttacctg aggatggagg tgacgaaatt aaaacagaag aagccaaacc tgctgaaact    840

tctgagcact catagtatac gattgcccct ggagcagtga agtccatttg gaccagaaaa    900

tgcaaattat ggtcacttca tagttgtgct ctcgttacat ctagaaaagt tcaacctacg    960
```

gcttatatta gttaccaatt tttttttcta tatacttcat atattttaag taaaggggtc 1020
aattgaagta acggataatt tacatatttt acttaaaagc atctcttctc attattgatt 1080
acttttgaa 1089

<210> SEQ ID NO 77
<211> LENGTH: 15
<212> TYPE: PRT
<213> ORGANISM: Arabidopsis thaliana

<400> SEQUENCE: 77

Phe Glu Ala His Leu Trp Asp Lys Ser Ser Trp Asn Ser Ile Gln
1 5 10 15

<210> SEQ ID NO 78
<211> LENGTH: 29
<212> TYPE: DNA
<213> ORGANISM: Artificial Sequence
<220> FEATURE:
<223> OTHER INFORMATION: A synthetic primer

<400> SEQUENCE: 78
aatggatccg gacaatgaag aagcgctta 29

<210> SEQ ID NO 79
<211> LENGTH: 24
<212> TYPE: DNA
<213> ORGANISM: Artificial Sequence
<220> FEATURE:
<223> OTHER INFORMATION: A synthetic primer

<400> SEQUENCE: 79
tccctcgagt cagaccaaat agtt 24

<210> SEQ ID NO 80
<211> LENGTH: 33
<212> TYPE: DNA
<213> ORGANISM: Artificial Sequence
<220> FEATURE:
<223> OTHER INFORMATION: A synthetic primer

<400> SEQUENCE: 80
tccctcgagt caagagctgc gtcgggtaga agc 33

<210> SEQ ID NO 81
<211> LENGTH: 39
<212> TYPE: DNA
<213> ORGANISM: Artificial Sequence
<220> FEATURE:
<223> OTHER INFORMATION: A synthetic primer

<400> SEQUENCE: 81
tccctcgagt catctcccag tccatctatg tctagtgac 39

<210> SEQ ID NO 82
<211> LENGTH: 36
<212> TYPE: DNA
<213> ORGANISM: Artificial Sequence
<220> FEATURE:
<223> OTHER INFORMATION: A synthetic primer

<400> SEQUENCE: 82
tccctcgagt cactgaatcg aattccaaga gctttt 36

<210> SEQ ID NO 83

<211> LENGTH: 38
<212> TYPE: DNA
<213> ORGANISM: Artificial Sequence
<220> FEATURE:
<223> OTHER INFORMATION: A synthetic primer

<400> SEQUENCE: 83
tccctcgagt cacagataaa cttgtttgcc tttcttgt 38

<210> SEQ ID NO 84
<211> LENGTH: 38
<212> TYPE: DNA
<213> ORGANISM: Artificial Sequence
<220> FEATURE:
<223> OTHER INFORMATION: A synthetic primer

<400> SEQUENCE: 84
tccctcgagt catgccggaa aattcaagat ggtgtcgg 38

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88
<211> LENGTH: 24
<212> TYPE: DNA
<213> ORGANISM: Artificial Sequence
<220> FEATURE:
<223> OTHER INFORMATION: A synthetic primer

<400> SEQUENCE: 88
taactcgagt tacgggaaaa cacc 24

<210> SEQ ID NO 89
<211> LENGTH: 27
<212> TYPE: DNA
<213> ORGANISM: Artificial Sequence
<220> FEATURE:
<223> OTHER INFORMATION: A synthetic primer

<400> SEQUENCE: 89
tgactcgagt cattcttctg aatatcc 27

<210> SEQ ID NO 90
<211> LENGTH: 32
<212> TYPE: DNA
<213> ORGANISM: Artificial Sequence
<220> FEATURE:
<223> OTHER INFORMATION: A synthetic primer

<400> SEQUENCE: 90
actggatccg gacaatgtct tctgattcgt cc 32

<210> SEQ ID NO 91
<211> LENGTH: 27
<212> TYPE: DNA
<213> ORGANISM: Artificial Sequence
<220> FEATURE:
<223> OTHER INFORMATION: A synthetic primer

<400> SEQUENCE: 91
tatctcgagt cactgcgaag gtggtgg 27

<210> SEQ ID NO 92
<211> LENGTH: 20
<212> TYPE: DNA
<213> ORGANISM: Artificial Sequence
<220> FEATURE:
<223> OTHER INFORMATION: A synthetic primer

<400> SEQUENCE: 92
tttcagtgtc ccttgtcgca 20

<210> SEQ ID NO 93
<211> LENGTH: 20
<212> TYPE: DNA
<213> ORGANISM: Artificial Sequence
<220> FEATURE:
<223> OTHER INFORMATION: A synthetic primer

<400> SEQUENCE: 93
tcaaggaaac ggagacgtgg 20

<210> SEQ ID NO 94
<211> LENGTH: 20
<212> TYPE: DNA
<213> ORGANISM: Artificial Sequence
<220> FEATURE:
<223> OTHER INFORMATION: A synthetic primer

<400> SEQUENCE: 94
tcaggtgcat ttgaagggct 20

<210> SEQ ID NO 95
<211> LENGTH: 20
<212> TYPE: DNA
<213> ORGANISM: Artificial Sequence
<220> FEATURE:
<223> OTHER INFORMATION: A synthetic primer

<400> SEQUENCE: 95
ctggtttagc cgcacaggta 20

<210> SEQ ID NO 96
<211> LENGTH: 20
<212> TYPE: DNA
<213> ORGANISM: Artificial Sequence
<220> FEATURE:
<223> OTHER INFORMATION: A synthetic primer

<400> SEQUENCE: 96
attgtccatc ccaccccaac 20

<210> SEQ ID NO 97
<211> LENGTH: 20
<212> TYPE: DNA
<213> ORGANISM: Artificial Sequence
<220> FEATURE:
<223> OTHER INFORMATION: A synthetic primer

<400> SEQUENCE: 97
aacagcatca gcaccctctc 20

<210> SEQ ID NO 98
<211> LENGTH: 20
<212> TYPE: DNA
<213> ORGANISM: Artificial Sequence
<220> FEATURE:
<223> OTHER INFORMATION: A synthetic primer

<400> SEQUENCE: 98
tggtcacaac tctgtcgtcg 20

<210> SEQ ID NO 99
<211> LENGTH: 20
<212> TYPE: DNA
<213> ORGANISM: Artificial Sequence
<220> FEATURE:
<223> OTHER INFORMATION: A synthetic primer

<400> SEQUENCE: 99
tctcgccgca ccttgtttat 20

<210> SEQ ID NO 100
<211> LENGTH: 20
<212> TYPE: DNA
<213> ORGANISM: Artificial Sequence
<220> FEATURE:
<223> OTHER INFORMATION: A synthetic primer

<400> SEQUENCE: 100
cggccaatcc cttaacgact 20

<210> SEQ ID NO 101
<211> LENGTH: 20
<212> TYPE: DNA
<213> ORGANISM: Artificial Sequence
<220> FEATURE:
<223> OTHER INFORMATION: A synthetic primer

<400> SEQUENCE: 101
ctctgtgtgg tggtgctgat 20

<210> SEQ ID NO 102
<211> LENGTH: 22
<212> TYPE: DNA
<213> ORGANISM: Artificial Sequence
<220> FEATURE:
<223> OTHER INFORMATION: A synthetic primer

<400> SEQUENCE: 102
agagcagtgg tttctccaga gg 22

<210> SEQ ID NO 103
<211> LENGTH: 22
<212> TYPE: DNA
<213> ORGANISM: Artificial Sequence
<220> FEATURE:
<223> OTHER INFORMATION: A synthetic primer

<400> SEQUENCE: 103
ttccgttgtg gtgatgccta gc 22

<210> SEQ ID NO 104

<211> LENGTH: 22
<212> TYPE: DNA
<213> ORGANISM: Artificial Sequence
<220> FEATURE:
<223> OTHER INFORMATION: A synthetic primer

<400> SEQUENCE: 104
gaccctgatg ttgatgttcg ct 22

<210> SEQ ID NO 105
<211> LENGTH: 22
<212> TYPE: DNA
<213> ORGANISM: Artificial Sequence
<220> FEATURE:
<223> OTHER INFORMATION: A synthetic primer

<400> SEQUENCE: 105
gagggatttg aagagagatt tc 22

<210> SEQ ID NO 106
<211> LENGTH: 1975
<212> TYPE: DNA
<213> ORGANISM: Solanum tuberosum

<400> SEQUENCE: 106
aagcttatgt tgccatatag agtagtttgt gatggtatac ttcataaact ttaacttatg 60
ttaaatttgt aatgataaaa tttttattgt aaattaaaaa ttacttataa aattgggcat 120
tataacatat gaaagacaaa ttgtgttaca tattttactt ttgactttaa tatgaatatt 180
tcaatttaaa tcattgtttt attttctctt tctttttaca ggtataaaag gtgaaaattg 240
aagcaagatt gattgcaagc tatgtgtcac cacgttattg atactttgga agaaattttt 300
acttatatgt ctttgtttag gagtaatatt tgatatgttt tagttagatt ttcttgtcat 360
ttatgcttta gtataatttt agttattttt attatatgat catgggtgaa ttttgataca 420 aatattttttg tcattaaata aattaattta tcacaacttg attactttca gtgacaaaaa 480
atgtattgtc gtagtaccct tttttgttga atatgaataa ttttttttat tttgtgacaa 540
ttgtaattgt cactacttat gataatattt agtgacatat atgtcgtcgg taaaagcaaa 600
cactttcagt gacaaaataa tagatttaat cacaaaatta ttaacctttt ttataataat 660
aaatttatcc ctaatttata catttaagga caaagtattt tttttatata taaaaaaatag 720 tctttagtga cgatcgtagt gttgagtcta gaaatcataa tgttgaatct agaaaaatct 780
catgcagtgt aaaataaacc tcaaaaagga cgttcagtcc atagaggggg tgtatgtgac 840
accccaacct cagcaaaaga aaacctccct tcaacaagga catttgcggt gctaaacaat 900
ttcaagtctc atcacacata tatttattat ataatactaa taaagaatag aaaaggaaag 960
gtaaacatca ttaaatcgtc tttgtatatt tttagtgaca actgattgac gaaatctttt 1020
tcgtcacaca aaatttttag tgacgaaaca tgatttatag atgatgaaat tatttgtccc 1080
tcataatcta atttgttgta gtgatcatta ctcctttgtt tgttttattt gtcatgttag 1140
tccattaaaa aaaaatatct ctcttcttat gtacgtgaat ggttggaacg gatctattat 1200
ataatactaa taaagaatag aaaaaggaaa gtgagtgagg ttcgagggag agaatctgtt 1260
taatatcaga gtcgatcatg tgtcaatttt atcgatatga ccctaacttc aactgagttt 1320
aaccaattcc gataaggcga gaaatatcat agtattgagt ctagaaaaat ctcatgtagt 1380
gtggggtaaa cctcagcaag gacgttgagt ccatagaggg gggtgtatgt gacaccccaa 1440
cctcagcaaa agaaaacctc ccctcaagaa ggacatttgc ggtgctaaac aatttcaagt 1500

-continued

```
ctcatcacac atatatatat attatataat actaataaat aatagaaaaa ggaaaggtaa   1560

acatcactaa cgacagttgc ggtgcaaact gagtgaggta ataaacatca ctaactttta   1620

ttggttatgt caaactcaaa gtaaaatttc tcaacttgtt tacgtgccta tatataccat   1680

gcttgttata tgctcaaagc accaacaaaa tttaaaaaca ctttgaacat ttgcaaaatg   1740

gcaactacta aaactttttt aattttattt tttatgatat tagcaactac tagttcaaca   1800

tgtgctaagt tggaagaaat ggttactgtt ctaagtattg atggaggtgg aattaaggga   1860

atcattccag ctatcattct cgaatttctt gaaggacaac ttcaggtatt gtaaaaatat   1920

tttttaatgt atgtgcgtaa gtgtgacact actactatag tcattctggg tacct        1975
```

```
<210> SEQ ID NO 107
<211> LENGTH: 194
<212> TYPE: PRT
<213> ORGANISM: Artificial Sequence
<220> FEATURE:
<223> OTHER INFORMATION: A synthetic protein

<400> SEQUENCE: 107

Met Glu Asn Glu Gln Ser Thr His Val His Phe Ala Ser Leu Ser Ser
1               5                   10                  15

Ser Ser Glu Arg Tyr Asn Glu Thr Phe Glu Glu Ile Lys Lys Ala Met
            20                  25                  30

Lys Lys Ser Val Gln Leu Lys Ala Glu Leu Ser Ala Lys Glu Arg Asn
        35                  40                  45

Leu Val Ser Val Gly Tyr Lys Asn Val Ile Ser Ala Arg Arg Ala Ser
    50                  55                  60

Leu Glu Ile Leu Ser Ser Ile Val Gln Lys Glu Glu Ser Lys Gly Asn
65                  70                  75                  80

Glu Glu Asn Val Lys Lys Leu Lys Asn Tyr Arg Asn Lys Val Glu Asp
                85                  90                  95

Glu Leu Ala Lys Ile Cys Asn Asp Ile Leu Ser Val Ile Asn Lys Gln
            100                 105                 110

Leu Ile Pro Ser Ser Thr Thr Val Asp Ser Ser Val Leu Phe Tyr Asn
        115                 120                 125

Met Leu Ala Asp Phe Ser Ser Asn Ala Glu Ser Lys Glu Ala Thr Asp
    130                 135                 140

Gln Ser Leu Asp Ala Tyr Lys Arg Leu Val Trp Tyr Gln Gln Phe Gln
145                 150                 155                 160

Leu Tyr Met Thr Leu Asn Trp Thr Ser Val Phe Leu Asn Ser Pro Glu
                165                 170                 175

Ser Ala Tyr Gln Leu Ala Lys Gln Ala Phe Asp Asp Ala Ile Asn Glu
            180                 185                 190

Phe Asp


<210> SEQ ID NO 108
<211> LENGTH: 20
<212> TYPE: PRT
<213> ORGANISM: Artificial Sequence
<220> FEATURE:
<223> OTHER INFORMATION: A synthetic protein

<400> SEQUENCE: 108

Leu Thr Glu Arg Glu Glu Val Ile Phe Leu Phe Pro Tyr Leu Pro Pro
1               5                   10                  15

Leu Met Ile Asp
```

20

<210> SEQ ID NO 109
<211> LENGTH: 241
<212> TYPE: PRT
<213> ORGANISM: Artificial Sequence
<220> FEATURE:
<223> OTHER INFORMATION: A synthetic protein

<400> SEQUENCE: 109

Met Glu Asn Glu Gln Ser Thr His Val His Phe Ala Ser Leu Ser Ser
1 5 10 15

Ser Ser Glu Arg Tyr Asn Glu Thr Phe Glu Glu Ile Lys Lys Ala Met
20 25 30

Lys Lys Ser Val Gln Leu Lys Ala Glu Leu Ser Ala Lys Glu Arg Asn
35 40 45

Leu Val Ser Val Gly Tyr Lys Asn Val Ile Ser Ala Arg Arg Ala Ser
50 55 60

Leu Glu Ile Leu Ser Ser Ile Val Gln Lys Glu Glu Ser Lys Gly Asn
65 70 75 80

Glu Glu Asn Val Lys Lys Leu Lys Asn Tyr Arg Asn Lys Val Glu Asp
85 90 95

Glu Leu Ala Lys Ile Cys Asn Asp Ile Leu Ser Val Ile Asn Lys Gln
100 105 110

Leu Ile Pro Ser Ser Thr Thr Val Asp Ser Ser Val Leu Phe Tyr Asn
115 120 125

Met Leu Ala Asp Phe Ser Ser Asn Ala Glu Ser Lys Glu Ala Thr Asp
130 135 140

Gln Ser Leu Asp Ala Tyr Lys Arg Leu Val Trp Tyr Gln Gln Phe Gln
145 150 155 160

Leu Tyr Met Thr Leu Asn Trp Thr Ser Val Phe Leu Asn Ser Pro Glu
165 170 175

Ser Ala Tyr Gln Leu Ala Lys Gln Ala Phe Asp Asp Ala Ile Asn Glu
180 185 190

Phe Asp Ile Ser Asp Glu Ser Asn Lys Asp Met Thr Leu Ile Ile Gln
195 200 205

Leu Leu Arg Asp Asn Leu Asn Met Trp Thr Leu Asp Leu Thr Glu Arg
210 215 220

Glu Glu Val Ile Phe Leu Phe Pro Tyr Leu Pro Pro Leu Met Ile Asp
225 230 235 240

Arg

<210> SEQ ID NO 110
<211> LENGTH: 198
<212> TYPE: PRT
<213> ORGANISM: Arabidopsis thaliana

<400> SEQUENCE: 110

Met Glu Asn Glu Gln Ser Thr His Val His Phe Ala Ser Leu Ser Ser
1 5 10 15

Ser Ser Glu Arg Tyr Asn Glu Thr Phe Glu Glu Ile Lys Lys Ala Met
20 25 30

Lys Lys Ser Val Gln Leu Lys Ala Glu Leu Ser Ala Lys Glu Arg Asn
35 40 45

Leu Val Ser Val Gly Tyr Lys Asn Val Ile Ser Ala Arg Arg Ala Ser
50 55 60

```
Leu Glu Ile Leu Ser Ser Ile Val Gln Lys Glu Glu Ser Lys Gly Asn
65                  70                  75                  80

Glu Glu Asn Val Lys Lys Leu Lys Asn Tyr Arg Asn Lys Val Glu Asp
                85                  90                  95

Glu Leu Ala Lys Ile Cys Asn Asp Ile Leu Ser Val Ile Asn Lys Gln
            100                 105                 110

Leu Ile Pro Ser Ser Thr Thr Val Asp Ser Ser Val Leu Phe Tyr Asn
        115                 120                 125

Met Leu Ala Asp Phe Ser Ser Asn Ala Glu Ser Lys Glu Ala Thr Asp
    130                 135                 140

Gln Ser Leu Asp Ala Tyr Lys Arg Leu Val Trp Tyr Gln Gln Phe Gln
145                 150                 155                 160

Leu Tyr Met Thr Leu Asn Trp Thr Ser Val Phe Leu Asn Ser Pro Glu
                165                 170                 175

Ser Ala Tyr Gln Leu Ala Lys Gln Ala Phe Asp Asp Ala Ile Asn Glu
            180                 185                 190

Phe Asp Asn Leu Thr Glu
        195


<210> SEQ ID NO 111
<211> LENGTH: 4
<212> TYPE: PRT
<213> ORGANISM: Artificial Sequence
<220> FEATURE:
<223> OTHER INFORMATION: A synthetic protein

<400> SEQUENCE: 111

Ala Met Lys Lys
1


<210> SEQ ID NO 112
<211> LENGTH: 13
<212> TYPE: PRT
<213> ORGANISM: Artificial Sequence
<220> FEATURE:
<223> OTHER INFORMATION: A synthetic protein

<400> SEQUENCE: 112

Glu Arg Asn Leu Val Ser Val Gly Tyr Lys Asn Val Ile
1               5                   10


<210> SEQ ID NO 113
<211> LENGTH: 5
<212> TYPE: PRT
<213> ORGANISM: Artificial Sequence
<220> FEATURE:
<223> OTHER INFORMATION: A synthetic protein

<400> SEQUENCE: 113

Ala Arg Arg Ala Ser
1               5


<210> SEQ ID NO 114
<211> LENGTH: 5
<212> TYPE: PRT
<213> ORGANISM: Artificial Sequence
<220> FEATURE:
<223> OTHER INFORMATION: A synthetic protein

<400> SEQUENCE: 114

Ile Leu Ser Ser Ile
1               5
```

<210> SEQ ID NO 115
<211> LENGTH: 13
<212> TYPE: PRT
<213> ORGANISM: Artificial Sequence
<220> FEATURE:
<223> OTHER INFORMATION: A synthetic protein

<400> SEQUENCE: 115

Gln Lys Glu Glu Ser Lys Gly Asn Glu Glu Asn Val Lys
1               5                   10

<210> SEQ ID NO 116
<211> LENGTH: 8
<212> TYPE: PRT
<213> ORGANISM: Artificial Sequence
<220> FEATURE:
<223> OTHER INFORMATION: A synthetic protein

<400> SEQUENCE: 116

Lys Val Glu Asp Glu Leu Ala Lys
1               5

<210> SEQ ID NO 117
<211> LENGTH: 8
<212> TYPE: PRT
<213> ORGANISM: Artificial Sequence
<220> FEATURE:
<223> OTHER INFORMATION: A synthetic protein

<400> SEQUENCE: 117

Cys Asn Asp Ile Leu Ser Val Ile
1               5

<210> SEQ ID NO 118
<211> LENGTH: 6
<212> TYPE: PRT
<213> ORGANISM: Artificial Sequence
<220> FEATURE:
<223> OTHER INFORMATION: A synthetic protein

<400> SEQUENCE: 118

Leu Ile Pro Ser Ser Thr
1               5

<210> SEQ ID NO 119
<211> LENGTH: 4
<212> TYPE: PRT
<213> ORGANISM: Artificial Sequence
<220> FEATURE:
<223> OTHER INFORMATION: A synthetic protein

<400> SEQUENCE: 119

Asp Gln Ser Leu
1

<210> SEQ ID NO 120
<211> LENGTH: 7
<212> TYPE: PRT
<213> ORGANISM: Artificial Sequence
<220> FEATURE:
<223> OTHER INFORMATION: A synthetic protein

<400> SEQUENCE: 120

Leu Asn Ser Pro Glu Ser Ala
1               5

<210> SEQ ID NO 121
<211> LENGTH: 11
<212> TYPE: PRT
<213> ORGANISM: Artificial Sequence
<220> FEATURE:
<223> OTHER INFORMATION: A synthetic protein

<400> SEQUENCE: 121

```
Gln Leu Ala Lys Gln Ala Phe Asp Asp Ala Ile
1               5                   10
```

<210> SEQ ID NO 122
<211> LENGTH: 212
<212> TYPE: PRT
<213> ORGANISM: Brassica napus

<400> SEQUENCE: 122

```
Met Glu Thr Glu Arg Glu Lys His Val Tyr Leu Ala Lys Leu Ser Glu
1               5                   10                  15

Gln Thr Glu Arg Tyr Asp Glu Met Val Glu Ala Met Lys Lys Val Ala
            20                  25                  30

Gln Leu Asp Val Glu Leu Thr Val Glu Glu Arg Asn Leu Val Ser Val
        35                  40                  45

Gly Tyr Lys Asn Val Ile Gly Ala Arg Arg Ala Ser Trp Arg Ile Leu
    50                  55                  60

Ser Ser Ile Glu Gln Lys Glu Glu Ser Lys Gly Asn Glu Glu Asn Val
65                  70                  75                  80

Lys Arg Ile Gln Asn Tyr Arg Lys Lys Val Glu Asp Glu Leu Ala Lys
                85                  90                  95

Val Cys Asn Asp Ile Leu Ser Val Ile Asp Lys His Leu Ile Pro Ser
            100                 105                 110

Ser Thr Ala Val Glu Ser Thr Val Phe Phe Tyr Lys Met Lys Gly Asp
        115                 120                 125

Tyr Tyr Arg Tyr Leu Ala Glu Phe Ser Ser Gly Ala Glu Arg Lys Glu
    130                 135                 140

Ala Ala Asp Gln Ser Leu Glu Ala Tyr Lys Ala Ala Val Ala Ala Ala
145                 150                 155                 160

Glu Thr Gly Leu Ala Pro Thr His Pro Val Arg Leu Gly Leu Ala Leu
                165                 170                 175

Asn Phe Ser Val Phe Tyr Tyr Glu Ile Leu Asn Ser Pro Glu Ser Ala
            180                 185                 190

Cys Gln Leu Ala Lys Gln Ala Phe Asp Asp Ala Ile Ala Glu Leu Asp
        195                 200                 205

Ser Leu Asn Glu
    210
```

<210> SEQ ID NO 123
<211> LENGTH: 196
<212> TYPE: PRT
<213> ORGANISM: Arabidopsis thaliana

<400> SEQUENCE: 123

```
Glu Asn Glu Gln Ser Thr His Val His Phe Ala Ser Leu Ser Ser Ser
1               5                   10                  15

Ser Glu Arg Tyr Asn Glu Thr Phe Glu Glu Ile Lys Lys Ala Met Lys
            20                  25                  30

Lys Ser Val Gln Leu Lys Ala Glu Leu Ser Ala Lys Glu Arg Asn Leu
        35                  40                  45
```

-continued

```
Val Ser Val Gly Tyr Lys Asn Val Ile Ser Ala Arg Arg Ala Ser Leu
    50                  55                  60

Glu Ile Leu Ser Ser Ile Val Gln Lys Glu Glu Ser Lys Gly Asn Glu
65                  70                  75                  80

Glu Asn Val Lys Lys Leu Lys Asn Tyr Arg Asn Lys Val Glu Asp Glu
                85                  90                  95

Leu Ala Lys Ile Cys Asn Asp Ile Leu Ser Val Ile Asn Lys Gln Leu
            100                 105                 110

Ile Pro Ser Ser Thr Thr Val Asp Ser Ser Val Leu Phe Tyr Asn Met
        115                 120                 125

Leu Ala Asp Phe Ser Ser Asn Ala Glu Ser Lys Glu Ala Thr Asp Gln
    130                 135                 140

Ser Leu Asp Ala Tyr Lys Arg Leu Val Trp Tyr Gln Gln Phe Gln Leu
145                 150                 155                 160

Tyr Met Thr Leu Asn Trp Thr Ser Val Phe Leu Asn Ser Pro Glu Ser
                165                 170                 175

Ala Tyr Gln Leu Ala Lys Gln Ala Phe Asp Asp Ala Ile Asn Glu Phe
            180                 185                 190

Asp Asn Leu Thr
        195


<210> SEQ ID NO 124
<211> LENGTH: 4
<212> TYPE: PRT
<213> ORGANISM: Artificial Sequence
<220> FEATURE:
<223> OTHER INFORMATION: A synthetic protein

<400> SEQUENCE: 124

Glu Arg Asn Leu
1


<210> SEQ ID NO 125
<211> LENGTH: 8
<212> TYPE: PRT
<213> ORGANISM: Artificial Sequence
<220> FEATURE:
<223> OTHER INFORMATION: A synthetic protein

<400> SEQUENCE: 125

Ser Val Gly Tyr Lys Asn Val Ile
1               5


<210> SEQ ID NO 126
<211> LENGTH: 5
<212> TYPE: PRT
<213> ORGANISM: Artificial Sequence
<220> FEATURE:
<223> OTHER INFORMATION: A synthetic protein

<400> SEQUENCE: 126

Ala Arg Arg Ala Ser
1               5


<210> SEQ ID NO 127
<211> LENGTH: 9
<212> TYPE: PRT
<213> ORGANISM: Artificial Sequence
<220> FEATURE:
<223> OTHER INFORMATION: A synthetic protein

<400> SEQUENCE: 127
```

Gln Lys Glu Glu Ser Lys Gly Asn Glu
1 5

<210> SEQ ID NO 128
<211> LENGTH: 4
<212> TYPE: PRT
<213> ORGANISM: Artificial Sequence
<220> FEATURE:
<223> OTHER INFORMATION: A synthetic protein

<400> SEQUENCE: 128

Lys Asn Tyr Arg
1

<210> SEQ ID NO 129
<211> LENGTH: 4
<212> TYPE: PRT
<213> ORGANISM: Artificial Sequence
<220> FEATURE:
<223> OTHER INFORMATION: A synthetic protein

<400> SEQUENCE: 129

Asp Ile Leu Ser
1

<210> SEQ ID NO 130
<211> LENGTH: 4
<212> TYPE: PRT
<213> ORGANISM: Artificial Sequence
<220> FEATURE:
<223> OTHER INFORMATION: A synthetic protein

<400> SEQUENCE: 130

Pro Ser Ser Thr
1

<210> SEQ ID NO 131
<211> LENGTH: 5
<212> TYPE: PRT
<213> ORGANISM: Artificial Sequence
<220> FEATURE:
<223> OTHER INFORMATION: A synthetic protein

<400> SEQUENCE: 131

Leu Asn Ser Pro Glu
1 5

<210> SEQ ID NO 132
<211> LENGTH: 7
<212> TYPE: PRT
<213> ORGANISM: Artificial Sequence
<220> FEATURE:
<223> OTHER INFORMATION: A synthetic protein

<400> SEQUENCE: 132

Leu Ala Lys Gln Ala Phe Asp
1 5

<210> SEQ ID NO 133
<211> LENGTH: 211
<212> TYPE: PRT
<213> ORGANISM: Glycine max

<400> SEQUENCE: 133

Glu Lys Glu Arg Glu Thr Gln Val Tyr Leu Ala Lys Leu Ser Glu Gln
1 5 10 15

Ala Glu Arg Tyr Glu Glu Met Val Glu Cys Met Lys Thr Ile Ala Lys
20 25 30

Leu Asp Leu Glu Leu Thr Val Glu Glu Arg Asn Leu Leu Ser Val Gly
35 40 45

Tyr Lys Asn Val Ile Gly Ala Arg Arg Ala Ser Trp Arg Ile Met Ser
50 55 60

Ser Ile Glu Gln Lys Glu Glu Ser Lys Gly Asn Glu Ser Asn Ala Lys
65 70 75 80

Leu Ile Lys Asn Tyr Arg Gln Lys Val Glu Glu Glu Leu Ser Lys Ile
85 90 95

Cys Ser Asp Ile Leu Ser Ile Ile Asp Gln His Leu Val Pro Ser Ser
100 105 110

Thr Ser Gly Glu Ala Thr Val Phe Tyr Tyr Lys Met Lys Gly Asp Tyr
115 120 125

Tyr Arg Tyr Leu Ala Glu Phe Lys Thr Asp Gln Asp Arg Lys Glu Ala
130 135 140

Ala Glu Gln Ser Leu Lys Gly Tyr Glu Ala Ala Leu Ala Thr Ala Ser
145 150 155 160

Thr Glu Leu Pro Ser Thr His Pro Ile Arg Leu Gly Leu Ala Leu Asn
165 170 175

Phe Ser Val Phe Tyr Tyr Glu Ile Leu Asn Ser Pro Glu Arg Ala Cys
180 185 190

His Leu Ala Lys Gln Ala Phe Asp Glu Ala Ile Ala Glu Leu Asp Thr
195 200 205

Leu Ser Glu
210

<210> SEQ ID NO 134
<211> LENGTH: 198
<212> TYPE: PRT
<213> ORGANISM: Arabidopsis thaliana

<400> SEQUENCE: 134

Met Glu Asn Glu Gln Ser Thr His Val His Phe Ala Ser Leu Ser Ser
1 5 10 15

Ser Ser Glu Arg Tyr Asn Glu Thr Phe Glu Glu Ile Lys Lys Ala Met
20 25 30

Lys Lys Ser Val Gln Leu Lys Ala Glu Leu Ser Ala Lys Glu Arg Asn
35 40 45

Leu Val Ser Val Gly Tyr Lys Asn Val Ile Ser Ala Arg Arg Ala Ser
50 55 60

Leu Glu Ile Leu Ser Ser Ile Val Gln Lys Glu Glu Ser Lys Gly Asn
65 70 75 80

Glu Glu Asn Val Lys Lys Leu Lys Asn Tyr Arg Asn Lys Val Glu Asp
85 90 95

Glu Leu Ala Lys Ile Cys Asn Asp Ile Leu Ser Val Ile Asn Lys Gln
100 105 110

Leu Ile Pro Ser Ser Thr Thr Val Asp Ser Ser Val Leu Phe Tyr Asn
115 120 125

Met Leu Ala Asp Phe Ser Ser Asn Ala Glu Ser Lys Glu Ala Thr Asp
130 135 140

Gln Ser Leu Asp Ala Tyr Lys Arg Leu Val Trp Tyr Gln Gln Phe Gln
145 150 155 160

Leu Tyr Met Thr Leu Asn Trp Thr Ser Val Phe Leu Asn Ser Pro Glu
165 170 175

Ser Ala Tyr Gln Leu Ala Lys Gln Ala Phe Asp Asp Ala Ile Asn Glu
180 185 190

Phe Asp Asn Leu Thr Glu
195

<210> SEQ ID NO 135
<211> LENGTH: 4
<212> TYPE: PRT
<213> ORGANISM: Artificial Sequence
<220> FEATURE:
<223> OTHER INFORMATION: A synthetic protein

<400> SEQUENCE: 135

Ala Met Lys Lys
1

<210> SEQ ID NO 136
<211> LENGTH: 13
<212> TYPE: PRT
<213> ORGANISM: Artificial Sequence
<220> FEATURE:
<223> OTHER INFORMATION: A synthetic protein

<400> SEQUENCE: 136

Glu Arg Asn Leu Val Ser Val Gly Tyr Lys Asn Val Ile
1 5 10

<210> SEQ ID NO 137
<211> LENGTH: 5
<212> TYPE: PRT
<213> ORGANISM: Artificial Sequence
<220> FEATURE:
<223> OTHER INFORMATION: A synthetic protein

<400> SEQUENCE: 137

Ala Arg Arg Ala Ser
1 5

<210> SEQ ID NO 138
<211> LENGTH: 5
<212> TYPE: PRT
<213> ORGANISM: Artificial Sequence
<220> FEATURE:
<223> OTHER INFORMATION: A synthetic protein

<400> SEQUENCE: 138

Ile Leu Ser Ser Ile
1 5

<210> SEQ ID NO 139
<211> LENGTH: 13
<212> TYPE: PRT
<213> ORGANISM: Artificial Sequence
<220> FEATURE:
<223> OTHER INFORMATION: A synthetic protein

<400> SEQUENCE: 139

Gln Lys Glu Glu Ser Lys Gly Asn Glu Glu Asn Val Lys
1 5 10

<210> SEQ ID NO 140
<211> LENGTH: 8
<212> TYPE: PRT
<213> ORGANISM: Artificial Sequence
<220> FEATURE:
<223> OTHER INFORMATION: A synthetic protein

<400> SEQUENCE: 140

Lys Val Glu Asp Glu Leu Ala Lys
1 5

<210> SEQ ID NO 141
<211> LENGTH: 8
<212> TYPE: PRT
<213> ORGANISM: Artificial Sequence
<220> FEATURE:
<223> OTHER INFORMATION: A synthetic protein

<400> SEQUENCE: 141

Cys Asn Asp Ile Leu Ser Val Ile
1 5

<210> SEQ ID NO 142
<211> LENGTH: 6
<212> TYPE: PRT
<213> ORGANISM: Artificial Sequence
<220> FEATURE:
<223> OTHER INFORMATION: A synthetic protein

<400> SEQUENCE: 142

Leu Ile Pro Ser Ser Thr
1 5

<210> SEQ ID NO 143
<211> LENGTH: 4
<212> TYPE: PRT
<213> ORGANISM: Artificial Sequence
<220> FEATURE:
<223> OTHER INFORMATION: A synthetic protein

<400> SEQUENCE: 143

Asp Gln Ser Leu
1

<210> SEQ ID NO 144
<211> LENGTH: 7
<212> TYPE: PRT
<213> ORGANISM: Artificial Sequence
<220> FEATURE:
<223> OTHER INFORMATION: A synthetic protein

<400> SEQUENCE: 144

Leu Asn Ser Pro Glu Ser Ala
1 5

<210> SEQ ID NO 145
<211> LENGTH: 11
<212> TYPE: PRT
<213> ORGANISM: Artificial Sequence
<220> FEATURE:
<223> OTHER INFORMATION: A synthetic protein

<400> SEQUENCE: 145

Gln Leu Ala Lys Gln Ala Phe Asp Asp Ala Ile
1 5 10

<210> SEQ ID NO 146
<211> LENGTH: 212
<212> TYPE: PRT
<213> ORGANISM: Brassica napus

<400> SEQUENCE: 146

-continued

```
Met Glu Thr Glu Arg Glu Lys His Val Tyr Leu Ala Lys Leu Ser Glu
1               5                   10                  15

Gln Thr Glu Arg Tyr Asp Glu Met Val Glu Ala Met Lys Lys Val Ala
            20                  25                  30

Gln Leu Asp Val Glu Leu Thr Val Glu Glu Arg Asn Leu Val Ser Val
        35                  40                  45

Gly Tyr Lys Asn Val Ile Gly Ala Arg Arg Ala Ser Trp Arg Ile Leu
    50                  55                  60

Ser Ser Ile Glu Gln Lys Glu Glu Ser Lys Gly Asn Glu Glu Asn Val
65                  70                  75                  80

Lys Arg Ile Gln Asn Tyr Arg Lys Lys Val Glu Asp Glu Leu Ala Lys
                85                  90                  95

Val Cys Asn Asp Ile Leu Ser Val Ile Asp Lys His Leu Ile Pro Ser
            100                 105                 110

Ser Thr Ala Val Glu Ser Thr Val Phe Phe Tyr Lys Met Lys Gly Asp
        115                 120                 125

Tyr Tyr Arg Tyr Leu Ala Glu Phe Ser Ser Gly Ala Glu Arg Lys Glu
    130                 135                 140

Ala Ala Asp Gln Ser Leu Glu Ala Tyr Lys Ala Ala Val Ala Ala Ala
145                 150                 155                 160

Glu Thr Gly Leu Ala Pro Thr His Pro Val Arg Leu Gly Leu Ala Leu
                165                 170                 175

Asn Phe Ser Val Phe Tyr Tyr Glu Ile Leu Asn Ser Pro Glu Ser Ala
            180                 185                 190

Cys Gln Leu Ala Lys Gln Ala Phe Asp Asp Ala Ile Ala Glu Leu Asp
        195                 200                 205

Ser Leu Asn Glu
    210
```